(12) United States Patent
Hunter et al.

(10) Patent No.: US 11,071,456 B2
(45) Date of Patent: *Jul. 27, 2021

(54) DEVICES, SYSTEMS AND METHODS FOR USING AND MONITORING MEDICAL DEVICES

(71) Applicant: CANARY MEDICAL INC., Vancouver (CA)

(72) Inventors: William L. Hunter, Vancouver (CA); Douglas R. Holberg, Wimberley, TX (US); Jeffrey M. Gross, Carlsbad, CA (US)

(73) Assignee: Canary Medical Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/655,962

(22) Filed: Oct. 17, 2019

(65) Prior Publication Data

US 2020/0281471 A1     Sep. 10, 2020

Related U.S. Application Data

(63) Continuation of application No. 15/078,604, filed on Mar. 23, 2016, now Pat. No. 10,492,686, which is a
(Continued)

(51) Int. Cl.
*A61B 5/00* (2006.01)
*G16H 40/63* (2018.01)
(Continued)

(52) U.S. Cl.
CPC .............. *A61B 5/0031* (2013.01); *A61B 5/00* (2013.01); *A61B 5/0024* (2013.01); *A61B 5/01* (2013.01); *A61B 5/026* (2013.01); *A61B 5/029* (2013.01); *A61B 5/02108* (2013.01); *A61B 5/036* (2013.01); *A61B 5/4851* (2013.01); *A61B 5/686* (2013.01); *A61B 5/6812* (2013.01); *A61B 5/6853* (2013.01); *A61B 5/6862* (2013.01); *A61B 5/7275* (2013.01); *A61B 17/74* (2013.01); *A61C 8/00* (2013.01); *A61F 2/0059* (2013.01); *A61F 2/07* (2013.01); *A61F 2/16* (2013.01); *A61F 2/2412* (2013.01); *A61F 2/32* (2013.01);
(Continued)

(58) Field of Classification Search
None
See application file for complete search history.

(56) References Cited

U.S. PATENT DOCUMENTS

| 4,894,728 A | 1/1990 | Goodman |
| 5,042,504 A | 8/1991 | Huberti |

(Continued)

FOREIGN PATENT DOCUMENTS

| CN | 1899222 A | 1/2007 |
| CN | 101495025 A | 7/2009 |

(Continued)

OTHER PUBLICATIONS

PCT International Search Report and Written Opinion dated Jul. 7, 2014, for PCT/US2014/028381.
(Continued)

*Primary Examiner* — Chico A Foxx

(57) ABSTRACT

Medical devices are provided, comprising a medical device and a sensor.

30 Claims, 34 Drawing Sheets

Related U.S. Application Data continuation-in-part of application No. PCT/US2015/050789, filed on Sep. 17, 2015.

(60) Provisional application No. 62/184,820, filed on Jun. 25, 2015, provisional application No. 62/051,855, filed on Sep. 17, 2014.

(51) Int. Cl.

| | | |
|---|---|---|
| *A61B 5/01* | (2006.01) | |
| *A61B 5/021* | (2006.01) | |
| *A61B 5/026* | (2006.01) | |
| *A61B 5/029* | (2006.01) | |
| *A61B 5/03* | (2006.01) | |
| *A61B 17/74* | (2006.01) | |
| *A61C 8/00* | (2006.01) | |
| *A61F 2/00* | (2006.01) | |
| *A61F 2/07* | (2013.01) | |
| *A61F 2/16* | (2006.01) | |
| *A61F 2/24* | (2006.01) | |
| *A61F 2/32* | (2006.01) | |
| *A61F 2/38* | (2006.01) | |
| *A61F 5/01* | (2006.01) | |
| *A61F 5/055* | (2006.01) | |
| *A61N 1/37* | (2006.01) | |
| *A61N 1/39* | (2006.01) | |
| *G16H 40/60* | (2018.01) | |
| *A61B 5/02* | (2006.01) | |

(52) U.S. Cl.
CPC ............ *A61F 2/389* (2013.01); *A61F 2/3859* (2013.01); *A61F 2/3877* (2013.01); *A61F 5/0123* (2013.01); *A61F 5/055* (2013.01); *A61N 1/3702* (2013.01); *A61N 1/3956* (2013.01); *G16H 40/60* (2018.01); *G16H 40/63* (2018.01); *A61B 5/021* (2013.01); *A61B 5/02014* (2013.01); *A61B 2560/0219* (2013.01); *A61B 2562/0219* (2013.01); *A61B 2562/0247* (2013.01); *A61B 2562/043* (2013.01); *A61B 2562/063* (2013.01)

(56) References Cited

U.S. PATENT DOCUMENTS

| | | | |
|---|---|---|---|
| 5,413,604 A | | 5/1995 | Hodge |
| 5,626,581 A | | 5/1997 | Staehlin et al. |
| 5,672,954 A | * | 9/1997 | Watanabe ............ H02J 7/1438 322/28 |
| 5,833,603 A | | 11/1998 | Kovacs et al. |
| 5,906,643 A | | 5/1999 | Walker |
| 6,019,794 A | | 2/2000 | Walker |
| 6,245,109 B1 | | 6/2001 | Mendes et al. |
| 6,358,202 B1 | | 3/2002 | Arent |
| 6,374,097 B1 | * | 4/2002 | Kudou ................. H04W 88/022 455/232.1 |
| 6,447,448 B1 | | 9/2002 | Ishikawa et al. |
| 6,610,101 B2 | | 8/2003 | Herr et al. |
| 6,620,168 B1 | * | 9/2003 | Lombardo ......... A61B 17/1735 606/102 |
| 6,706,071 B1 | | 3/2004 | Wolter |
| 6,712,778 B1 | | 3/2004 | Jeffcoat et al. |
| 7,009,511 B2 | | 3/2006 | Mazar et al. |
| 7,097,662 B2 | | 8/2006 | Evans, III et al. |
| 7,130,695 B2 | | 10/2006 | Czygan et al. |
| 7,141,026 B2 | | 11/2006 | Aminian et al. |
| 7,190,273 B2 | | 3/2007 | Liao et al. |
| 7,383,071 B1 | | 6/2008 | Russell et al. |
| 7,450,332 B2 | | 11/2008 | Pasolini et al. |
| 7,463,997 B2 | | 12/2008 | Pasolini et al. |
| 7,553,923 B2 | | 6/2009 | Williams et al. |
| 7,559,951 B2 | | 7/2009 | DiSilvestro et al. |
| 7,813,808 B1 | | 10/2010 | Doron et al. |
| 7,922,771 B2 | | 4/2011 | Otto et al. |
| 7,924,267 B2 | | 4/2011 | Sirtori |
| 8,029,566 B2 | | 10/2011 | Lozier et al. |
| 8,080,064 B2 | * | 12/2011 | Dietz ...................... A61F 2/389 623/20.32 |
| 8,109,890 B2 | | 2/2012 | Kamiar et al. |
| 8,176,922 B2 | * | 5/2012 | Sherman ................. A61F 2/38 128/899 |
| 8,244,368 B2 | * | 8/2012 | Sherman ................. A61F 2/30 607/62 |
| 8,317,869 B2 | * | 11/2012 | Cloutier ................ A61F 2/3859 623/20.3 |
| 8,551,023 B2 | * | 10/2013 | Sherman ............... A61B 5/4585 600/587 |
| 8,634,928 B1 | | 1/2014 | O |
| 8,721,643 B2 | | 5/2014 | Morgan et al. |
| 8,876,739 B2 | | 11/2014 | Salarian et al. |
| 8,996,892 B1 | | 3/2015 | Chu et al. |
| 9,019,098 B2 | | 4/2015 | Okano |
| 9,307,932 B2 | | 4/2016 | Mariani et al. |
| 9,549,742 B2 | * | 1/2017 | Berend ................ A61B 17/155 |
| 9,820,858 B2 | * | 11/2017 | Harris .................. A61B 17/155 |
| 10,070,973 B2 | * | 9/2018 | Sherman ............... A61F 2/4657 |
| 10,492,686 B2 | | 12/2019 | Hunter et al. |
| 10,596,009 B2 | * | 3/2020 | Mines ................. A61F 2/30734 |
| 2002/0024450 A1 | | 2/2002 | Townsend et al. |
| 2003/0069644 A1 | | 4/2003 | Kovacevic et al. |
| 2003/0204267 A1 | | 10/2003 | Hazebrouck et al. |
| 2004/0019382 A1 | | 1/2004 | Amirouche et al. |
| 2004/0019384 A1 | | 1/2004 | Kirking et al. |
| 2004/0083003 A1 | * | 4/2004 | Wasielewski ....... A61L 27/3629 623/20.21 |
| 2004/0204766 A1 | | 10/2004 | Siebel |
| 2004/0211580 A1 | | 10/2004 | Wang et al. |
| 2004/0243148 A1 | | 12/2004 | Wasielewski |
| 2004/0243244 A1 | * | 12/2004 | Otto ....................... A61F 2/3886 623/20.27 |
| 2005/0010299 A1 | | 1/2005 | Disilvestro |
| 2005/0010301 A1 | | 1/2005 | Disilvestro et al. |
| 2005/0012610 A1 | | 1/2005 | Liao et al. |
| 2005/0242666 A1 | * | 11/2005 | Huscher ............... B60R 16/0232 307/10.1 |
| 2005/0245992 A1 | | 11/2005 | Persen et al. |
| 2006/0009856 A1 | | 1/2006 | Sherman et al. |
| 2006/0030945 A1 | | 2/2006 | Wright |
| 2006/0069403 A1 | | 3/2006 | Shalon et al. |
| 2006/0142670 A1 | | 6/2006 | DiSilvestro et al. |
| 2006/0184067 A1 | | 8/2006 | Clark et al. |
| 2006/0224088 A1 | | 10/2006 | Roche |
| 2006/0229730 A1 | | 10/2006 | Railey et al. |
| 2006/0271112 A1 | | 11/2006 | Martinson et al. |
| 2006/0271199 A1 | | 11/2006 | Johnson |
| 2006/0282168 A1 | | 12/2006 | Sherman et al. |
| 2007/0004994 A1 | | 1/2007 | Sherman |
| 2007/0005141 A1 | | 1/2007 | Sherman |
| 2007/0034013 A1 | * | 2/2007 | Moon .................... G01D 5/2412 73/780 |
| 2007/0088442 A1 | | 4/2007 | Cima et al. |
| 2007/0089518 A1 | | 4/2007 | Ericson et al. |
| 2007/0126696 A1 | | 6/2007 | Boillot |
| 2007/0179628 A1 | * | 8/2007 | Rochetin ................ A61F 2/389 623/20.34 |
| 2007/0179739 A1 | | 8/2007 | Donofrio et al. |
| 2007/0211022 A1 | | 9/2007 | Boillot |
| 2007/0211023 A1 | | 9/2007 | Boillot |
| 2007/0233065 A1 | * | 10/2007 | Donofrio ............... A61B 8/4472 606/309 |
| 2007/0233267 A1 | | 10/2007 | Amirouche et al. |
| 2007/0234819 A1 | | 10/2007 | Amirouche et al. |
| 2007/0238984 A1 | | 10/2007 | Maschke et al. |
| 2007/0238992 A1 | | 10/2007 | Donofrio et al. |
| 2007/0239282 A1 | | 10/2007 | Caylor et al. |
| 2007/0288194 A1 | | 12/2007 | Boillot |
| 2008/0027679 A1 | | 1/2008 | Shklarski |
| 2008/0033527 A1 | | 2/2008 | Nunez et al. |
| 2008/0048878 A1 | | 2/2008 | Boillot |

(56) References Cited

U.S. PATENT DOCUMENTS

| | | |
|---|---|---|
| 2008/0065225 A1 | 3/2008 | Wasielewski et al. |
| 2008/0076972 A1 | 3/2008 | Dorogusker et al. |
| 2008/0088436 A1 | 4/2008 | Reeves et al. |
| 2008/0214903 A1 | 9/2008 | Orbach |
| 2008/0215609 A1* | 9/2008 | Cleveland ......... G06F 16/24556 |
| 2008/0235621 A1 | 9/2008 | Boillot |
| 2008/0300597 A1 | 12/2008 | Morgan et al. |
| 2008/0300659 A1 | 12/2008 | Matos |
| 2008/0306325 A1 | 12/2008 | Burnett et al. |
| 2009/0005708 A1 | 1/2009 | Johanson et al. |
| 2009/0005876 A1 | 1/2009 | Dietz et al. |
| 2009/0012372 A1 | 1/2009 | Burnett et al. |
| 2009/0048524 A1 | 2/2009 | Wildau et al. |
| 2009/0088756 A1 | 4/2009 | Anderson |
| 2009/0119222 A1 | 5/2009 | O |
| 2009/0157146 A1 | 6/2009 | Linder et al. |
| 2009/0264894 A1 | 10/2009 | Wasielewski |
| 2009/0299228 A1 | 12/2009 | Lozier et al. |
| 2010/0100011 A1 | 4/2010 | Roche |
| 2010/0145337 A1 | 6/2010 | Janna et al. |
| 2010/0152621 A1 | 6/2010 | Janna |
| 2010/0191100 A1 | 7/2010 | Anderson et al. |
| 2010/0204551 A1 | 8/2010 | Roche |
| 2010/0204802 A1 | 8/2010 | Wilson et al. |
| 2010/0204955 A1 | 8/2010 | Roche et al. |
| 2010/0249533 A1 | 9/2010 | Pierce et al. |
| 2010/0249787 A1 | 9/2010 | Roche |
| 2010/0249790 A1 | 9/2010 | Roche |
| 2010/0262160 A1 | 10/2010 | Boyden et al. |
| 2010/0285082 A1 | 11/2010 | Fernandez |
| 2010/0287422 A1 | 11/2010 | Miyazaki |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1* | 12/2010 | Stein ..................... A61B 5/4528 73/862.636 |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331738 A1 | 12/2010 | Stein et al. |
| 2010/0331894 A1 | 12/2010 | Stein |
| 2010/0332152 A1 | 12/2010 | Stein |
| 2011/0004076 A1 | 1/2011 | Janna et al. |
| 2011/0019595 A1 | 1/2011 | Magar et al. |
| 2011/0054272 A1 | 3/2011 | Derchak |
| 2011/0060220 A1 | 3/2011 | Roche et al. |
| 2011/0063094 A1 | 3/2011 | Meiertoberens et al. |
| 2011/0077736 A1 | 3/2011 | Rofougaran |
| 2011/0087306 A1 | 4/2011 | Goossen |
| 2011/0098576 A1 | 4/2011 | Hollstien |
| 2011/0160572 A1 | 6/2011 | McIntosh et al. |
| 2011/0160583 A1 | 6/2011 | Roche et al. |
| 2011/0160616 A1* | 6/2011 | Stein ..................... A61B 5/4528 600/587 |
| 2011/0196501 A1 | 8/2011 | Michelson |
| 2011/0200052 A1 | 8/2011 | Mungo et al. |
| 2011/0213221 A1 | 9/2011 | Roche |
| 2011/0288805 A1 | 11/2011 | Dejnabadi et al. |
| 2011/0319755 A1* | 12/2011 | Stein ..................... A61F 2/4657 600/437 |
| 2012/0035868 A1 | 2/2012 | Roche et al. |
| 2012/0095526 A1 | 4/2012 | Roche |
| 2012/0116310 A1 | 5/2012 | Forsell |
| 2012/0123498 A1 | 5/2012 | Gross |
| 2012/0123716 A1 | 5/2012 | Clark |
| 2012/0130687 A1 | 5/2012 | Otto et al. |
| 2012/0152017 A1 | 6/2012 | Stein et al. |
| 2012/0157839 A1 | 6/2012 | Stein |
| 2012/0157884 A1 | 6/2012 | Stein et al. |
| 2012/0190940 A1 | 7/2012 | Stein et al. |
| 2012/0191206 A1 | 7/2012 | Stein et al. |
| 2012/0216611 A1 | 8/2012 | Stein et al. |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232834 A1 | 9/2012 | Roche et al. |
| 2012/0283600 A1 | 11/2012 | Stein |
| 2012/0330367 A1 | 12/2012 | Roche et al. |
| 2013/0011008 A1 | 1/2013 | Ikezoye et al. |
| 2013/0023794 A1 | 1/2013 | Stein et al. |
| 2013/0023795 A1 | 1/2013 | Stein et al. |
| 2013/0079668 A1 | 3/2013 | Stein et al. |
| 2013/0079669 A1* | 3/2013 | Stein ..................... A61B 5/6882 600/587 |
| 2013/0079670 A1* | 3/2013 | Stein ..................... A61F 2/4657 600/587 |
| 2013/0079671 A1 | 3/2013 | Stein et al. |
| 2013/0079672 A1* | 3/2013 | Stein ..................... A61F 2/3859 600/587 |
| 2013/0079674 A1 | 3/2013 | Stein et al. |
| 2013/0079675 A1 | 3/2013 | Stein et al. |
| 2013/0079790 A1 | 3/2013 | Stein et al. |
| 2013/0079884 A1* | 3/2013 | Stein ..................... A61B 5/4528 623/18.11 |
| 2013/0197656 A1 | 8/2013 | Conrad |
| 2013/0215979 A1 | 8/2013 | Yakovlev et al. |
| 2013/0225949 A1 | 8/2013 | Roche |
| 2013/0225982 A1 | 8/2013 | McIntosh et al. |
| 2013/0226034 A1 | 8/2013 | Stein et al. |
| 2013/0252610 A1 | 9/2013 | Kim et al. |
| 2013/0261450 A1 | 10/2013 | Stein et al. |
| 2013/0268081 A1 | 10/2013 | Stein et al. |
| 2013/0317367 A1* | 11/2013 | Shuler .................. A61B 5/0075 600/473 |
| 2013/0325019 A1* | 12/2013 | Thomas ............. A61B 17/1735 606/88 |
| 2013/0338455 A1 | 12/2013 | Gradel et al. |
| 2013/0338770 A1 | 12/2013 | Boyden et al. |
| 2014/0025338 A1 | 1/2014 | Blount et al. |
| 2014/0031063 A1 | 1/2014 | Park et al. |
| 2014/0085102 A1* | 3/2014 | McCormick ........... H04B 7/185 340/870.01 |
| 2014/0094715 A1 | 4/2014 | Stein et al. |
| 2014/0107796 A1 | 4/2014 | Stein et al. |
| 2014/0135589 A1 | 5/2014 | Osorio |
| 2014/0135616 A1 | 5/2014 | Stein et al. |
| 2014/0135624 A1 | 5/2014 | Stein et al. |
| 2014/0135773 A1 | 5/2014 | Stein et al. |
| 2014/0136143 A1 | 5/2014 | Stein et al. |
| 2014/0148676 A1 | 5/2014 | Stein et al. |
| 2014/0171754 A1 | 6/2014 | Stein et al. |
| 2014/0180697 A1 | 6/2014 | Torok et al. |
| 2014/0188007 A1 | 7/2014 | Stein et al. |
| 2014/0194707 A1 | 7/2014 | Stein et al. |
| 2014/0200584 A1 | 7/2014 | Stein et al. |
| 2014/0256324 A1 | 9/2014 | Mohanty et al. |
| 2014/0257047 A1 | 9/2014 | Sillay et al. |
| 2014/0275815 A1 | 9/2014 | Stein et al. |
| 2014/0275849 A1 | 9/2014 | Acquista |
| 2014/0276240 A1* | 9/2014 | Stein ..................... A61B 5/1072 600/595 |
| 2014/0276241 A1 | 9/2014 | Stein et al. |
| 2014/0276885 A1 | 9/2014 | Stein et al. |
| 2014/0276887 A1 | 9/2014 | Stein et al. |
| 2014/0277542 A1 | 9/2014 | Stein et al. |
| 2014/0288464 A1* | 9/2014 | Stein ..................... A61F 2/4657 600/595 |
| 2014/0328253 A1 | 11/2014 | Lee et al. |
| 2014/0330105 A1 | 11/2014 | Roche |
| 2015/0032217 A1 | 1/2015 | Bojarski et al. |

(56) References Cited

U.S. PATENT DOCUMENTS

| | | | |
|---|---|---|---|
| 2015/0039093 A1* | 2/2015 | McTighe | A61F 2/4014 623/23.14 |
| 2015/0057775 A1 | 2/2015 | Dong | |
| 2015/0080901 A1 | 3/2015 | Stein | |
| 2015/0335290 A1 | 11/2015 | Hunter | |
| 2016/0029952 A1 | 2/2016 | Hunter | |
| 2016/0038087 A1 | 2/2016 | Hunter | |
| 2016/0081762 A1 | 3/2016 | Stein et al. | |
| 2016/0166201 A1 | 6/2016 | Stein et al. | |
| 2016/0192878 A1* | 7/2016 | Hunter | A61B 5/0031 623/20.14 |
| 2016/0310077 A1 | 10/2016 | Hunter et al. | |
| 2016/0340177 A1* | 11/2016 | Takada | G01C 19/5628 |
| 2017/0119316 A1 | 5/2017 | Herrmann et al. | |
| 2017/0119472 A1 | 5/2017 | Herrmann et al. | |
| 2017/0138986 A1* | 5/2017 | Kern | G01R 31/67 |
| 2017/0156632 A1 | 6/2017 | Swiston et al. | |
| 2017/0181825 A1 | 6/2017 | Hunter | |
| 2017/0189553 A1 | 7/2017 | Hunter | |
| 2017/0196478 A1 | 7/2017 | Hunter | |
| 2017/0196499 A1 | 7/2017 | Hunter | |
| 2017/0196508 A1 | 7/2017 | Hunter | |
| 2017/0196509 A1 | 7/2017 | Hunter | |
| 2017/0252187 A1 | 9/2017 | Chapman et al. | |
| 2018/0000380 A1 | 1/2018 | Stein et al. | |
| 2018/0055443 A1 | 3/2018 | Stein et al. | |
| 2018/0125365 A1 | 5/2018 | Hunter et al. | |
| 2018/0177607 A1 | 6/2018 | Trabish et al. | |
| 2018/0177611 A1 | 6/2018 | Trabish et al. | |
| 2018/0177612 A1 | 6/2018 | Trabish et al. | |
| 2018/0235546 A1 | 8/2018 | Hunter | |
| 2019/0038361 A1 | 2/2019 | Wasielewski | |
| 2019/0038425 A1 | 2/2019 | Otto et al. | |
| 2019/0290451 A1 | 9/2019 | Trabish et al. | |
| 2020/0054215 A1 | 2/2020 | Roche | |

FOREIGN PATENT DOCUMENTS

| | | |
|---|---|---|
| CN | 101773387 A | 7/2010 |
| CN | 202036215 U | 11/2011 |
| DE | 19924676 A1 | 11/2000 |
| EP | 2018825 A1 | 1/2009 |
| EP | 1814471 B1 | 3/2010 |
| JP | 2005520630 A | 7/2005 |
| JP | 2006055629 A | 3/2006 |
| JP | 2007535372 A | 12/2007 |
| JP | 2011514812 A | 5/2011 |
| WO | 1997033513 A1 | 9/1997 |
| WO | 2004016204 A1 | 2/2004 |
| WO | 2004091419 A2 | 10/2004 |
| WO | 2005120203 | 12/2005 |
| WO | 2006105098 A2 | 10/2006 |
| WO | 2006113394 A2 | 10/2006 |
| WO | 2008035089 A1 | 3/2008 |
| WO | 2008103181 A1 | 8/2008 |
| WO | 2008152549 A2 | 12/2008 |
| WO | 2009148847 A2 | 12/2009 |
| WO | 2010111678 A2 | 9/2010 |
| WO | 2012006066 A1 | 1/2012 |
| WO | 2012061825 A2 | 5/2012 |
| WO | 2012103549 A1 | 8/2012 |
| WO | 2013044117 A1 | 3/2013 |
| WO | 2013044127 A1 | 3/2013 |
| WO | 2013044157 A1 | 3/2013 |
| WO | 2013044160 A2 | 3/2013 |
| WO | 2013044165 A2 | 3/2013 |
| WO | 2013044174 A2 | 3/2013 |
| WO | 2014053956 A1 | 4/2014 |
| WO | 2014100795 A1 | 6/2014 |
| WO | 2014144070 A1 | 9/2014 |
| WO | 2014144107 A1 | 9/2014 |
| WO | 2014209916 A1 | 12/2014 |
| WO | 2015038979 A1 | 3/2015 |
| WO | 2015200704 A1 | 12/2015 |
| WO | 2015200707 A1 | 12/2015 |
| WO | 2015200718 A1 | 12/2015 |
| WO | 2015200720 A2 | 12/2015 |
| WO | 2015200722 A2 | 12/2015 |
| WO | 2015200723 A1 | 12/2015 |
| WO | 2016044651 A1 | 3/2016 |
| WO | 2016174612 A1 | 11/2016 |
| WO | 2016180653 A1 | 11/2016 |
| WO | 2016180654 A1 | 11/2016 |
| WO | 2017152153 A1 | 9/2017 |
| WO | 2017165717 A1 | 9/2017 |
| WO | 2018119360 A1 | 6/2018 |

OTHER PUBLICATIONS

PCT International Search Report and Written Opinion dated Oct. 15, 2014, for PCT/US2014/043736.
PCT International Search Report and Written Opinion dated Feb. 1, 2016, for PCT/US2015/050789.
PCT International Search Report and Written Opinion dated Aug. 2, 2017, for PCT/US2017/023916.
PCT International Search Report and Written Opinion dated Oct. 30, 2020, for PCT/US2020/036516.
European Partial Search Report dated Jun. 13, 2017, for 14817352.9.
European Partial Search Report dated Oct. 16 2018 for 15842678.3.
European Full Extended Search Report dated Nov. 12, 2018 for 15812631.8.
European Extended Search Report dated Feb. 5, 2019 for 15842678.3.
Arami, Arash et al., "Instrumented Prosthesis for Knee Implant Monitoring", 2011 IEEE International Conference on Automation Science and Engineering, Trieste, Italy, Aug. 24-27, 2011, pp. 828-835.
Arami, Arash et al., "Accurate Measurement of Concurrent Flexion-Extension and Internal-External Rotations in Smart Knee Prostheses", IEEE Transactions on BioMedical Engineering, v. 60, No. 9, Sep. 2013, pp. 2504-2510.
Bosch Sensortec Data Sheet for BMI160 Small, low power inertial measurement unit, Doc Rev 0.8, Release Date Feb. 10, 2015, No. BST-BMI160-DS000-07, 110 pp.
Bosch for BMI160 Small, low power inertial measurement unit, Jan. 15, 2015, , 2 pp.
Bosch Press Release, "Bosch Sensortec launches first IMU with sub 1mA current consumption", Jun. 25, 2014, 3 pp.
Ebrahim, A. F., et al., "The use of fiber Bragg grating sensors in biomechanics and rehabilitation applications: The state-of-the-art and ongoing research topics", Sensors, 2012, v 12, No. 10, pp. 12890-12929.
Forchelet, David et al. "Enclosed Electronic System for Force Measurements in Knee Implants", Sensors 2014, vol. 14, pp. 15009-15021.
Graichen, F., et al., "Hip endoprosthesis for in vivo measurement of joint force and termperative", Journal of Biomechanics, 1999, v 32, No. 10, pp. 1113-1117.
Heinlein, Bernd et al., "Design, calibration and pre-clinical testing of an instrumented tibial tray", Journal of Biomechanics, vol. 40, 2007, pp. S4-S10.
Jacq, Caroline et al., "Investigation of Polymer Thick-Film Piezoresistors for Medical Writst Rehabilitation and Artificial Knee Load Sensors", Procedia Engineering, vol. 87, 2014, pp. 1194-1197.
Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.
Li, Yiming et al., "Wireless Sensor Networks in Healthcare", Chinese Journal of Medical Instrumentation, v. 37, No. 5, Dec. 31, 2013, pp. 351-354.
Park, Min-Ho, MD et al., "Using a Tibial Short Extension Stem Reduces Tibial Component Loosening After Primary Total Knee Arthroplasty in Severely Varus Knees: Long-term Survival Analysis with Propensity Score Matching," The Journal of Arthroplasty, vol. 33, 2018, pp. 2512-2517.

(56) References Cited

OTHER PUBLICATIONS

Simoncini, Matteo; "Design and integration of an instrumented knee prosthesis", Thesis No. 6379 (2014), École Polytechnique Fédérale de Lausanne.

Xie, Xiang et al., "A Review of the Implantable Electronic Devices in Biology and Medicine", ACTA Electronica Sinica, vol. 32, No. 3, Mar. 2004, pp. 462-467.

Zimmer® NexGen® RH Knee Brochure 8 pp.

\* cited by examiner

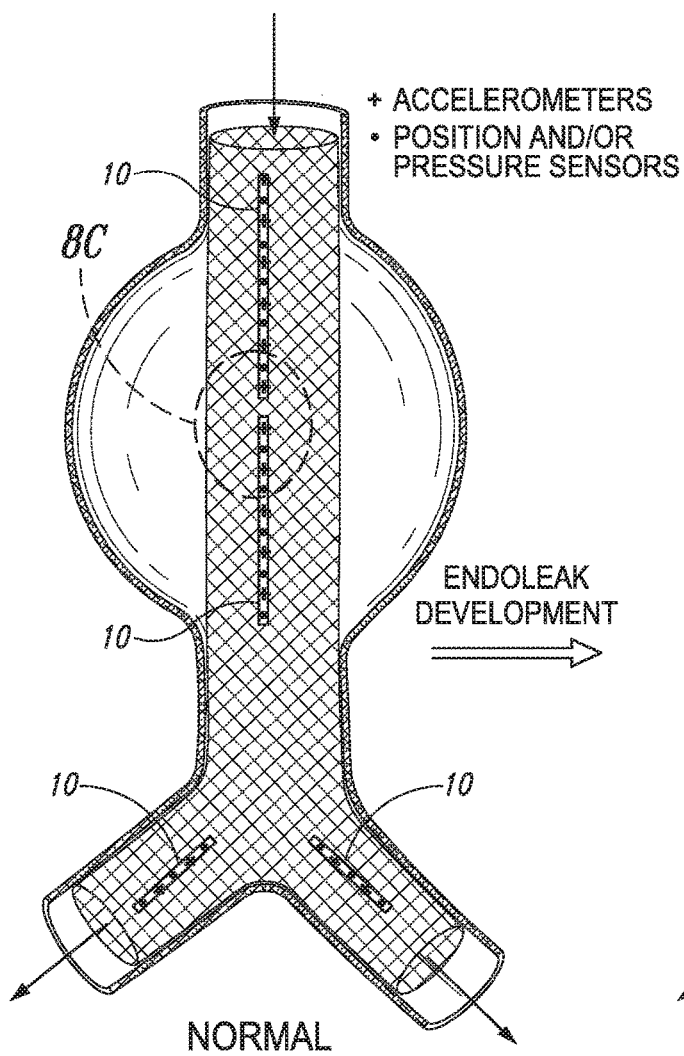
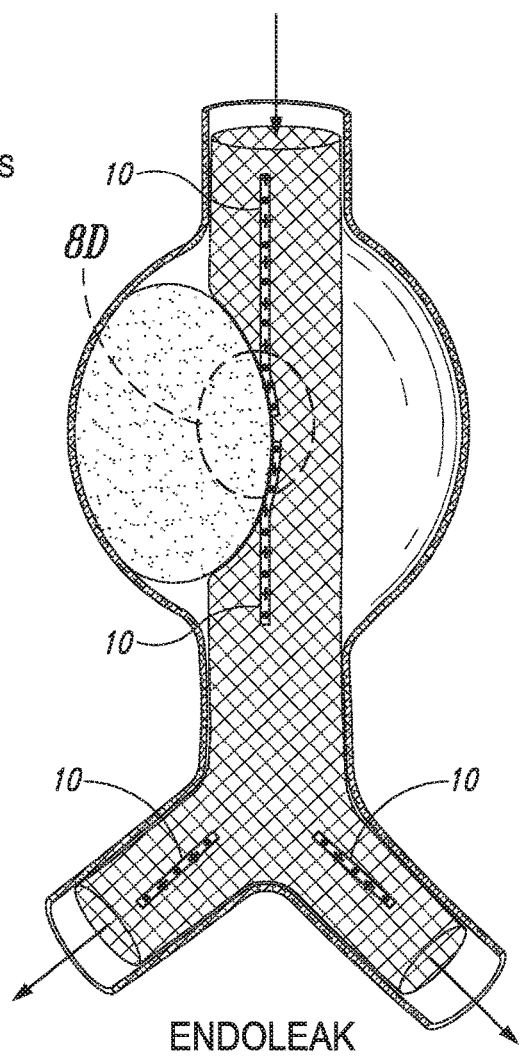
FIG. 8A — NORMAL
FIG. 8B — ENDOLEAK
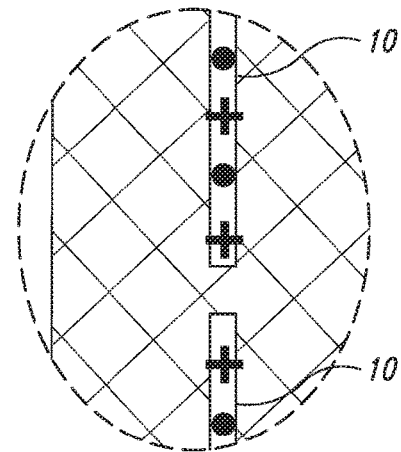
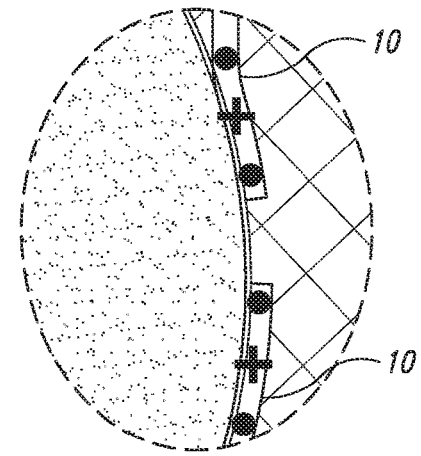
FIG. 8C
FIG. 8D

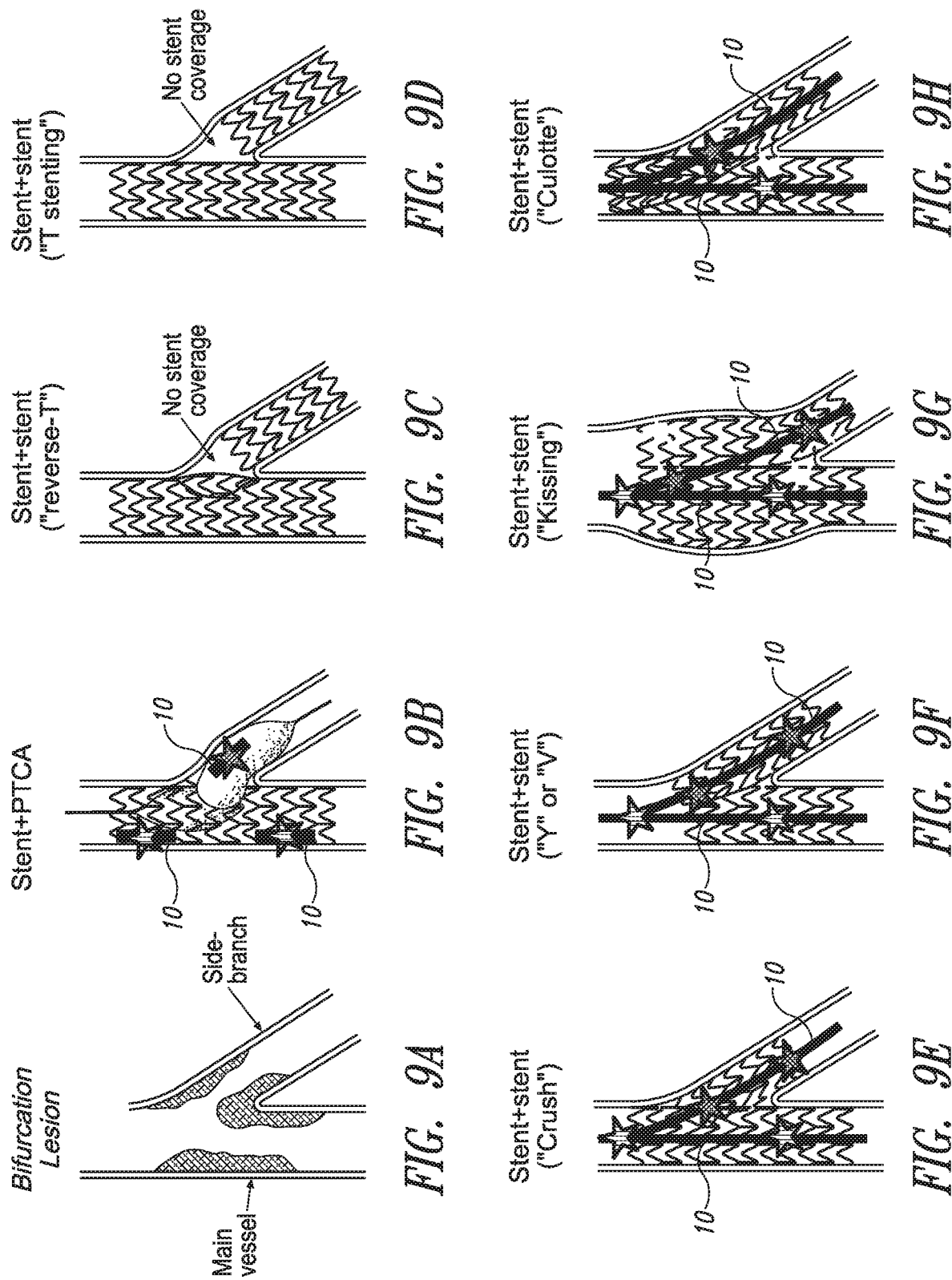

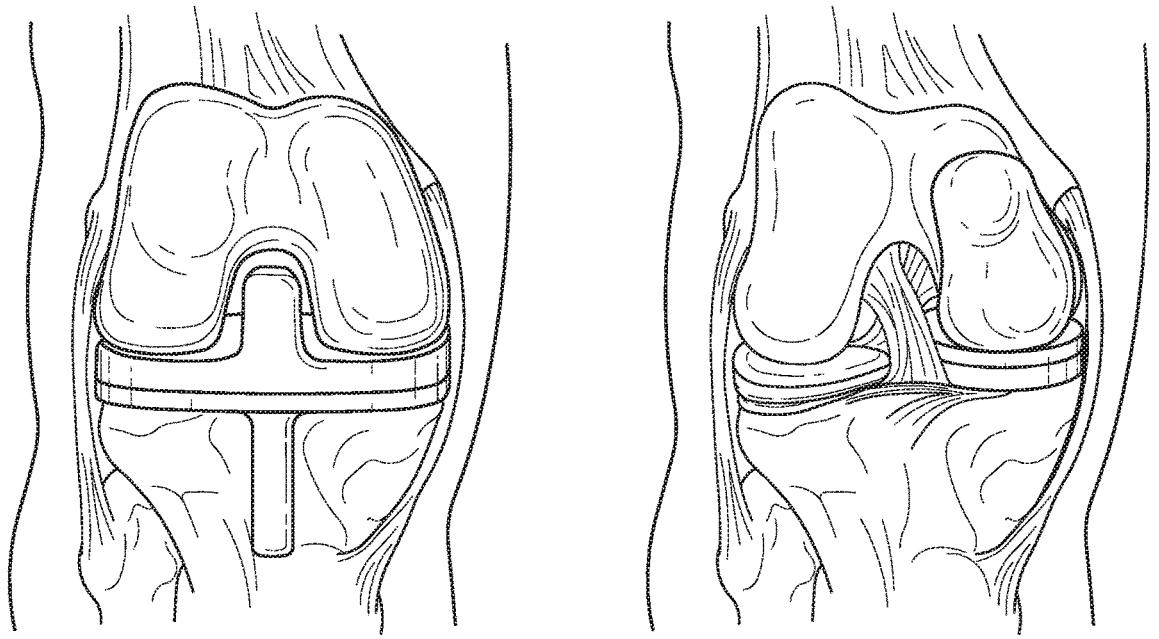
TOTAL UNICOMPARTMENTAL
*FIG. 14*
*FIG. 15A*
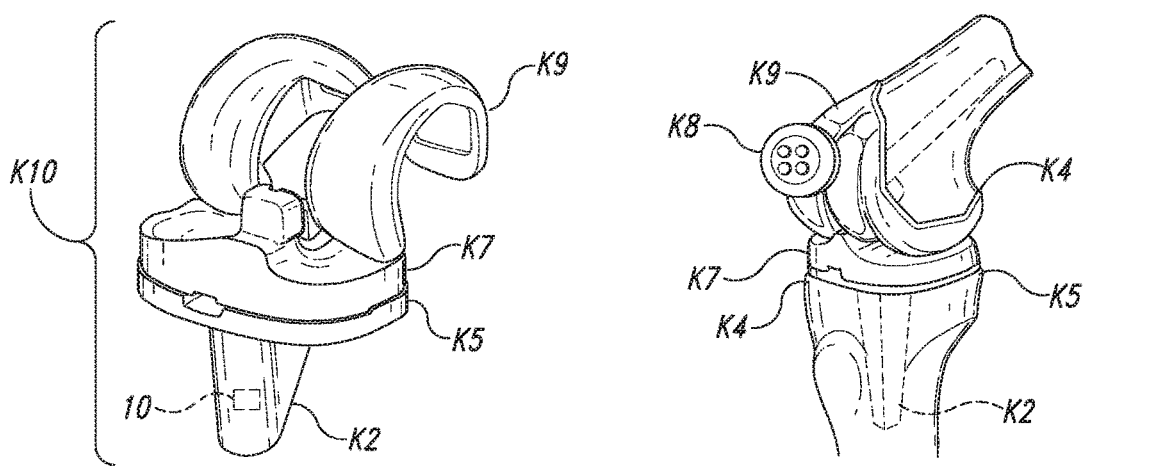

DEVICES, SYSTEMS AND METHODS FOR USING AND MONITORING MEDICAL DEVICES

CROSS-REFERENCE TO RELATED APPLICATIONS

This application is a continuation of U.S. patent application Ser. No. 15/078,604, filed Mar. 23, 2016, which is a continuation-in-part of International Application No. PCT/US2015/050789, filed Sep. 17, 2015, which claims the benefit under 35 U.S.C. § 119(e) of U.S. Provisional Patent Application No. 62/051,855 filed Sep. 17, 2014, and U.S. Provisional Patent Application No. 62/184,820 filed Jun. 25, 2015, all applications are incorporated herein by reference in their entireties.

FIELD OF THE INVENTION

Technical Field

The present invention relates generally to medical devices, and more specifically, to devices and methods for monitoring the placement, efficacy, durability and performance of a wide variety of temporary and/or permanently implantable medical devices.

Background

DESCRIPTION OF THE RELATED ART

Medical devices and implants have become commonplace in modern medicine. Typically, medical devices and implants are manufactured to replace, support, or enhance an anatomical or biological structure. Examples of medical devices include cardiovascular implants such as implantable cardioverter defibrillators, pacemakers, stents, stent grafts, bypass grafts, catheters and heart valves; orthopedic implants such as hip and knee prosthesis; spinal implants and hardware (spinal cages, screws, plates, pins, rods and artificial discs); intrauterine devices; orthopedic hardware used to repair fractures and soft tissue injuries (casts, braces, tensor bandages, plates, screws, pins and plates); cochlear implants; aesthetic implants (breast implants, fillers); dental implants: medical polymers; and artificial intraocular eye lenses.

Unfortunately, various complications may arise during insertion of the medical device or implant (whether it is an open surgical procedure or a minimally invasive procedure). For example, a surgeon may wish to confirm correct anatomical alignment and placement of the implant within surrounding tissues and structures. This can however be difficult to do during the procedure itself, making corrective adjustments difficult.

In addition, a patient may experience a number of complications post-procedure. Such complications include neurological symptoms, pain, malfunction (blockage, loosening, etc.) and/or wear of the implant, movement or breakage of the implant, inflammation and/or infection. While some of these problems can be addressed with pharmaceutical products and/or further surgery, they are difficult to predict and prevent; often early identification of complications and side effects is difficult or impossible.

The present invention discloses novel medical devices and implants which can overcome many of the difficulties and limitations found with previous medical devices and implants, methods for constructing and monitoring these novel medical devices and implants, and further provides other related advantages.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, medical devices and implants (also referred to as 'medical devices') are provided comprising a medical device along with one or more ISMs ("Implantable Sensor Modules") which can be utilized to monitor the integrity and efficaciousness of the medical device.

Representative examples of medical devices and implants include, for example, cardiovascular devices and implants such as implantable cardioverter defibrillators, pacemakers, stents, stent grafts, bypass grafts, catheters and heart valves; orthopedic implants such as hip and knee prosthesis; spinal implants and hardware (spinal cages, screws, plates, pins, rods and artificial discs); a wide variety of medical tubes, cosmetic and/or aesthetic implants (e.g., breast implants, fillers); a wide variety of polymers; intrauterine devices; orthopedic hardware (e.g., casts, braces, tensor bandages, external fixation devices, tensors, slings and supports) and internal hardware (e.g., K-wires, pins, screws, plates, and intramedullary devices (e.g., rods and nails)); cochlear implants; dental implants; medical polymers, a wide variety of neurological devices; and artificial intraocular eye lenses.

The ISMs may be positioned on the inside of the medical device, within the body of the medical device, or on the outer/inner surface (or surfaces) of the medical device, and/or between the medical device and any device that might be utilized to deliver the implant, as well as cements, sutures and glues that may also be utilized within a surgical procedure. Within certain embodiments, the sensors are of the type that are passive and thus do not require their own power supply. Within certain embodiments, the sensors are of the type that are subservient to another sensor, where the subservient sensor needs a power supply but since the subservient sensor only sends information to another, close by sensor, the subservient sensor does not need a large power supply such as is needed by sensor that sends information outside of the body.

Within one embodiment of the invention, the ISM is a self-contained module having one or more sensors as described herein, a sensor interface, a processor interface, battery management, and a wireless interface. Within preferred embodiments of the invention the ISM will be less than 5, 4, 3, 2, or 1 cubic centimeter in size, and more preferably, less than 5.0, 4.5, 4.0, 3.5, 3.0, 2.5, 2.0, 1.5, 1.0, 0.9, 0.8. 0.7, 0.6, 0.5, 0.4, 0.3, 0.2, or 0.1 cubic centimeters in size. Within various embodiments the ISM can be comprised of a solid outer core, or composed of flexible materials (e.g., a degradable or non-degradable outer polymeric surface). Within certain embodiments the ISM may be relatively square and solid, and yet with in other embodiments very thin, malleable and lengthy (as compared to its width and/or height). It can be constructed for a number of different applications (e.g., for insertion or implantation into any of the medical devise or implants provided herein).

ISMs can also be utilized in delivery devices which are associated with, or used along with the medical device and implant. Representative examples include drills, drill guides, mallets, guidewires, catheters, balloons, trocars, endoscopes, bone tunneling catheters, microsurgical tools and general surgical tools.

In addition, further components or compositions may be delivered along with the medical device and implant which also can have or contain an ISM, including for example, fillers such as sutures, glues, collagen, fibrin, growth factors, barriers, hemostats, bone cement and polymers such as PMMA.

Within preferred embodiments of the above, the ISM, medical device, medical delivery device and filler are all provided in a sterile form (e.g., ETO sterilized), non-pyrogenic, suitable for use in humans and in a kit containing components suitable for a particular surgery. Within further embodiments one or more of the components may be provided together as a kit.

Representative examples of sensors which may be contained within an ISM and which are suitable for use within the present invention include accelerometers (acceleration, tilt, vibration, shock and rotation sensors), pressure sensors, contact sensors, position sensors, chemical sensors, tissue metabolic sensors, mechanical stress sensors, auditory sensors and temperature sensors. Within particularly preferred embodiments the sensor is a wireless sensor, or a sensor connected to a wireless microprocessor. Within further embodiments the medical device, delivery device or surgical tool can have more than one type of the above-noted sensors.

According to various embodiments, sensors can be placed into an ISM at different locations in order to monitor the operation, movement, anatomical location, medical imaging (both of the medical device and the surrounding tissues), function, physical integrity, wear, performance, potential side effects, medical status of the patient and the medical status of the medical device and its interface with the live tissue of the patient. Live, continuous or intermittent, in situ, monitoring of patient activity, patient function, medical device activity, medical device function, medical device performance, medical device placement, medical device forces and mechanical stresses, medical device and surrounding tissue anatomy (imaging), mechanical, functional and physical integrity of the medical device, and potential local and systemic side effects is provided. In addition, information is available on many aspects of the medical device and its interaction with the patient's own body tissues, including clinically important measurements not currently available through physical examination, medical imaging and diagnostic medical studies.

According to one embodiment, the ISM has one or more sensors to provide evaluation data of any motion or movement of the medical device. Motion sensors and accelerometers can be used to accurately determine the movement of the medical device and to determine if there is movement between the device and surrounding tissue (e.g., bone, blood vessels, soft tissues, organs). Such evaluation can be utilized to help reduce the incidence of improper placement, alignment and deployment during surgical placement, migration/breakage/wear during medical and physical examination post-operatively, and malfunction or side effects during normal daily activities after the patient returns home.

According to another embodiment, ISMs having contact sensors are provided between the medical device and implant and the surrounding tissue and/or between articulated components of the device/implant itself (e.g., in the case of orthopedic devices or implants, stent grafts, overlapping stents, heart valves, etc.). In other embodiments, vibration sensors are provided to detect the vibration between the medical device and/or the surrounding tissue. In other embodiments, ISMs having strain gauges are provided to detect the strain between the medical device and the surrounding tissue and/or between articulated components of the device/implant itself (e.g., in the case or orthopedic devices, stent grafts, multiple stents, heart valves, etc.). Sudden increases in strain may indicate that too much stress is being placed on the medical device, which may increase damage to the body and/or breakage, cracking and/or damage to the device.

According to other embodiments, accelerometers are provided in the ISM which detect vibration, shock, tilt and rotation of the device/implant and by extension the surrounding tissue itself. According to other embodiments, sensors are provided in the ISM for measuring surface wear, such as contact or pressure sensors, which may be embedded at different depths within the medical device in order to monitor contact of the medical device with surrounding tissues, or degradation of the medical device over time (e.g., in the context of a biodegradable or bioerodible implants and devices, or surfaces subject to repeated rubbing or wear such as joint surfaces or heart valve leaflets). In other embodiments, ISMs are provided with position sensors, as well as other types of sensors, which indicate potential problems such as movement, migration, pressure on surrounding anatomical structures, alignment, breakage, cracking and/or bending of the medical device in actual use over a period of time.

Within further embodiments, the medical device can contain one or more ISMs with sensors at specified densities in specific locations. For example, the medical device can have a density of sensors of greater than one, two, three, four, five, six, seven, eight, nine, or ten sensors [e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these] per square centimeter of the device/implant. Within other embodiments, the medical device can have a density of sensors of greater than one, two, three, four, five, six, seven, eight, nine, or ten sensors [e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these] per cubic centimeter of the device.

The multiple sensors do not need to be identical. For example, within certain embodiments, the sensors include a sensor that is subservient to another sensor, where the subservient sensor needs a power supply but since the subservient sensor only sends information to another, close by sensor, the subservient sensor does not need a large power supply such as is needed by sensor that sends information outside of the body. Accordingly, a subservient sensor may be smaller than a sensor that needs a sufficient large power supply to send information outside of the body.

Within certain embodiments of the invention, the medical device is provided with a specific unique identifying number, and within further embodiments, each of the ISMs and/or each of the sensors on, in or around the medical device each have either a specific unique identification number, or a group identification number [e.g., an identification number that identifies the sensor as accelerometers (acceleration, tilt, vibration, shock and rotation sensors), pressure sensors, contact sensors, position sensors, chemical sensors, tissue metabolic sensors, mechanical stress sensors and temperature sensors]. Within yet further embodiments, the specific unique identification number or group identification number is specifically associated with a position on, in or around the medical device.

Within other aspects of the invention methods are provided for monitoring an anatomically-implanted medical device comprising the steps of transmitting a wireless electrical signal from a location outside the body to a location inside the body; receiving the signal at a sensor positioned on, in or around a medical device located inside the body; powering the sensor using the received signal; sensing data at the sensor; and outputting the sensed data from the sensor to a receiving unit located outside of the body.

Within another aspect of the invention methods are provided for monitoring an anatomically-implanted medical device comprising the steps of transmitting a wireless electrical signal from a location outside the body to a location inside the body; receiving the signal at ISM implanted on or within a medical device located inside the body; sensing data at the sensor; and outputting the sensed data to a location outside of the body. Within one embodiment, the sensed data may be output to a location outside of the body by a further implantable module that does not contain sensors, or which is designed to coordinate and distribute sensed data between one or more ISMs. For example, the one or more ISMs may include a subservient sensor which needs a power supply but since the subservient sensor only sends information to another, close by sensor, the subservient sensor does not need a large power supply such as is needed by sensor that sends information outside of the body.

Within related aspects of the invention, a subject may have more than one implanted ISM. Furthermore, multiple ISMs may be 'connected', in that, they can be designed to communicate with each other, and can perform different functions. For example, within one aspect of the invention methods are provided for monitoring two or more anatomically-implanted medical devices comprising the steps of transmitting a wireless electrical signal from a location outside the body to a location inside the body; receiving the signal at one of a plurality of ISMs implanted on or within a medical device located inside the body; receiving said signal at ISM implanted on or within a medical device located inside the body; processing said signal and transmitting to one or more other ISMs implanted on or within a medical device located inside the body; sensing data at a sensor in one or more of the other ISMs; and outputting the sensed data from one or more of the other ISMs to the one of a plurality of ISMs; processing the data received from the one or more of the other ISMs; and outputting processed data to a receiving unit located outside of the body. Within various embodiments, one of the plurality of ISMs receiving said signal from outside the body may not necessarily contain sensors, or be utilized to provide sensor data, but rather, for example, for signal processing. Within yet other embodiments an implantable module can be utilized solely to receive, send and/or store signals. Such implantable modules may be utilized to coordinate and transmit signals within a subject, to locations outside of the subject. These implantable modules may include a subservient ISM that can send information only to a closely located ISM.

Within other aspects of the invention methods are provided for imaging a medical device as provided herein, comprising the steps of (a) detecting the location of one or more ISMs having sensors in or on the medical device, any associated anatomical or radiological "landmarks", and/or associated medical delivery device or surgical tool; and (b) visually displaying the relative anatomical location of said one or more ISMs having one or more sensors, such that an image of the medical device is created. Within various embodiments, the step of detecting may be done over time, and the visual display may thus show positional movement over time. Within certain preferred embodiments the image which is displayed is a three-dimensional image.

The imaging techniques provided herein may be utilized for a wide variety of purposes. For example, within one aspect, the imaging techniques may be utilized during a surgical procedure in order to ensure proper anatomical placement, alignment, deployment and functioning of the medical device. Particularly in orthopedic reconstructive surgery (joint replacement) proper alignment and motion is critical, while in trauma surgery and fracture reduction, proper alignment and immobilization of the bone fragments is critical to obtaining a good outcome; therefore, allowing the surgeon to be able to see the implant's position in "real time" (particularly in procedures where direct vision is not possible) would be beneficial for achieving proper anatomical placement, alignment and immobilization. Within other embodiments, the imaging techniques may be utilized post-operatively in order to examine the medical device, examine the interface with surrounding tissues, and/or to compare operation, integrity, alignment and/or movement of the device/implant over time.

The integrity of the medical device can be wirelessly interrogated and the results reported on a regular basis. This permits the health and status of the patient to be checked on a regular basis or at any time as desired by the patient and/or physician. Furthermore, the medical device can be wirelessly interrogated when signaled by the patient to do so (via an external signaling/triggering device) as part of "event recording"—i.e. when the patient experiences a particular event (e.g. pain, injury, instability, etc.) she/he signals/triggers the device/implant to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention, methods are provided for detecting and/or recording an event in a subject with one of the medical devices provided herein, comprising interrogating one of the ISMs on the medical device as provided herein at a desired point in time. Within one aspect of the invention, methods are provided for detecting and/or recording an event in a subject with the medical device as provided herein, comprising the step of interrogating at a desired point in time the activity of one or more of the ISMs having sensors within the medical device, and recording said activity. Within various embodiments, interrogation may be accomplished by the subject and/or by a health care professional. Within related embodiments, the step of recording may be performed with one or more wired devices, or, wireless devices that can be carried, or worn (e.g., a cellphone, watch or wristband, shoe, and/or glasses).

Within yet other aspects of the invention methods, devices are provided suitable for transmitting a wireless electrical signal from a location outside the body to a location inside the body; receiving the signal at one of the aforementioned sensors positioned on, in or around the medical device located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the ISM, or on the medical device, or on an associated device (e.g., an associated medical device, or an external device such as a cellphone, watch, wristband, and/or glasses). During a visit to the physician, the data can be downloaded via a wireless sensor, and the doctor is able to obtain data representative of real-time performance of the medical implant, and any associated medical device.

The advantages obtained include more accurate monitoring of the medical device and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIGS. 8A-8D illustrate the development of an endoleak from the beginning of the leak (8A) to substantial formation of the leak (8B). FIGS. 8C and 8D are a blown up images of 8A and 8B, respectively, which depicts the movement of the ISM sensors during development of the endoleak.

FIG. 9A-9H are a schematic of various types of stent placement, and contact sensors which can aid in this placement. FIG. 9A illustrates a site of bifurcation with stenosis occurring at multiple points in the vessel. FIG. 9B illustrates a stent with PTCA. FIG. 9C illustrates a stent plus stent deployment (also referred to as a "reverse-T"). FIG. 9D illustrates a stent plus stent deployment (referred to as "T stenting"). FIG. 9E illustrates a stent plus stent deployment referred to as a "Crush". FIG. 9F illustrates a stent plus stent deployment referred to as a "Y" or "V". FIG. 9G illustrates a stent plus stent deployment referred to as "Kissing".

FIG. 9H illustrates a stent plus stent deployment referred to as a "Culotte".

FIG. 14 is an isometric view of a total knee replacement.

FIG. 15A is an exploded view of the total knee replacement of FIG. 14.

FIG. 26A illustrates a knee brace having ISMs; FIG. 26B a neck brace.

DETAILED DESCRIPTION OF THE INVENTION

Figure 1:
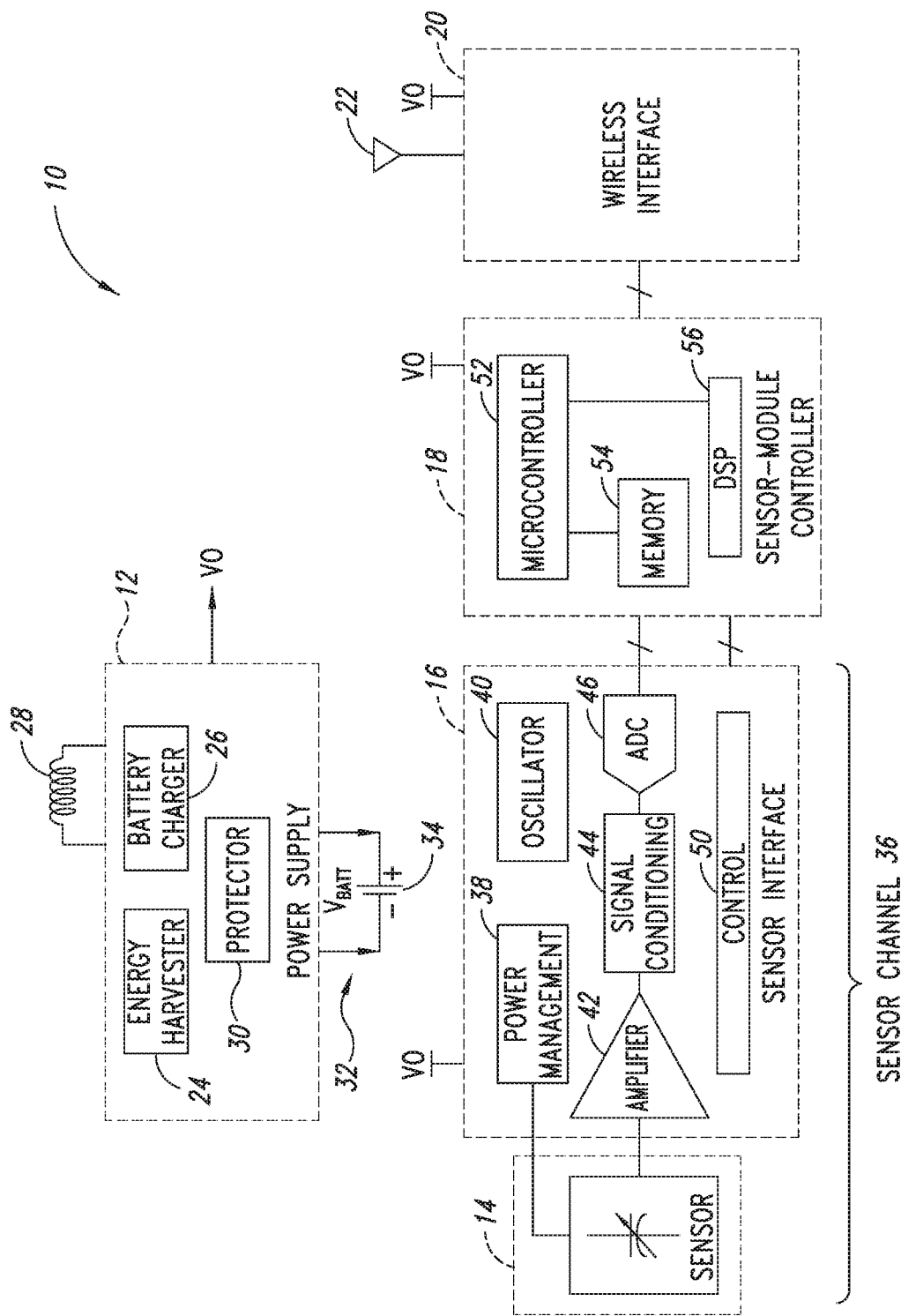
FIG. 1 is a diagram of a sensor module, according to an embodiment.

Briefly stated the present invention provides a variety of medical devices and implants that can be utilized to monitor the placement, location, anatomy, alignment, immobilization, performance, healing, integrity, wear, side effects, and/or efficaciousness of the medical device, and any associated medical devices and or device delivery instruments. Prior to setting forth the invention however, it may be helpful to an understanding thereof to first set forth definitions of certain terms that are used hereinafter.

"Medical device" refers to an instrument, apparatus, constructed element or composition, machine, implement, or similar or related article that can be utilized to diagnose, prevent, treat or manage a disease or other condition(s). The medical devices provided herein may, depending on the device and the embodiment, be implanted within a subject, utilized to deliver a device to a subject, or, utilized externally on a subject. In many embodiments the medical devices provided herein are sterile, and subject to regulatory requirements relating to their sale and use. Representative examples of medical devices and implants include, for example, cardiovascular devices and implants such as implantable cardioverter defibrillators, pacemakers, stents, stent grafts, bypass grafts, catheters and heart valves; orthopedic implants (e.g., total or partial arthroplastic joints such as hip and knee prosthesis); spinal implants and hardware (spinal cages, screws, plates, pins, rods and artificial discs); a wide variety of medical tubes, cosmetic and/or aesthetic implants (e.g., breast implants, fillers); a wide variety of polymers, bone cements, bone fillers, scaffolds, and naturally occurring materials (e.g., heart valves, and grafts from other naturally occurring sources); intrauterine devices; orthopedic hardware (e.g., casts, braces, tensor bandages, external fixation devices, tensors, slings and supports) and internal hardware (e.g., K-wires, pins, screws, plates, and intramedullary devices (e.g., rods and nails)); cochlear implants; dental implants; medical polymers, a wide variety of neurological devices; and artificial intraocular eye lenses.

"Sensor" refers to a device that can be utilized to measure one or more different aspects of a body tissue (anatomy, physiology, metabolism, and/or function) and/or one or more aspects of the medical device. Representative examples of sensors suitable for use within the present invention include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor and/or a Unique Device Identification number ("UDI") with which the sensors can provide unique information of the associated Medical device for tracking purposes of the Medical Device manufacturer, the health care system, and regulatory requirements.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE-The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm³ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, on the inside of a medical device, within the body of the medical device, on the outer surfaces (or inner surfaces) of the medical device, between the medical device and other medical devices or implants, and/or between the medical device and any device that might carry or deliver it (e.g., a delivery device, injection device, or surgical instrument). When the phrase "placed in a medical device" or "placed in a medical implant" is utilized, it should be understood to refer to any of the above embodiments (or any combination thereof) unless the context of the usage implies otherwise.

The sensors may be placed in the medical device alone, or along with an associated medical device which might be utilized in a desired surgical procedure. For example, within certain embodiments, the medical device and/or medical device kit comprises sensors at a density of greater than 1, 2, 3, 4, 5, 6, 7, 8, 9, 10 or greater than 10 sensors per square centimeter. Within other aspects, the medical device and/or medical device kit comprises sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within the medical device, medical device, or kit as described herein.

In various embodiments, the sensors may be placed within specific locations and/or randomly throughout the medical device and/or associated devices. In addition, the sensors may be placed in specific patterns (e.g., they may be arranged in the pattern of an X, as oval or concentric rings around the orthopedic implant and/or associated devices).

"Implantable Sensor Module" or "ISM" is a sensing device which is configured to be implanted in, or otherwise attachable to, a living subject, such as a human subject, and is configured to sense one or more physical quantities, to generate a signal that represents the sensed quantity, and to transmit the signal to a remote receiver. The ISM may have one or more sensors as provided above. The ISM may be implanted into a subject directly, or, within one or more medical devices which are implanted within a subject. Within an embodiment, the signal may contain information encoded to represent one or more of a magnitude, phase, and type of the sensed physical quantity.

Within one embodiment of the invention, the ISM is a self-contained module having one or more sensors as described herein, a sensor interface, a processor interface, battery management, and a wireless interface. Within preferred embodiments of the invention the ISM will be less than 5, 4, 3, 2, or 1 cubic centimeter in size, and more preferably, less than 5.0, 4.5, 4.0, 3.5, 3.0, 2.5, 2.0, 1.5, 1.0, 0.9, 0.8. 0.7, 0.6, 0.5, 0.4, 0.3, 0.2, or 0.1 cubic centimeters in size. Within various embodiments the ISM can be comprised of a solid outer core, or composed of flexible materials (e.g., flexible/malleable alloys, a degradable or non-degradable outer polymeric surface). Within related embodiments, the ISM can be comprised of flexible circuitry (including for example, single and double-sided flexible circuits. Within certain embodiments the ISM may be relatively square and solid, and yet with in other embodiments very thin, pliable and lengthy (as compared to its width and/or height). It can be constructed for a number of different applications (e.g., for insertion, attachment or implantation into any of the medical devices or implants provided herein).

Representative Embodiments of Medical Devices and Medical Uses of Sensor-Containing Medical Devices In order to further understand the various aspects of the invention provided herein, the following sections are provided below:

A. Implantable Sensor Modules;
B. Implantable Medical Devices (including B1—Stent Grafts; B2—Stents; B3—Hips; B4—Knees; B5—Tubes; B6—Implants; B7—Spinal Implants; B8—Orthopedic Hardware; B9—Polymers; B10—Heart Valves; and B11 Methods of Manufacture);
C. Use of Medical Devices Having ISMs to Deliver Therapeutic Agent(s);
D. Methods for Monitoring Infection in Medical devices;
E. Further Uses of ISM-containing Medical Devices or Implants in Healthcare;
F. Generation of Power from Medical Devices or Implants;
G. Medical Imaging and Self-Diagnosis of Assemblies Comprising Medical Devices or Implants, Predictive Analysis and Predictive Maintenance;
H. Methods of Monitoring Assemblies Comprising Medical Devices or Implants; and
I. Collection, Transmission, Analysis, and Distribution of Data from Assemblies Comprising Medical Devices or Implants.

A. Implantable Sensor Modules

As noted above, the present invention provides ISM's suitable for implantation in, or otherwise being attached (internally or externally) to a living subject [e.g., by implantation into a medical device and/or attachment to a medical device which is then surgically placed internally (hip and knee replacements, stents, heart valves, etc.) or applied to the outside of the body (casts, braces, tensors, external fixation devices, etc.)]. FIG. 1 is a diagram of a sensor module 10, according to one embodiment of the invention. The sensor module 10 is configured to be implantable in, or otherwise attachable to, a living subject, such as a human subject, and is configured to sense a physical quantity, to generate a signal that represents the sensed quantity, and to transmit the signal to a remote receiver (not shown in FIG. 1) for processing. The ISM may be implanted into a subject directly, within one or more medical devices which are implanted within a subject, or, within (or attached to) a medical device that is affixed to the outside of the body. Within an embodiment, the signal may contain information encoded to represent one or more of a magnitude, phase, and type of the sensed physical quantity.

The sensor module 10 may be suitable for applications that call for the sensing of one or more biological quantities (biological quantities are physical quantities) of the subject in which the module is implanted or to which the module is attached. For example, the sensor module 10 may sense one or more of the electrical signals generated by the subject's heart, and may generate a signal that represent an electrocardiogram of the heart; the device that receives the signal may then generate a visual representation of the electrocardiogram in response to the signal. Other applications include, but are not limited to, sensing one or more parameters (e.g., contact, pressure, position, movement, wear, stability, level of bone attachment) related to an artificial joint, brain activity, organ function, blood flow, digestion, and/or drug effectiveness.

The sensor module 10 includes a power supply 12, one or more sensors 14, a sensor interface 16, a sensor-module controller 18, a wireless interface 20, and an antenna 22. The supply 12, sensor(s) 14, channel 16, controller 18, interface 20, and antenna 22 may be disposed on one or more integrated-circuit dies that are respectively disposed in one or more integrated-packages to form one or more integrated circuits (ICs); and these one or more ICs may be disposed in (not shown in FIG. 1), is implantable in, or otherwise attachable too, a subject. Or, the sensor(s) 14 and the antenna 20, or any other of the afore-mentioned components, may be not be disposed on an IC die, but may be discrete components.

The power supply 12 is configured to generate a regulated supply signal (e.g., a regulated supply voltage $V_O$) to power the other components of the sensor module 10, and includes an energy harvester 24, a battery charger 26, a power coil 28, a protector 30, and a battery receptacle 32 for receiving a battery 34, according to an embodiment.

The regulated supply voltage $V_O$ may be in, for example, an approximate range of 1-24 Volts (V), according to an embodiment. Furthermore, although not shown in FIG. 1, the power supply 12 may generate more than one regulated supply signal.

The energy harvester 24 is configured to convert an environmental stimulus into an electrical current or voltage for charging the battery 34, according to an embodiment. For example, the harvester 24 may convert, into a battery-charging electrical current or voltage, one or more of body heat from the subject in which the sensor module 10 is implanted or otherwise attached, kinetic energy generated by the subject's movement, changes in pressure (e.g., barometric pressure or pressure within the subject, such as the subject's blood pressure), energy generated by an electrochemical reaction within the subject's body, radio-frequency (RF) energy (e.g., ambient RF transmissions), and light.

The battery charger 26 includes the power coil 28, which is configured to generate a voltage and current in response to a near magnetic field generated by a power unit (not shown in FIG. 1), according to an embodiment; such near-magnetic-field charging may be similar to a technique for powering a smart card. For example, the battery charger 26 and coil 28 may be used to charge the battery 34 while the energy harvester 24 is unable to generate enough energy to charge the battery to a voltage level sufficient for proper operation of the sensing module 10.

The protector 30 protects the battery 34 from overcharging or other conditions that may damage the battery, and also protects the power supply 12 in case a load current drawn from the regulated voltage $V_O$ (or from another regulated supply signal that the power supply generates) exceeds a predetermined safe threshold. The protector 30 may also monitor temperature of battery 34 and make appropriate adjustments of safe thresholds. For example, the protector 30 may disable the energy harvester 24 and the battery charger 26 if the voltage across the battery 34 exceeds a predetermined safe threshold, and may also generate some type of alarm to indicate a malfunction. And, the protector 30 may limit the load current drawn from $V_O$ (or from another regulated supply signal) to a safe limit, or may otherwise disable the power supply 12 if the load current exceeds a predetermined safe threshold; for example, the protector may implement such a limit or disabling if the node carrying $V_O$ is short-circuited to ground.

And the battery 34 may be any type of rechargeable battery, such as a lithium-ion battery, that is suitable for use in an electronic device that is implantable in, or otherwise attachable to, a biological subject.

Still referring to FIG. 1, the one or more sensors 14 are each configured to sense a respective physical quantity within, or otherwise influenced by, the body of the subject in which the module 10 is implanted or to which the module is attached, and are each configured to generate a respective sensor signal that represents one or more of a magnitude, phase (if applicable), and type of the respective sensed quantity. Examples of such a physical quantity include, but are not limited to, a relative or absolute position of the sensor module 10, a movement (e.g., acceleration, velocity, rotation) of the sensor module, and the following quantities in the vicinity of the sensor module: an electric field, voltage, or current, a magnetic field, a temperature, a pressure (e.g., blood pressure), radiation, electrical conductivity, an optical intensity, a spatial or temporal differential in the physical quantity (e.g., a temperature differential, a pressure differential, or a voltage differential), a biological marker (e.g., a tumor marker, bacterial marker or DNA fragment), a chemical composition of a substance, and a chemical reaction or a byproduct thereof. Examples of the one or more sensors 14 include, but are not limited to, the following types of sensors: global-positioning-system (GPS), accelerometer, Hall-effect, electrical (e.g., current, voltage, and conductivity), magnetic, thermal, pressure, radiation, optical, quantity-differential, capacitive, inductive, and microelectromechanical (MEMS). And examples of the sensor signal include an analog or digital voltage or current.

The sensor interface 16, which, together with the sensor(s) 14, forms a sensor channel 36, includes a power-management circuit 38, an oscillator 40, an amplifier 42, a signal conditioner 44, an optional analog-to-digital converter (ADC) 46, and a control circuit 50, according to an embodiment.

The power-management circuit 38 is configured to convert $V_O$ from the power supply 12 into one or more other supply voltages or supply currents for the sensor 14 and the circuits of the sensor interface 16. The power manager 38 may provide power to the sensor using a conductor or by induction using a coil. Sensor 14 may provide a signal to sensor interface 16 using one or more conductors or by induction using a coil. The coil used to provide power to sensor 14 may be the same coil that receives the signal from sensor 14. Alternatively, the coil used to provide power to sensor 14 may be separate from the coil that receives a signal from sensor 14.

The oscillator 40 generates one or more clock signals for the digital and mixed-signal circuits of the sensor interface 16, and, depending on the types of the one or more sensors 14, may generate an analog reference signal for the sensor(s) 14. For example, a sensor 14 may generate a sensor signal by modifying one or more of the frequency, amplitude, and phase of such an analog reference signal in response to a respective physical quantity. Examples of the oscillator 40 include a ring oscillator, an operational-amplifier-based oscillator, or other digital or analog oscillator.

The amplifier 42 is configured to amplify the sensor signal generated by a sensor 14, according to an embodiment. Although shown as a having a single-ended input and a single-ended output, the amplifier 42 may have one or both of a differential input and a differential output. Examples of the amplifier 42 include an operational amplifier (e.g., having a feedback configuration), a transconductance ($g_m$) amplifier (e.g., having an open-loop configuration), and a low-noise amplifier (LNA). If there are more than one sensor 14, then the sensor interface 16 may include a respective amplifier 42 for each sensor, or a mux that selects which sensor output is input to amplifier 42. The gain of amplifier 42 may be controlled by one or more of the signal conditioner 44, the ADC 46.

The signal conditioner 44 is configured to condition the amplified sensor signal from the amplifier 42 for reception by the ADC 46 if present, or for reception by the sensor-module controller 18 if the ADC is not present. For example, the conditioner 44 may be configured to adjust the amplitude and the DC offset of the amplified sensor signal so that it is compatible with the dynamic input range of the ADC 46, to remove noise from, or to otherwise filter, the amplified sensor signal, or to equalize the amplified sensor signal. In addition, the signal conditioner 44 may be configured to add error-correction coding (ECC) to the amplifier sensor signal.

If present, the ADC 46 is configured to convert the conditioned sensor signal from the analog domain to the digital domain; but if the sensor 14 is configured to generate the sensor signal in the digital domain, then the amplifier 42 and the signal conditioner 44 may be digital circuits, and the ADC 46 may be omitted as described above.

And the control circuit 50 is configured to control the operations of one or more of the power manager 38, oscillator 40, amplifier 42, signal conditioner 44, and ADC 46, and may be configured to control the operations of one or more other components of the sensor interface 16. For example, the control circuit 50 may include, or be coupled to, a memory (not shown in FIG. 1) that stores configuration data or programming instructions for the sensor(s) 14 or for the sensor interface 16, and may configure the sensor(s) 14 or the interface 16 in response to this data or these instructions upon power up of the sensor module 10. Furthermore, the control circuit 50 may be configured to control communications between the interface 16 and the sensor-module controller 18.

Still referring to FIG. 1, the sensor-module controller 18 is configured to control the operations of the power supply 12, the sensor channel 36, the wireless interface 20, and other components of the sensor module 10, according to an embodiment, and includes a microcontroller or microprocessor 52, a memory 54, and a co-controller or co-processor, such as a digital-signal processor (DSP) 56, according to an embodiment. For clarity, hereinafter the microcontroller/microprocessor 52 is referred to as a microcontroller, it being understood that the microcontroller may instead be a microprocessor.

The microcontroller 52, in cooperation with the DSP 56, is configured to process the signal from the sensor channel 36, to generate data from the processed signal, and to condition the signal for transmission by the wireless interface 20. For example, if the sensor 14 measures temperature, then the microcontroller 52 may convert the signal from the sensor interface 16 into a temperature value in units of Fahrenheit or Celsius; or, if the sensor measures pressure, then the microcontroller may convert the signal from the sensor interface into a pressure value in units of Pascal.

The memory 54 may include volatile memory and non-volatile memory, according to an embodiment. For example, the volatile memory may be configured to store the operating system and one or more applications executed by the microcontroller 52, and the non-volatile memory may be programmed to store configuration information for the sensor module 10, such configuration information including, but not limited to, the type of the sensor 14, the frequency signal generated by the oscillator, the gains of the amplifier 42 and the signal conditioner 44, and the level of the voltage $V_O$ generated by the power supply 12.

And the wireless interface 20 is configured to receive the data from the sensor-module controller 18, to modulate one or more carrier signals with the data, and to transmit, via the antenna 22, the modulated carrier signal(s) to a remote device (not shown in FIG. 1) for use by, e.g., the subject in which the sensor module 10 is implanted or attached, or to his/her physician. For example, the wireless interface 20 may be configured to operate according to a specification such as, but not limited to, one of the following specifications: Bluetooth®, near-field communication (NFC), Zig-Bee (IEEE 802.15), WiFi, wireless local area network (WLAN, IEEE 802.11).

Furthermore, the wireless interface 20 may be configured to receive a signal from a remote device (not shown in FIG. 1) via the antenna 22, and to provide this signal to the supply-module controller 18. For example, such a signal may include sensor-module configuration data or program instructions, or may include a request that the sensor-module 10 transmit specified data to the remote device. Examples of the remote device include, but are not limited to, a smart phone or tablet computer (FIG. 4), a computer system (FIG. 5), or another sensor module 10 (FIG. 6).

Still referring to FIG. 1, the operation of the sensing module 10 during a sensing mode is described, according to an embodiment.

The power supply 12 generates the regulated supply voltage $V_O$ (and perhaps one or more other regulated supply signals) from the voltage $V_{BATT}$ across the battery 34. For example, if the battery voltage $V_{BATT} > V_O$, then the power supply 12 steps down $V_{BATT}$ to $V_O$; the power supply may include a buck converter to perform such a voltage step down. Alternatively, if $V_{BATT} < V_O$, then the power supply 12 steps up $V_{BATT}$ to $V_O$; the power supply may include a boost converter to perform such a voltage step up.

The sensor 14 senses a physical quantity that the sensor is configured to sense, and provides to the sensor interface 16 a sensor signal that represents the sensed quantity.

The sensor interface 16 amplifies, conditions, and, if the sensor signal is an analog signal, converts the conditioned sensor signal to the digital domain via the amplifier 42, signal conditioner 44, and ADC 46, respectively.

The sensor-module controller 18 processes the conditioned (and possibly ADC converted) sensor signal from the interface 16, and generates data representing the sensed quantity. The controller 18 may store the generated data in the memory 54 for later retrieval, or may provide the data to the wireless interface 20.

And if the sensor-module controller 18 provides the data to the wireless interface 20, then the wireless interface modulates one or more carriers signals with the data from the sensor-module controller 18, generates a transmission signal from the one or more carriers signals, and transmits the transmission signal to a remote device (not shown in FIG. 1) via the antenna 22. In the event that the sensor is a subservient sensor, the wireless signal will be transmitted to another ISM which is in close proximity to the subservient ISM. A subservient sensor may generally have a smallwe battery than does a sensor that transmits signal to a remote device.

Still referring to FIG. 1, the operation of the sensing module 10 during a data-receiving mode is described, according to an embodiment.

The power supply 12 generates the regulated supply voltage $V_O$ (and perhaps one or more other regulated supply signals) from the voltage $V_{BATT}$ across the battery 34 as it does during the above-described sensing mode.

The wireless interface 20 senses a signal being received by the antenna 22 and notifies the sensor-module controller 18.

In response to the wireless interface 20 sensing the received signal, the sensor-module controller 18 instructs the wireless interface to demodulate, and, if necessary, decode, the received signal, recover the data from the signal, and provide the data to the sensor-module controller.

The sensor-module controller 18 analyzes the recovered data, and takes appropriate action. For example, if the data is configuration data, then the sensor-module controller 18 may load this data into a non-volatile portion of the memory 54, and initiate a configuration cycle so as to configure, or reconfigure, one or more portions of the sensing module 10 in response to the configuration data. Or, if this data is a command, then the sensor-module controller 18 may execute the command. For example, if the command is a request for the sensor module 10 to send specified other data to a remote device (not shown in FIG. 1), then the controller 18 sends the requested data via the wireless interface 20, which modulates one or more carrier signals with the requested data, generates a transmission signal from the one or more carriers signals, and transmits the transmission signal to a remote device via the antenna 22 as described above in conjunction with the sensing mode.

Still referring to FIG. 1, alternate embodiments of the sensor module 10 are contemplated. For example, any of the functions performed by the sensor module 10 may be performed either by dedicated hardware, configurable hardware [e.g., a field-programmable gate array (FPGA)], a microprocessor or microcontroller executing program instructions, or a combination or sub-combination of dedicated hardware, configurable hardware, and a microprocessor or microcontroller executing program instructions. Furthermore, although the sensor module 10 is described as including components disposed in a single housing, the sensor module may include multiple housings/pieces linked together wirelessly and/or operating independently. For example, two ISMs may be in wireless communication, where one ISM is subservient to another sensor in the sense that the subservient ISM send information only to an ISM that is capable of sending wireless signal to a remote device. The subservient sensor needs a power supply but since the subservient sensor only sends information to another, close by sensor, the subservient sensor does not need a large power supply such as is needed by sensor that sends information outside of the body. Moreover, although described as being implantable or otherwise attachable to a subject, the sensor module 10 may be configured to be disposed remotely from a subject, or to be ingested or inhaled by a subject.

Figure 2:
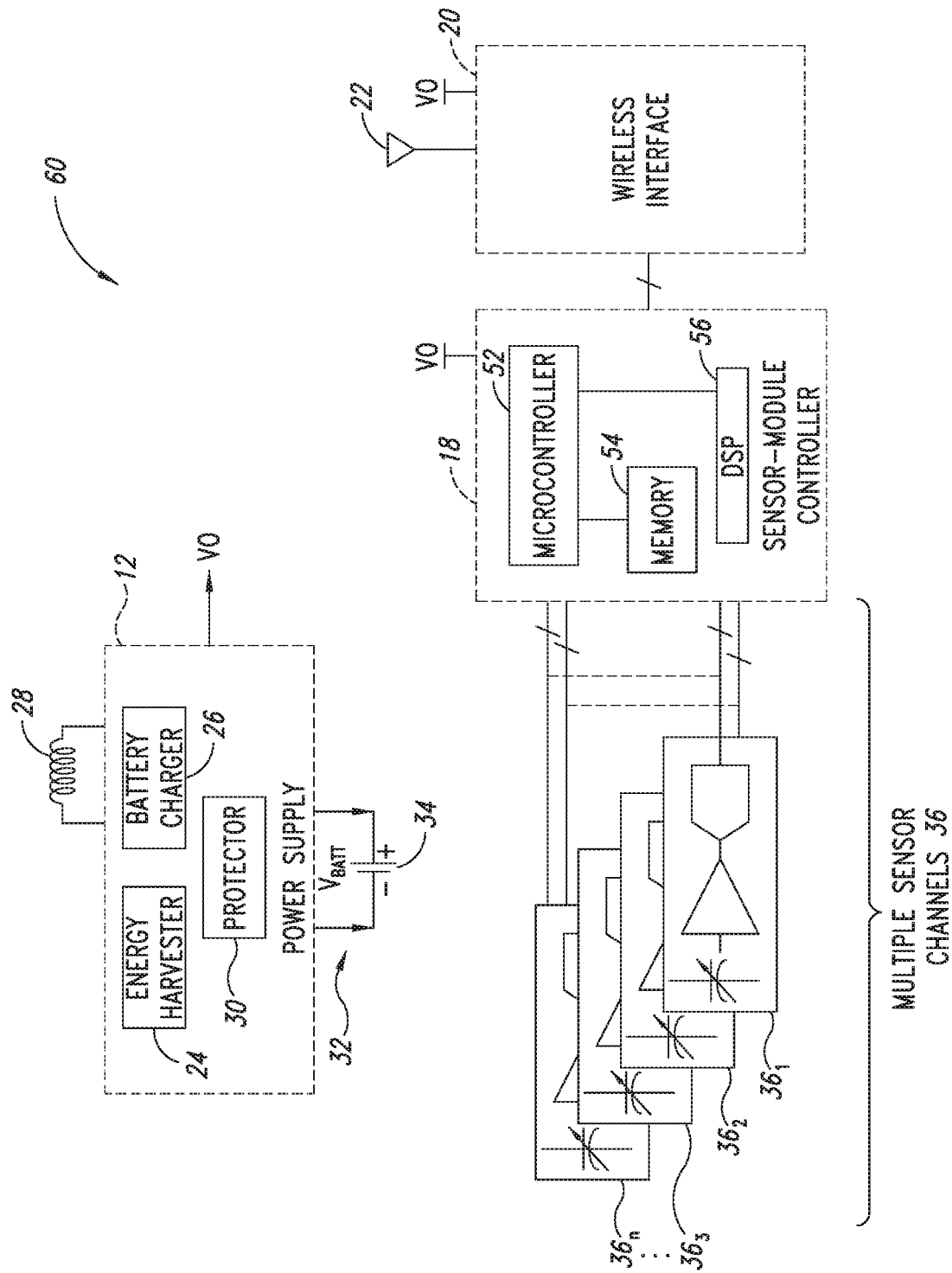
FIG. 2 is a diagram of a sensor module that includes multiple sensing channels, according to an embodiment.

FIG. 2 is a diagram of a sensor module 60, according to an embodiment. The sensor module 60 is similar to the sensor module 10 of FIG. 1, except that the sensor module 60 includes multiple sensor channels $36_1$-$36_n$, each of which may have one or more sensors 14.

Figure 3:
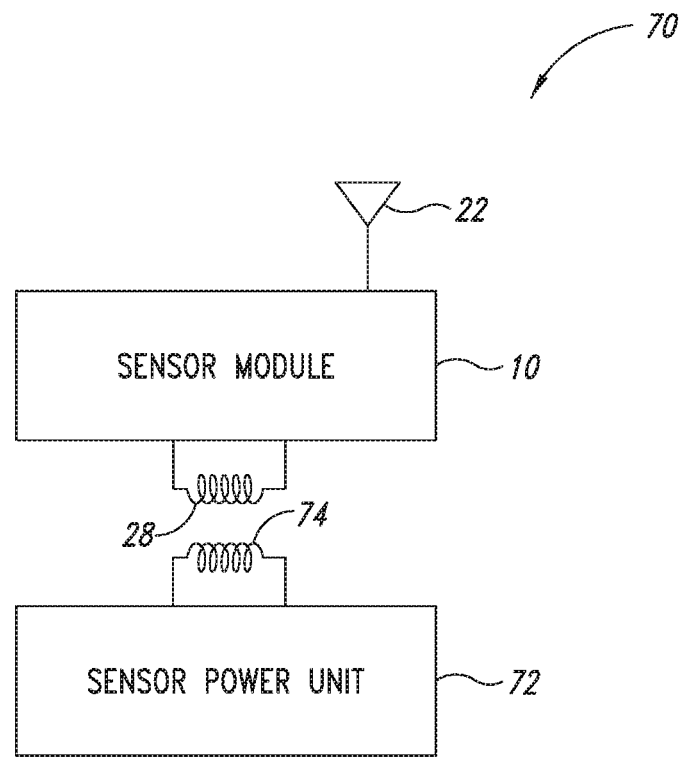
FIG. 3 is a diagram of a sensor-module power system, according to an embodiment.

FIG. 3 is a diagram of a sensor-module power-transfer system 70, according to an embodiment.

The system 70 includes the sensor module 10 of FIG. 1, and includes a sensor power unit 72 having a power coil 74. The sensor power unit 72 is configured to provide energy to the sensor module 10 in a manner similar to the manner in which a smart-card reader may power a smart card.

In operation during a power-transfer mode of the sensor module 10, one first positions the power coil 74 in near-field proximity (e.g., in an approximate range of 0-4 inches) to the power coil 28 of the sensor module.

Next, one activates the power unit 72, which generates, across the coil 74, an alternating (AC) voltage, which causes an alternating (AC) current to flow through the coil.

Because the power coil 74 is in near-field proximity to the power coil 28, the coils are magnetically (i.e., inductively) coupled such that each coil acts as a respective winding of a transformer. This coupling occurs even though the coil 28 may be implanted in a subject such that items like air, clothing, and biological materials (e.g., skin or other tissue, and blood) separate the coils 28 and 74.

Due to the inductive coupling between the coils 28 and 74, the magnetic flux generated by the AC current flowing through the coil 74 magnetically induces an AC current through, and an AC voltage across, the coil 28.

Consequently, the charger 26 of the power supply 12 (FIG. 1) is configured to use the induced AC current through, and the induced AC voltage across, the coil 28 to charge the battery 34 (FIG. 1), or the power supply 12 may include circuitry that is configured to directly power the sensor module 10 from the induced AC current and voltage.

After the power-transfer mode is complete, one deactivates the sensor power unit 72 and removes the coil 74 from near-field proximity with the coil 28.

Still referring to FIG. 3, alternate embodiments of the sensor-module power system 70 are contemplated. For example, the system 70 may include the sensor module 60 of FIG. 2 instead of the sensor module 10 of FIG. 1. Or the system 70 may include more than one sensor module (e.g., one or more of one or both sensor modules 10 and 60) or more than one power unit 72. Furthermore, as described above in conjunction with FIG. 1, while the coil 74 is not in near-field proximity with the sensor module 10, or while the power unit 72 is inactive, the power supply 12 of FIG. 1 may convert other sources of energy (e.g., kinetic energy, temperature-induced energy, pressure-induced energy) into a voltage and current suitable to charge the battery 34 (FIG. 1) or to power the sensor module 10.

Figure 4:
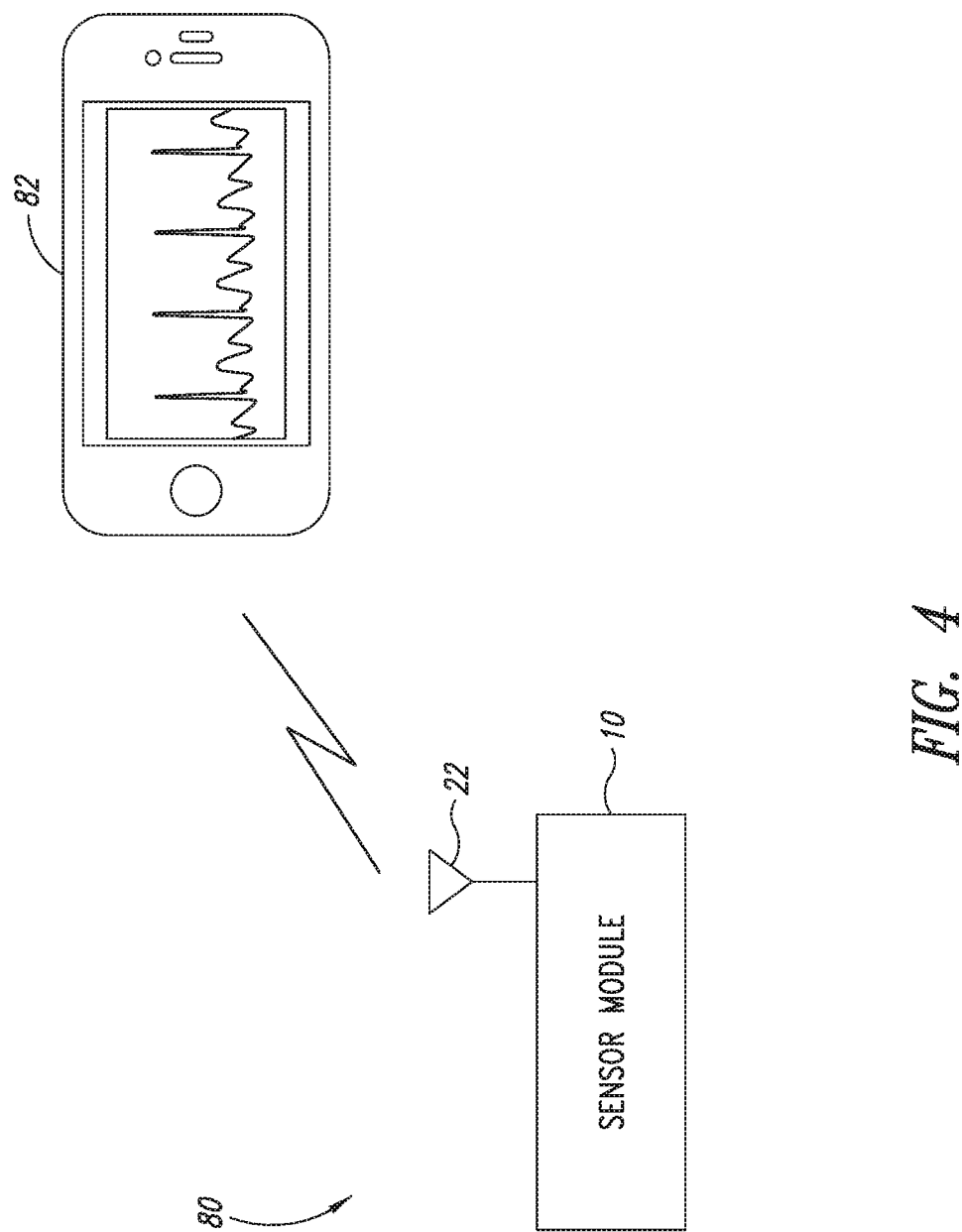
FIG. 4 is a diagram of a sensor-module data system, according to an embodiment.

FIG. 4 is a diagram of a sensor data system 80, according to an embodiment.

The sensor data system 80 includes the sensor module 10 of FIG. 1 and a remote data-receiving device 82.

The remote data-receiving device 82 may be, or include, a smart phone or tablet computer having circuitry sufficient to receive, demodulate, and recover sensor data from the wireless signal that the sensor module 10 transmits via the antenna 22. And the device 82 may also be configured to analyze, or otherwise process, the recovered sensor data. For example, the device 82 may be configured to display the recovered sensor data (e.g., an electrocardiogram), to make a recommendation or warning (e.g., "blood sugar level low") in response to the sensor data, or to store the sensor data for later processing by the device 82 or by another device or for later review by a medical professional.

Still referring to FIG. 4, the operation of the sensor data system 80 is described, according to an embodiment.

First, the device 82 notifies the sensor module 10 that the device would like to receive sensor data, or the sensor module notifies the device that the sensor module would like to send sensor data to the device.

Next, the sensor module 10 and the device 82 establish communications using, e.g., a handshake technique.

Then, the sensor module 10 transmits a signal including the sensor data according to a communications protocol such as Bluetooth® or NFC.

Next, the device 82 receives the transmitted signal and recovers the data therefrom.

Then, the sensor module 10 notifies the device 82 when all of the data has been transmitted.

Next, the device 82 notifies the sensor module 10 that it has received all of the data, or that it needs the sensor module to resend some or all of the data (e.g., due to a communications error).

Then, the sensor module 10 notifies the device 82 if it has more data to send, or the device requests additional data from the sensor module. If the sensor module 10 sends additional data, then it does so according to the same procedure described above.

After the sensor module 10 is finished transmitting all available or requested data, it notifies the device 82, which acknowledges this notification to the sensor module.

Next, the sensor module 10 and the device 82 cease communicating with one another.

Then, the device 82 may display a representation of the recovered data, may make a recommendation or warning based on the recovered data, may transmit the data to another device, such as to a computer system at a doctor's office, via, e.g., a phone system, or may store the data for later access.

Still referring to FIG. 4, alternate embodiments of the sensor data system 80 are contemplated. For example, the system 80 may include the sensor module 60 of FIG. 2 instead of the sensor module 10 of FIG. 1. Or the system 80 may include more than one sensor module (e.g., one or more of one or both sensor modules 10 and 60) or more than one device 82. Furthermore, the data that the sensor module 10 sends to the remote device may be sensor-module-status data instead of, or in addition to, sensor data. Moreover, the remote device 82 may send data, such as configuration data or command data, to the sensor module 10.

Figure 5:
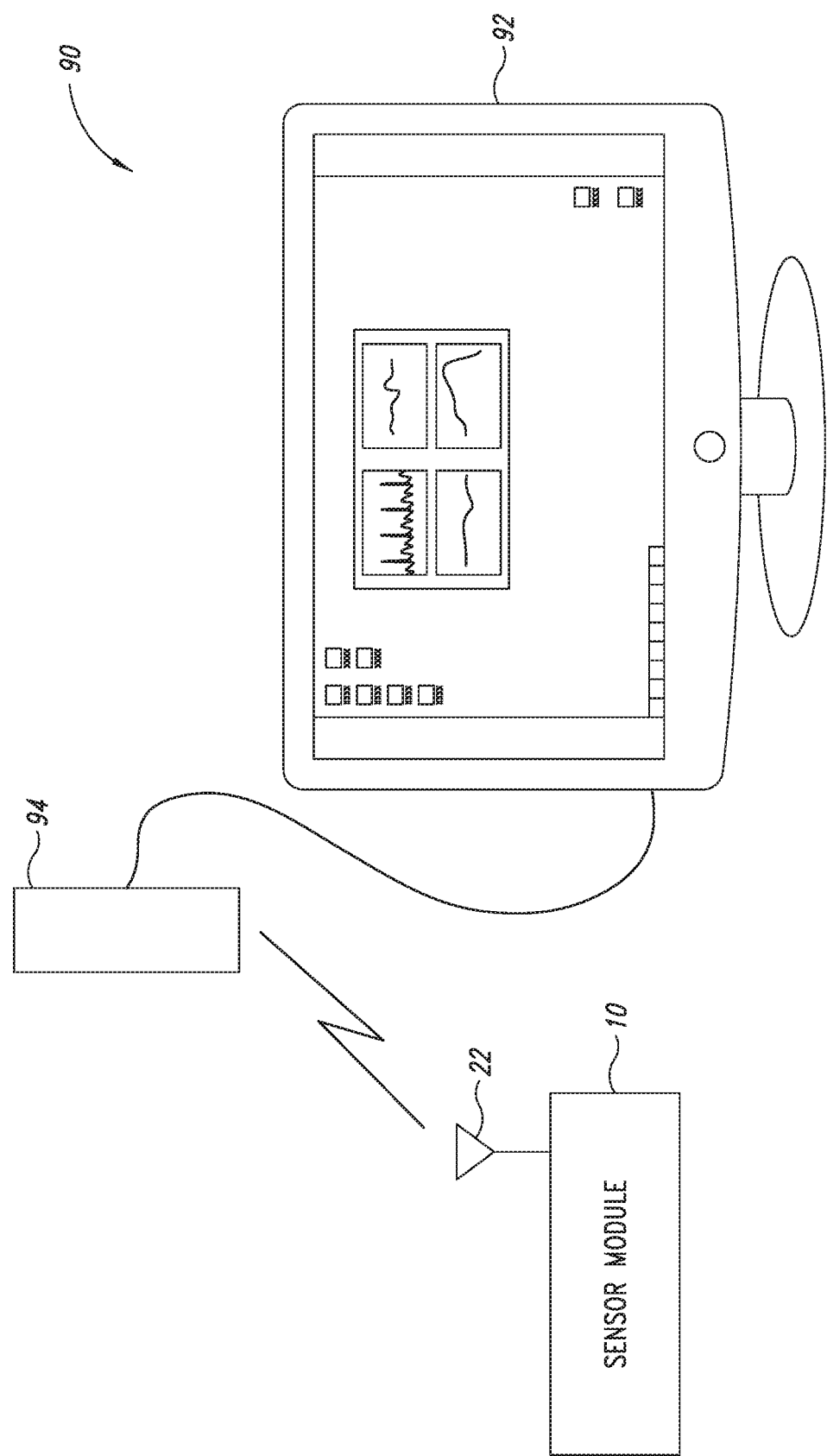
FIG. 5 is a diagram of a sensor-module data system, according to another embodiment.
Figure 6:
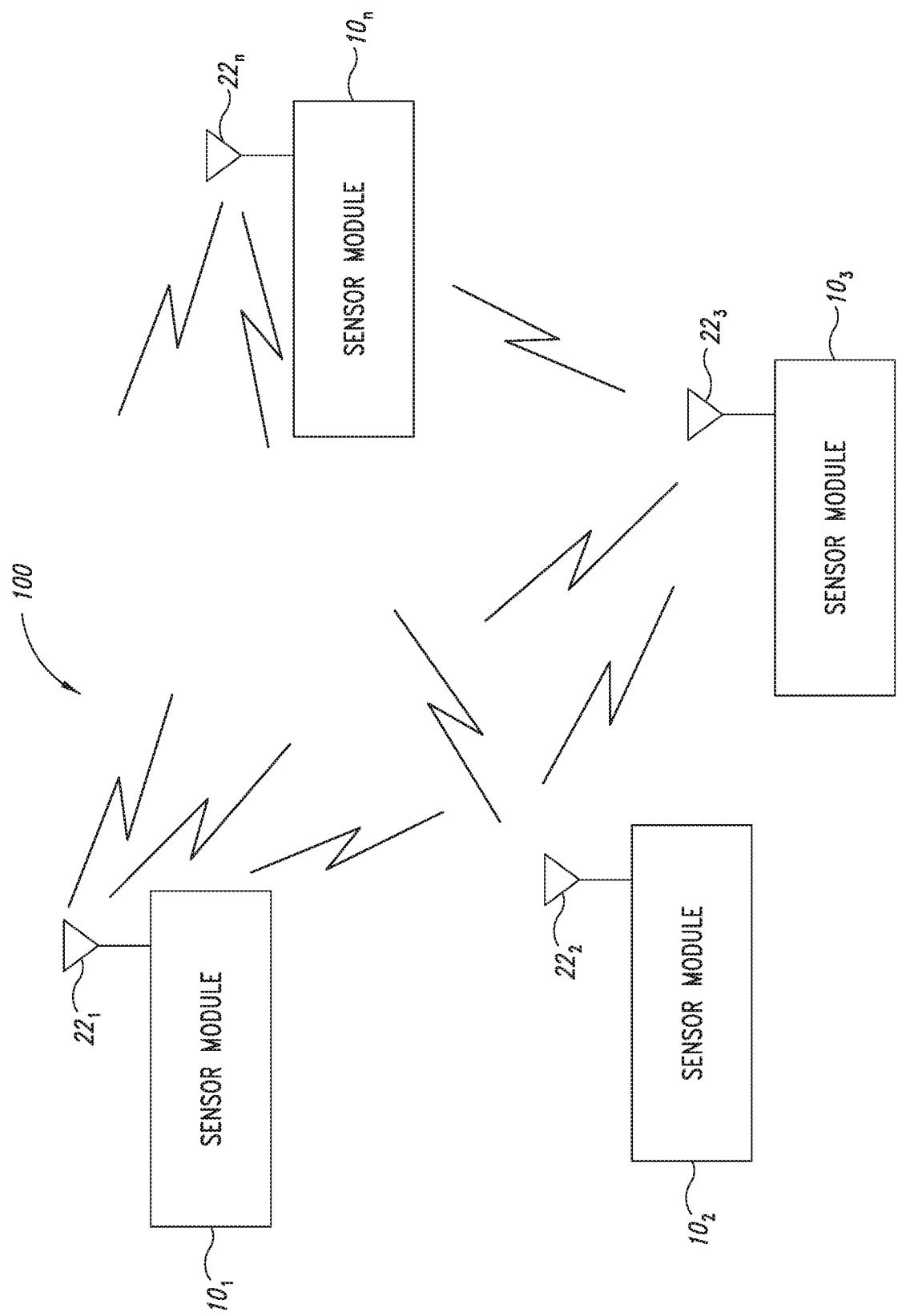
FIG. 6 is a diagram of a sensor-module network, according to an embodiment.

FIG. 5 is a diagram of a sensor data system 90, according to an embodiment.

The sensor data system 90 can be similar to the sensor data system 80 of FIG. 4, except that instead of the device 82, the system 90 includes a computer system 92 having a communication interface (e.g., a Bluetooth® interface) 94. The computer system 92 and the interface 94 can be configured to perform, together or separately, the operations that the device 82 of FIG. 4 is described as performing.

Still referring to FIG. 5, alternate embodiments of the sensor data system 90 are contemplated. For example, the system 90 may include the sensor module 60 of FIG. 2 instead of the sensor module 10 of FIG. 1. Or the system 90 may include more than one sensor module (e.g., one or more of one or both sensor modules 10 and 60) or more than one computer system 92. Furthermore, the data that the sensor module 10 sends to the computer system 92 may be sensor-module-status data instead of, or in addition to, sensor data. Moreover, the computer system 92 may send data, such as configuration data or command data, to the sensor module 10.

FIG. 6 is a diagram of a sensor-module network 100, according to an embodiment.

The network 100 includes multiple sensor modules 10 (FIG. 1), which are configured to communicate with one another using, e.g., ZigBee or another multi-node wireless-network protocol. For example, the sensor modules 10 may be implanted in, or otherwise attached to, a same subject, or in or to two or more different subjects.

Still referring to FIG. 6, the operation of the sensor-module network 100 is described, according to an embodiment.

First, when an initiating one of the modules 10 in the network 100 is ready to communicate with a responding one of the modules, the initiating module first determines if the communication channel is clear, i.e., that there are no other sensor modules currently using the channel for inter-module communications.

If the initiating module 10 determines that the communication channel is clear, then it notifies the responding sensor module that the initiating sensor module would like to receive sensor data or other data from the responding sensor module, or the initiating sensor module notifies the responding sensor module that the initiating sensor module would like to send sensor data or other data to the responding sensor module.

Next, the initiating and responding sensor modules 10 establish communications using, e.g., a handshake technique, and also inform the remaining sensor modules that the communication channel is being used.

Then, the initiating sensor module 10 transmits a signal including the sensor data; or, if the initiating sensor module is requesting data, then the responding sensor module transmits a signal to the initiating sensor module.

Next, the one of the initiating and responding sensor module 10 that is to receive the data receives the transmitted signal and recovers the data therefrom.

Then, the transmitting one of the initiating and responding sensor modules 10 notifies the receiving one of the initiating and responding sensor modules when all of the data has been transmitted.

Next, the receiving one of the initiating and responding sensor modules 10 notifies the transmitting one of the initiating and responding sensor modules that it has received all of the data, or that if needs the transmitting one of the initiating and responding sensor modules to resend some or all of the data (e.g., due to a communications error).

Then, the transmitting one of the initiating and responding sensor modules 10 notifies the receiving one of the initiating and responding sensor modules if it has more data to send, or the receiving one of the initiating and responding sensor modules requests additional data from the transmitting one of the initiating and responding sensor modules. If the transmitting one of the initiating and responding sensor modules 10 sends additional data, then it does so according to the same procedure.

After the transmitting one of the initiating and responding sensor modules 10 is finished transmitting all available or requested data, it notifies the receiving one of the initiating and responding sensor modules, which acknowledges this notification to the transmitting one of the initiating and responding sensor modules.

Next, the initiating and responding sensor modules 10 cease communicating with one another.

Then, the receiving one of the initiating and responding sensor modules 10 may use the recovered data for any suitable purpose.

Still referring to FIG. 6, alternate embodiments of the sensor-module network 100 are contemplated. For example, the network 100 may include sensor modules 60 of FIG. 2 instead of sensor modules 10 of FIG. 1. Or the network 100 may include one or more of one or both sensor modules 10 and 60.

Still referring to FIG. 6, alternate embodiments of the sensor-module network 100 are contemplated. For example, the network 100 may employ a master-slave protocol where only one of the sensor modules serves as master, sending and receiving data to a plurality of sensors simultaneously or one at a time, and receiving data from sensor modules one at a time; whereas the master sensor module, in the alternative, may not contain any sensors. The master sensor module sends and receives data from a transceiver outside the body.

B. Temporary and Permanent Implantable Medical Devices and their Use

B.1. Stent Grafts 0.401

Within one embodiment of the invention, stent grafts are provided having one or more ISMs as described herein. Briefly, "stent graft", as utilized herein, refers to a device comprising a graft or covering (composed of a textile, polymer, or other suitable material such as biological tissue) which maintains the flow of fluids (e.g., blood) from one portion of a vessel to another, and an endovascular scaffolding or stent (including expandable and balloon-inflatable stent structures) that holds open a body passageway and/or supports the graft or covering. Endovascular stent grafts may be used to treat a variety of vascular conditions, including treating abdominal aortic aneurysms and thoracic aortic aneurysms (referred to as "EVAR"—endovascular aortic aneurysm repair), atherosclerosis, peripheral vascular disease or other vascular diseases. Endovascular stent grafts are also used in dialysis grafts and dialysis fistulas to treat obstructions or aneurysms that occur at the site of vascular access in hemodialysis patients. Non-vascular stent grafts can be used in a variety of other body passageways such as the esophagus, colon, bile duct, urethra and ureter to name a few examples. Within certain embodiments, the stent graft has at least two openings (and within further embodiments, three or more openings), an outer (adluminal) surface, and an inner (luminal) surface. Within certain embodiments the stent graft is an "articulated" or "segmented" stent graft; these multi-component stent grafts are inserted as separate segments which are then assembled inside the body (artery or other body passageway) into their final configuration. Within other embodiments, the stent graft is fenestrated (e.g.

FEVAR—fenestrated endovascular aortic aneurysm repair) with holes in the graft body material that maintain the patency of important blood vessels (or side branches). With certain embodiments, the stent graft has a Unique Device Identification ("UDI") number.

Within embodiments of the invention one or more ISMs, and/or sensors may be placed on (the luminal side or abluminal side), and/or within a stent grafts (e.g., within the metallic struts of the stent graft or embroidered into the fabric of the stent graft). Representative examples of sensors placed on a stent graft are provided in PCT Publication No. WO2014/100795, which is hereby incorporate by reference in its entirety.

B.1.A. Stent Grafts and Endoleaks

As noted above, stent grafts are typically utilized in a wide variety of medical procedures to open up and/or maintain the lumen of a body passageway (e.g. artery, gastrointestinal tract, urinary tract). They are most commonly used however for vascular procedures, e.g., in the treatment of aortic aneurysm disease. An aortic aneurysm (AA) is a dilatation of the aorta that usually results from underlying disease (typically atherosclerosis) causing weakness in the vessel wall. As the aneurysm progressively grows (dilates) in size over time, the risk of it bursting or rupturing rapidly increases; a condition which if not promptly treated, leads to massive hemorrhage and death. Stent grafts are inserted into an aneurysm, not only to simply hold open the diseased vessel, but also to bridge across the dilated vascular segment from healthy vessel to healthy vessel.

Briefly, a stent graft is inserted over a guide wire, from the femoral or iliac artery and deployed within the aneurysm, resulting in maintenance of blood flow from an aorta of acceptable (usually normal) caliber above the aneurysm to a portion of aorta or iliac artery(s) of acceptable (usually normal) caliber below the aneurysm. The aneurysm sac is thus excluded from the circulation. Blood within the excluded aneurysm sac thromboses and thus has no flow within it, presumably reducing the pressure and thus its tendency to burst.

Presently available stent grafts, however, have a number of limitations such as endoleaks, migration, detachment, wear and durability issues, rupture, stenosis, kinking and malpositioning. For example, current stent grafts are prone to persistent leakage of blood around the area of the stent graft and into the aneurysm sac (a condition known as an "endoleak"). Hence, pressure within the aneurysm sac is not reduced, stays at or near arterial pressure, and the aneurysm remains at risk for rupture. Endoleaks are among the most common and the most clinically dangerous complications of stent graft placement and the early detection and treatment of endoleaks remains a significant medical problem. Stent grafts of the present invention have, within certain embodiments, pressure detecting sensors that are able to detect elevated pressure within the aneurysm sac and warn the patient and/or the attending physician that there may be a potential endoleak. Pressure sensors contained within an ISM that is itself contained within a stent graft (e.g., within the metallic struts of the stent graft or embroidered into the fabric of the stent graft) or attached to a stent graft can recognize adluminal (the outer surface of the graft in contact with the blood vessel wall) pressure rising; this is suggestive that pressure within the aneurysm sac is becoming elevated and that the aneurysm is no longer excluded from the circulation. Since most endoleaks are asymptomatic to the patient (rupture is often the first symptom), a gradual or rapid increase in stent graft adluminal pressure (or aneurysm wall pressure) is an important early indicator that medical care should be sought and that investigation into its underlying cause is warranted. Currently, there is no such continuous monitoring and early detection system available to recognize endoleaks and embodiments of the present invention will greatly facilitate the identification and early treatment of this potentially fatal complication of stent graft treatment.

There are 5 common types of perigraft leakage (endoleak), and corrective measures can vary depending upon the underlying cause. Stent grafts of the present invention contain, within certain embodiments, ISMs comprising one or more sensors of various types including but not limited to fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like, which are capable of providing information useful to the physician for determining which type of endoleak might be present.

The first type of endoleak (Type I Endoleak) occurs when there is direct leakage of blood around the stent graft (either proximally or distally) and into the aneurysm sac. This type of endoleak can be persistent from the time of insertion because of poor sealing between the stent graft and vessel wall, or can develop later because the seal is lost. In addition, this problem can develop due to changes in the position or orientation of the stent graft in relation to the aneurysm as the aneurysm grows, shrinks, elongates or shortens with time after treatment. Type I endoleaks also commonly occur if the stent graft "migrates downstream" from its initial point of placement as a result of being shifted distally by the flow of blood and arterial pulsations. Representative stent grafts can have an ISM with contact and/or position sensors implanted/affixed to the proximal end of the stent graft to detect loss of contact with the vessel wall which could be indicative of a potential Type I endoleak. IMRs could also be located at the distal ends of the stent graft (as well as within the body of the stent graft) to assist in the identification of a Type I endoleak. Stent grafts equipped with an ISM (or ISMs) having pressure and contact sensing devices can indicate the suspected presence of an endoleak through the detection of elevated adluminal pressure; furthermore loss of contact with the vessel wall (as detected by the contact sensors) at the proximal and/or distal ends of the graft would suggest the presence of a Type I endoleak, while loss of contact of the body of the stent graft with the vessel wall would suggest the location, size and extent of the endoleak present in the aneurysm sac. Lastly, ISMs having position sensors and/or accelerometers concentrated at the proximal and/or distal ends of the stent graft (as well as in the body of the stent graft) can detect movement (migration) of the stent graft from its original point of placement (a common cause of Type I Endoleaks) and also aid in determining the size and location of the endoleak (by detecting deformations of the stent graft wall).

As noted above, within certain embodiments of the invention specific sensors can be identified by their USI, as well as by their positional location within the stent graft. Hence, a more comprehensive image or analysis of the overall function of the stent graft (and of the patient's response to the stent graft) can be ascertained based upon knowledge of the location and activities of a group of sensors collectively. For example, a collection of sensors, when analyzed as a group could be utilized to ascertain the specific type of endoleak, the degree and the location of the endoleak. In addition, the collection of sensors could be utilized to assess a variety of other conditions, including for example, kinking or deformation of the stent graft, and stenosis of the stent graft.

The second type of perigraft leak (Type II Endoleak) can occur because there are side arteries extending out the treated segment of blood vessel (typically the lumbar arteries, testicular arteries and/or the inferior mesenteric artery). Once the aneurysm is excluded by the stent graft, flow can reverse within these blood vessels and continue to fill the aneurysm sac around the stent graft. Representative stent grafts can have ISMs with contact and/or position sensors (ideally an ISM would be incorporated to the proximal and distal ends of the stent graft, as well as well potentially as within the body of the stent graft) to assist in the identification of a Type II endoleak. Stent grafts equipped with ISMs having pressure and contact sensing devices can indicate the suspected presence of an endoleak through the detection of elevated adluminal pressure; furthermore continued contact with the vessel wall (as detected by the contact sensors) at the proximal and/or distal ends of the graft would suggest the endoleak could be a Type II, while loss of contact of the body of the stent graft with the vessel wall would suggest the location, size and extent of the endoleak present in the aneurysm sac. Lastly, ISMs having position sensors and/or accelerometers concentrated at the proximal and distal ends of the stent graft would confirm that the stent graft had not migrated from its original point of placement, while those in the body of the stent graft would aid in determining the size and anatomical location of the endoleak (by detecting deformations of the stent graft wall) which could suggest the blood vessel responsible for the Type II endoleak.

The third type of endoleak (Type III Endoleak) can occur because of disarticulation of the device (in the case of modular or segmented devices). Due to the complicated vascular anatomy, the diversity of aneurysm shapes and the need to custom fit the stent graft to a particular patient, many stent grafts are composed of several segments that are inserted separately and constructed within aorta into their final configuration. Disarticulation of the device at the junction points can develop due to improper placement or deployment, or due to changes in shape of the aneurysm as it grows, shrinks, elongates or shortens with time after treatment. Representative segmented stent grafts can have ISMs having contact and/or position sensors implanted/affixed to the stent graft at the articulation points to assist in assessing the integrity of the seal between stent graft segments. During placement of the stent graft, ISMs having complimentary (paired/matched) contact sensors on the respective articulated segments can confirm that a precise and accurate connection has been achieved during construction of the device. Should a Type III endoleak develop, gaps/discontinuities between contact sensors on complimentary segments can be detected to ascertain both the location and extent of the endoleak present.

A fourth type of endoleak (Type IV Endoleak) occurs due to the development of holes within the graft material through which blood can leak into the aneurysm sac. Continuous pulsation of the vessel causes the graft material to rub against the metallic stent tynes eventually leading to fabric wear and graft failure. Representative stent grafts have ISMs with fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like that are incorporated within the body of the stent graft (e.g., within the metallic struts of the stent graft or embroidered into the fabric of the stent graft) to assist in the identification of a Type IV endoleak. Should a defect develop in the graft material, the embedded ISM sensors will aid in determining the size and location of the endoleak by detecting deformations and defects of the stent graft wall. In extreme cases, stent graft wall defects can lead to rupture of the stent graft; a condition that can be detected early as a result of embodiments of this invention.

The final type of endoleak (Type V Endoleak) is a leak of unknown origin. Representative stent grafts equipped with ISMs having fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like can indicate the suspected presence of an endoleak through the detection of elevated adluminal pressure. Furthermore, loss of contact with the vessel wall detected by contact sensors, changes in position sensors and/or movements detected by accelerometers can detect changes in the stent graft and assist in determining the size and location of the endoleak (by detecting deformations of the stent graft wall).

Figure 10:
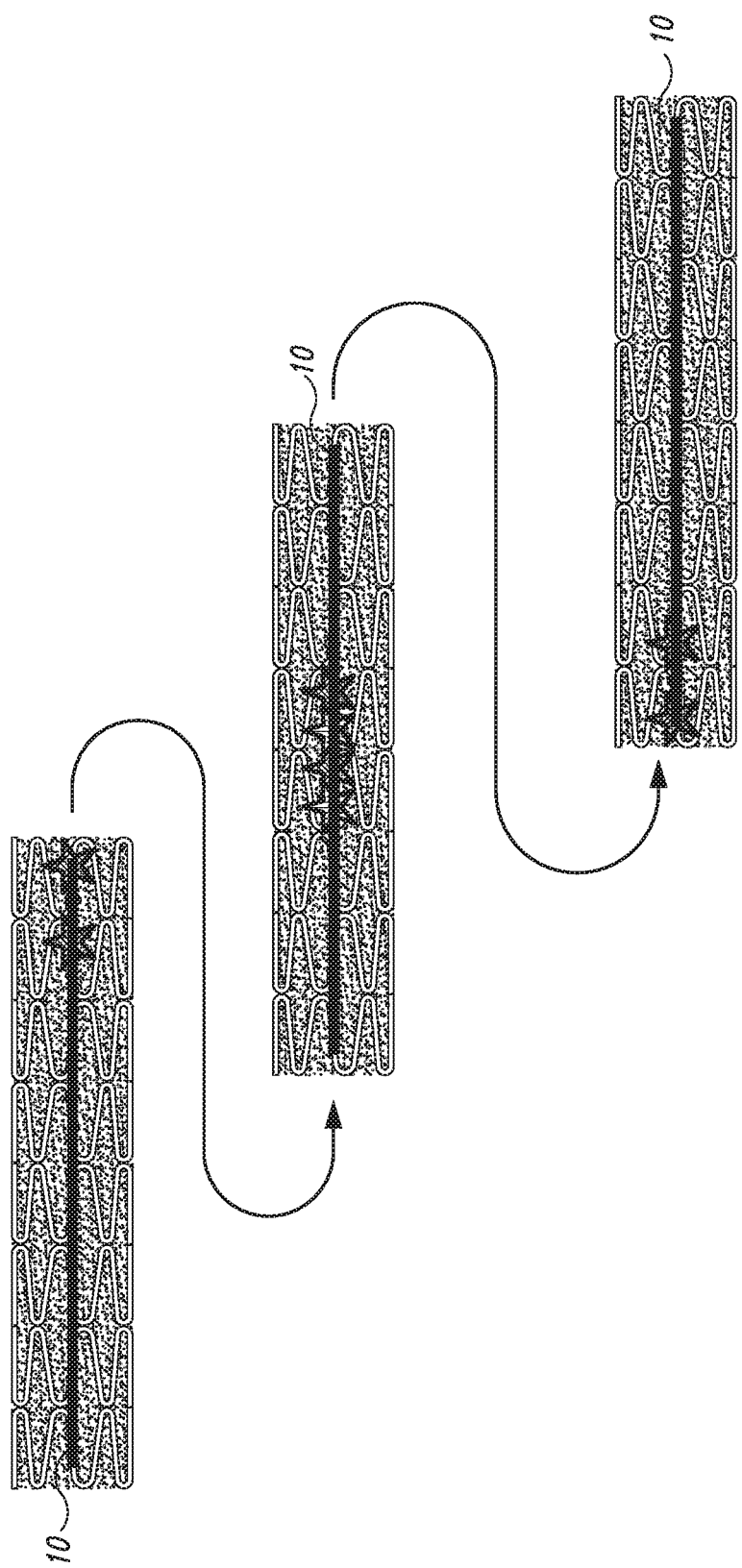
FIG. 10 is a schematic illustration of an ISM having contact sensors that can be utilized to aid and or assist the placement of overlapping stents.

The integration of data from the fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the can produce a computer reconstruction of the stent graft wall that can serve a function similar to medical "imaging" of the device (see e.g., FIGS. 9 and 10). Stent grafts of the present invention containing ISMs, within certain embodiments, can provide sensing information to serve a variety of important clinical functions.

For example, this information is useful to the clinician during initial placement of the stent graft to determine if it is correctly placed anatomically, if there is leakage around the graft, if stent graft segments are correctly assembled, to detect kinking or deformation of the graft, to ascertain if there is uniform blood flow through the device—to name but a few important functions. Malpositioning of the stent graft, either at the time of placement or due to subsequent movement/migration, is a common complication of stent graft therapy. ISM-containing stent grafts of the present embodiment can be used to confirm proper initial placement, assembly and deployment and any ensuing disarticulation or migration. Detachment of the graft as a whole (from the artery), or detachment of individual graft segments from each other is another problematic complication of stent graft insertion and ongoing therapy. Stent grafts of the present invention have the ability to detect movement/detachment of the entire stent graft, as well as movement and/or detachment of individual segments, providing the clinician and patient with valuable diagnostic information. Kinking of the stent graft during deployment and/or as the result of subsequent movement after placement is also a significant clinical problem if it develops. Stent grafts of the present invention have ISMs with position sensors and accelerometers distributed throughout the stent graft capable of detecting deformation and kinking of the stent graft.

In some cases, the lumen of the stent graft can become narrowed and restrict blood flow through the graft due to external compression (such as an endoleak), stenosis (the growth of thickened vascular tissue called neointimal hyperplasia on the inner surface of the stent graft), or the formation of a blot clot. Stent grafts of the present invention have a variety of ISM containing sensors capable of detecting and differentiating types of stenosis. Blood flow, fluid pressure and blood volume sensors located on the luminal surface are able to detect the presence and location of a stenosis due to the increased blood flow speed and increased blood (and pulse) pressure at the site of a stenosis (relative to normal segments of the graft). Stenosis due to external compression (such as the presence of an endoleak as discussed above) will be experienced as such (increased blood flow speed and increased pressure). Stenosis due to neointimal hyperplasia or luminal clot formation will be detected as "dead spots" and/or altered readings on the luminal surface as ISMs having blood flow sensors, blood metabolic and/or chemistry sensors (e.g., for blood and/or other fluids) will become covered by vascular tissue or clot and will cease to register; while ISM adluminal pressure sensors and accelerometers will not show changes in adluminal pressure or stent graft wall deformation (as would occur with an endoleak). ISMs having metabolic sensors and chemistry sensors are capable of determining the difference between stenosis (normal pH and physiologic readings) and clot (lowered pH and altered physiologic readings).

As mentioned, stent grafts are often placed in arteries (typically the aorta) in anatomic locations where important arterial side branches originate. Of greatest importance are the renal arteries, but the lumbar, testicular, inferior mesenteric and internal iliac arteries can be affected by an aortic aneurysm. To maintain patency of these arteries (and prevent them from being obstructed by the placement of the stent graft), stent grafts with holes (or fenestrations) have been developed that allow blood flow through the graft and into the arteries that branch out from the aorta. FEVAR (fenestrated endovascular aortic aneurysm repair) is a form stent graft design and treatment that maintains the patency of important blood vessels that originate from the aorta. Stent grafts of the present invention have ISMs possessing blood flow sensors, fluid pressure sensors, pulse pressure sensors, blood volume sensors and/or blood chemistry and metabolic sensors at the fenestration sites to monitor blood flow through the side branches. Stent grafts of the present invention may also have ISMs having position sensors, contact sensors and/or accelerometers at the fenestration sites to monitor patency of the side branches (due to stenosis and/or kinking, migration and obstruction of the arterial branches by the stent graft itself).

In addition, patients requiring stent grafts often have extensive cardiovascular disease resulting in impaired cardiac and circulatory function. For example, patients receiving stent grafts are at an increased risk for myocardial infarction (heart attack), congestive heart failure, renal failure and arrhythmias. The aorta is the largest blood vessel to originate from the heart; therefore, monitoring certain hemodynamic and metabolic parameters within the aorta can provide the clinician with very important information regarding the patient's cardiac, renal and circulatory function. Stent grafts of the present invention contain ISMs having fluid pressure sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors, temperature sensors, and the like, suitable for such purposes. Representative stent grafts of the present invention can have ISMs with pressure sensors, pulse pressure sensors, pulse contour sensors, blood volume sensors, blood flow sensors on and/or within the stent graft which can be used by one of ordinary skill in the art to calculate and monitor important physiologic parameters such as cardiac output (CO), stroke volume (SV), ejection fraction (EV), systolic blood pressure (sBP), diastolic blood pressure (dBP), mean arterial pressure (mAP), systemic vascular resistance (SVR), total peripheral resistance (TPV) and pulse pressure (PP). For example, the FloTrac/Vigileo (Edwards Life Sciences, Irvine, Calif.) uses pulse contour analysis to calculate stroke volume (SV) and systemic vascular resistance (SVR); the pressure recording analytical method (PRAM) is used by Most Care (Vytech, Padora, Italy) to estimate cardiac output (CO) from analysis of the arterial pressure wave profile. Changes in cardiac output (CO), stroke volume (SV) and ejection fraction (EF) and cardiac index (CI) can be an important in detecting complications such myocardial ischemia and infarction; they can also assist the clinician in implementation and adjusting cardiac medications and dosages. ISMs having pulse pressure sensors, pulse contour sensors and heart rate sensors contained on and within stent grafts of the present invention can assist in the detection and monitoring of cardiac arrhythmias and heart rate abnormalities; they can also be used to monitor the patient's response to cardiac medications that effect heart rate and rhythm. Systolic blood pressure (sBP), diastolic blood pressure (dBP), mean arterial pressure (mAP), systemic vascular resistance (SVR) and total peripheral resistance (TPV) readings can be used by the clinician to monitor the dosage and effect of blood pressure lowering medications and pressor (blood pressure increasing) agents.

As described above, patients requiring stent grafts often have concurrent medical problems related to cardiovascular disease such as renal impairment or renal failure. The renal arteries originate from the aorta, often in close approximation to the typical location of stent graft placement; therefore, monitoring certain hemodynamic and metabolic parameters within the aorta can provide the physician and patient with very important "real time" information regarding ongoing renal function. Stent grafts of the present invention can contain ISMs having circulatory sensors (as described herein) as well as chemistry sensors (e.g., for blood and/or other fluids) and metabolic sensors (e.g., for blood and/or other fluids) suitable for monitoring kidney function. Examples of blood chemistry and metabolic sensors of utility for this embodiment include, but are not limited to, Blood Urea Nitrogen (BUN), Creatinine (Cr) and Electrolytes (Calcium, Potassium, Phosphate, Sodium, etc.). Furthermore, combining metabolic data with hemodynamic data and urinalysis can allow the clinician to calculate the Glomerular Filtration Rate (GFR) which is a very useful measure of kidney function. This information would be of particular utility in the management of dialysis patients to monitor the timing, effectiveness, and frequency of dialysis therapy.

Finally, due to the numerous complications described above, there is long term uncertainty about the utility of stent graft technology as a treatment for aortic aneurysm. Although much more invasive and traumatic, standard open surgical aneurysm repair is extremely durable and effective. Uncertainties about endovascular stent grafts include whether they will lower the aneurysm rupture rate, rate of perigraft leak (endoleak), device migration, ability to effectively exclude aneurysms over a long term, and device rupture or disarticulation. Stent grafts containing ISMs of the present invention, with their ability to detect and monitor many (if not all) of the aforementioned complications, are an important advancement of stent graft therapy as a whole.

Representative examples of sensors placed on a stent graft are provided in PCT Publication No. WO2014/100795, which is hereby incorporate by reference in its entirety).

B.1.B. Representative Embodiments of Stent Grafts and Endoleaks

Figure 7:
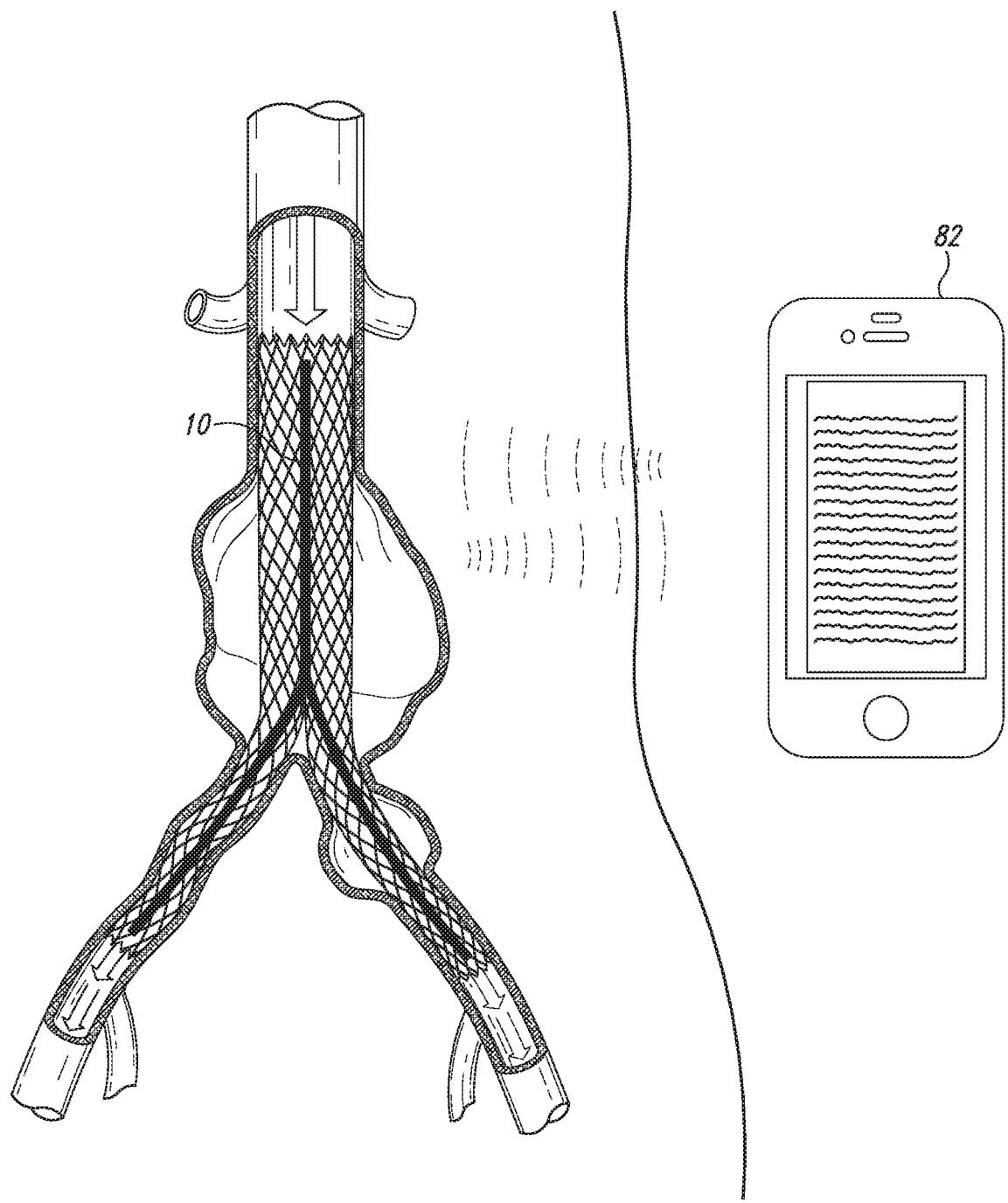
FIG. 7 is a schematic illustration of an ISM positioned on a stent graft within a patient which is being probed for data and outputting data, according to one embodiment of the invention.

Representative examples of stent grafts having ISMs are shown in FIGS. 7 and 8. Briefly, FIG. 7 illustrates an abdominal aortic aneurism of the type which may occur in patients. A stent graft has been positioned inside the aneurism to form a stent graft which is in physical contact with a blood vessel wall proximally and distally (and "seals" or excludes the aneurysm from the circulation). While such stent grafts are beneficial to reduce pressure in the aneurism sac and significantly increase the health of the patient, sometimes difficulties occur in which blood gets around or through the stent graft leading to various types of endoleaks. In order to monitor the health of the patient, it is desirable to identify any one of the five types of endoleaks (discussed above) which may occur in a stent graft. In addition, it is desirable to monitor cardiac output, blood flow, blood volume, and various characteristics of the blood internal to the stent graft.

FIG. 7 also illustrates that one or more ISMs can be positioned in, on, or within the wall of the stent graft (e.g., within the metallic struts of the stent graft or embroidered into the fabric of the stent graft) in order to sense various conditions of the stent graft relative to the blood vessel, the circulation, and the status of the aneurism. Although the ISM (or ISMs) can be located wherever is practical (e.g., multiple ISMs can be located in bands, proximally, distally, and/or circumferentially throughout the stent), particularly important locations include the proximal end (and to a lesser extent the distal ends) of the stent graft and the section of the graft adjacent to the aneurysm sac. For example, one or more ISMs containing one or more pressure sensors can be located at the proximal and distal ends of the stent graft, as well as within the aneurism sac in order to sense the fluid pressure at various locations along the outer wall of the stent graft and within the aneurism sac. Additionally, the ISMs may include one or more contact sensors and be located at the distal end of the stent graft, the proximal end of the stent graft, and various locations along the stent graft in contact with the aneurysm wall in order to determine whether the stent is in physical contact with the blood vessel wall. The ISM contact sensors may be of a type of physical pressure sensors, whereas the ISM pressure sensors are fluid pressure sensors. In addition, one or more position markers can be placed in the ISM and located to determine whether or not the ISM (and hence the stent graft) has moved relative to the blood vessel wall, since movement of the stent graft is one of the conditions which causes endoleak and failure.

Within various embodiments the ISMs may be powered by one or more batteries that is located on the outside of the stent graft (e.g. positioned such that it would be located within a site of an aneurysm. Similarly, other components of an ISM may likewise be located on a stent graft such that, once deployed, they would be located within the site of an aneurysm.

An ISM with sensors which are in contact with the inner (luminal) wall of the stent graft can both monitor the integrity of the stent graft and also the properties of the blood flowing through the stent graft. Accordingly, the ISM sensors on the luminal surface of the stent graft may include a pulse analyzer to determine the pulse properties of the patient. It may also include a plurality of blood pressure sensors to sense the blood pressure of the patient. It may include both blood flow and blood volume detectors to calculate the cardiac output of the patient. In addition, the stent graft provides an excellent location in order to determine various blood properties, such as the pH, the glucose level, the oxygen content, the cholesterol level, and other properties of the arterial blood as it flows by. Thus, a variety of different luminal sensors in an ISM can be utilized to sense for both the integrity of the stent graft as well as the properties of the blood flowing through the stent graft.

The ISM sensors used can also include accelerometers and motion sensors to detect movement of the stent graft due to heart beats, migration or other physical changes. Changes in the position of the accelerometers and/or motion sensors over time can be used as a measurement of changes in the position of the stent graft and/or vascular wall over time. Such positional changes can be used as a surrogate marker of vascular and stent graft anatomy—i.e. they can form an "image" of the stent graft and/or vascular wall to provide information on the size, shape and location of endoleaks, kinking of the stent graft, disarticulation of a segmented stent graft, stenosis with the stent graft, clot formation, and/or stent graft movement/migration.

For example, as shown in FIG. 8 is an enlargement of the proximal end of the stent graft showing the location of an ISM containing various sensors which can perform sensing functions for both for the integrity of the stent graft and the blood properties of the patient. More specifically, FIG. 8A shows development of an endoleak, which eventually becomes more complete (FIG. 8B). As shown in the blown-up images (FIGS. 8C and 8D), an ISM located in the stent graft wall adjacent to the aneurysm sac will possess sensors that will be moved from their typical (original) specified position, to a different position, as a result of the endoleak. The movement, rate of movement, pressure, and other metrics of measurement (depending upon the type of sensors contained in the ISM) can be interrogated at a single time point, as well as over a time course to follow the progression of the endoleak (and the success/failure of treatment attempts to correct it). Moreover, the three-dimensional spacial deformation of the stent graft (and four-dimensional if time is also considered), may be determined based upon the movement, pressure, and other metrics of the ISM sensors and used to provide sizing and anatomical location of the endoleak.

The, collection of data from the ISM sensors can also be utilized to ensure proper placement of the stent graft (e.g., that no leaks are present at the time of placement), complete articulation of the stent graft, full deployment (expansion) of the stent graft, and that the stent graft is appropriately positioned (e.g., relative to the aneurysm and arterial branches of the aorta).

B.2. Stents

Within one embodiment of the invention, stents are provided having one or more ISMs as described herein. Briefly, "stent" refers to a medical device that can be utilized to hold open body structures and/or passageways, and can be utilized to treat and/or prevent a wide variety of diseases and/or conditions resulting from lumen narrowing or obstruction; whether due to an injury or external compression of the vessel wall (a benign or malignant tumor, abscess, cyst), a disease process occurring within the vessel wall (e.g., cancer, atherosclerosis, inflammation, scarring or stenosis), a disease processes occurring on the surface (or in the lumen) of the vessel wall (thrombus, atherosclerosis, restenosis, tumor growth, inflammation and scarring, biliary and urinary "stones", mucous impaction, etc.), and/or an operation or other medical intervention causing damage to the vessel.

Stents can be used in a wide variety of variety of tubular body passageways to preserve the normal movement of luminal materials (blood, digestive contents, digestive enzymes and bile, air, urine, reproductive materials) through them, including for example, vascular structures (e.g., coronary, carotid, cerebral, vertebral, iliac, femoral, popliteal, tibial, mesenteric, pulmonary, and other branches of these arteries; large veins such as the superior and inferior vena cava and veins of the neck, upper and lower extremities), gastrointestinal structures (e.g., esophagus, duodenum, small intestine, colon, biliary tract and pancreatic ducts), pulmonary structures (e.g., to hold open the trachea, bronchi, or bronchioles), urinary system structures (collecting system, ureters, urethra), female and male reproductive system structures (e.g., to maintain patency of the fallopian tubes, prostatic urethra), sinus structures in the head and skull (maxillary sinus, frontal sinus, lacrimal duct), and inner ear structures (tympanostomy tubes).

Typically, stents are composed of metallic or polymeric components, and have a unitary structure, or multiple components (e.g., a bifurcated stent system). Stents may be non-degradable, partially degradable, or fully degradable. In addition, stents may be coated with one or more different compositions, including both polymers and drugs (including biologics and stem cells). Representative examples of stents include those disclosed in U.S. Pat. Nos. 6,852,153, 7,942,923, 7,753,947, 7,879,082, and 8,287,588, as well as various publications (see, e.g., "Open Stent Design: Design and analysis of self expanding cardiovascular stents", by Craig S. Bonsignore, CreateSpace Independent Publishing Platform, November 2012, and "Coronary Stents" by Sigwart and Frank (eds.), Springer, 2012)

Within preferred embodiments the stents of the present invention have a Unique Device Identification ("UDI") number, and each of the sensors of the ISM located within the stent have a Unique Sensor Identification ("USI").

In addition, within various embodiments of the invention one or more ISMs, and/or sensors may be placed on (the luminal side or abluminal side), and/or within a stent (e.g., within the metallic struts of the stent or embroidered into the fabric of a "covered" stent). Representative examples of sensors placed on a stent are provided in PCT Application No. PCT/US2014/028323, which is hereby incorporate by reference in its entirety).

B.2.A. Stents and their Use

As noted above, stents are used to open up and maintain the lumen of a diseased body passageway (e.g. artery, gastrointestinal tract, urinary tract), but have found their greatest utility in the management of vascular disease. Briefly, a stent is inserted into body a lumen to physically hold open structures and/or passageways (typically tubular organ structures such as blood vessels, the gastrointestinal tract, the urinary tract, the sinuses of the skull, the respiratory tract, or the male and female reproductive tracts) which have become blocked or partially obstructed thereby reducing or eliminating the movement of materials (typically fluids, solids or air) through them. The stent is usually placed percutaneously (e.g. vascular stents are often inserted into the vasculature via the femoral artery in the groin or the radial artery in the arm and then maneuvered through the blood stream under radiological guidance until they reach the diseased blood vessel) or via insertion through a natural orifice (e.g. the mouth, nose, anus, urethra) and placed under direct vision (endoscopy) into the affected organ (lungs, GI tract, urinary tract). Most often the stent is delivered to the deployment site in a compressed form and then expanded into place (often by inflating a balloon with the stent or through the use of "self-expanding" stents) to open the organ lumen back up to its original size and shape. The symptoms of blockage or obstruction (e.g. chest pain, claudication, neurological deficit, dysphagia, bowel obstruction, jaundice, difficulty breathing, infertility, urinary obstruction, sinus pain) depend upon the organ affected and restoration of normal anatomy and lumen function is the goal of stent treatment. Stent failure can be due to a multitude of causes but includes things such improper placement, improper sizing, incomplete opening or deployment of the stent, tissue ingrowth into the stent lumen (restenosis, tumor cell growth, inflammation), luminal obstruction (clot, biliary stone, kidney stone), stent fracture, stent kinking and stent migration. Stents containing ISM sensors able to assist the physician in their proper placement and deployment, and stents capable of ongoing monitoring to detect evidence of partial and/or complete obstruction, would have significant benefits over existing devices.

Within various embodiments an ISM containing sensors can be positioned on/in the stent in a location where the sensors are exposed to the blood flowing through the stent (on the luminal surface of the stent). A wide variety of sensors can be placed in an ISM on the luminal wall of the stent, within the stent, and/or, on the outer (adluminal) wall of the stent (for example, part of the stent strut itself can be composed of an ISM such that the sensors are in contact with all aspects—luminal, internal, adluminal—of the stent). Representative sensors that can be utilized within one or more ISMs on/in a stent include fluid pressure sensors, contact sensors, position sensors, pulse pressure sensors, blood volume sensors, blood flow sensors, blood chemistry sensors, blood (and tissue) metabolic sensors, accelerometers, mechanical stress sensors, vibration sensors and temperature sensors.

Figure 11:
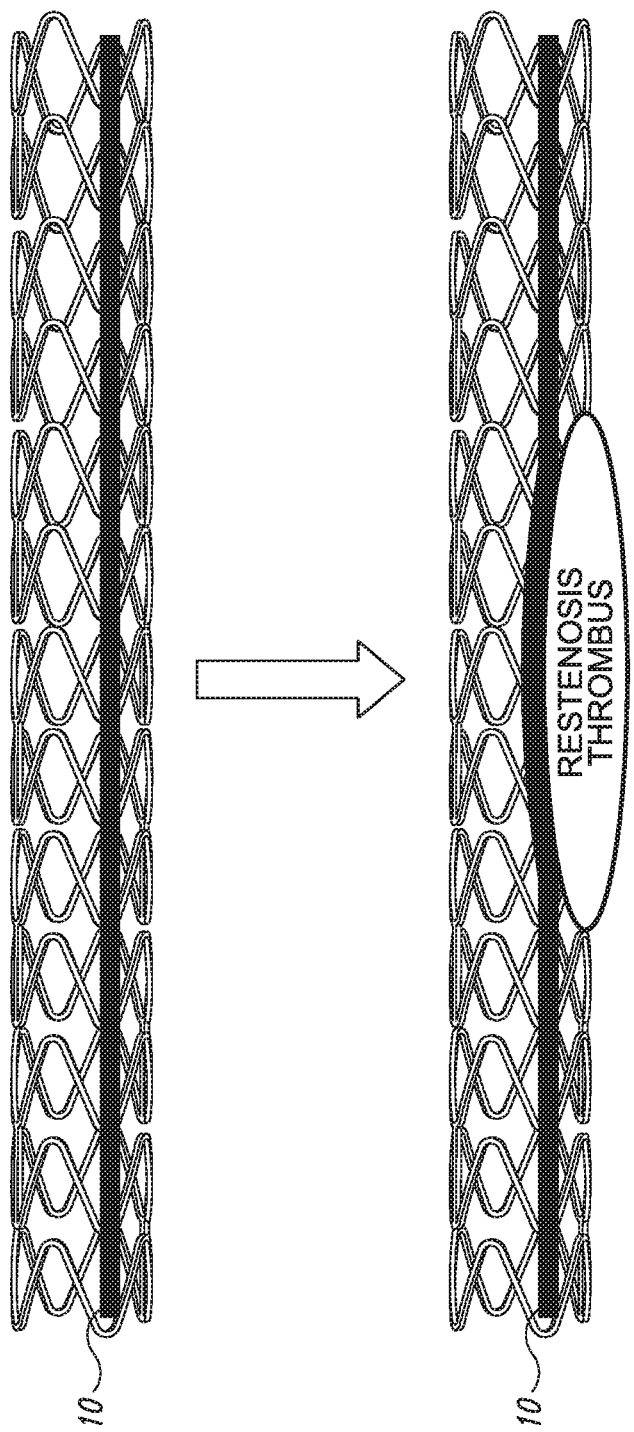
FIG. 11 illustrates the medical imaging of vasculature by an ISM having sensors which can detect positional movement due to vascular pathology (e.g., restenosis or thrombus formation).

Within various embodiments, vascular stents (coronary, peripheral and cerebral) of the present invention can have one or more ISMs with variety of sensors capable of detecting and differentiating types of normal vascular healing versus stenosis, restenosis, and/or thrombosis. For example, as generally shown in FIG. 11, an ISM can be contained within or on the strut or tynes of a vascular stent and contain sensors that detect blood flow, fluid pressure and blood volume on the luminal surface such that they are able to detect the presence and location of a stenosis due to the increased blood flow speed and increased blood (and pulse) pressure at the site of a stenosis (relative to normal pressures). Stenosis due to neointimal hyperplasia or clot formation can be detected as "dead spots" and/or altered readings on the luminal surface as an ISM having blood flow sensors, blood metabolic and/or blood chemistry sensors that become covered by vascular tissue or clot will no longer obtain readings; however, "upstream" sensors will show increased pressure and decreased flow rates, while sensors "downstream" from the obstruction will show decreased pressure and increased flow rates (a "jet" effect). An ISM having metabolic sensors and chemistry sensors are capable of determining the difference between stenosis (normal pH and physiologic readings) and clot (lowered pH and altered physiologic readings). Lastly, complete coverage of the luminal surface of the stent in the absence of altered pressure, blood flow rates, stent deformation and metabolic/chemistry readings is suggestive of normal healing; that the stent has become endothelialized (covered with the cells that line the body's blood vessels). This indicator of healthy and complete incorporation of the stent within the blood vessel wall (i.e. the stent is no longer exposed to the elements of the bloodstream) has an important clinical consequence—it alerts the clinician that it may be possible to discontinue the patient's (costly and dangerous) anticoagulant therapy since the risk of subacute and delayed thrombosis is now markedly reduced. In the case of biodegradable stents, complete coverage of the luminal surface of the stent and incorporation of it into the vessel wall means that dissolution of the stent is now safe (i.e. stent fragments will not be released into the blood stream).

In addition, subjects requiring stents often have extensive cardiovascular disease resulting in impaired cardiac and systemic circulatory function. For example, subjects receiving stents are at an increased risk for myocardial infarction (heart attack), cerebral vascular accidents (stroke), congestive heart failure, renal failure and arrhythmias. The coronary arteries are critical to the functioning of the heart, and hence, monitoring certain hemodynamic and metabolic parameters within these arteries can provide the clinician with very important information regarding the subject's cardiac, renal and circulatory function. Coronary stents of the present invention can contain one or more ISMs with fluid pressure sensors, contact sensors, position sensors, pulse pressure sensors, blood volume sensors, blood flow sensors, blood chemistry sensors, blood metabolic sensors, accelerometers, mechanical stress sensors, temperature sensors, and the like, suitable for such purposes. Representative stents of the present invention can be utilized by one of ordinary skill in the art to calculate and monitor important physiologic parameters such as cardiac output (CO), stroke volume (SV), ejection fraction (EV), systolic blood pressure (sBP), diastolic blood pressure (dBP), mean arterial pressure (mAP), systemic vascular resistance (SVR), total peripheral resistance (TPV) and pulse pressure (PP). For example, the FloTrac/Vigileo (Edwards Life Sciences, Irvine, Calif.) uses pulse contour analysis to calculate stroke volume (SV) and systemic vascular resistance (SVR); the pressure recording analytical method (PRAM) is used by Most Care (Vytech, Padora, Italy) to estimate cardiac output (CO) from analysis of the arterial pressure wave profile. Changes in cardiac output (CO), stroke volume (SV) and ejection fraction (EF) and cardiac index (CI) can be an important in detecting complications such myocardial ischemia and infarction; they can also assist the clinician in implementation and adjusting cardiac medications and dosages. ISMs with pulse pressure sensors, pulse contour sensors and heart rate sensors contained on and within stents of the present invention can assist in the detection and monitoring of cardiac arrhythmias and heart rate abnormalities; they too can be used to monitor the subject's response to cardiac medications that effect heart rate and rhythm. Systolic blood pressure (sBP), diastolic blood pressure (dBP), mean arterial pressure (mAP), systemic vascular resistance (SVR) and total peripheral resistance (TPV) readings can be used by the clinician to monitor the dosage and effect of blood pressure lowering medications and pressor (blood pressure increasing) agents. It is obvious that peripheral and cerebral vascular stents implanted in other arteries (renal, iliac, femoral, carotid, etc.) are capable of monitoring virtually all of the above cardiac/vascular parameters as well.

Vascular stents of the present invention can contain ISMs with circulatory sensors (as described herein) as well as blood chemistry sensors and blood metabolic sensors suitable for monitoring kidney function. Examples of blood chemistry and metabolic sensors of utility for this embodiment include, but are not limited to, Blood Urea Nitrogen (BUN), Creatinine (Cr) and Electrolytes (Calcium, Potassium, Phosphate, Sodium, etc.). Furthermore, combining metabolic data with hemodynamic data and urinalysis can allow the clinician to calculate the Glomerular Filtration Rate (GFR) which is a very useful measure of kidney function. This information would be of particular utility in the management of dialysis subjects to monitor the timing, effectiveness, and frequency of dialysis therapy.

Within one embodiment of the invention the stent may also comprise an ISM with one or more temperature sensors. These sensors may be utilized to track both the discrete temperature of the blood, vessel wall and surrounding environment, but the change of temperature overtime. Such change in temperature may be utilize to diagnose a possible developing infection (or other disease or condition), and allow a physician or care-giver to treat the infection (or other disease or condition) prior to a full onset B.2.B. Stents with Sensors Located within the Stent As noted above, within various aspects of the invention ISMs with sensors as described herein can be contained within the stent, including for example, within the tines of a stent, or within holes in the struts of the stent, or within the struts themselves. As utilized herein, "holes" should be understood to include openings that run entirely through a stent, as well as cavities, depressions, wells, or other openings or partial openings which permit insertion of a sensor within the stent. Representative examples of stents include those described within U.S. Pat. Nos. 7,208,010, and 7,179,289.

Within yet other embodiments, an ISM is designed to be placed, in, within, or on a stent, and one or more individual sensors which communicate with the ISM placed in, within, or on the stent.

B.2.C. Stent Placement, Deployment and Connections

Stents of the present invention, within certain embodiments, can provide sensing information to serve a variety of important clinical functions. It is widely accepted that the greater the amount of trauma experienced by the vessel wall during stent placement and deployment, the higher the probability that the stent will ultimately become obstructed (often due to restenosis). Causes of vessel trauma during placement include inaccurate sizing (stents too large for the vessel), difficult placement and deployment (requiring extensive manipulation to place the stent), long lesions, overlapping stents, over-inflation of the balloon or over-expansion of the stent, complicated lesions (including stenting at branch points) and placing stents in tortuous vessels. Accurate placement, sizing, deployment, and full expansion of stents continues to be a challenge, particularly in the vasculature, where primarily indirect visualization techniques, such as angiography, are used for stent positioning; angiography (radio-opaque dye running through the bloodstream) shows only the vascular luminal anatomy and gives no information about the vessel wall anatomy (which is often the critical diseased segment being treated) and only limited information about the stent itself. "Real Time" sensing information from the stent containing an ISM is useful to the clinician during placement of the stent to determine: if it is correctly implanted anatomically, if the stent is appropriately sized for the vessel in which it is placed, if it is completely opened (deployed) during balloon expansion (or during self-expansion), if it exerts too much (or too little) pressure against the vessel wall, if stent segments are correctly assembled, if there is an optimal amount of overlap between adjacent stents, if there is kinking or deformation of the stent, if there is cracking or fracturing of the stent, and if there is uniform flow through the device—to name but a few important functions. Stents of the present invention can allow the operating physician to monitor many valuable parameters that can lead to better and less traumatic stent placement and deployment.

Improper sizing of the stent relative to the vessel wall in which it is placed can significantly increase the risk of failure (particularly due to restenosis); stents with ISM sensors able to detect the amount, presence and/or absence of pressure and contact with the vessel wall can assist in matching the stent size and degree of expansion (deployment) to that of the vessel wall. Incomplete opening of all, or parts of the stent (known as "incomplete malaposition"—areas where the stent is not in full contact with the vessel wall and it projects into the arterial lumen), increases the risk of subsequent clotting (thrombosis) and stent failure. ISM position sensors, contact sensors and accelerometers contained within the stent can be used to identify and correct areas of incomplete opening (deployment) during stent insertion and furthermore can confirm that the stent has "locked" into the fully opened position. Improper positioning (malpositioning) of the stent, either at the time of placement or due to subsequent movement/migration, is also a common complication of stent therapy. ISM sensor-containing stents of the present invention can be used to confirm proper initial placement and any ensuing migration or relocation within the vessel. Movement of the stent as a whole, or detachment of individual stent segments from each other is another problematic complication of stent insertion and ongoing therapy. Stents of the present invention have the ability to detect movement/detachment of the entire stent, as well as movement and/or detachment of individual segments (or fragments), providing the clinician and patient with valuable diagnostic information. Kinking of the stent during deployment and/or as the result of subsequent movement after placement is also a significant clinical problem if it develops. Stents of the present invention have ISM components containing position sensors and accelerometers distributed capable of detecting deformation and kinking of the stent. Stent cracking and fracture can be a problem with all stents, but particularly in peripheral stents of the lower limb (due to movement of the limb or bending of the stent across the knee joint), as well as in polymeric degradable stents (coronary, peripheral and non-vascular) that can become fragile during the polymeric degradation process. ISMs having vibration sensors, position sensors, location sensors and accelerometers located within the stent device could alert the clinician and the patient to the development of this complication prior to it developing into an acute emergency.

Within various aspects of the invention assemblies are provided wherein a stent may be composed of a unitary component which is combined with another stent, or of multiple components which need to be placed in the appropriate configuration to ensure proper utility. When the patient has arterial disease and vessel narrowing at branching points in the vascular tree, it is often necessary to use stents (or stent components) than can be placed together in situ to match the anatomy of the obstructed segment. For example, FIG. 9 is a schematic illustration of various types of multiple stent placements, wherein ISMs with contact sensors can be utilized to ensure proper placement, configuration, and attachment (overlap) of the various stent segments. FIG. 9A illustrates a site of bifurcation with stenosis occurring at multiple points in the vessel. FIG. 9B illustrates a stent with PTCA (along with ISMs and representative sensors). FIG. 9C illustrates a stent plus stent deployment (also referred to as a "reverse-T"). FIG. 9D illustrates a stent plus stent deployment (referred to as "T stenting"). FIG. 9E illustrates a stent plus stent deployment referred to as a "Crush" (along with ISMs and representative sensors). FIG. 9F illustrates a stent plus stent deployment referred to as a "Y" or "V" (along with ISMs and representative sensors). FIG. 9G illustrates a stent plus stent deployment referred to as "Kissing". FIG. 9H illustrates a stent plus stent deployment referred to as a "Culotte" (along with ISMs and representative sensors). In each case, stents containing an ISM with multiple sensors (the "stars" in FIG. 9), such as contact sensors (potentially "matched" or complimentary for adjacent or overlapping stents) used to confirm accurate positioning and assembly; accelerometers used to corroborate anatomical location and conformation; position sensors used to monitor movement; flow sensors used to validate vascular patency; and pressure/vessel wall sensors used to verify full deployment and accurate vessel sizing. Taken collectively, this sensing information can create a 3-dimensional image of the vascular and stent anatomy and greatly improve the data available from angiography alone. This dramatically increases the chances of accurate, safe and effective deployment of multiple stents in complicated vascular lesions.

FIG. 10 is a schematic illustration of ISM sensors (the "stars" in FIG. 10) that can be utilized to aid and or assist the placement of overlapping stents. Overlapping stents are used in the treatment of long lesions or tortuous lesions where a single stent is insufficient to span the entire length of the diseased segments. While often effective, overlapping stents are more prone to failure and the rate of failure is directly proportional to the degree of overlap between adjacent stents; too much overlap increases failure risk, while too little—particularly if there is a gap between the two stents—is equally problematic. Stents containing ISMs with contact sensors can be used to confirm both the presence and the extent of overlap between adjoining stents. In a preferred embodiment the ISM contact sensors between stents are "matched," or complementary, confirming when the ideal amount of overlap has been achieved between neighboring stents. Furthermore, ISM pressure sensors, position sensors and accelerometers can be used to confirm that the overlapping segments are equally deployed to ensure that there is not a "mismatch" in lumen size in the two stents where they overlap.

B.2.D. Partially or Fully Biodegradable Stents

As noted above, stents of the present invention (including for example, vascular (e.g., coronary, carotid, cerebral, vertebral, iliac, femoral and arteries of the lower extremities), gastrointestinal (e.g., esophageal, duodenal, colonic, biliary and pancreatic), pulmonary (e.g., to hold open the trachea, bronchus, or bronchi), head and neck (sinus, lacrimal, tympanostomy), and genitourinary (e.g., ureteral and urethral, prostate, fallopian tube) may be comprised of one or more biodegradable polymers. Such stents may be fully, or partially biodegradable and or resorbable. Representative examples of such stents include for example U.S. Patent App. Nos. 2009/0192588, 2007/0270940, and 2003/0104030, and U.S. Pat. Nos. 6,387,124, 6,869,443 and 7,044,981.

Placement of ISMs having sensors as described herein on or within a biodegradable or partially biodegradable stent (at varying depths within the polymer) allows a determination of degradation of the stent, as well as, optionally, the rate of biodegradation or resorption of the stent. Hence, within one aspect of the invention methods are provided for determining degradation of a stent are provided, comprising the steps of a) providing to a body passageway of a subject an assembly comprising a stent and one or more ISMs having sensors, and b) detecting a change in a sensor, and thus determining degradation of the stent. Within various embodiments the ISM has sensors capable of detecting one or more physiological (e.g., contact, fluid flow, pressure and/or temperature) and/or locational (e.g., location within the subject) parameters. Within further embodiments the step of detecting is a series of detections over time, and optionally, the method may further comprise the step of determining the rate of degradation of the stent, and/or estimating the time for complete degradation of the stent. Within still further embodiments, the stent can determine luminal coverage of the device by healing tissue and therefore confirm that the stent is embedded within the vessel wall (reducing or eliminating the possibility that stent fragments are released into the luminal fluids).

Within one embodiment the biodegradable stent is an esophageal, ureteral, urethral, sinus, vascular, or prostatic stent and degradation of the stent can be monitored by detecting the loss or movement of ISM sensors over a period of time.

B.2.E. Stent Coatings

Within certain embodiments of the invention the stents provided herein can have one or more coatings on one or more surfaces of the stent. Coatings can be provided on stents for a variety of purposes. Coatings may be biodegradable, or non-biodegradable, or a combination of these. Typically, many coatings are polymer-based (e.g., polymers comprised of polyurethane, polyester, polylactic acid, polyamino acid, polytetrafluroethylene, tephlon, Gortex®), although non-polymer coatings may also be utilized.

Representative examples of suitable coatings include those described in, for example, U.S. Pat. Nos. 8,123,799, 8,080,051, 8,001,925, 7,553,923, and 5,779,729, all of which are incorporated by reference in their entirety.

B.3. Prosthetic Hip Joints

Within one embodiment of the invention, prosthetic hip joints are provided having one or more ISMs as described herein. Briefly, "hip replacement" as that term is utilized herein, may take a variety of different forms and may involve replacement of all or portions of the patient's hip joint with synthetic materials. In total hip replacement (THR), both the femoral head and the acetabulum are replaced. In a hemi (partial) hip arthroplasty, only the femoral head is replaced while the patient's own acetabulum is retained. The femoral component of a hip replacement may be a single piece with the head and stem as an integral, complete unit, or it may be constructed in several pieces, such as a femoral stem which is then coupled to a separate femoral head piece and neck section (which is often done to provide the patient with custom fitting for length and/or femoral head size). The femoral component can be cemented in place with PMMA bone cement (cemented hip) or it can be fitted precisely within the medullary canal of the femur and held in place without cement (AML—anatomic medullary locking—stem design). Similarly, the acetabular component of a THR can also be a single piece coupled to the hip socket to receive the femoral head, or be a two-piece component with a shell coupled to the pelvic bone and an inner liner attached to the shell. The acetabular component of a THR can be held in place with screws and/or cement or it can be affixed without cement.

Currently, the various components may be made of the same material, for example, all portions can be made of metal, or individual components can be made from a variety of different materials. For example, it is common for the acetabular component to have a metal shell with an outer surface coating to facilitate bone attachment and ingrowth, and an inner lining made from polyethylene, ultrahigh molecular weight polyethylene, ceramic, or surgical-grade stainless steel. Similarly, there may be several different combinations of materials used in the construction of the femoral head. For example, the femoral head can be composed of metal, usually cobalt chromium (but also stainless steel or titanium), or a ceramic material, while the femoral stem is typically metal (stainless steel, titanium, or cobalt chromium) and often possesses a surface coating to encourage incorporation of the implant within the femur.

As utilized herein the terms "hip implant" "prosthetic hip" or "hip replacement" or "hip replacement or portion thereof" or "medical device" should be understood, unless the specific context requires otherwise, to refer to any or all of the various components that go into making a total hip prosthesis, including for example, the femoral stem, femoral head, and acetabular assembly, as well as their various subcomponents. "Hip replacement prosthesis" should be understood to refer to either a partial or total hip replacement prosthesis.

Within various embodiments of the invention one or more ISMs, and/or sensors may be placed on or within a hip replacement. Representative examples of sensors placed on a hip replacement are provided in PCT Application No. PCT/US2014/028323, which is hereby incorporate by reference in its entirety).

B.3.A. Medical Uses of Hip Replacements

Hip replacement is carried out when the patient loses sufficient use of the hip so as to result in disability, loss of movement and function, impaired ambulation, and/or continuous joint pain and discomfort. Common causes of impaired hip function leading to total or partial hip replacement include trauma (typically a hip fracture; often at the femoral neck), avascular necrosis of the hip, or various types of arthritis (such as rheumatoid arthritis or osteoarthritis). In most patients, the operation is successful in improving ambulation, restoring function and reducing pain; as a result, it is one of the most common orthopedic procedures in the Western World.

B.3.B. Representative Embodiments of Hip Implants

Hip replacement prostheses are described in more detail in PCT Application No. PCT/US2014/028381, which is hereby incorporated by reference in its entirety. Briefly, the prosthesis typically, is comprised of an acetabular shell in which an acetabular liner is placed. It also includes a femoral assembly which includes two components, a femoral head and a femoral implant or femoral stem (also having a femoral neck) (see generally, FIG. 12).

One or more ISMs having sensors can be positioned within the prosthesis in order to monitor, in situ, the real-time operation of the patient activity and the prosthesis performance. In one embodiment, an ISM having contact sensors can be placed within the acetabular shell. These sensors detect and record contact between adjacent parts, such as the between the acetabular shell and the pelvis and/or between the acetabular shell and the bone cement (if present) and/or between the bone cement (if present) and the pelvis, and can detect loosening of the prosthesis and its connection to the surrounding cement (if present) and/or pelvic bone. Loosening of the acetabulum is a common complication that occurs (typically over 8-12 years) when bone loss takes place in the pelvic bones surrounding the acetabulum (e.g., due to a process known as osteolysis). Erosion of the bone around the implant may be caused by material debris (metal, ceramic, and/or polyurethane fragments) generated by friction between the femoral head and acetabular cup entering the pelvic tissues surrounding the acetabulum and causing inflammation and bone loss. Other potential causes of inflammation and osteolysis are implant vibration and motion, mechanical wear and tear, lack of biocompatibility between the implant materials and the surrounding bone, metal allergy, and lack of biocompatibility between the bone cement and the surrounding bone. In addition, an ISM having contact sensors may indicate that the acetabular shell is positioned further from the pelvic bone than desired as a result of material debris being built up over time and/or the presence of inflammation between the shell and the pelvic bone. An ISM having contact sensors can also be placed within the bone cement (if present) so as to collect data on the physical contact between the bone cement and the acetabular prosthesis and/or between the bone cement and the pelvic bone.

Within various embodiments, an ISM having contact sensors may also be positioned at various locations on the two surfaces of the acetabular liner. The contact sensors can therefore sense the contact (and/or movement) between the acetabular liner and the acetabular shell (these sensors could be "paired" so as to detect shifting between the acetabular liner and shell), as well as contact between the femoral head and the acetabular liner. Similarly the ISM having contact sensors can be positioned at various locations on the femoral head to detect contact between the femoral head and the acetabular liner. Thus, in the embodiment, an ISM having a variety of contact sensors are provided in order to monitor contact between the bone and the acetabular component, and between the femoral head and the acetabular liner. Dislocation of the femoral head from the natural or synthetic acetabulum of a prosthetic hip is a common complication of hip replacement occurring shortly after surgery (particularly while the surrounding supportive tissues are healing from surgery); ISM sensors on the femoral head and/or acetabulum can alert the patient and the healthcare provider if joint dislocation has occurred. Partial or incomplete dislocation (subluxation) of the hip joint can also occur and may not be readily evident to the patient or the physician; contact sensors on the femoral head and/or acetabulum can determine of the joint is functioning (tracking) correctly and if subluxation (even if subclinical or asymptomatic) is occurring.

Additional (or alternative) ISMs having contact sensors can be positioned on or within the femoral stem as well, to monitor contact between the femoral stem and the femur and/or contact between the femoral stem and the surrounding bone cement (if present). An ISM having contact sensors on and/or within the femoral shaft can detect loosening of the prosthesis and its connection to the surrounding cement (if present) and/or the femur. Loosening of the femoral shaft is a common complication that occurs when (typically over 8-12 years), bone loss occurs in the femoral canal surrounding the femoral shaft due to osteolysis. As described above, erosion of the bone around the implant may be caused by material debris (metal, ceramic, and/or polyurethane fragments) generated by friction between the femoral head and acetabular cup entering the femoral tissues surrounding the femoral prosthesis and causing inflammation and bone loss. Other potential causes of inflammation and osteolysis are implant vibration and motion, mechanical wear and tear, lack of biocompatibility between the implant materials and the surrounding bone, metal allergy, and lack of biocompatibility between the bone cement and the surrounding bone. In addition, ISMs containing contact sensors can also be used to detect and record contact between connecting parts in a modular femoral prosthesis, such as the between the femoral head, femoral neck and/or the femoral stem. These ISMs, can be used to insure that the connecting elements of a modular femoral prosthesis are properly aligned and fitted.

Within other embodiments, ISMs having strain gauges can be positioned a various places on or within a prostheses particularly the femoral stem, but also the femoral neck and the femoral head, in order to detect strain encountered between the prosthesis and the surrounding bone. A decrease in strain may indicate that there is bone resorbtion (loss), which could lead to loosening of the prosthesis, or fractures. The strain sensors provide a different data point than the contact sensors, which merely specify whether there is current contact between adjacent structures and thus provide a good indication of whether there is abutting contact between two surfaces. However, they do not provide an indication of the strain that is present in either of the surfaces, on the other hand, the strain sensors output data indicative of the mechanical strain forces being applied across the implant which, if not corrected, can be a harbinger of future loosening and prosthesis failure. In addition, an ISM having strain gauges may be of the type which indicates the strain which is being exhibited between two surfaces, such as between the acetabular liner and the pelvic bone or between the acetabular shell and the acetabular liner.

Within other embodiments an ISM is provided with accelerometers that can be positioned at various locations in and on the femoral shaft, femoral neck and femoral head. Accelerometers provide the benefit of being able to detect acceleration, vibration, shock, tilt, and rotation of various components. They permit the ability to measure performance of the prosthesis under various conditions and over long periods of time.

Shortly after the hip has been replaced, the leg will be mobilized, at first passively, then actively; shortly thereafter, the patient will begin gradual weight bearing on the joint. The ISM accelerometers will measure the movement of the hip socket during movement, including during ambulation as the leg swings forward, hits the ground, plants, is lifted off the ground, and the body is propelled forward. In addition, the accelerometers will measure the impact of the foot hitting the ground and the effect of the force being transferred through the femur to the pelvic bones and any vibration, shock or rotation which may occur at different locations in the prosthesis. As the patient continues to improve their range of motion postoperatively, the acceleration experienced at different locations in the prosthetic hip joint, can be monitored. It will be expected that as the patient heals from the surgery, activity levels will progressively increase, ambulation will improve, steps will be more rapid (and fluid) and, in addition, greater stride length will be achieved with each step. This may result in greater impact every time the foot hits the ground, which can be measured over time (and compared to previous values) by the various accelerometers positioned on the femoral head, in the femoral stem, and/or in other locations on the prosthesis. Postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Figures 12, 13:
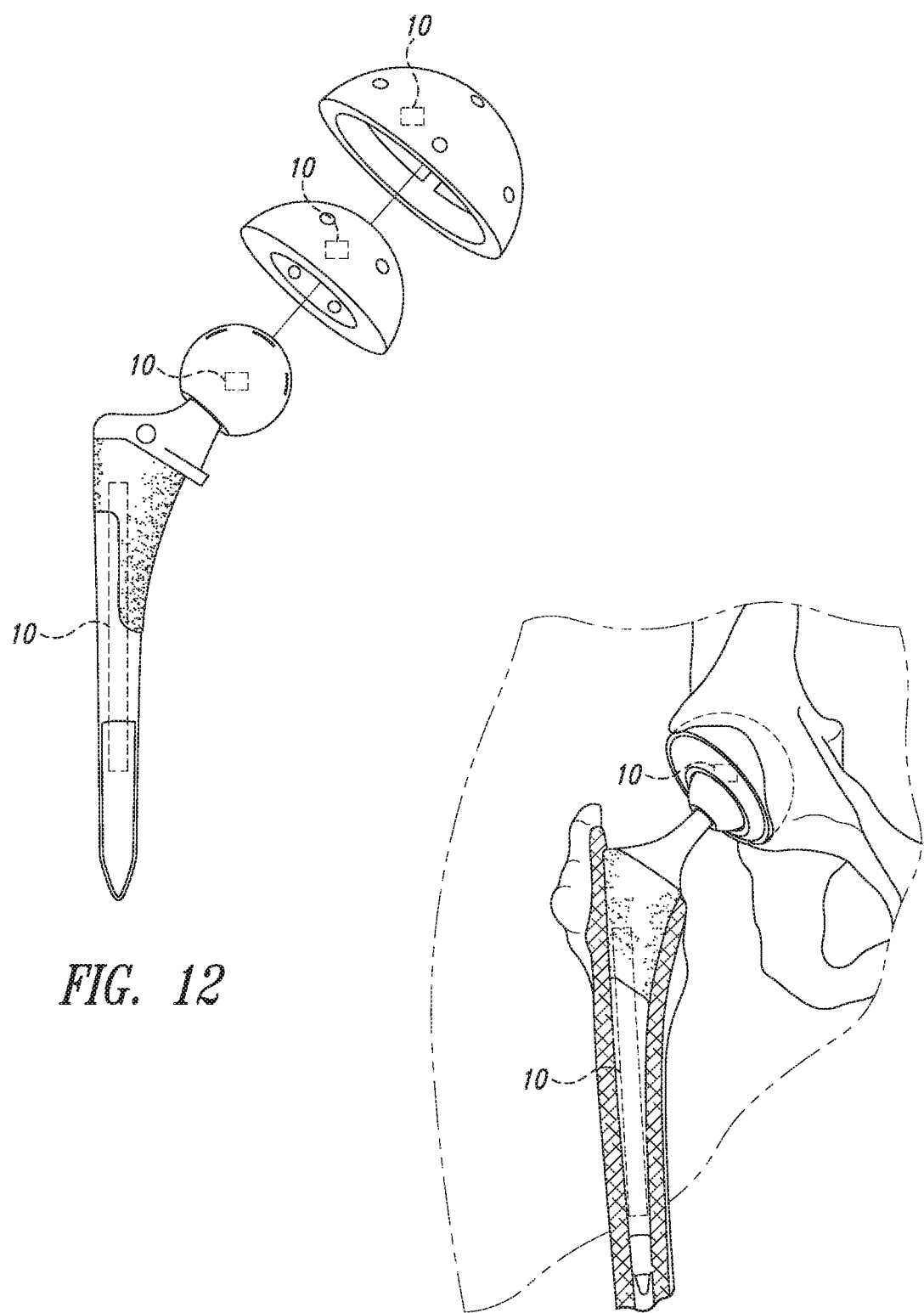
FIG. 12 is a representative example of an implantable hip prosthesis.
FIG. 13 is an illustration of an implanted hip prosthesis having several ISMs.

Within certain embodiments of the invention, the ISM is a unitary implantable device such as is shown in FIG. 13. For an ISM collecting mechanical data (position, motion, vibration, rotation, shock, tilt, steps), the implanted ISM sensors (accelerometers, position sensors, pedometers) have the advantage of not requiring either direct physical contact with the surface of the device or with patient tissues; only a secure and immobile attachment within the prosthetic joint is needed. In a particularly preferred embodiment, the ISM containing multiple mechanical sensors (as described above) is placed within the internal canal of the femoral stem; a location that provides more than enough space to insert and seal an ISM with multiple sensor functions and battery capability. Furthermore, the motion of the stem of a total hip joint that occurs during normal activities (such as walking) can provide opportunities to power the ISM.

The sensors used in the ISM for contact, strain and accelerometers can be an acceptable type of those generally available and as described herein.

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion (discussed later) and prosthesis performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, stiffness, time of day, compliance and timing of medication use (pain medications, anti-inflammatories), recent activity and exercise levels, patient strength, mental status, language barriers, the nature of their doctor-patient relationship, or even the patient's ability to accurately articulate their symptoms—to name just a few. Continuous monitoring or at repeated periodic intervals as a means to manage battery life and data collection can allow the patient and the physician to monitor progress objectively by supplying information about patient function under numerous conditions and circumstances, to evaluate how performance has been affected by various interventions (pain control, exercise, physiotherapy, anti-inflammatory medication, rest, etc.), and to compare rehabilitation progress versus previous function and future expected function. Better therapeutic decisions and better patient compliance can be expected when both the doctor and the patient have the benefit of observing the impact of various treatment modalities on patient rehabilitation, activity, function and overall performance.

As will be readily evident given the disclosure provided herein, the ISMs described and claimed herein can comprise a variety of different sensors within different locations of the ISM on and/or within the prosthetic hip. In addition, within various embodiments of the invention one or more sensors may be placed separate from the ISM (but still be, optionally, able to communicate with, and be controlled, by the ISM). Representative examples of sensors placed on a hip prosthesis are provided in PCT Application No. PCT/US2014/028381, which is hereby incorporated by reference in its entirety.

B.3.C. Coatings on Hip Implants

Within certain embodiments of the invention the hip implants are provided that can have one or more coatings on one or more surfaces of the prosthesis. Coatings can be provided on hip implant for a variety of purposes. Coatings may be biodegradable, or non-biodegradable, or a combination of these. Representative examples of coatings are polymer-based (e.g., polymers comprised of polyurethane, polyester, polylactic acid, polyamino acid, polytetrafluoroethylene, tephlon, Gortex®), although non-polymer coatings may also be utilized. Within certain embodiments of the invention, one or more ISMs containing sensors, as described herein, may be disbursed throughout the coating (e.g., even in a random manner).

B.4. Prosthetic Knee Joints

Within one embodiment of the invention, knee replacements are provided having one or more ISMs as described herein. Briefly, "knee replacement" or "knee prosthesis" as that term is utilized herein, may take a variety of different forms and may involve replacement of all (total knee replacement) or portions (partial knee replacement) of the patient's knee joint with synthetic materials. In total knee replacement (TKR), both the femoral side and the tibial side are replaced. In a partial, or unicompartmental, knee replacement, only one or two portions (surfaces—tibial or femoral; or compartments—medial, lateral or patellar) of the knee are replaced.

The various components of a TKR can typically include a femoral implant, a patellar implant, and a tibial implant (which can be composed of a tibial plate—with or without a stem—and a tibial liner). Currently, the various components can be made from a variety of different materials, including for example, polyethylene, ultrahigh molecular weight polyethylene, ceramic, surgical-grade stainless steel, cobalt chromium, titanium, and various ceramic materials. Within certain devices, the femoral implant (typically made of a metal such as stainless steel, titanium, or cobalt chromium) can be designed with a bone surface coating to encourage incorporation of the implant within the femur and the tibial plate (and stem) can also have a surface coating to encourage incorporation into the tibia. Representative examples of the various components of a knee replacement are described in U.S. Pat. Nos. 5,413,604, 5,906,643, 6,019,794 and 7,922,771.

"Bone Cement" refers to a material that can be administered between the prosthetic hardware and the surrounding bone and hardens in place when cooled (or otherwise activated); it is an agent used to secure one or more of the components (the prosthetic femur surface, the tibial plate/stem, the patellar "button") of the prosthesis to the appropriate bony tissue (femur, tibia, tibial medulla, patella). Bone cement is often composed of PMMA (polymethylmethacrylate) or PMMA and MMA copolymer blends. It should be noted that bone screws and/or other metallic (or polymeric) securing devices can also be used to assist in anchoring the prosthetic components to the surrounding bony tissues.

The present invention provides knee prosthesis (which may include a full or a partial implant), medical devices (e.g., a portion of a knee implant, and/or components or materials which are useful in the process of implanting the device), and kits (e.g., a knee prosthesis, medical device, and additional necessary materials such as bone cement and any associated delivery devices), all of which can have one or more of the ISMs provided herein. The knee prosthesis, medical devices and kits as provided herein (including related materials such as bone cement) are preferably sterile, non-pyrogenic, and/or suitable for use and/or implantation into humans. However, within certain embodiments of the invention the knee prostheses, medical devices and/or kits can be made in a non-sterilized environment (or even customized to an individual subject), and sterilized at a later point in time.

B.4.A. Knee Prosthesis, Medical Devices and Kits and their Use

Knee replacement is carried out when the patient loses sufficient use of the knee so as to result in disability, loss of movement and function, impaired ambulation, and/or continuous joint pain and discomfort. Common causes of impaired knee function leading to total or partial knee replacement include various types of arthritis (such as rheumatoid arthritis or osteoarthritis, and trauma (for example, previous knee ligament injuries or cartilage/meniscus tears). In most patients, the operation is successful in improving ambulation, restoring normal daily function and reducing pain; as a result, it is a very common orthopedic procedure in the Western World.

FIG. 14 shows a total knee joint of a type known in the art, as well as a unicompartmental (medial compartment) knee replacement. FIG. 15 illustrates the components and materials of a typical artificial joint (K10), including a metallic tibial plate (K5) and tibial stem (K2) (present in this Figure, although some tibial plate components do not have stems), a polyethylene articulating surface (K7), cement used to hold the various components in place (K4), patellar "button" prosthesis (K8), and the femoral knee component (K9).

Figure 15B:
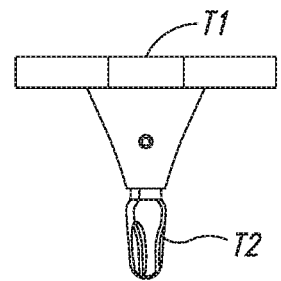
FIG. 15B depicts a tibial plate with attached tibial extension.
Figure 15C:
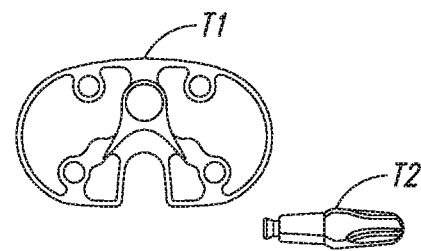
FIG. 15C depicts a tibial extension separated from a tibial plate.
Figure 15D:
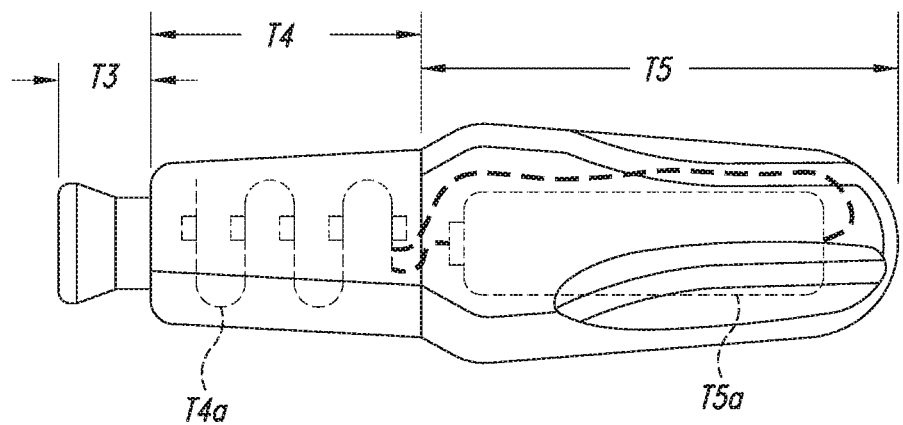
FIG. 15D depicts a tibial extension.

Within one embodiment of the invention an ISM may be placed within a tibial extension. For example, a portion of an artificial joint as shown in FIG. 15B may be composed of a tibial plate (FIG. 15C T1) and a tibial extension (FIG. 15C T2). The tibial extension (FIG. 15D) may be comprised of various aspects, including a screw engagement (T3), a first portion (T4) and a second portion (T5), which optionally may be ribbed to assist with bone engagement. It is also understood that the screw engagement (T3) may be configured alternatively as a press-fit cylinder, a threaded cylinder, or other means that can be accepted into a mating unit on a tibial plate to effect fixation. Within certain embodiments of the invention an ISM as described herein may be placed within a tibial extension (e.g., within portion T4). Within certain embodiments the extension is formed into two pieces with a joint located at the maximum outer dimension of T5. The tibial extension containing an ISM (e.g., T4a) can be sealed at a joint using glue, threads, ultrasonic weld, or any combination of the foregoing. Within further embodiments, a battery (e.g., T5a) which powers the ISM may also be placed within the body of the tibial extension (e.g. within portion T5). Although a standard battery is provided in FIG. 15D T5a merely for purposes of illustration, the battery may also be designed to have a shape which conforms to the ribbed segment in order to maximize the battery volume and hence its power capacity. Such shape also provides the additional benefit of inhibiting rotation of the battery within the tibial extension when the joint is in motion. It is also understood that the tibial extension containing the ISM can be configured as an extension for any total arthroplasty joint where the extension is placed into the medullary canal of bone used to seat the arthroplasty device in the patient. Particularly preferred ISMs for use in this aspect of the invention can be made with flexible circuitry (e.g., as shown in FIG. 15D T4a), a nd have an accelerometer, and gyroscope for measurement of the movement of the artificial joint. Additionally, ISMs suitable for use herein may include one or more of: a temperature sensor, a magnetometer, a radio transceiver, an energy harvester, a signal processor, a microcontroller, and piezoelectric sensor.

Figure 16:
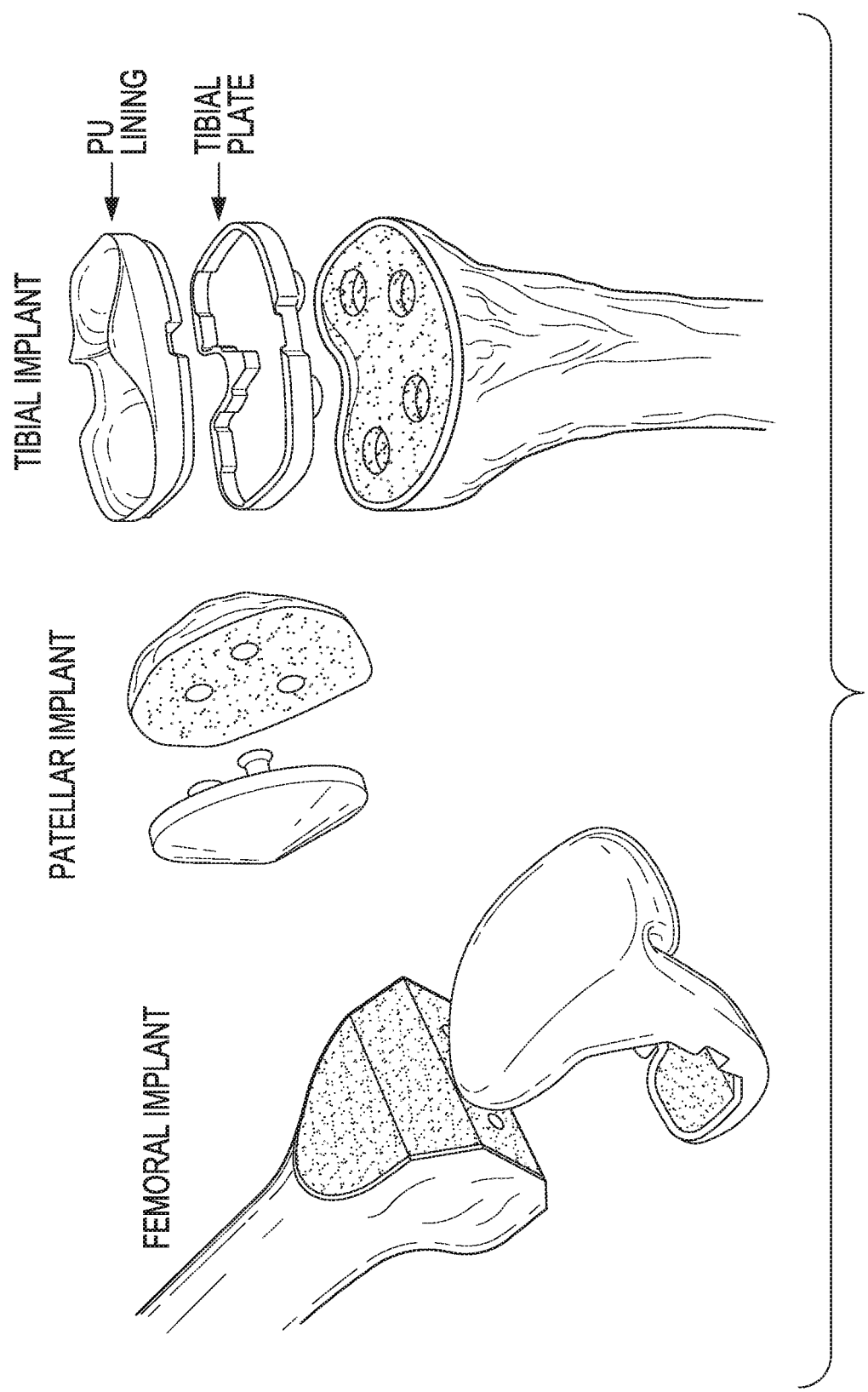
FIG. 16 shows the total knee replacement within a patient.

FIG. 16 depicts another typical TKR, with a femoral component, a tibial plate, a tibial lining and a patellar button which may be attached with screws and/or cement to the underlying bone (in FIG. 16 the tibial plate is attached to the tibia by screws and/or cement as opposed to a stemmed tibial plate as depicted in FIG. 15).

Figure 17:
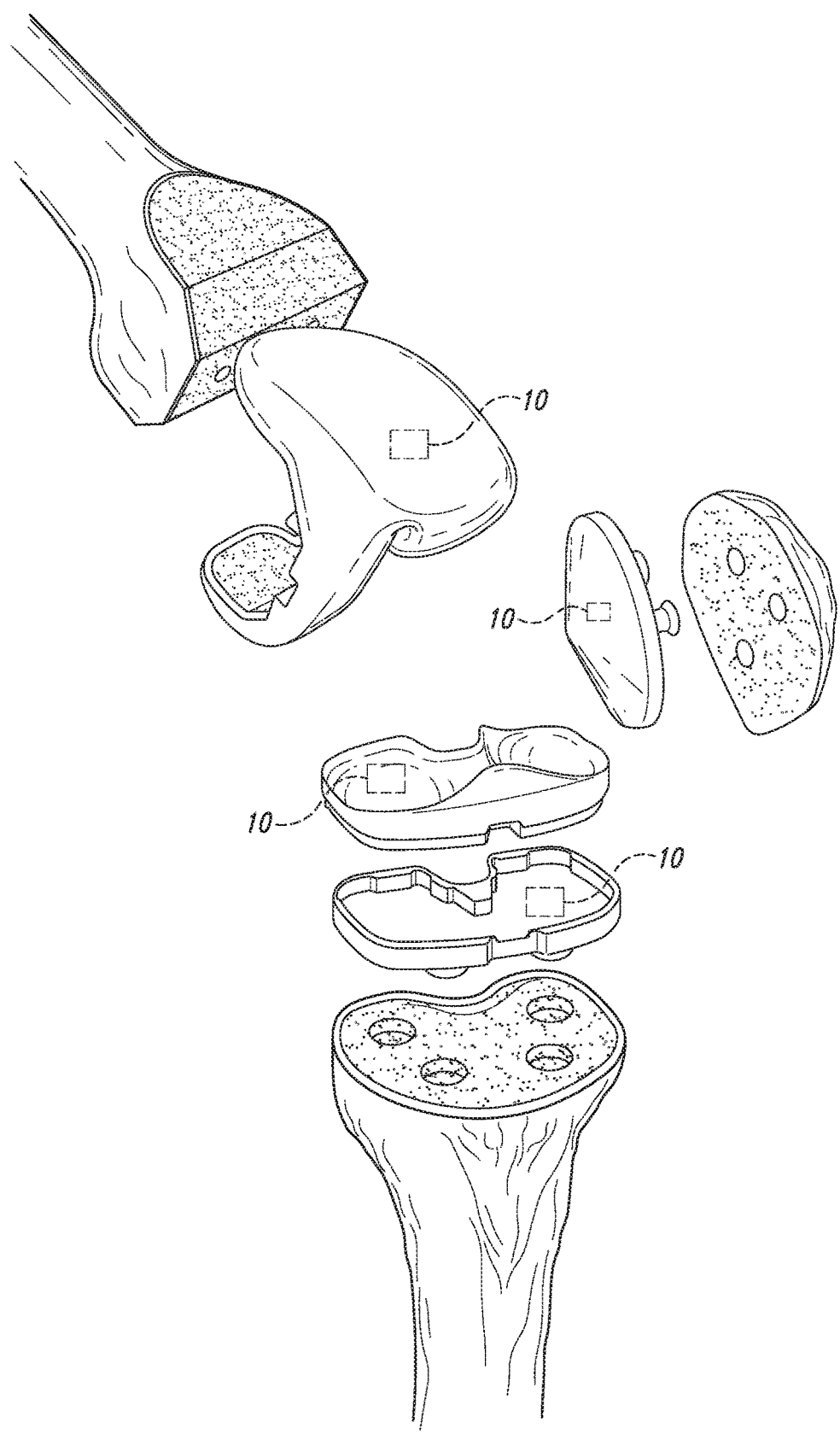
FIG. 17 is a side view of a total assembled knee with examples of different sensor locations.

FIG. 17 illustrates a representative prosthesis having one or more ISMs (10) positioned in or on the prosthesis in order to monitor, in situ, the real-time operation of the prosthesis, levels of patient function and activity, and the prosthesis performance acutely and over time. Note that in a knee prosthesis containing a tibial stem (as in FIG. 15), the inner canal of the tibial stem is a preferred location for the placement of an ISM.

As an example, one or more ISMs having contact sensors can be provided for placement or attachment on or within the tibial component (the liner, plate or stem), femoral component, and/or patellar components ("button") of a knee prosthesis. The ISM can also be contained within the bone cement (if present).

Within other aspects of the invention methods are provided for imaging a knee replacement or medical device containing one or more ISMs as provided herein, comprising the steps of (a) detecting the location of one or more sensors within an ISM in a knee replacement or medical device; and (b) visually displaying the location of said one or more sensors, such that an image of the knee replacement or medical device is created. Within various embodiments, the step of detecting may be done over time, and the visual display may thus show positional movement over time. Within certain preferred embodiments the image which is displayed is a three-dimensional image.

The imaging techniques provided herein may be utilized for a wide variety of purposes. For example, within one aspect, the imaging techniques may be utilized during a surgical procedure in order to ensure proper placement, alignment and working of the knee replacement or medical device. Within other embodiment, the imaging techniques may be utilized post-operatively in order to examine the knee replacement or medical device, and/or to compare operation and/or movement of the device over time.

Within one embodiment, a prosthetic knee containing one or more ISMs equipped with contact or pressure sensors can be used to detect loosening of the prosthesis and its connection to the surrounding cement (if present) and/or bone. For example, an ISM having contact or pressure sensors located on/in the tibial component (and/or on/in the bone cement around the tibial component), can detect loosening of the tibial component within the tibia; this can be detected acutely during surgery and alert the surgeon that some intra-operative adjustment is required. Progressive loosening of the tibial component within the tibia over time (as compared to post-operative levels) is a common complication that occurs when bone loss takes place (e.g., due to a process known as osteolysis); this too can be detected by the ISM contact or pressure sensors on/in the tibial component (and/or on/in the surrounding bone cement). Furthermore, ISM contact or pressure sensors located between segments of the tibial component (e.g. between the tibial plate and the tibial liner) can detect abnormal movement, loosening, or wear between component segments; these sensors can be "matching" (i.e. "paired" between adjacent components) so as to also allow accurate fitting during (and after) surgical placement.

Hence, in one embodiment ISMs having contact or pressure sensors are provided in order to monitor contact between the tibia and the tibial component, between the femur and the femoral component, between the patella and the patellar component, between the complimentary segments of the individual prosthetic components, and between the various articular surfaces present (medial and lateral tibial-femoral joint; the patellar-femoral joint) of a multi-compartmental or uni-compartmental prosthetic knee joint. Specifically, full or partial dislocation (subluxation) of the femoral prosthetic joint surface from the natural or synthetic tibial joint surface (medial, lateral or both) of a prosthetic knee is a common complication of knee replacement, often occurring shortly after surgery (particularly during the post-operative recovery period when the surrounding muscles and ligaments are still healing from surgery). ISM contact sensors on the femoral component articular surface and/or tibial component articular surface can alert the patient and the healthcare provider if joint dislocation or subluxation has occurred. This is of particular value in the detection of subclinical partial or incomplete dislocation (subluxation) of the knee joint which may not be readily evident to the patient or the physician; this is of greatest concern during early mobilization and post-operative rehabilitation efforts. Additionally, an ISM having contact or pressure sensors on the various knee components can determine of the joint is functioning and aligning (tracking) correctly during movement and activity. This is particularly true with respect to the movement of the knee cap, as accurate patellar tracking can be difficult to accurately measure clinically; accurate measurement of patellar tracking, both intra-operatively and post-operatively, would be beneficial.

In other embodiment ISMs having one or more strain gauges (or sensors) are provided, including for example, on and/or within the femoral condyle prosthesis-bone interface, on and or within the tibial bone—metal plate (and stem if present) interface, and on or within the patellar prosthesis (patellar "button")—patellar bone interface. In some embodiments (and to the extent space permits), the ISM having strain gauges can be contained on/within the bone cement (if present) used to secure the prosthesis to the surrounding bone, and in still other embodiments the strain gauges are contained on/within both the prosthetic components and the bone cement (PMMA).

Within various embodiments ISMs having strain gauges can be positioned at various locations on the tibial component to detect strain encountered between the tibial prosthesis and the surrounding tibial bone (and/or bone cement if present). Many tibial prostheses contain a stem that extends into the medullary canal of the tibia to enhance anchoring and stability. A decrease in strain in the tibial prosthesis and/or tibial bone cement may indicate that conditions are present that could potentially lead to bone resorbtion (loss) in all, or parts, of the tibial canal; bone resorbtion can lead to loosening of the prosthesis, or to tibial fracture (conversely, increased strain would favour bone growth in the region). Therefore, ISMs having strain sensors can provide an indication of the strain that is present in the tibial shaft and measure the most important mechanical strain forces being applied across the implant which, if mal-aligned or not corrected, have a high probability of resulting in loosening and prosthesis failure. An increase of strain may also indicate bone hypertrophy (growth), which can be a source of pain. The same dynamic exists in the interface between the femoral and patellar prosthetic components (and/or bone cement) and the femur and patellar; ISMs having strain gauges of the present invention can be used to monitor for these purposes as well. "Real life" strain information would not just be beneficial to the doctor and patient, who could use the data to determine the (positive and negative) effects of various activities on prosthetic-bone health, but also to manufacturers who could use it to design better prostheses.

Similarly, in other embodiments ISMs are provided having one or more accelerometers that can be located throughout the implant, including ISMs having accelerometers distributed on and within the femoral condyle prosthesis, on and within the tibial plate (and stem if present) and tibial liner, and on or within the patellar prosthesis (patellar "button"). In some embodiments, the ISM having accelerometers are on/within the prosthetic components themselves (tibial, femur and patellar segments), while in others the ISM having accelerometers are contained on/within the bone cement (if present) used to secure the prosthesis to the surrounding bone, and in still other embodiments the accelerometers are contained on/within both the prosthetic components and the bone cement (PMMA).

ISMs having accelerometers provide the benefit of being able to detect acceleration, vibration, shock, tilt, and rotation of various components. They permit the ability to measure performance of the prosthesis (K10) under various conditions and over long periods of time.

During knee replacement surgery, the prosthetic joint will be moved through a full range of motion and stability testing to assess prosthetic function and mobility prior to surgical closure. The ISMs having accelerometers can provide the surgeon with accurate, numeric, quantitative range of motion data at that time; this data can be compared to expected values to assess efficacy of the implantation surgery and can serve as a baseline value for comparison to functional values obtained post-operatively. Any abnormalities in vibration (indicative of an inadequate anchoring of the prosthesis in the surrounding bone), tilt (indicative of improper tracking and/or alignment of the tibial-femoral joint and the patellar-femoral joint), rotation (indicative of dislocation or subluxation), and/or range of motion can be addressed at this time and allow the surgeon to make adjustments intra-operatively. Shortly after the knee has been replaced, the leg will be mobilized post-operatively, at first passively, then actively; shortly after recovering from the procedure, the patient will begin gradual weight bearing on the joint. The ISM accelerometers can measure the movement and tracking of the knee joint during movement, including during ambulation as the leg swings forward, hits the ground, plants, is lifted off the ground, and the body is propelled forward. In addition, the accelerometers can measure the impact of the foot hitting the ground and the effect of the force being transferred through the tibia to the knee joint and any vibration, shock or rotation which may occur at different locations in the prosthesis. As the patient continues to improve their range of motion postoperatively, the acceleration experienced at different locations in the prosthetic knee joint, can be monitored. It will be expected that as the patient heals from the surgery, activity levels will progressively increase, ambulation will improve and increase, steps will be more rapid (and fluid) and, in addition, greater stride length will be achieved with each step. The effects of exercise and various activities can be monitored by the various accelerometers and can be compared to patient's subjective experiences to determine which life activities are improving (or inhibiting) post-operative recovery and rehabilitation.

In another embodiment, one or more ISMs containing position sensors are provided for inclusion or attachment throughout the implant, including ISM containing position sensors distributed on and within the femoral condyle prosthesis, distributed on and within the tibial plate (and stem if present) and tibial liner, and distributed on within the patellar prosthesis (patellar "button"). In some embodiments, the ISM containing position sensors are on/within the prosthetic components themselves (tibial, femur and patellar segments), while in others the position sensors are contained on/within the bone cement (if present) used to secure the prosthesis to the surrounding bone, and in still other embodiments the position sensors are contained on/within both the prosthetic components and the bone cement (PMMA).

ISMs having positional sensors as described herein can be utilized to provide accurate positional data (intra-operatively and post-operatively) for the prosthetic knee joint, including the measurement of flexion and extension, to enhance the accuracy of a physical exam by providing 3 dimensional data of the implant, to detect full and partial dislocation (subluxation) of the tibial-femoral (knee) joint and/or the patella-femoral joint, and to determine proper tracking and alignment of the knee joint and the patella.

Within another embodiment ISMs can be placed in any of the polymer components of the medical device. Representative polymers that can, within certain embodiments, be utilized, include polyethylene, highly crosslinked polyethylene, ultra-high molecular weight polyethylene, polyether ether ketone ("PEEK"), carbon fiber reinforced PEEK, and/or vitamin E stabilized highly crosslinked polyethylene (HXLPE) (as described in greater detail below under the section entitled "Medical Polymers".

For an ISM collecting mechanical data (position, motion, vibration, rotation, shock, tilt, steps), the implanted ISM sensors (accelerometers, position sensors, pedometers) have the advantage of not requiring either direct physical contact with the surface of the device or with patient tissues; only a secure and immobile attachment within the prosthetic joint is needed. In a particularly preferred embodiment, an ISM with multiple mechanical sensors (as described above) is placed within the internal canal of the tibial stem; a location that provides more than enough space to insert and seal an ISM with multiple sensor functions and battery capability. Furthermore, the motion of the stem of a total knee joint that occurs during normal activities (such as walking) can provide opportunities to power the ISM.

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion and prosthesis performance under various "real world" conditions. Continuous monitoring or at repeated periodic intervals as a means to manage battery life and data collection can allow the patient and the physician to monitor progress objectively by supplying information about patient function under numerous conditions and circumstances, to evaluate how performance has been affected by various interventions (pain control, exercise, physiotherapy, anti-inflammatory medication, rest, etc.), and to compare rehabilitation progress versus previous function and future expected function.

As will be readily evident given the disclosure provided herein, the ISMs described and claimed herein can comprise a variety of different sensors within different locations of the ISM. In addition, within various embodiments of the invention one or more sensors may be placed separate from the ISM (but still be, optionally, able to communicate with, and be controlled by, the ISM). Representative examples of sensors placed on a knee prosthesis are provided in PCT Application No. PCT/US2014/043736, which is hereby incorporated by reference in its entirety).

B.4.B. Use of a Knee Prosthesis, Medical Device or Kit Having Sensors to Measure Degradation or Wearing of an Implant As noted above, within various aspects of the present invention knee prosthesis, medical devices and kits are provided which can detect and monitor the degradation of an implant. For example, within one embodiment of the invention, a method is provided for degradation of a knee replacement, medical device or kit, comprising the steps of a) providing to a subject a knee replacement, medical device or kit having one or more ISMs containing sensors as described herein, and b) detecting a change in an ISM sensor, and thus determining degradation of the knee replacement, medical device or kit. Within various embodiments the ISM sensor(s) can detect one or more physiological and/or locational parameters. Within another embodiment, the ISM sensor(s) can detect contact, fluid flow, pressure and/or temperature. Within yet another embodiment the ISM sensors can detect a location within the subject.

When a knee prosthesis degrades or is damaged, ISM sensors can detect a change so that a determination of damage and/or degradation can be made. For example, a sensor that was previously embedded within a polymer portion of a device, upon degradation may be exposed to fluid forces, and pressures where none existed before. Hence, within preferred embodiments of the invention degradation can be detected over a period of time.

B.5. Medical Tubes

Within yet another embodiment of the invention medical tubes are provided having one or more ISMs as described herein. Briefly, a "medical tube" refers to a generally cylindrical, closed, water-tight body, and as utilized herein, can be used in a wide variety of medical procedures (e.g., the tubes are generally sterile, non-pyrogenic, and/or suitable for use and/or implantation into humans). For example, tubes can be utilized to: 1) bypass an obstruction (e.g., in the case of Coronary Artery Bypass Grafts, or "CABG" and peripheral bypass grafts) or open up an obstruction (balloon dilation catheters, angioplasty balloons); 2) to relieve pressure (e.g., shunts, drainage tubes and drainage catheters, urinary catheters); 3) to restore or support anatomical structures (e.g., endotracheal tubes, tracheostomy tubes, and feeding tubes); and 4) for access (e.g., CVC catheters, peritoneal and hemodialysis catheters). Representative examples of tubes include catheters (as discussed in more detail below), auditory or Eustachian tubes, drainage tubes, tracheotomy tubes (e.g., Durham's tube), endobronchial tubes, endotracheal tubes, esophageal tubes, feeding tubes (e.g., nasogastric or NG tubes), stomach tubes, rectal tubes, colostomy tubes, and a wide variety of vascular grafts (e.g., bypass grafts).

Tubes may be composed of synthetic materials (e.g., silicone, polyurethane and rubber), composed of non-synthetic components (e.g., harvested vein and artery grafts for bypass), or some combination of these [e.g., artificial blood vessels having a synthetic polymer scaffold, and naturally occurring cells (e.g., fibroblasts) which produce matrix materials for the vessel (e.g., collagen)].

"Catheter" as that term is utilized herein, refers to a thin tube that is commonly used for a wide variety of medical conditions, and in a wide variety of medical procedures.

Typically, they are inserted into a body cavity, lumen, duct, or vessel. Catheters are often inserted into the body by first advancing a flexible, metallic guidewire to the desired anatomical location; the catheter is then placed over the guidewire and maneuvered into position and the guidewire is then removed. In this manner they can, depending on the indication or procedure, allow for drainage, administration of fluids (e.g., saline solutions, drugs, etc.), provide access for various medical or surgical instruments, and/or of themselves be utilized to perform a wide variety of surgical procedures (such as balloon catheters used to dilate an obstructed body passageway). Catheters may be used either temporarily, or for extended periods of time (even permanently), and may have one, two, three, or more lumens or channels.

Catheters may be composed of a wide variety of materials (including for example metals such as nitinol), although most are made from polymers. Catheters may be made of either biodegradable or non-biodegradable polymers (or combinations of these). Typical polymers that are used in the construction of catheters include silicone, nylon, polyurethane, and polyethylene terephthalate. As will be readily evident given the disclosure provided herein, the catheter can be designed suitable to the intended use, and may be designed in a wide variety of forms and shapes (see e.g., FIG. 18 for an example of a balloon-based catheter having an ISM with various sensors).

Catheters can be utilized for a wide variety of clinical indications and procedures, including for example, for 1) draining fluids or eliminating obstructions through the placement of catheters via natural body orifices, such as: draining the urinary tract (e.g., the bladder or kidney) via the urethra with Foley catheters, intermittent (Robinson) catheters and ureteric catheters; accessing the GI tract through anal catheters, and suction catheters; reaching the respiratory system through the nose and mouth with pulmonary catheters; entering the reproductive system via the vagina (female) or urethra (male); 2) draining bodily fluids or relieving an obstruction through a surgically created access into an anatomical space or cavity; e.g., peritoneal catheters (placed in the abdominal cavity for ascites, dialysis), chest tubes (placed in the pleural space for pneumothorax, pleural effusion, chylothorax, infection), pericardial drainage tubes (in the heart), CNS drainage catheters or shunts (placed in the cerebrospinal fluid for hydrocephalus, infection, inflammation, obstruction); 3) drainage catheters which are surgically placed percutaneously or intraoperatively to drain collections of sterile fluid or abscesses elsewhere [can be placed virtually anywhere, including the thorax (heart, lungs), abdomen (liver, biliary drainage catheters), knees, hips, urinary tract (ureters, kidneys, prostate, bladder), reproductive tract (uterus, fallopian tubes), GI tract (anal fistulas, other fistulas, abcesses, stomas, colostomies), soft tissues (abscesses, seromas, compartment syndromes) to name a few]; 4) intervenous catheters [e.g. peripheral i.v.'s, central venous catheters (CVCs), peripherally-inserted central venous catheters (PICCs), arterial (e.g. hemodialysis access grafts and catheters, arterial catheters), and peritoneal (e.g. peritoneal dialysis catheters, peritoneal catheters) catheters that are placed for the administration of fluids (e.g., intravenous administration of fluids, medication, direct administration of a desired substance (e.g., a drug) to a desired location), access, dialysis or nutrition (nasogastric tubes, feeding tubes, total parental nutrition tubes, gastric tubes); 5) catheters placed for the implementation of a medical or surgical procedure or device [e.g., coronary angioplasty, peripheral angioplasty, angiography, dilation of an artery and/or placement of a stent, balloon septostomy, balloon sinuplasty, catheter-based ablation, balloon dilation catheters (esophageal, biliary, tracheal, bronchial, urethral, etc.)]; and 6) catheters placed for the direct measurement of a biological function or value (e.g., arterial or venous blood pressure, cardiac function, and intracranial pressure).

Commonly available catheters include Foley-catheters for the drainage of urine, ureteral catheters, central venous catheters (CVCs, PICCs, ports) for the administration of drugs and fluids, and Swan-Ganz catheters utilized principally for diagnostic purposes in the pulmonary artery. Representative examples of catheters are described in U.S. Pat. Nos. 8,491,569, 8,469,989, 8,460,333, 8,359,082, 8,246,568, 8,285,362, 8,257,420, 8,317,713, 8,328,829, 8,262,653, 6,966,914, 5,989,213, 5,509,897, 4,772,268, and U.S. Publication Nos. 2012/0310158, 2012/0283641, 2012/0239032, 2012/0253276, all of which are incorporated by reference in their entirety. Within one limited embodiment of the invention a balloon catheter which is utilized to deploy a stent or at stent graft can be optionally excluded, to the extent said exclusion is specifically stated or claimed.

Representative examples of intravascular catheters and balloon dilation catheters (including drug delivery catheters and balloon catheters are described in U.S. Pat. Nos. 5,180,366; 5,171,217; 5,049,132; 5,021,044; 6,592,568; 5,304,121; 5,295,962; 5,286,254; 5,254,089; 5,112,305, 5,318,531, 5,336,178, 5,279,565, 5,364,356, 5,772,629, 5,810,767, 5,941,868, 5,362,309, 5,318,014, 5,315,998, 5,304,120, 5,282,785, 5,267,985, 5,087,244, 5,860,954, 5,843,033, 5,254,089, 5,681,281, 5,746,716, 6,544,221, 6,527,739, 6,605,056, 6,190,356, 5,279,546, 5,236,424, 5,226,888; 5,181,911, 4,824,436, 4,636,195, 5,087,244, 6,623,452, 5,397,307, 4,636,195, 4,994,033, 5,362,309 and 6,623,444; U.S. patent application Publication Nos. 2002/0138036, 2002/0068869, 2005/0186243; and PCT Publication Nos. WO 01/15771; WO 93/08866, WO 92/11890, WO 92/11895, WO 94/05361; WO 96/04955 and WO 96/22111, all of which are incorporated by reference in their entirety.

"Guidewire" refers to a medical device which is utilized to position another medical device (e.g., an intravenous catheter, endotracheal tube, central venous line, balloon catheter, or gastric feeding tube), or to localize a tumor (e.g., during a breast biopsy). Representative examples of guidewires are described in U.S. Pat. Nos. 4,787,884, 5,911,734, 5,910,154, 6,676,682, 6,936,065, 6,964,673, and 7,691,123 and U.S. Publication Nos. 2006/0100694, and 2007/0027522, all of which are incorporated by reference in their entirety.

B.5.A. Catheters, Tubes and their Use

B.5.A.1. Balloon Catheters and their Use

Figure 18:
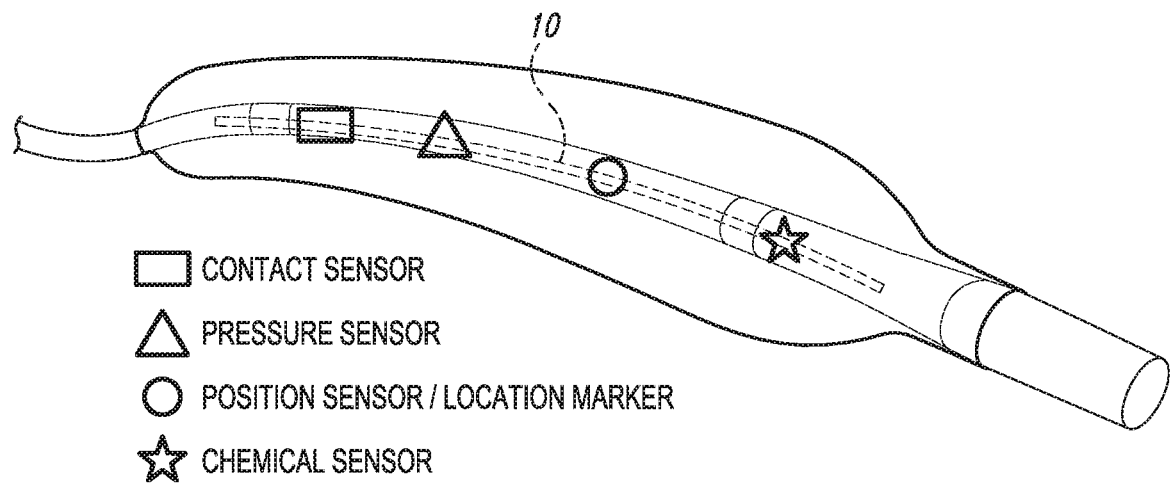
FIG. 18 illustrates one embodiment wherein an ISM having sensors of various types are deployed throughout a balloon catheter.

As noted above, within various embodiments of the invention, balloon catheters (and their associated medical devices, e.g., stents and/or guidewires), are provided with one or more ISMs having one or more of the sensors described herein. For example, FIG. 18 illustrates a balloon catheter having one or more ISMs containing a variety of sensors positioned in or on the balloon catheter (and/or potentially the guidewire) in order to monitor, in situ, the real-time operation of the catheter, the inflation and deflation of the balloon, the forces exerted by the balloon against adjacent tissues or devices (e.g. stents), flow levels through and around the balloon, and the catheter performance acutely and over time. The ISM containing sensors may be positioned inside the balloon catheter, within the walls of the balloon catheter, or on the outer surface of the balloon catheter. While in certain embodiments, ISMs containing contact sensors, pressure sensors, and positions sensors can be utilized as shown in FIG. 18, a wide variety of other sensors can also be used within the ISM that is placed in, on, or within the balloon catheter, including for example, fluid pressure sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, mechanical stress sensors, and temperature sensors.

For example, balloon catheters containing an ISM can be inserted via a guidewire into a stenosed artery (such as a coronary artery or peripheral artery). ISMs having contact sensors able to monitor the surface of the balloon can be utilized to measure contact with the vessel wall during inflation, deployment and deflation. Specifically, the balloon is expanded, thereby expanding the artery (coronary artery or peripheral artery); ISMs having pressure sensors can monitor pressure in the balloon, and the pressure which is exerted against the vascular wall. Within preferred embodiments the pressure is monitored and, if needed, adjusted in order to prevent injury to the vascular wall due to excessive pressure. The drop in pressure during deflation of the balloon can also be monitored to confirm that it is safe to withdraw the balloon catheter from the treated vascular lesion. Similarly, ISMs containing contact sensors can be used to monitor contact of the balloon with the vessel wall during balloon deflation to confirm that it is safe to withdraw the balloon catheter from the treated vascular lesion. ISMs containing position sensors can be utilized in balloon catheters and guidewires, in order to assist in placement of the balloon catheter, (and placement of a stent, if desired), and for medical imaging. The ISM position sensors contained in or on the balloon can be utilized to provide an image of vascular anatomy, pre- and post-inflation anatomy, confirmation of full balloon inflation and deflation, confirmation of stent placement and confirmation of full stent expansion and deployment (if present).

In other embodiments, balloons containing ISMs with sensors can be utilized to assist the placement of a balloon-expandable stent. For example, FIG. 9A illustrates a site of bifurcation with stenosis occurring at multiple points in the vessel. FIG. 9B illustrates a stent with PTCA to open up a side branch. In this case, (potentially "matched" or complimentary) contact sensors on an ISM in the stent and the balloon can be used to confirm accurate assembly; ISM accelerometers on the stent and the balloon can be used to confirm anatomical location and conformation; ISM position sensors on the stent and the balloon can monitor movement; ISM flow sensors on the stent and the balloon can confirm vascular patency; and ISM pressure/vessel wall sensors on the stent and the balloon can confirm full deployment and accurate vessel sizing. Taken collectively, this sensing information can create a 3-dimensional image of the vascular and stent anatomy and physiology and greatly improve the data available from angiography alone. This dramatically increases the chances of accurate, safe and effective deployment of multiple stents in complicated vascular lesions.

It should be readily evident given the disclosure provided herein that the above ISM-containing balloon catheters and associated medical devices containing ISM sensors can be utilized in the management of non-vascular disease. Balloon catheters are used to open up obstructed body passageways and lumens in many other tissues, such as, but not restricted to, the sinuses, respiratory tract, gastrointestinal tract, biliary tract, urinary tract and reproductive tract. While the size, shape and purpose of the balloon catheter (and associated devices) may vary, the type, placement and role of various ISM sensors is analogous to that described above for the vascular system. In summary, a wide variety of ISMs having multiple sensor types may be placed on and/or within balloon catheters and associated devices (such as guidewires) described herein, in order to provide "real time" information and feedback to a health care provider. Such ISM-containing balloons can be used by a surgeon during a surgical procedure safely and effectively open up an obstructed body passageway, to confirm proper placement, verify anatomy, ensure effective dilation (and elimination of the obstruction), monitor forces exerted on surrounding tissues, follow full balloon inflation and deflation, and to detect the strain/forces encountered in a balloon procedure.

In this embodiment, the balloon catheters and associated devices (such as guidewires) provided herein can contain one or more ISMs having one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. The above ISMs may be continuously monitored in order to provide a 'real-time' data, imaging, and changes in function over the course of the procedure, and to better understand the conditions which balloon catheters are exposed to in clinical practice.

B.5.A.2. Central Venous Catheters and their Use

Within other embodiments of the invention central venous catheters are provided having at least one ISM having one or more sensors placed thereon. Briefly, central venous catheters (also referred to as "central lines", "CVC"s) are catheters that are most typically placed into the great veins of the body [usually the superior vena cava (SVC), or the inferior vena cava (IVC)] via access through the large vein of the neck [e.g., the internal jugular vein), the chest (e.g., the subclavian vein or axillary vein), or the groin (e.g., the femoral vein)] when reliable, longer term vascular access is required. However, CVCs can also be inserted peripherally (e.g., placed into the peripheral vasculature system such as the veins of the arm and then advanced through the venous system until the tip reaches the SVC), and in this instance are commonly referred to as "Peripherally Inserted Central Catheters" or "PICC"s. CVCs are utilized to deliver medication and/or fluids to a subject, to obtain blood for testing, and for measuring pressure (typically at the distal tip of the catheter).

CVCs can be 'non-tunneled' (i.e., fixed at the site of insertion), and 'tunneled' (i.e., passed under the skin from the insertion site, to a separate exit site). One type of catheter similar to a 'tunneled' catheter is a "port", which although similar, differs in that it is left entirely under the skin. In this case, medications and fluids can be injected directly through the skin into the port, or, for some types of ports, into a reservoir contained in the port. The term "Central Venous Catheter" or "CVC" used herein should be interpreted to include PICCs, Ports, Tunneled CVCs and Non-tunneled CVCs.

Common complications of central lines include pneumothorax, central line associated bloodstream infections (CRBSI), thrombosis, hemorrhage, and the formation of hematomas or seromas at the insertion site.

Hence, central venous catheters of the present invention can be utilized which have one or more ISMs having at least one of the sensors described herein. For example, within one embodiment, central venous catheters of the present invention can have an ISM with one or more fluid flow sensors. Such ISMs can, within various embodiments be located on the inner (luminal) surfaces of the catheter the outer (adluminal or blood contacting) surfaces of the catheter, throughout the catheter, and/or (in a preferred embodiment) located at tip of the catheter. The ISMs with flow sensors can be utilized to measure fluid flow through the catheter lumen. If at least one ISM with a flow sensor is located proximally and at least one ISM with a flow sensor is located at the tip, it is possible to determine if and where a blockage has occurred; for example from the formation of a fibrin sheath, catheter stenosis, catheter thrombosis, or catheter kinking (e.g., there would be decreased luminal fluid flow rate prior to a narrowing and increased luminal fluid flow rate following an narrowing; there would be no fluid flow before or after a complete obstruction). The ability to monitor flow rates would be valuable in normal operation and during/after procedural attempts to "reopen" obstructed catheters.

Within other embodiments, ISMs having pressure sensors can be incorporated into a central venous catheter on the inner (luminal) wall, outer (abluminal) wall, and/or within the body of the catheter itself. Such ISMs are able to measure pressure within or exerted against the catheter wall. Increased pressures can be suggestive of stenosis, thrombosis or kinking upstream from a narrowing or obstructing event, whereas decreased pressures would be seen downstream from a narrowing and (little or) no pressure would be seen downstream from an obstruction. Having the ability to measure pressure (proximally and distally) throughout the catheter allows for functional monitoring of the central venous catheter (in normal operation and during/after attempts to "reopen" obstructed catheters), and the capability to detect events prior to a complication developing.

Within yet other embodiments, ISMs are provided having contact sensors which can be incorporated into a central venous catheter on the inner (luminal) wall, outer (abluminal) wall, and/or within the body of the catheter itself to measure contact between the luminal and adluminal surfaces and the surrounding environment. Sustained foreign body contact on either surface could be indicative of the formation of a fibrin sheath, thrombosis, biofilm formation or infection; sustained contact at the tip could indicate that the catheter has become pushed up against the vascular wall and needs to be repositioned. In yet another embodiment, an ISM containing chemical sensors can be placed primarily on the adluminal (blood contacting) surface in order to measure a wide variety of metabolic parameters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.).

Within other embodiments, an ISM having position sensors can be placed in, on or within the catheter in order to allow imaging of the catheter, and detection of changes and/or movement over time. Position sensors on an ISM within a CVC catheter are useful during placement of the catheter to ensure advancement into the SVC, but not the right atria of the heart; post-placement, they can be used to determine if the catheter has migrated proximally or distally (into the right atrium) with time.

Within yet other embodiments, an ISM having chemical and/or temperature sensors can be incorporated into a CVC such that it is blood contacting (on the adluminal surface) and can be utilized to monitor changes in temperature, which could suggest the presence of an infection or a developing infection.

In a particularly preferred embodiment, an ISM containing multiple sensors (flow sensor, position sensor, accelerometer, pressure sensor, contact sensors, chemical sensors, temperature sensors) is located at the tip of the catheter such that it has both luminal and adluminal surface exposure.

In summary, one or more ISMs containing a wide variety of sensors may be placed on and/or within the central venous catheters described herein, in order to provide "real time" information and feedback to a health care provider (during placement, repositioning or "reopening" procedures), to detect proper anatomical placement, vascular anatomy, alignment, forces exerted on surrounding tissues, and to detect changes encountered during placement and subsequent manipulation or repositioning procedures. For example, the central venous catheters (CVCs, PICCs, Ports) provided herein can have one or more ISMs having one or more contact sensors, strain gauge sensors, pressure sensors, fluid pressure sensors, position sensors, accelerometers, shock sensors, rotation sensors, vibration sensors, tilt sensors, pressure sensors, blood chemistry sensors, blood metabolic sensors, mechanical stress sensors and temperature sensors.

B.5.A.3. Dialysis Catheters and their Use

Within other embodiments, specialized central venous catheters can be utilized in hemodialysis procedures (typically when dialysis is only needed for a short period of time or as a bridge to permanent dialysis procedures—see later). Briefly, a hemodialysis catheter (or alternatively—"acute dialysis catheter") is a specialized CVC placed into the central circulation that is used for exchanging blood to and from a hemodialysis machine. Typically, the catheter has two lumens, one for venous flow and the other for arterial flow. The arterial lumen withdraws blood from the patient and carries it to the hemodialysis machine, and the venous lumen returns blood to the patient (after the blood has been treated by the dialysis machine). Typically, flow rates of dialysis catheters range from between 200 and 500 milliliters per minute. If the patient requires long term dialysis therapy, a 'chronic' dialysis catheter can be utilized, which typically includes a cuff that is buried beneath the skin (and which is believed to aid as a barrier to infection). Common complications of hemodialysis catheters include fibrin sheath formation, clotting, biofilm formation, infection and kinking. Hence, hemodialysis catheters of the present invention can be utilized which have one or more of the ISMs described herein. For example, within one embodiment hemodialysis catheters of the present invention can have one or more ISMs having a blood flow sensor. Such ISMs can, within various embodiments be located on the inner (luminal) surfaces of the catheter, the outer (adluminal) surface of the catheter, and within the walls of the catheter; in a preferred embodiment, the ISM containing a blood flow sensor is located at the tip of the catheter such that it can measure flow in both the arterial and the venous lumen. They can be utilized to measure fluid flow through the catheter. By comparing the readings of ISM flow sensors at different locations in the hemodialysis catheter (i.e. the difference between proximal and distal readings), a determination of blockage (and the extent of a blockage; for example from the formation of a fibrin sheath, catheter stenosis, catheter thrombosis, or catheter kinking) can be determined (e.g., there would be decreased fluid/blood flow prior to a narrowing and increased fluid/blood flow following an narrowing; there would be no fluid/blood flow before or after a complete obstruction). The ability to monitor flow rates would be valuable in normal operation and during/after procedural attempts to "reopen" obstructed catheters. Within other embodiments, ISMs having pressure sensors can be incorporated into a hemodialysis catheter on the inner (luminal) wall, outer (adluminal) wall, and/or within the body of the catheter itself. Such sensors are able to measure pressure within or exerted against the catheter wall. Increased pressures can be suggestive of stenosis, thrombosis or kinking upstream from a narrowing or obstructing event, whereas decreased pressures would be seen downstream from a narrowing and (little or) no pressure would be seen downstream from an obstruction. Having the ability to measure pressure at different points in the catheter allows for functional monitoring of the hemodialysis catheter (in normal operation and during/after attempts to "reopen" obstructed catheters), and the capability of detecting events prior to a complication developing.

Within yet other embodiments, ISMs having contact sensors can be placed on the luminal and adluminal surfaces of the hemodialysis catheter in order to measure contact between the luminal and adluminal surfaces and the surrounding environment. Sustained foreign body contact on either surface could be indicative of the formation of a fibrin sheath, thrombosis, biofilm formation or infection; sustained contact at the tip could indicate that the catheter has become pushed up against the vascular wall and needs to be repositioned.

In yet another embodiment, ISMs having chemical sensors can be placed primarily on the adluminal (blood contacting) surface in order to measure a wide variety of metabolic parameters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.). Many of these parameters are important in the monitoring the need, effectiveness, timing and frequency of dialysis treatments and would be a great assistance to the clinician managing a renal patient; similarly comparing values in the arterial arm of the catheter, the venous arm of the catheter and the systemic circulation would also provide useful clinical data.

Within other embodiments, ISMs having position sensors can be placed on or within the hemodialysis catheter (e.g., on both the luminal and adluminal surfaces, and within the catheter material itself) in order to allow imaging of the catheter, and detection of changes and/or movement over time. Position sensors are useful during placement of the catheter to ensure advancement into the proper anatomical location; post-placement, they can be used to determine if the catheter has migrated proximally or distally with time.

Within yet other embodiments ISMs having chemical and temperature sensors can be utilized to monitor changes in temperature which could be suggestive of the presence of an existing infection, biofilm formation or a developing infection.

In a particularly preferred embodiment, an ISM containing multiple sensors (flow sensor, position sensor, accelerometer, pressure sensor, contact sensors, chemical sensors, temperature sensors) is located at the tip of the catheter such that it has both luminal and adluminal surface exposure to both the arterial and venous lumens of the dialysis catheter.

In summary, one or more ISMs with a wide variety of sensors may be placed on and/or within the hemodialysis catheters described herein, in order to provide "real time" information and feedback to a health care provider (or during placement or subsequent manipulation or "reopening" procedures), to detect proper placement, vascular anatomy, alignment, forces exerted on surrounding tissues, and to detect changes encountered during placement and subsequent manipulation or repositioning procedures. For example, the hemodialysis catheters (acute and chronic) provided herein can have one or more ISMs having contact sensors, strain gauge sensors, pressure sensors, fluid pressure sensors, position sensors, accelerometers, shock sensors, rotation sensors, vibration sensors, tilt sensors, pressure sensors, blood chemistry sensors, blood metabolic sensors, mechanical stress sensors and temperature sensors. The above sensors may be continuously monitored in order to provide a 'real-world' activity, patency, and changes in function over time, to evaluate patient physiology, and to better manage the dialysis patient.

B.5.A.4. Drainage Catheters and their Use

Within other embodiments of the invention, drainage catheters are provided having one or more ISMs placed thereon. Briefly, drainage catheters are typically placed in order to drain fluid (e.g., surgical fluids, blood, peritoneal fluids, CSF, biliary fluids, joint fluids, intestinal fluids, pus, an abscess, pleural fluids, or urine to name a few) from a body structure. In the context of urinary drainage, Foley catheters, which are designed to drain urine from the bladder, and ureteral catheters which are designed to allow flow of urine from the kidneys, are commonly utilized in a wide variety of medical procedures. Drainage catheters are typically made of polymers such as silicon or rubber, but other materials (including biodegradable polymers) can also be utilized. In the case of a Foley catheter, the catheter typically has two separated lumens, one of which allows urine to drain (typically to a collection bag), and the other has a valve which allows inflation of a balloon at the distal end of the catheter which is inflated within the bladder after insertion in order to ensure that the catheter doesn't inadvertently fall out.

Common complications of drainage catheters include infections, kinking of the catheter, biofilm build-up (resulting in potential obstruction and infection), breaking of the balloon (as well as overinflating or failing to inflate the balloon) and the accumulation of obstructing foreign bodies (urinary stones, biliary stones, blood/clot, inflammatory tissue, fibrotic tissue, infectious tissue) on the luminal surface.

Hence, drainage catheters of the present invention can be utilized which have one or more of the ISMs described herein. For example, within one embodiment, drainage catheters of the present invention can have one or more ISMs having flow sensors. Such sensors can, within various embodiments be located on the inner (luminal) surfaces, adluminal surfaces of the catheter, throughout the catheter, and/or concentrated at the ends of the catheter. They can be utilized to measure fluid flow through the catheter. By comparing the readings of ISMs containing flow sensors at different points in the drainage catheter, a determination of blockage (and the extent of a blockage; for example from the formation of a clot, stone, or catheter kinking) can be determined (e.g., there would be decreased fluid flow prior to a narrowing and increased fluid flow following an narrowing; there would be no fluid flow before or after a complete obstruction). The ability to monitor flow rates would be valuable in normal operation and during/after procedural attempts to "reopen" obstructed drainage catheters.

Within other embodiments, ISMs having pressure sensors can be incorporated into a drainage catheter on the inner (luminal) wall, outer (adluminal) wall, and/or within the body of the catheter itself. Such sensors are able to measure pressure within, or exerted against, the catheter wall. Increased pressures can be suggestive of narrowing, thrombosis, foreign body obstruction, or kinking upstream from a narrowing or obstructing event, whereas decreased pressures would be seen downstream from a narrowing and (little or)

no pressure would be seen downstream from an obstruction. Having the ability to measure pressure within the drainage catheter allows for functional monitoring of the catheter (in normal operation and during/after attempts to "reopen" obstructed catheters), and the capability of detecting events prior to a complication developing.

Within yet other embodiments, ISMS having contact sensors can be placed on and throughout the drainage catheter in order to measure contact between the luminal and adluminal surfaces and the surrounding environment. Sustained foreign body contact on either surface could be indicative of the formation of a fibrin sheath, thrombosis, stone formation, biofilm formation or infection; sustained contact at the tip could indicate that the catheter has become pushed up against the luminal wall (or an adjacent tissue) and needs to be repositioned.

Within other embodiments, ISMs having chemical sensors can be utilized to measure a wide variety of physiological parameters, including for example: 1) urinary function (e.g., measurement of nitrate, sodium, potassium, calcium and phosphate); 2) presence of cells (e.g., white cells which may suggest an infection, and/or red cells which may indicate trauma, stones, infections, and/or a malignancy); 3) protein/proteinuria (indicative of diabetes, kidney or liver disease, hyperthyroidism, etc.); 4) glucose (to measure diabetes); and various other chemicals (e.g., ketones, bilirubin, urobilinogen, hemoglobin, creatinine, catecholamines, dopamine, cortisol, phenylalanine) and characteristics of the urine (e.g., specific gravity, osmolality, pH, presence of bacteria, and hcG); 5) the presence of bacteria (in all cases suggestive of infection).

Within other embodiments, ISMs having position sensors can be placed throughout the drainage catheter (e.g., on both the luminal and adluminal surfaces, and within the catheter material itself) in order to allow imaging of the catheter, and detection of changes and/or movement over time. Position sensors are useful during placement of the catheter to ensure advancement into the proper anatomical location (prior to balloon inflation, if present, such as in Foley catheters); post-placement, they can be used to determine if the catheter has migrated proximally or distally with time.

Within yet other embodiments ISMs having chemical and/or temperature sensors can be utilized to monitor changes in temperature, which could suggest the presence of an infection, biofilm formation, or a developing infection.

In a particularly preferred embodiment, an ISM containing multiple sensors (flow sensor, position sensor, accelerometer, pressure sensor, contact sensors, chemical sensors, temperature sensors) is located at the tip of the drainage catheter such that it has both luminal and adluminal surface exposure.

Taken collectively, ISMs having one or more of a wide variety of sensors as described herein can be utilized to detect, measure and assess a number of factors relevant to the function of the kidneys (and/or bladder) and any other organ in which the drainage catheter is placed (liver, pleural space, CSF, joint, etc.). Such drainage catheters can provide "real time" information and feedback to a health care provider (or during placement or subsequent manipulation or "reopening" procedures), to detect proper placement, anatomy, alignment, forces exerted on surrounding tissues, and to detect changes encountered during placement and subsequent manipulation or repositioning procedures. For example, the drainage catheters provided herein can one or more ISMs with one or more contact sensors, strain gauge sensors, pressure sensors, fluid pressure sensors, position sensors, accelerometers, shock sensors, rotation sensors, vibration sensors, tilt sensors, pressure sensors, chemistry sensors, metabolic sensors, mechanical stress sensors and temperature sensors. The above sensors may be continuously monitored in order to provide a 'real-world' activity, patency, and changes in function over time, to evaluate patient physiology, and to better manage the drainage catheter patient.

B.5.A.6. Vascular Grafts and their Use

Within other embodiments of the invention, ISMs can be placed on a variety of vascular grafts. Briefly, medical grafts are hollow tubes or cylinders that are utilized to allow fluids (typically blood) to flow from one place to another. Medical grafts may be obtained from natural materials (e.g., saphenous vein or mammary artery grafts), constructed from natural and/or artificial materials (e.g., bioengineered grafts or blood vessels), or constructed from entirely synthetic materials (e.g., vascular grafts comprised of polymers such as polytetrafluoroethylene or "PTFE" or dacron). Representative examples of medical grafts are disclosed in U.S. Pat. Nos. 5,556,426, 5,628,786, 5,641,373, 6,863,686, and 8,062,354.

Within one embodiment of the invention, one or more ISMs containing multiple sensors (flow sensor, position sensor, accelerometer, pressure sensor, contact sensors, chemical sensors, temperature sensors) is located at the distal end of the bypass graft (made from natural materials) such that it has luminal surface exposure. For example, during Coronary Artery Bypass Grafting (or "CABG" procedures), arteries or veins from elsewhere in the body can be grafted onto the coronary arteries to bypass atherosclerotic narrowings and improve blood supply to the myocardium (e.g., wherein saphenous veins are utilized for coronary artery bypass, and a mammary artery is used for a coronary artery bypass).

Within other embodiments of the invention, synthetic vascular grafts can be utilized to bypass an obstruction (e.g., synthetic vascular bypass grafts can be utilized to bypass an obstruction in the lower limb). Hence, grafts which have ISMs of the present invention have a wide variety of utilities. For example, within one embodiment, grafts of the present invention can have ISMs with one or more blood flow sensors. Such ISMs containing blood flow sensors can, within various embodiments be located on the inner (luminal) surfaces of the graft, on the outer (adluminal) surfaces of the graft, throughout the graft (e.g., woven into the fabric of a synthetic graft, or incorporated into the metal of a "supported" graft), and/or concentrated at the ends of the graft (i.e. the proximal and distal vascular anastomoses). They can be utilized to measure blood flow through the graft. By comparing the readings of sensors from one part of the graft to another part of the graft, a determination of partial narrowing (and the extent of narrowing) can be determined (e.g., there would be an decreased blood flow prior to a narrowing or stenosis, and increased blood flow following a narrowing). If the vascular graft was completely obstructed, there would be no flow through the graft (before or after the obstruction). The ability to monitor flow rates would be valuable in normal operation and during/after procedural attempts to "reopen" obstructed catheters.

Within other embodiments, ISMs having pressure sensors can be incorporated into a graft [e.g., on the outer (adluminal) walls, the inner (luminal) walls and/or within the body of the graft itself (as described above for flow sensors)]. Such sensors are able to measure pressure in or against the vessel wall. Increased pressures can be suggestive of stenosis, thrombosis or kinking upstream from an obstructing event, whereas decreased pressures would be seen downstream from a narrowing and (little or) no pressure would be seen downstream from an obstruction. Having the ability to measure pressure throughout the vascular allows for functional monitoring of the graft (in normal operation and during/after attempts to "reopen" obstructed grafts), and the capability of detecting events prior to a complication developing.

Within yet other embodiments ISMs having contact sensors can be placed on and throughout the graft in order to measure contact (integrity of the seal) between the bypass graft and the vessel to which it is attached (the anastomosis) in order to identify leaks or anastomotic failure (during and after surgical placement). Contact sensors on the luminal surface of the graft could also detect the presence of unwanted accumulated luminal surface materials such as restenosis tissue, fibrin or biofilm and alert the clinician to potential problems.

Within further embodiments ISMs having chemical sensors can also be placed on and throughout the graft in order to measure a wide variety of important metabolic paramaters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.).

Within other embodiments ISMs can be provided with sufficient number of position sensors (e.g., on both the luminal and adluminal surfaces, and within the graft material itself) in order to allow imaging of the graft, and detection of changes (such as bending or kinking) and/or movement over time.

In a particularly preferred embodiment, an ISM containing multiple sensors (flow sensor, position sensor, accelerometer, pressure sensor, contact sensors, chemical sensors, temperature sensors) is located at both anastomoses of a bypass graft, such that it has luminal surface exposure.

Taken collectively, ISMs within vascular grafts can be utilized to detect, measure and assess a number of factors relevant to cardiac function. For example, blood flow rate detectors, blood pressure detectors, and blood volume detectors (e.g., to measure blood volume over a unit of time) can be placed within (on the luminal side), and on other parts of the vascular graft in order to measure systolic and diastolic pressure, cardiac output, ejection fraction, cardiac index and systemic vascular resistance.

Within other embodiments of the invention, vascular grafts (synthetic grafts and native grafts such as arteriovenous fistulas) can be utilized in a hemodialysis procedure. Briefly, a hemodialysis access graft is a vascular graft that is implanted by a vascular surgeon as an artificial, high-flow, interposition graft (or direct anastomosis) between an artery and a vein (typically in the forearm or the thigh) to provide permanent access for hemodialysis (native arteries and veins tend to collapse and close after being repeatedly instrumented numerous times). Once mature and suitable for use, the hemodialysis access graft (or AV fistula) is used as a permanent site into which to insert another catheter that is used for exchanging blood to and from a hemodialysis machine. Typically, that catheter has two lumens, one for venous flow and the other for arterial flow (as described in a previous section above). Common complications of hemodialysis access grafts include clotting, stenosis (narrowing of the graft most often occurring at the graft-venous anastomosis, but also occasionally at the arterial-graft anastomosis), infection and kinking. Hence, hemodialysis access grafts of the present invention can be utilized which have one or more ISMs having one or more sensors described herein. For example, within one embodiment, hemodialysis access grafts of the present invention can have an ISM with one or more blood flow sensors. Such ISMs with blood flow sensors can, within various embodiments be located on the inner (luminal) surfaces of the access graft, within the walls of the access graft (e.g., woven into the fabric of a synthetic graft, or incorporated into the metal of a "supported" graft)—and/or concentrated at the various locations (e.g., the ends—the anastomoses—of the access graft). The ISMs with blood flow sensors can be utilized to measure blood flow through the hemodialysis access graft. By comparing the readings of ISM flow sensors at various locations in the grafts (for example the arterial and venous anastomses), a determination of partial narrowing (and the extent of narrowing) can be determined (e.g., there would be a decreased blood flow prior to a narrowing or stenosis, and increased blood flow following a narrowing). If the access graft was completely obstructed, there would be no flow through the graft (before or after the obstruction). The ability to monitor flow rates would be valuable in normal operation and during/after procedural attempts to "reopen" obstructed dialysis catheters (a common interventional procedure).

Within other embodiments, ISMs which have pressure sensors can be incorporated into a dialysis access graft [e.g., on the outer (adluminal) walls, on the inner (luminal) walls, or within the body of the access graft itself as described above]. Such sensors are able to measure pressure in or against the access graft wall. Increased pressures within the graft can be suggestive of stenosis (typically at the graft-vein anastomsis, but occasionally at the artery-graft anastomosis), thrombosis or kinking upstream from an obstructing event, whereas decreased pressures would be seen downstream from a narrowing and (little or) no pressure would be seen downstream from an obstruction. Having the ability to measure pressure throughout the vascular allows for functional monitoring of the graft (in normal operation and during/after attempts to "reopen" obstructed grafts), as well as the capability of detecting events prior to a clinical complication developing.

Within yet other embodiments, ISMs having contact sensors can be placed on at the ends of the hemodialysis access graft in order to measure contact (integrity of the seal) between the access graft and the vessel to which it is attached (i.e. the arterial and venous anastomosis) in order to identify leaks or anastomotic failure (during and after surgical placement). Contact sensors in ISMs on the luminal surface of the graft could also detect the presence of surface materials such as restenosis tissue, fibrin (clot) or biofilm and alert the clinician to potential problems. In yet another example, ISMs having chemical sensors can also be placed on and/or within the access graft such that the sensors have luminal exposure in order to measure a wide variety of metabolic paramaters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.); parameters which are very important in the clinical management of a patient with late-stage renal disease.

Within other embodiments ISMs having position sensors can be placed throughout the hemodialysis access graft (e.g., on both the luminal and adluminal surfaces, and within the access graft material itself) in order to allow imaging of the access graft, and detection of changes (bending, kinking) and/or movement over time.

Taken collectively, one or more ISMs having wide variety of sensors as described herein can also be utilized to detect, measure and assess a number of factors relevant to cardiac function. For example, blood flow rate detectors, blood pressure detectors, and blood volume detectors (e.g., to measure blood volume over a unit of time) can be placed within (on the luminal side), and on other parts of the access graft in order to measure systolic and diastolic pressure, and estimate systemic vascular resistance. Within particularly preferred embodiments ISMs having one or more blood flow rate detectors, blood pressure detectors, and blood volume detectors can also be utilized to calculate cardiac output, ejection fraction and cardiac index (which are key clinical measurements that are valuable in monitoring cardiac-compromised patients, which many renal patients are). For example, an ISM containing high-fidelity pressure transducers can be located on, in, or within a hemodialysis access graft in order to measure the timing and pressure of pulsations. Such measurements can be utilized to assess stroke volume and systemic vascular resistance, and also provide continuous cardiac output monitoring and heart rate monitoring. Within yet other embodiments chemical and temperature sensors can be utilized to monitor changes in temperature, and/or the presence of an infection or a developing infection. With repeated instrumentation of the access graft, the incidence of infection is quite high and monitoring for its presence prior to the onset of clinical symptoms is of great value to the management of the patient.

In a particularly preferred embodiment, an ISM containing multiple sensors (flow sensor, position sensor, accelerometer, pressure sensor, contact sensors, chemical sensors, temperature sensors) is located at one or both ends of the hemodialysis access catheter (i.e. at the arterial and venous anastomoses) such that it has luminal surface exposure.

In summary, ISMs with a wide variety of sensors may be placed on and/or within hemodialysis access grafts described herein, in order to provide "real time" information and feedback to a health care provider (or a surgeon during a surgical procedure to implant a hemodialysis access graft, or an interventionalist performing a procedure to open up an obstructed hemodialysis access graft), to detect proper placement, vascular anatomy, alignment, cardiac output, renal function, infection, and to detect any changes encountered before, during or after an interventional procedure. For example, the hemodialysis access grafts provided herein can have one or more ISMs with one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. The above sensors may be continuously monitored in order to provide a 'real-world' activity, healing, and changes in function over time, to evaluate patient activity, and to better understand the conditions which hemodialysis access grafts are exposed to in the real world.

B.5.A.7. Other Medical Tubes and their Use

Within other embodiments a wide variety of medical tubes are provided which may have ISMs with one or more sensors. Representative examples of medical tubes include tympanostomy tubes, endotracheal tubes, tracheostomy tubes, nasogastric tubes, gastric tubes, feeding tubes, colostomy tubes, rectal tubes, and chest tubes.

For example within one embodiment one or more ISMS having one or more sensors can be placed on an endotracheal tube. Briefly, an endotracheal tube is a type of catheter that is inserted into the trachea for the primary purpose of establishing and maintaining a patent airway. The tube may be orotracheal (inserted into the mouth, nasotracheal (inserted into the nose), or via a tracheostomy (e.g., inserted via a hole or incision in the trachea).

Within other embodiments the tube having one or more ISMs having one or more sensors can be a drainage tube such as a chest tube. Briefly, chest tubes (also referred to as 'chest drains', thoracic catheters, tube thoracostomy and intercostal drains) are flexible tubes that can be inserted through the chest wall and into the pleural space or mediastinum. Such tubes can be utilized to remove air (e.g., pneumothorax), fluid (e.g., pleural effusion, blood, chyle), and infectious material (e.g., empyema, pus)

Chest tubes come in a range of sizes (e.g., 6 Fr to 40Fr), can have multiple drainage fenestrations, and optionally, be marked for distance (or length) of the tube, as well as contain radiopaque markers. They are available in a wide variety of configurations (e.g., right angle, trocar, flared, and tapered), and may be coated in an effort to prevent thrombus formation or clogging. Such tubes can be made from a wide variety of materials, including polyvinyl chloride ("PVC"), silicone, latex, and polyurethane.

Tubes (e.g., tympanostomy tubes, endotracheal tubes, tracheostomy tubes, nasogastric tubes, gastric tubes, feeding tubes, colostomy tubes, rectal tubes, and chest tubes) can suffer from a variety of complications, such as improper placement, damage to (or penetration into) surrounding tissues, narrowing, obstruction, movement/migration and infection, For example, endotracheal tubes have been found to cause a number problems, including aspiration, improper placement, airway obstruction, perforation of the esophagus or trachea, development of a sore throat, pneumonia, narrowing, as well as arrhythmia, hypertension, increased intracranial pressure, increased intraocular pressure, bronchospasms, laryngospasms, vocal cord damage, retropharyngeal abcesses, nerve injury, and fistulas.

Hence, tubes of the present invention can be utilized which have one or more ISMs having a flow sensor as described herein. For example, within one embodiment chest tubes and endotracheal tubes of the present invention are provided with ISMs which have one or more flow sensors. Such sensors can, within various embodiments be located on the inner (luminal) surfaces of the tube, the outer (adluminal) surface of the tube, within the tube, and/or concentrated at the ends of the tube. They can be utilized to measure fluid flow through the tube, such as air flow (endotracheal tubes, chest tubes in pneumothorax; note other tubes as described above may have other body fluids passing through them). By comparing the readings of sensors throughout the tube, a determination of partial narrowing (and the extent of narrowing) can be determined (e.g., there would be decreased air flow prior to a narrowing or stenosis, and increased air flow following a narrowing). If the tube was completely obstructed, there would be no flow through the tube lumen (before or after the obstruction). The ability to monitor flow rates would be valuable in normal operation and during/after procedural attempts to "reopen" obstructed tubes.

Within other embodiments, ISMs containing pressure sensors can be incorporated into a tube [e.g., on the outer (adluminal) walls, the inner (luminal) walls and/or within the body of the tube itself]. Such sensors are able to measure pressure in or against the tube wall. Increased pressures (e.g. ventilation pressures in endotracheal tubes) can be suggestive of stenosis (narrowing), obstruction or kinking upstream from an obstructing event, whereas decreased pressures would be seen downstream from a narrowing and (little or) no pressure would be seen downstream from an obstruction. Monitoring pressure in the inflation cuff of an endotracheal tube can ensure that proper inflation is present; not too much pressure so as to lead to mucosal damage to the surrounding trachea, but not too little so as to allow fluids to pass by the cuff and aspiration to occur. Having the ability to measure pressure at different locations within the tube allows for functional monitoring of the tube (in normal operation and during/after attempts to "reopen" obstructed tubes), as well as the capability of detecting events prior to a clinical complication developing.

Within yet other embodiments, ISMs containing contact sensors are placed on or within the tube in order to measure contact (integrity of the seal) between the tube and the tissue in which it is placed in order to identify leaks, cracks, or migration of the tube (during and after surgical placement). ISM contact sensors with access to the luminal surface of the tube could detect the presence of fibrous/inflammatory tissue or biofilm formation and alert the clinician to potential problems. Monitoring contact on the surface of the inflation cuff of an endotracheal tube can ensure that proper inflation is present; creating a sufficient seal between the cuff and the tracheal mucosa such that fluids are unable to pass by the cuff and allow aspiration to occur.

Within other embodiments, ISMs having chemical sensors are located on or within medical tubes for the purpose of measuring a wide variety of physiological parameters, including for example: 1) tissue chemistry (e.g., measurement of nitrate, sodium, potassium, calcium and phosphate); 2) the presence of cells (e.g., white cells which may suggest an infection, and/or red cells which may indicate trauma, erosions/ulcers, penetration of the device into a blood vessel); 3) protein, serous fluid); 4) glucose ketones, bilirubin, urobilinogen, hemoglobin, osmolality, pH, presence of bacteria, tumor markers.

Within other embodiments ISMs containing position sensors are located on or within a medical tube (e.g., on both the luminal and adluminal surfaces, and within the tube material itself) in order to allow imaging of the tube, and detection of changes and/or movement of the tube over time. For example, improper placement of endotracheal tubes (usually inadvertent placement in the esophagus) is a very dangerous complication; 50% of misplacements in the Emergency Room result in death. Position sensors able to better define the anatomical position and placement of the medical tube (in "real time") would be of great utility. Many other tubes (e.g. proper chest tube placement in the area of pleura requiring decompression/drainage and not in adjacent tissues—lung, heart, pericardium) would similarly benefit. Post-insertion, many tubes can move from their initial site of placement (e.g., tympanostomy tubes often fall out, endotracheal tubes can migrate into one of the bronchi to produce uneven ventilation, chest tubes can move from the required drainage area) and would benefit from the ability to monitor their movement and current location.

Within yet other embodiments ISMs are provided with chemical and/or temperature sensors which can be utilized to monitor changes in temperature, and/or the presence of an infection or a developing infection.

Taken collectively, a wide variety of tubes are provided with ISMs having one or more sensors as described herein, which can be utilized to detect, measure and assess a number of factors relevant to the function numerous implanted tubes. In a particularly preferred embodiment, an ISM containing multiple sensors (flow sensor, position sensor, accelerometer, pressure sensor, contact sensors, chemical sensors, temperature sensors) is located at the distal end of the medical tube (i.e. at the tissue contacting end) such that it has luminal surface exposure.

In summary, one or more ISMs containing a wide variety of sensors may be placed on and/or within the medical tubes described herein, in order to provide "real time" information and feedback to a health care provider (or a physician during an insertion or follow-up procedure), to detect proper placement, anatomy, alignment, forces exerted on surrounding tissues (and entry into, damage to, non-target tissues), integrity, flow, surface conditions, patency and movement/migration of the implanted tube and to detect and monitor the properties of the fluids flowing through them. For example, the tubes (e.g., tympanostomy tubes, endotracheal tubes, tracheostomy tubes, nasogastric tubes, gastric tubes, feeding tubes, colostomy tubes, rectal tubes, and chest tubes) provided herein can have one or more ISMs with one or more contact sensors, strain gauge sensors, pressure sensors, fluid pressure sensors, position sensors, accelerometers, shock sensors, rotation sensors, vibration sensors, tilt sensors, pressure sensors, chemistry sensors, metabolic sensors, mechanical stress sensors and temperature sensors.

The above sensors may be continuously or intermittently monitored in order to provide a 'real-world' function, healing, and changes in function over time, to evaluate patient responses, and to better understand the conditions which tubes are exposed to in the real world.

As will be readily evident given the disclosure provided herein, the ISMs described and claimed herein can comprise a variety of different sensors within different locations of the ISM. In addition, within various embodiments of the invention one or more sensors may be placed separate from the ISM (but still be, optionally, able to communicate with and be controlled by the ISM). Representative examples of sensors placed on a medical tube are provided in U.S. Provisional No. 62/017,086, which is hereby incorporated by reference in its entirety).

B.6. Implants

Within one embodiment of the invention implants are provided having one or more ISMs as described herein. Briefly, "implant" as that term is utilized herein, refers to an artificial or synthetic prosthesis that has, or can be, implanted into a body. Implants are typically utilized to augment or replace a structure within the body, and have been utilized in a wide variety of aesthetic applications, including for example, for facial (e.g., lips, chin, nasal, nasal/labial fold and malar implants), penile, and body contouring (e.g., breast, pectoral, calf, buttocks, abdomen and biceps/triceps) implants.

"Surrounding Implant" as that term is utilized herein, refers to an artificial or synthetic implant or implanted material that is placed into the implant pocket where the aesthetic implant will ultimately be inserted. When an aesthetic implant is inserted into the body, a "pocket," or surgically created anatomical space, is first dissected into the tissue which will receive the aesthetic implant. A "surrounding implant" is typically a gel, adhesion barrier, hemostat, glue, and/or adhesive that is placed into the implant pocket such that it lies between the aesthetic implant and the host tissue (bags or other devices can placed around the aesthetic implant for the same purpose). Generally, the role of the "surrounding implant" is to prevent or minimize (at least initially) the contact between the aesthetic implant and the host tissue in an attempt to reduce scarring and capsular contraction.

Implants can be composed of a wide variety of materials, but utilizing breast implants as an example, they are typically comprised of an elastomeric outer surface or 'shell', and an interior 'filling'. With respect to the shell, silicone is the most commonly used elastomer, which may be either smooth, or textured. With respect to the filling, most implants are filled with either silicone, or saline (although other compositions have been suggested, including for example, peanut oil, sunflower oil, soy oil and polypropylene string).

Within various embodiments, the implants may contain more than one internal filling (e.g., in different compartments), and may be coated (polymers, gels, drugs) and/or textured on the outer shell or provided with a bag in order to reduce the incidence of capsular contractions. In addition, implants can be provided in different sizes, and different shapes, and even customized to specific anatomical requirements. Within yet other embodiments one implant can be delivered to one location in the breast (e.g., subfascially), and another implant delivered to a different location (e.g., subglandularly).

Representative examples of implants are described in U.S. Pat. Nos. 4,995,882, 6,251,137, 6,464,726, 8,420,077 and U.S. Publication Nos. 2006/0136056, 2009/0099656, 2011/0184277, 2014/0088700. Representative examples of implant delivery devices include U.S. Pat. No. 8,550,090 and U.S. Publication Nos. 2014/0074235, and 2014/0074236.

The implants and medical devices provided herein are preferably sterile, non-pyrogenic, and/or suitable for use and/or implantation into humans. However, within certain embodiments of the invention the medical devices and/or kits may be made in a non-sterilized environment (or even customized or "printed" for an individual subject), and sterilized at a later point in time.

Figure 19:
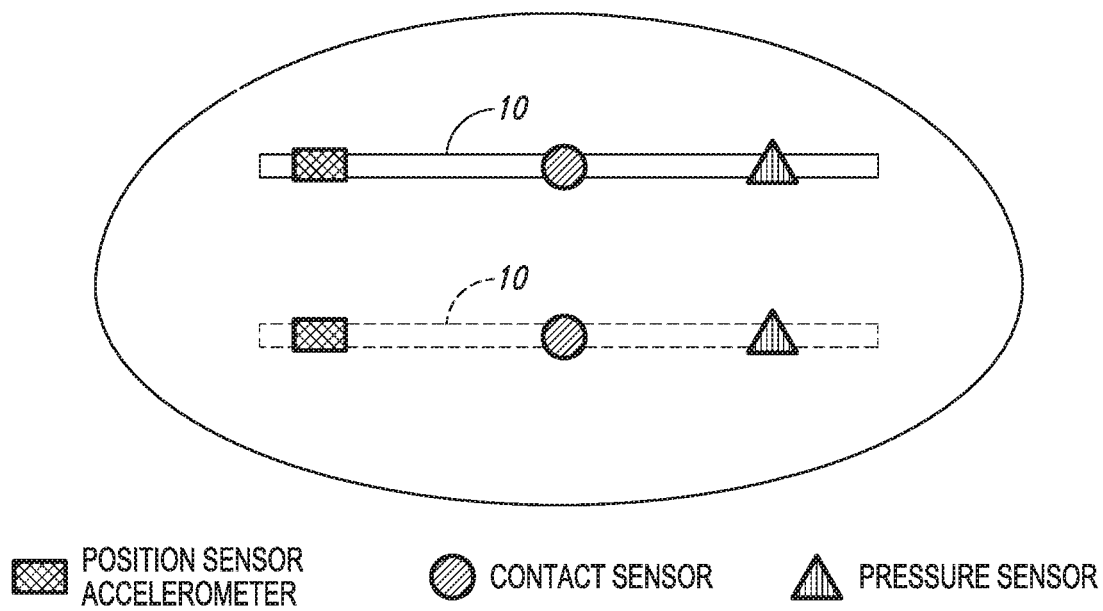
FIG. 19 illustrates one embodiment wherein sensors of various types are deployed by an ISM on the surface of an aesthetic (breast) implant.
Figure 20A:
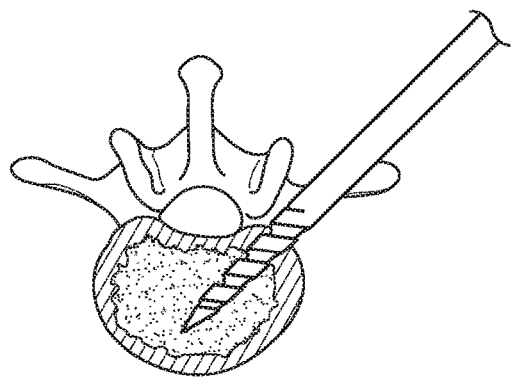
FIGS. 20A-20E illustrate one embodiment called vertebroplasty wherein an ISM is placed into the body of the body of a vertebrae, followed by injection of bone cement (without the use of a balloon). These Figures illustrate one embodiment wherein, a hole is created in the vertebral body (FIG. 20A) through a bone tunneling catheter; introduction of an ISM (FIG. 20B); and introduction of a delivery device (FIG. 20C) which allows injection of the bone cement directly into the collapsed bone. The compression fracture is corrected and supported through the injection of bone cement into the vertebral body (as shown in FIGS. 20D and 20E) to restore the normal height of the vertebra.
Figure 20B:
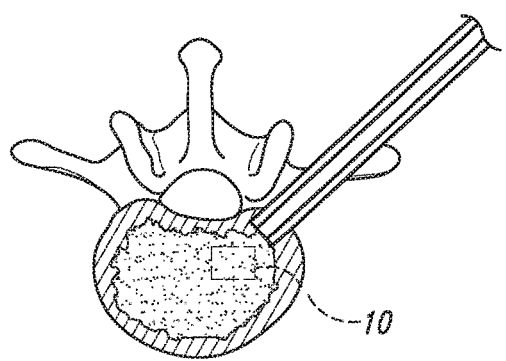
Figure 20C:
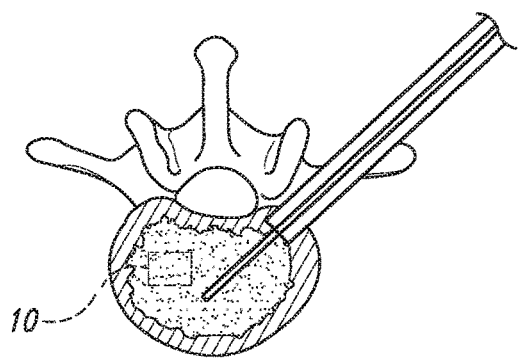
Figure 20D:
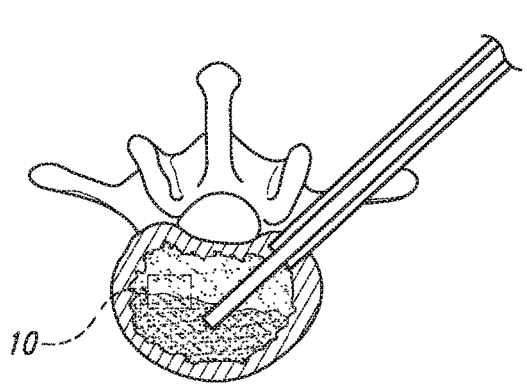
Figure 20E:
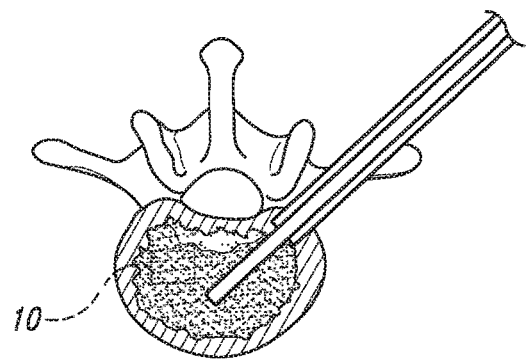

Within one embodiment of the invention, implants are provided with an ISM having one or more sensors as shown in FIG. 19. For example, the ISM having one or more position sensors and/or accelerometers can be placed within the 'filling' of the implant, or on or within the 'shell' of an implant. Such sensors are capable of providing: a) an image of the implant (or 'real-time' imaging of the implant); b) assistance during placement of the implant, and confirmation subsequent to implant of the correct anatomical location (e.g., by way of the aforementioned imaging, or by comparison with external markers); and c) confirmation of full inflation (i.e. not folded or wrinkled in situ). In addition, such sensors are useful in confirming that the implant is operating as expected [e.g., a) confirming that it has not moved or migrated; b) confirming that scarring or capsular contraction has not begun; c) confirming that the integrity of the implant is sound (i.e., that there are no leaks), or by determination of a leak from the surface of the implant; and d) confirming that the implant is not wrinkled or folded]. Sensors can also be utilized to ensure that acute complications are not developing (e.g., the development of a hematoma, seroma, granuloma, abscess, or other mass in the tissues surrounding the implant that applies external pressure to the implant itself).

Within other embodiments, implants are provided with one or more ISMs possessing contact sensors and/or pressure sensors. As noted above, the contact and/or pressure sensors can be placed within the 'filling' of the implant, or, on or within the 'shell' of the implant. Such sensors are capable of providing: a) an image of the implant (or 'real-time' imaging of the implant); b) assistance during placement of the implant, and confirmation subsequent to implant of the correct anatomical location (e.g., by way of the aforementioned imaging, or by comparison with external markers); and c) confirmation of full inflation (i.e. not folded or wrinkled in situ). In addition, such sensors are useful in confirming that the implant is operating as expected [e.g., a) confirming that it has not moved or migrated; b) confirming that scarring or capsular contraction has not begun; and c) confirming that the integrity of the implant is sound (i.e., that there are no leaks), or by determination of a leak from the surface of the implant; and d) confirming that the implant is not wrinkled or folded]. Sensors can also be utilized to ensure that acute complications are not developing (e.g., the development of a hematoma, seroma, granuloma, abscess, or other mass in the tissues surrounding the implant that applies external pressure to the implant itself).

Within yet other embodiments implants are provided with one or more ISMs possessing one or more accelerometers. Such accelerometers can be utilized to a) determine the durability of the implant based upon 'real-world' conditions; b) determine if different implants are better in certain patients (based upon activity levels, impact, forces, weight, etc.); and c) assist manufacturers in the design of new implants, product improvements, and collection of clinical data. Moreover, it would allow the evaluation of performance of different devices under similar conditions, and the ability of the patient to monitor their progress at home.

Within other embodiments implants are provided with one or more ISMs possessing one or more temperature sensors and/or chemical or metabolic sensors. Such sensors can be utilized to detect the presence of infection, seroma, hematoma and inflammation and allow for rapid or preemptive intervention (e.g., administration of antibiotics before a full-blown infection has developed, drainage of a subclinical hematoma or seroma, or undertake measures to reduce inflammation in an effort to lower the chance of a capsular contracture developing).

It should be obvious to one of skill in the art that ISMs containing the same sensors can be incorporated into a surrounding implant for the same purposes as described above.

As will be evident given the disclosure provided herein, a wide variety of other sensors may also be utilized within the ISM, including for example, pulse pressure sensors, heart rate sensors, glucose sensors, or sensors to detect tumor (particularly breast cancer) markers.

As will be readily evident given the disclosure provided herein, the ISMs described and claimed herein can contain a variety of different sensors within different locations of the ISM. In addition, within various embodiments of the invention one or more sensors may be placed separate from the ISM (but still be, optionally, able to communicate with and be controlled by the ISM). Representative examples of sensors placed on an implant are provided in U.S. Provisional No. 62/017,099, which is hereby incorporated by reference in its entirety).

B.7. Spinal Implants

Within one embodiment of the invention, spinal implants are provided having one or more ISMs as described herein. Briefly, "spinal device and or spinal implant" as those terms are utilized herein, refers to a wide variety of devices (typically hardware) and implants (typically biomaterials like bone cement and bone grafts) that can be implanted into, around, or in place of part of a subject's spine (typically in an interventional or surgical procedure), and which can be utilized to facilitate vertebral body fracture repair, fusion of vertebrae, correct degenerative disc disease (DDD), to stabilize the spinal column, and to correct deformities due to disease and/or injury. Spinal devices/implants are typically permanent, but in some cases may be temporary. Representative examples of spinal devices and implants include, for example: spinal cages (e.g., U.S. Pat. Nos. 5,425,772, 6,247,847, 6,428,575, 6,746,484, 7,722,674, 7,744,599, 7,988,713, 8,172,905, and U.S. Patent App. Nos. 2004/0082953, 2011/0015742, 2012/0046750, 2013/0053894, and 2013/0158669): pedicle screws and associated devices (e.g., U.S. Pat. Nos. 7,678,137, 8,361,121 and U.S. Patent App. Nos. 2005/0187548, 2006/0195086, 2008/0154309 and 2009/0287255); artificial discs and associated assemblies (e.g., U.S. Pat. Nos. 5,676,701, 8,226,723, and U.S. Patent App. Nos. 2006/0293753, 2007/0088439, 2007/0179611, 2008/0133014, 2011/0054617, and 2012/0232662); spinal rods and associated assemblies (e.g. U.S. Patent App. Nos. 2003/0050640, 2004/0015166, 2007/0118122, 2008/0306528, 2009/0177232, 2011/0245875, 2013/0211455, and 2013/0231703), spinal plates and their assemblies (e.g., U.S. Pat. Nos. 8,246,664, 8,262,594, 8,343,223, and U.S. Patent App. Nos. 2009/0210008, 2010/0069968, and 2013/0006367); and vertebroplasty/kyphoplasty balloons and bone cement (see e.g., US 2007/0100449, US 2009/0299373); all of which are incorporated by reference in their entirety.

Spinal device/implants may be composed of a wide variety of materials (including for example metals such as titanium, titanium alloys, and/or stainless steel), although other materials can also be utilized, including polymers (e.g., polymethylmethacrylate or "PMMA", poly-ether-ether-ketone or "PEEK" for cervical cages and anterior thoracolumbar implants, and bone graft material that can be allographic, xenographic or synthetic); growth factors (e.g., bone morphogenic protein); and non-polymeric materials such as silicon nitride.

"Spinal Implant Surgical Device" or "Spinal Implant Delivery Device" refers to devices that can be utilized to introduce a spinal implant into a patient, and/or to surgical tools and devices that can be utilized to operate on the spine. Representative examples include guidewires, trocars, bone tunnel catheters, electrothermal catheters, endoscopes, microsurgical instruments, surgical instruments, kyphoplasty balloons, and bone cement injection devices to name a few.

The medical devices, implants and kits provided herein are preferably sterile, non-pyrogenic, and/or suitable for use and/or implantation into humans. However, within certain embodiments of the invention the medical devices and/or kits may be made in a non-sterilized environment (or even customized or "printed" for an individual subject), and sterilized at a later point in time.

B.7.A. Vertebroplasty and Kyphoplasty Procedures

Within various aspects of the invention spinal device/implants and associated medical devices are provided with ISMs suitable for use in a wide variety of vertebroplasty and kyphoplasty procedures. Briefly, vertebral compression fractures can result from the sudden collapse of the vertebral body, and result in the rapid onset of back pain, numbness, tingling, weakness, spinal cord compression, and cauda equine syndrome (e.g., extremity weakness, paraplegia, urinary retention, urinary/fecal incontinence, sexual dysfunction, sciatica, decreased ankle reflex, and saddle anesthesia). It is typically found in patients with osteoporosis, but can occur due to other causes (e.g., trauma, lytic lesions from metastatic or primary tumors, infections, and osteogenesis imperfecta).

For vertebroplasty procedures, bone cement (e.g., polymethylmethacrylate or "PMMA") is injected percutaneously into the fractured vertebral body in order restore normal vertebral height and anatomy so as to relieve the pain and symptoms associated with compression fractures. Using a percutaneous approach or a small surgical incision, a hole is created in the wall of the vertebral body by a specialized bone tunneling catheter, followed by introduction of a delivery catheter into the vertebral body at the site of the fracture. Bone cement is then injected into the cancellous bone of the collapsed vertebral body until sufficient PMMA material has been injected to restore the vertebra to its normal height and anatomy (the cement hardens and supports the fractured bone).

Kyphoplasty is a specialized form of vertebroplasty. In kyphoplasty procedures, a balloon is first inserted into the cancellous bone of the vertebral compression fracture and then inflated in order to restore normal vertebral height and spinal shape (kyphosis) and to create a void. The balloon is then removed and PMMA is injected into the void created by the balloon and allowed to harden in place to form a solid support structure within the fractured vertebrae. A number of medical instruments can be utilized to complete a kyphoplasty, including, an introducing needle, an injector for the bone cement, bone needles, guidewires, bone tunnel catheters, balloon introducing catheters and a kyphoplasty balloon catheter.

Within various embodiments of the invention, ISMs containing sensors may be placed in some or all of the spinal implants and associated devices used for vertebroplasty and/or kyphoplasty.

For example, as shown in FIG. 20, a hole is created in the vertebral body (FIG. 20A) through a bone tunneling catheter; an ISM is introduced (FIG. 20B); followed by a delivery device (FIG. 20C) which allows injection of the bone cement directly into the collapsed bone. The compression fracture is corrected and supported through the injection of bone cement into the vertebral body (as shown in FIGS. 20D and 20E) to restore the normal height of the vertebra.

Figure 21:
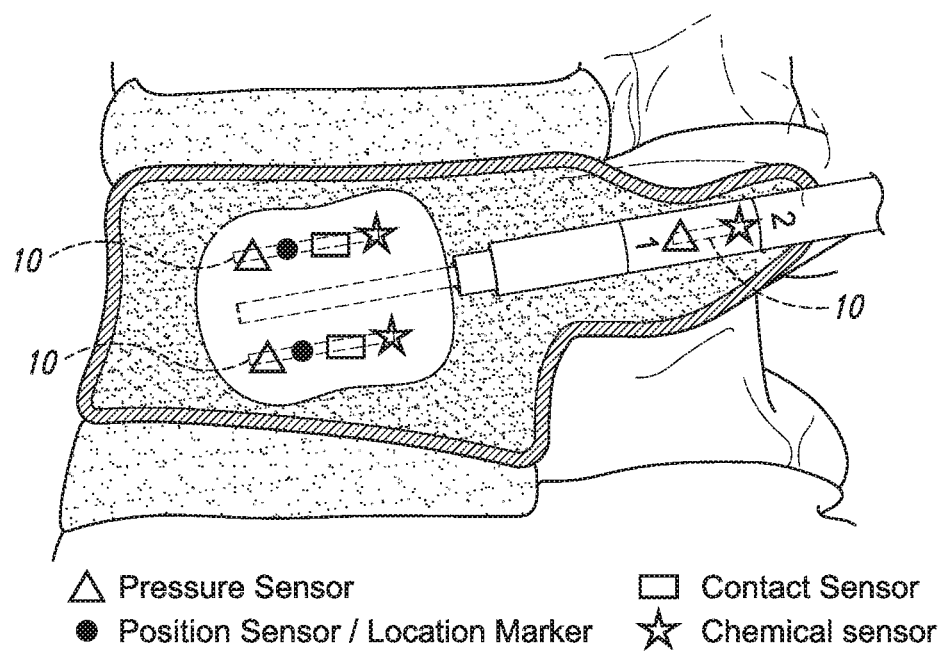
FIG. 21 illustrates one embodiment wherein one or more ISMs are placed on and/or within a kyphoplasty balloon.

Similarly, as shown in FIG. 21, one or more ISMs can be placed on, or within the kyphoplasty balloon. The ISM can have pressure sensors in order to monitor pressure exerted on the cancellous bone by the kyphoplasty balloon (particularly during inflation) and to optimize the inflation pressure (preventing over-inflation leading to potential tissue damage) and deflation pressure (ensuring the balloon is fully deflated before attempting to remove the device). ISMs containing contact sensors can also be placed on or within the kyphoplasty balloon in order to monitor contact between the balloon and the cancellous bone of the vertebral body. Similarly, ISMs containing position sensors/location markers can be placed on or within the kyphoplasty balloon in order to assist in accurate placement of the insertion device, the balloon, and bone cement into the compression fracture. Position sensors and location markers are also useful to monitor the expansion of the vertebral body (by, for example monitoring the position of the balloon walls as the balloon is progressively inflated) to achieve a more precise expansion; one that can be more accurately matched to the anatomical deficit present. "Visualization" via the ISM sensors present on the balloon assist with accurate placement, optimum expansion, more precise measurement of deficit correction and safe deflation and extraction; all completed in "real time" during the procedure. In a preferred embodiment, one or more ISMs contained on or within the kyphoplasty balloon contain several sensors including position sensors, location markers, accelerometers, pressure sensors, and contact sensors.

ISMs having sensors may have a variety of additional uses, including to assist in identifying vertebral anatomy (e.g., to measure the exact vertebral height restored and proper kyphosis during kyphoplasty), to prevent accidental placement of the kyphoplasty instruments into surrounding tissues (the spinal cord, spinal nerves, etc.), to confirm full (or optimal) balloon inflation and deflation, to confirm restoration of vertebral height and kyphosis after kyphoplasty, and to image the void where bone cement will be injected, to more precisely match the volume to be injected, and to prevent overfilling and/leakage of the bone cement. Within various embodiments of the invention ISMs, or passive sensors along with the ISMs can be added to the bone cement, and utilized to interrogate various aspects of the procedure (as noted above), as well as ultimate success and maintenance of the procedure (See FIGS. 20 and 21). An ISM containing accelerometers can be placed within the bone cement in order to detect acceleration, vibration, shock, tilt and rotation of the cement within the vertebral body. Such sensors may be utilized to create 2D and 3D imaging data which show the size and shape of the filled void, movement and/or dissolution of the bone cement, and potentially complications such as leakage or impingement of the cement into the spinal cord and/or around the spinal nerves. Within preferred embodiments the image data can be collected over time, in order to visually show changes (e.g., a "movie" or "moving images") detected by the sensors.

In a preferred embodiment, one or more ISMs contained within the bone cement contain several sensors including position sensors, location markers, accelerometers, pressure sensors, and contact sensors in order to monitor spinal anatomy, function and the development of side effects.

Optionally, ISMs containing chemical sensors and placed within the bone cement can be utilized to monitor pH, calcium content, and other parameters (e.g., in order to predict and/or monitor the progression of osteoporosis, tumor growth and/or bone metabolism). Similarly, temperature sensors, can be utilized to monitor the temperature of the cement (the cement is above body temperature when initially inserted before hardening), as well as indicate any possible early signs of inflammation or infection.

The above described ISMs within bone cement can be utilized to monitor pressure, location, position, contact and other measures (temperature, pH, etc.) during both placement and in subsequent follow-up. Once implanted, the ISM contained within the bone cement is identical, regardless of whether it is administered as part of vertebroplasty (FIG. 20) or kyphoplasty (FIG. 21).

The above ISM containing sensors may be continuously monitored in order to provide a 'real-world' range of motion for the spine, to assist in detecting any decrease in spinal health, to collect and compare procedure performance data over time, to evaluate patient function, and to better understand the conditions which spinal implants are exposed to in the real world.

B.7.B. Intervertebral Disc Disease/Spinal Fusion

Injury and/or disease of the intervertebral disc can result in substantive, chronic neck and/or back pain and/or neurological symptoms. Examples of chronic disc problems include degenerated discs, bulging discs, herniated discs, thinning discs, and disc degeneration with osteophyte formation.

In order to address problems associated with intervertebral disc injuries or disease, spinal fusion surgery is often indicated. In this surgery, two or more adjacent vertebrae (vertebral bodies) are fused together by creating a 'bony bridge' across the damaged/diseased intervertebral disc, for example, by using autologous or allograph bone tissue. For posterolateral spinal fusion a bony fusion is created between the transverse processes of the vertebrae, while in an interbody spinal fusion the bone graft is created between the bodies of the vertebrae in the area usually occupied by the intervertebral disc. In the latter case the disc is often removed entirely and is typically replaced by a plastic or titanium cage to maintain alignment and height and promote bone growth. Fusion may also be augmented by fixation devices, including metal screws (including pedicle screws and a rod), rods or plates to connect the screws, and wires.

Spinal fusion devices, and spinal fusion surgery in general can be associated with many complications, both during the surgery, as well as post-surgically. Typical complications include vertebral subluxation (abnormal movement between the vertebra), collapse of structural elements and loss of support, tissue-reaction against the device, infection, pseudo-arthritis, failure to heal properly (i.e., delayed union or non-union of the vertebrae) and problems with the implanted devices themselves such as: hardware fracture, loosening and/or migration; pedicle screw breakage, loosening or movement: and transitional syndrome (i.e., stress placed on nearby vertebrae due to the fusion).

Within various embodiments of the invention ISMs having one or more sensors can be placed on the instruments and fixation devices described herein in order to assist placement of the medical device and/or implant, and to monitor for efficacy subsequent to surgery. For example, ISMs can be placed on rods which are affixed by pedicle screws (FIG. 22A), as well as on plates which can be utilized to fuse to vertebrae together (FIG. 22B). It should be evident given the disclosure provided herein that the ISMs can also be placed on or within the pedicle screws, wires and/or other hardware used in spinal fusion.

Figure 22A:
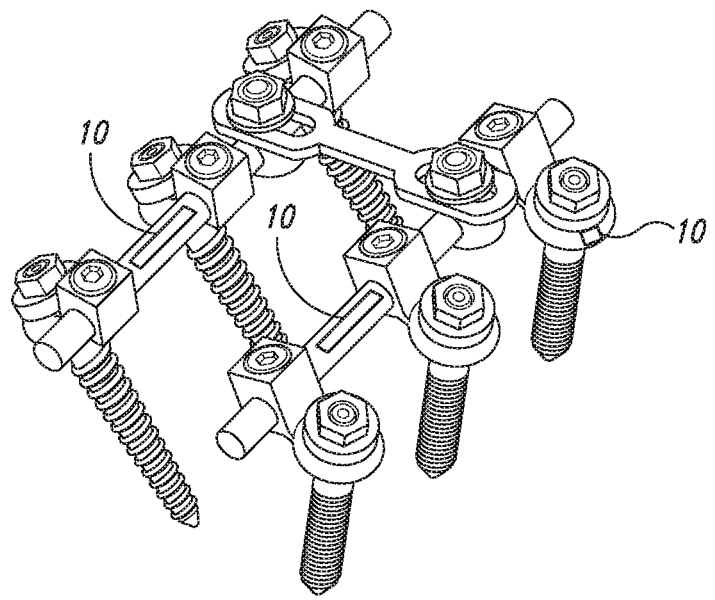
FIGS. 22A and 22B illustrate a variety of spinal fusion implants, including pedicle screws affixed to rods (FIG. 22A), and a spinal plate retained by screws (FIG. 22B).
Figure 22B:
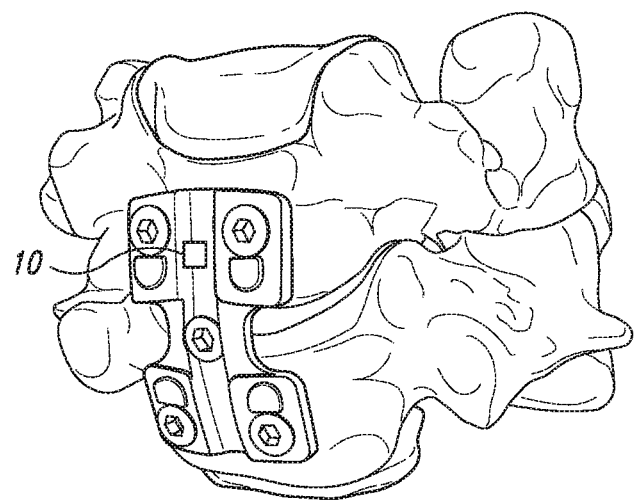

For example, the ISMs shown in FIGS. 22A and 22B can have position sensors that can be utilized to assess the range of motion of the spinal segment (flexion and extension of the spinal segment, adduction and rotation of the spinal segment), to enhance the accuracy of physical exam (from 3D data which may be utilized to produce an image, and to assess position and movement of the spine and the device, to assess if there is subluxation between the segments), to monitor spinal and device anatomy (alignment, kyphosis), to assess the contact and interaction between adjacent device components (e.g., between screws, plates rods and/or wires), and to monitor for breakage, bending, loosening and/or movement of any of the implant parts. Collection of data from position sensors will also allow for both short-term and long-term assessment of product performance, as well as assessment of healing and patient recovery.

The ISMs shown in FIGS. 22A and 22B can also have contact sensors that can be utilized to detect the space, movement and integrity of the bond between the hardware and the surrounding tissues, and the integrity of the connections between the various different pieces of hardware (disconnection of the hardware components), bending or breakage of the hardware pieces, and to detect loosening and/or osteolysis associated with the hardware (bone loss in the tissues surrounding the implanted devices; particularly for screws). Collection of data from contact sensors will also allow for both short-term and long-term assessment of product performance, as well as assessment of healing and patient recovery.

The ISMs shown in FIGS. 22A and 22B can also have accelerometers and/or strain gauges that can be utilized to indicate strains (and/or repetitive strains over time) that can result in destructive bone remodeling. In addition, the sensors can detect and record the magnitude, direction of acceleration, orientation, vibration and shock of a given strain. Hence, loosening of screw in bone, movement between components, vertebral subluxation (spondylolisthesis), breakage and/or failure of components, and the collapse of structural elements (including damage to the surrounding bone) can also be monitored and recorded. The data can also be integrated and utilized to create a 2D and/or 3D image of the hardware and spinal anatomy, both at a single point as well as over time based upon real-world stresses. Such sensors also allows for the continuous monitoring of the device in order to assess both short-term and long-term assessment of product performance, as well as assessment of healing and patient recovery.

A wide variety of other sensors (alone or in combination) can also be contained within the ISMs shown in FIGS. 22A and 22B, including for example, one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors.

B.7.C. Degenerative Disc Disease (DDD)/Interbody Fusion/Spinal Cages

Degenerative Disc Disease, also known as spondylosis, is typically a disease associated with aging (although it can also be caused by injury or trauma), and can be associated with chronic neck and/or back pain and peripheral nervous symptoms (numbness, tingling, weakness, bowel and bladder problems). Fibrocartilage typically develops in the intervertebral disc as a result of aging or repeated injury. Contents of the nucleus pulposis (the inner, gelatinous part of the disc) can bulge or herniate through weakened areas of the annulus fibrosis and come into contact with the spinal cord or the spinal nerves. It is the pressure from the bulging or herniated disc on the spinal cord or the spinal nerves that leads to the pain and neurological symptoms described previously.

Spinal cages have been developed in order to assist with interbody fusion, and can be utilized to treat Degenerative Disc Disease, herniated discs, and low grade spondylolisthesis. They are typically small, hollow cylindrical devices composed of titanium, titanium alloys, stainless steel, or polymers. They can be filled with bone graft material (allograft or autograft) and/or growth factors (e.g. bone morphogenic protein, BMP)

A wide variety of spinal cages are presently available commercially from a number of manufacturers (e.g., BAK from Sulzer Spine Tech, Ray TFC from Stryker, Contact Fusion Cage from Synthes, and Interfix Cage and LT Cage from Medtronic). Spinal cages can be manufactured to be placed between the vertebral bodies of the spine in a specific orientation (e.g., a vertebral body side and a vertical side). Furthermore, the vertical sides can be flattened to allow the placement of two cages side-by-side in the intervertebral space. The spinal cage can be packed during surgery with autologous or allogeneic bone graft material, with or without other factors such as bone morphogenic proteins ("BMPs"), in order to assist in bone growth through the perforated walls of the cage, and the formation of a bony fusion between the vertebrae.

Figure 23:
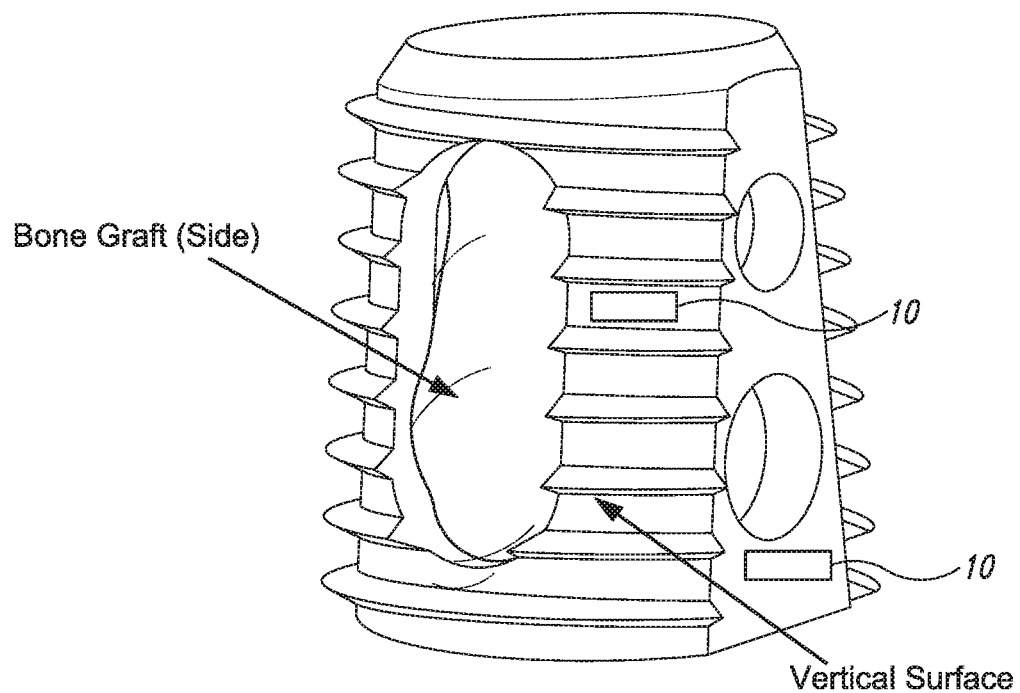
FIG. 23 illustrate a spinal (interbody) cage having an ISM.

Within various embodiments of the invention, ISMs having sensors can be placed on and/or within a spinal cage (e.g., as shown in FIG. 23). For example, an ISM having position sensors can be placed on and/or within a spinal cage and/or within the bone graft material. The sensors can be utilized to detect and monitor location and fixation of the affected spinal cage, movement of the cage within the intervertebral space, to monitor breakage and/or wear of the spinal cage, and to monitor the anatomy, contact and interaction between adjacent components (particularly when more than one cage is used). For example, during placement, the ISM position sensors can be utilized to determine if the cages are correctly placed, if spinal alignment is correct, and if intervertebral spacing is optimal; following placement, the ISM position sensors can monitor any movement, migration, or breakage of the spinal cage; furthermore, they can be used to follow the progress of bony fusion as spinal cage movement should become progressively less as new bone growth successfully fuses the two segments together (and "locks" the cages within the bone mass); conversely, ongoing positional movement or increasing positional movement would be cause for concern that fusion is not progressing as expected. ISM positional sensors therefore allow for the continuous monitoring of the device, spinal anatomy (alignment, spacing, etc.) and bony fusion in order to assess both short-term and long-term product performance, as well as assessment of healing and patient recovery.

Within other embodiments, ISMs containing contact and/or pressure sensors can be placed on or within the spinal cage (as shown in FIG. 23) and/or within the bone graft material. Within certain embodiments of the invention two cages are provided with ISMs which allow "matching" sensor placement, in order to allow an analysis of movement and/or migration between the different (paired) pieces of spinal cage hardware. Contact sensors can also be utilized to detect space, movement, and the integrity of bond between the hardware and the developing bony tissue. For example, increasing contact and/or decreasing pressure between the hardware and the surrounding tissue is suggestive of ongoing fusion (i.e. the new bone growth is assuming the compressive forces and decreasing the dependence on the cage), while eventual contact/pressure stabilization suggests healing is almost complete; such measurements can guide rehabilitation and physiotherapy decisions. On the other hand, lessening of contact between the bone tissue and the cage might suggest inadequate bone growth, failure of fusion, or failure of the device; increasing pressure on the cage in this context would suggest that the device (and not the new bone growth) is taking a disproportionate amount of the compressive forces between the intervertebral bodies. The sensors also allow for the continuous monitoring of the device in order to assess both short-term and long-term product performance, as well as assessment of healing and patient recovery and can help guide activity and recovery regiments.

Within yet other embodiments, ISMs containing accelerometers and/or strain gauges can be placed on or within the spinal cages (as shown in FIG. 23) and/or within the bone graft material. The ISM accelerometers can be utilized to detect and record the magnitude, direction of acceleration, orientation, vibration and shock of a given strain. Hence, detection of vibration/movement may indicate loosening within the fused disc, movement between paired spinal cage components (if more than one cage is used), breakage/failure of the spinal cage, migration of the cage(s), vertebral subluxation (spondylolisthesis), collapse of structural elements and loss of support, as well as damage to surrounding new bone. Data which is generated from the sensors can also be integrated and utilized to create a 2D and/or 3D image of the hardware and spinal anatomy, both at a single time point, as well as over time, based upon real-world stresses. Accelerometers can provide the clinician with an understanding of the overall movement and stability of the affected spinal segment—the flexion, extension and rotation of the spinal segment (which if bony fusion is successful, should all decrease with time). Such sensors also allow for the continuous monitoring of the implanted device in order to monitor both short-term and long-term product performance, as well as assessment of healing and patient recovery. This data is helpful in monitoring patient progress and the effects of specific rehabilitation efforts as well as identifying potential activities/actions that are detrimental to recovery.

As will be evident given the disclosure provided herein, in addition to the above noted sensors, the ISM on the spinal cage of FIG. 23 (or in the bone graft material) may also have a variety of sensors, including for example, one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors.

B.7.D. Artificial Discs

Within various aspects of the present invention, intervertebral disc damage (e.g., injury or disease such as Degenerative Disc Disease) may also be treated utilizing artificial discs (i.e., by complete replacement of the damaged disc with a prosthetic replacement). The intent of an artificial disc is, unlike a spinal fusion, to preserve motion between the vertebrae, e.g., to provide for more natural spinal flexion, extension and rotation. Representative artificial discs include the Charite Lumbar Disc (DePuy), Prodisc Lumbar Disc (Synthes), ProDisc Cervical Disc (Synthes) and the Maverick Lumbar Dis (Medtronic). Typically, the intervertebral disc is completely excised by the surgeon via an anterior (abdominal) approach, and plates (usually composed of titanium or titanium alloys) are placed over the vertebral bodies. A core piece (usually comprised of a polymer such as polyethylene) is sized to provide the correct height and positioned between the plates in order to complete the artificial disc.

Figure 24:
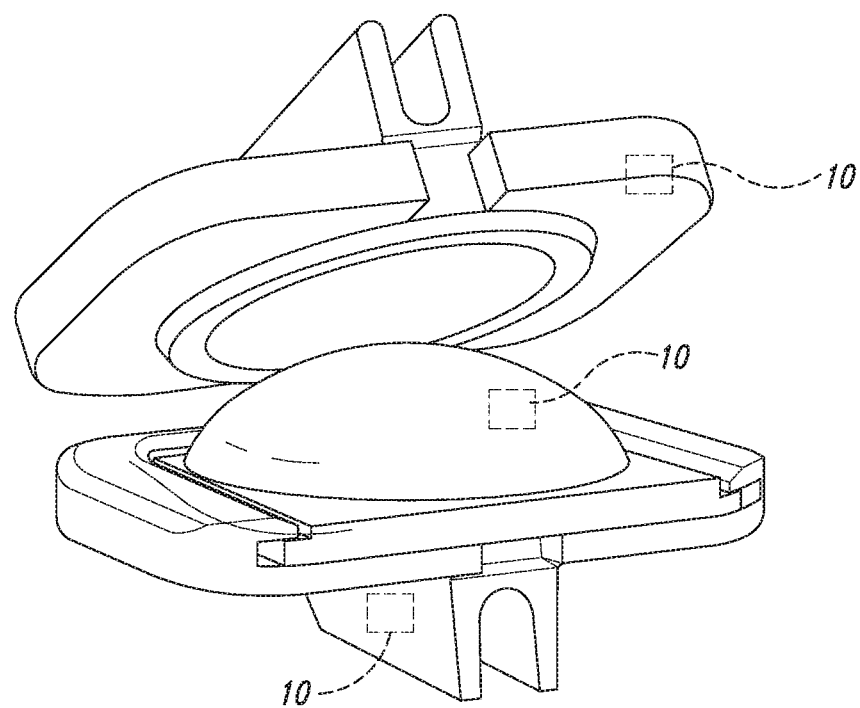
FIG. 24 illustrate an artificial intervertebral disc having an ISM.

Within an embodiment of the invention, artificial discs are provided with one or more ISMs (see, e.g., FIG. 24). For example, within one embodiment, artificial discs are provided with an ISM having one or more positions sensors placed on and/or within the artificial disc (i.e., on or within the metallic plates, and/or on/within the articular core piece between the plates). For artificial discs that a cemented in place, the one or more ISMs can also be contained within the bone cement. Intraoperatively, the ISM position sensors can be utilized by the surgeon to determine accurate placement, alignment and spinal anatomy (medical imaging). Postoperatively, the ISM Position sensors can be utilized to detect and accurately monitor flexion, extension and rotation of the artificial disc (precise, numeric measurements of all motion), and to assess, measure and evaluate the range of motion of the spinal segment. The ISM position sensors can also be utilized to determine and monitor the location and fixation of the artificial disc, movement of the artificial disc, to monitor the anatomy, contact and interaction between adjacent components (detect normal component movement and abnormal component movement such as artificial joint dislocation or subluxation), and to monitor migration, breakage and/or wear of the artificial disc. It also allows for the continuous monitoring of the device in order to assess both short-term and long-term product performance, as well as assessment of healing and patient recovery.

Within other embodiments, the ISM of FIG. 23 can have one or more contact sensors, and be placed on and/or within the artificial disc (i.e., on or within the metallic plates, and/or on/within the articular core piece between the plates); for cemented prostheses, the ISM can be contained within the bone cement). Intraoperatively, the ISM contact sensors can be utilized by the surgeon to determine accurate placement, alignment and contact between the metallic plates and the surrounding tissues and between the components of the artificial disc (the metallic plates and the articular core). Postoperatively, the ISM contact sensors can also be utilized to detect space, movement, and the integrity of bond between the disc hardware (the metallic plates) and bone, and to detect increasing movement (which could be suggestive of osteolysis); to monitor articular surface contact (to identify artificial joint dislocation or subluxation); and to detect and/or monitor wear, erosion, migration and/or failure or breakage of the device. An ISMs can also be placed at critical depth within the polymeric articular core to notify the patient and physician when the amount of surface wear of the synthetic articular component has become concerning. The sensors also allow for the continuous monitoring of the device in order to assess both short-term and long-term product performance, as well as assessment of healing and patient recovery.

Within other embodiments, the ISMs of FIG. 23 can have one or more accelerometers and/or strain gauges and can be located on and/or within the artificial disc (e.g., on or within the metallic plates, and/or on/within the articular core piece between the plates); for cemented prostheses, the ISM can be contained within the bone cement). The ISM accelerometers can be utilized to detect and record the magnitude, direction of acceleration, orientation, vibration and shock of a given strain. Hence, detection of vibration/movement may indicate loosening of the prosthetic disc from the surrounding bone (improper fixation or osteolysis); or within the artificial disc, vibration/movement may be an indicator of migration/breakage/failure of the artificial disc, vertebral artificial joint subluxation or dislocation, collapse of the structural elements and loss of support, as well as damage to surrounding new bone. Data which is generated from the ISM accelerometers can also be integrated and utilized to create a 2D and/or 3D image of the hardware and spinal anatomy, both at a single point as well as over time based upon real-world stresses. ISM accelerometers can provide the clinician with an understanding of the overall movement and stability of the affected spinal segment—the flexion, extension and rotation of the spinal segment containing the artificial disc. Such sensors also allow for the continuous monitoring of the device under "real world" conditions in order to assess both short-term and long-term performance, as well as assessment of healing and patient recovery. This data is helpful in monitoring patient progress and the effects of specific rehabilitation efforts as well as identifying potential activities/actions that are detrimental to recovery.

In summary, a wide variety of ISMs having sensors may be placed on and/or within the artificial disc (i.e., on or within the metallic plates, and/or on/within the articular core piece between the plates; for cemented prostheses, the ISMs can also be contained within the bone cement) in order to provide an evaluation of performance in the clinic as well as in 'real-world' settings, to detect loosening between the prosthesis and the surrounding bone, to detect joint subluxation or dislocation, to monitor spinal anatomy and alignment, to detect infection and/or inflammation, to detect the strain encountered in the prosthesis, to detect acceleration and impact events, and to detect articular surface wear in the metal plates and/or polymer components (if present). For example, the ISM contained on or within an artificial disc can have a combination of one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors.

B.7.E. Microdiscetomy

Within various aspects of the present invention, devices and methods are provided for treating herniated discs. Briefly, unlike a typical vertebrae, a tear in the Annulus Fibrosis of the disc allows the soft, central Nucleus Pulposis to herniate out through the Annulus. This may occur for a variety of reasons, e.g., trauma, lifting, repeated injury, or may be idiopathic in nature. Such herniated discs may be initially treated conservatively with rest, anti-inflammatory medication, and physiotherapy, but in certain cases, surgery may be required if the nerve roots or spinal cord are involved and neurological symptoms (numbness, weakness, tingling, paralysis, bowel or bladder dysfunction) are present.

In a typical surgical procedure, a patient is anesthetized, and a small incision is made in the back. The spinal muscles and ligaments are separated, and a small amount of the facet joint may be removed. The herniated disc material is then removed endoscopically.

Within various embodiments, microdiscectomy tools containing ISMs with sensors, as described herein, are provided. For example, within one embodiment microdiscectomy tools containing ISMs with contact sensors are provided which can be utilized to monitor contact between the rongeur and nerve root, spinal cord and/or surrounding nerve tissue. Microdiscectomy tools containing ISMs with pressure sensors may be utilized to monitor pressure exerted on the nerve tissue during dissection, and to prevent tissue damage and nerve injury from excessive pressure. Microdiscectomy tools containing ISMs with position sensors and accelerometers can be utilized to assist in resection of herniated disc tissue, and used for medical imaging (e.g., to provide an image of spinal and disc anatomy, the herniated segment, and disc wall) pre and post-resection. Within certain embodiments of the invention, a naturally occurring or synthetic nucleus-like material may be reinjected back into the disc (see generally, Eur Spine J. 2009 November; 18(11): 1706-1712. Published online 2009 August 18). Within preferred embodiments, the naturally occurring or synthetic nucleus-like material may contain one or more ISMs having sensors to monitor pressure, position, contact and/or movement within the nucleus, as well as leaks or ruptures of the disc and inflammation and/or infection of the disc.

Within other aspects of the invention, Intradiscal Electrothermal Annuloplasty can be utilized to treat, for example, Degenerative Disc Disease. For example, an electrothermal catheter can be inserted along the back inner wall of the disc. The catheter can then be heated, thereby thickening collagen fibers which make up the disc wall (and sealing any ruptures in the disc wall), and cauterizing sensitive nerve endings.

Within various embodiments of the invention electrothermal catheters are provided comprising one or more ISMs having sensors that can be utilized in the process of Intradiscal Eletrothermal Annuloplasty. For example, ISMs having contact sensors can be utilized to monitor contact between the electrothermal catheter and the inner wall of the annulus. ISMs having pressure sensors can be utilized to monitor the pressure in the annulus, to aid in avoiding perforation through the annulus, and to confirm the integrity/sealing of the annulus post-procedure. ISMs having position sensors and accelerometers can be utilized to assist in catheter placement, and used for medical imaging (e.g., to confirm correct catheter placement and to image spinal anatomy and disc anatomy, both pre and post-treatment). In addition, ISMs having temperature sensors can be utilized to control the heat of the catheter, in order to ascertain and maintain the correct operating temperature (and prevent thermal injury to non-target tissues).

In summary, one or more ISMs having one or more sensors may be placed on and/or within microdiscectomy and electrothermal catheter tools in order to provide "real time" information and feedback to the surgeon during the procedure, to detect instrument placement, spinal and disc anatomy, forces exerted on surrounding tissues, and to detect the physiologic conditions encountered in an interventional procedure. For example, the microdissectomy and electrothermal tools can have one or more ISMs having one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors.

As will be readily evident given the disclosure provided herein, the ISMs described and claimed herein can contain a variety of different sensors within different locations of the ISM. In addition, within various embodiments of the invention one or more sensors may be placed separate from the ISM (but still be, optionally, able to communicate with and be controlled by the ISM). Representative examples of sensors placed on a spinal implant or spinal device, or spinal implant surgical delivery device are provided in U.S. Provisional No. 62/017,106, which is hereby incorporated by reference in its entirety).

B.8. Orthopedic Hardware

Within one embodiment of the invention, ISMs are provided in orthopedic hardware and/or orthopedic implants. "Orthopedic device and/or orthopedic implant" as those terms are utilized herein, refers to a wide variety of devices (typically hardware) and implants (typically biomaterials like bone cement, glues, adhesives, hemostats and bone grafts) that can be implanted into, around, or in place of part of a subject's musculoskeletal system (e.g., bone), in order to facilitate treatment of the disease, injury or disorder. Representative conditions that may be treated include musculoskeletal trauma (e.g., falls, trauma, motor vehicle accidents, projectile injuries), sports injuries, degenerative diseases (such as osteoarthritis and other forms of arthritis, osteoporosis), infections (osteomyelitis), tumors (primary and metastatic bone tumors), and congenital disorders (deformities, osteogenesis imperfect).

Orthopedic devices and implants can be utilized both externally and internally to correct musculoskeletal injuries and deformities. Representative examples of external orthopedic devices and implants include, for example: casts (e.g., made of plaster of paris, polyurenthane, fiberglass, or thermoplastics; see, e.g., U.S. Pat. Nos. 4,308,862, 4,817,590, 6,053,882), braces (see e.g., U.S. Pat. Nos. 4,862,878 and 5,437,617), tensor bandages (e.g., elastic bandages which are stretchable and can create localized pressure; e.g., Kendall Tensor Elastic Bandages), slings, supports and braces (e.g., ACE Adjusted Padded Sling, and Flexibrace), (see generally "Orthopedic Taping, Wrapping, Bracing & Padding", Joel W. Beam, F. A. David Company, 2006).

Representative examples of internal hardware and implants include K-wires (Kirschner wires), pins (Steinmann pins), screws, plates, and intramedullary devices (e.g., rods and nails) and associated devices. Briefly, intramedullary rods or nails (including for example interlocking nails, Küntscher nails, Ender's nail, Grosse-Kempf (GK) nails, Gamma nails, and Rush nails) are long metal rods which are implanted into the medullary cavity of a long bone (e.g., a femur, humerus, or tibia), thereby providing greater stability and support to the bone during healing. Kirschner wires (or "K-wires") are sharpened, smooth pins which are utilized to hold bone fragments together, or to serve as an anchor for skeletal traction. K-wires come in a variety of sizes and shapes, and within certain embodiments may be threaded. Orthopedic screws, pins and plates are utilized in a wide variety of orthopedic procedures to secure, stabilize, mend, fix, replace, or immobilize bone (or bone fragments). Representative orthopedic implants include Smith Peterson nails for fracture of the neck of the femur, McLaughlin's plate (which along with Smith Peterson nails are used for intertrochanteric factures), Buttress plates for condylar fractures of the tibia, the Condylar blade plate for condylar fractures of the femur, Dynamic compression plates, Steinmann pins for skeletal traction, Talwalkar nails for fractures of the radius and ulna, and Moore's pin for fractures of the head of the femur. Representative examples of the above devices, implants and devices are described in Oxford Textbook of Orthopedics and Trauma, Oxford University Press, 2002; (see also U.S. Pat. Nos. 6,565,573, 7,044,951, 7,686,808, 7,811,311, 7,905,924, 8,048,134, and 8,361,131) all of the above of which are incorporated by reference in their entirety.

Orthopedic devices or implants may be composed of a wide variety of materials (including for example metals such as titanium, titanium alloys, and/or stainless steel), although other materials can also be utilized, including polymers (e.g., polymethylmethacrylate or "PMMA", poly-ether-ether-ketone or "PEEK", and bone graft material that can be allographic, xenographic or synthetic); and non-polymeric materials such as silicon nitride.

Within certain embodiments of the invention, ISMs can be placed into orthopedic devices which are traditionally made of metallic materials (e.g., plates) by a variety of different means. For example, within one embodiment small holes, cavities, or openings can be placed into a device (e.g., through use of a laser), and one or more sensor inserted into the opening. Within other embodiments, a surface of a metallic device can be coated with one or more polymers which contain or comprise one or more ISMs having one or more sensors. Within other embodiments, the ISM can be inserted into the "shaft" of the device (intermedullary rods, pins or nails; dynamic hip screws) or attached to the device surface.

"Orthopedic implant surgical device" or "orthopedic implant delivery device" refers to devices that can be utilized to introduce an orthopedic implant into a patient, and/or to surgical devices that can be utilized to operate on the bone. Representative examples include power drills, power screw devices, and power saw devices, mallets, hammers, and chisels all of which are composed of selected sterilizable components. Other examples include glue, hemostat, and bone cement injection devices.

The medical devices (e.g., orthopedic devices and implants, orthopedic delivery devices, etc.) and kits provided herein are preferably sterile, non-pyrogenic, and/or suitable for use and/or implantation into humans. However, within certain embodiments of the invention the medical devices and/or kits may be made in a non-sterilized environment (or even customized or "printed" for an individual subject), and sterilized at a later point in time.

B.8.A. External Orthopedic Devices: Casts, Splints, Braces, Tensors, Slings and Supports As noted above, within various aspects of the invention, external orthopedic devices or implants and associated medical devices are provided for use in a wide variety of orthopedic procedures.

For example, within one embodiment of the invention ISMs can be placed onto, within, and/or under casting material (e.g., typically plaster of paris on a mesh, fiberglass mesh, or a polymer—based composition such as polyurethane or a thermoplastic polymer), in order to form a cast. Within other embodiments one or more ISMs can be placed on the surface of, within, and/or under the 3-D printed cast.

Such ISMs can be utilized for a variety of purposes. For example, one of the complications associated with casts is the development of points of pressure between the cast and the skin, which can result in tissue sores, pain, and even tissue necrosis. ISMs having pressure sensors can be utilized to detect pressures during placement of the cast, as well as over the period that the cast is in place. The pressure sensors can be utilized to monitor inappropriate or dangerous increases in pressure (which can occur, for example, with inflammation occurring in the days following injury or after ambulation), and to serve as a basis to alert a patient, health care provider, or other entity or object as discussed in more detail below.

ISMs having accelerometers and/or position sensors can be utilized in casts in order to monitor joint movement and immobilization, and to ensure that too much stress is not placed on the casted body part. Proper fracture healing often requires not only immobilization of the bone fragments, but also the immobilization of the joints above and below the fracture. Accelerometers and/or position sensors can help to ensure that the underlying structure (e.g., bone) maintains proper alignment and that the related joints are adequately immobilized. In addition, the ISM accelerometers and position sensors can be utilized to monitor twisting, torque, flexion, extension and bending, all of which may lead to complications such as inadequate or improper healing.

Within certain embodiments, ISMs having external accelerometers and/or position sensors may be correlated with sensors which have been placed within the body (e.g., implanted by injection or surgically, or associated with an internal orthopedic implant as described in more detail below).

Figure 25A:
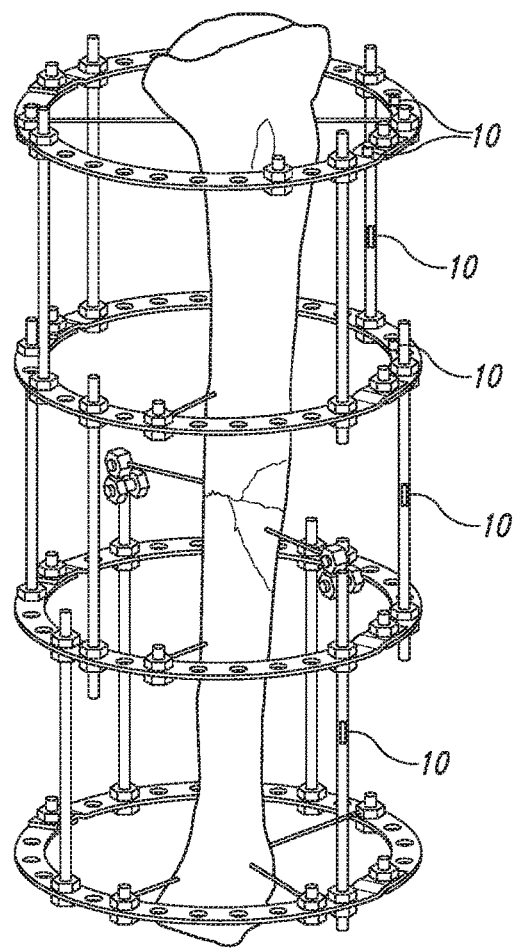
FIGS. 25A-25C illustrate the use and placement of an external fixation device (including the use of screws, pins and clamps) on a bone (FIG. 25A), and an external fixation device having several ISMs placed on it (FIG. 25B) implanted on the arm (FIG. 25C).
Figure 25B:
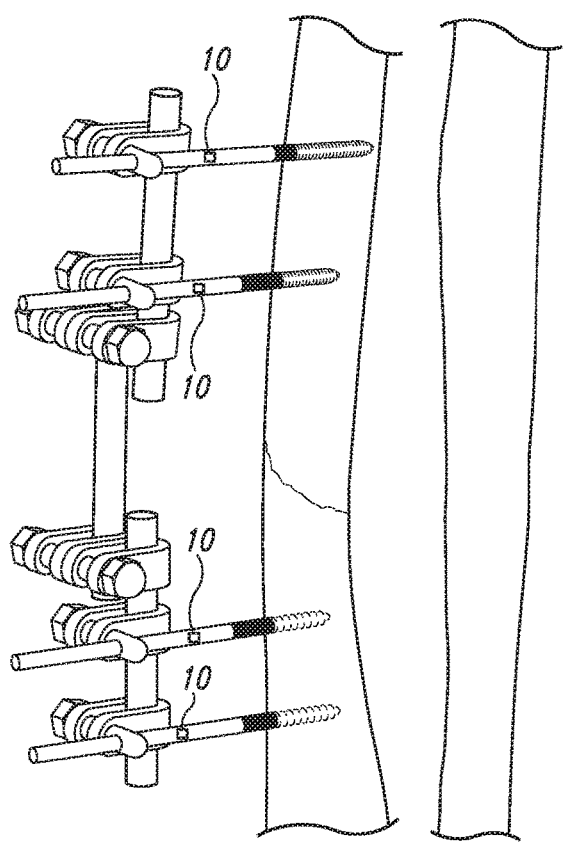
Figure 25C:
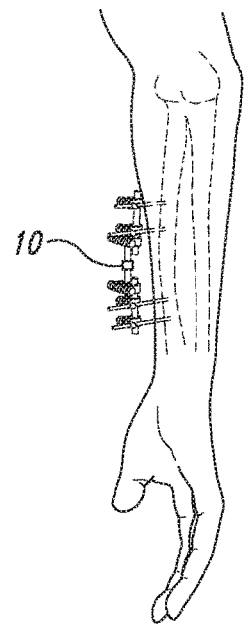

For example, as shown in FIG. 25, ISMs (e.g. ISMs having one or more of accelerometers, position sensors, pressure sensors, etc.) can be placed on an external support structure (e.g. see FIG. 25A). ISMs (e.g. ISMs having one or more of accelerometers, position sensors, pressure sensors, etc.) can be placed on various aspects of the support structure (including for example on external screws, pins, clamps or other supporting structures), as well as on various aspects of the orthopedic devices or implants inserted on or into a bone (e.g., the radius as shown in FIG. 25B implanted on the arm (FIG. 25C). Movement between the internal (implanted) sensors and external sensors can be utilized to assess whether anatomical segments have become misaligned, and whether such misalignment might need to be adjusted or corrected in a further procedure.

Within yet other embodiments ISMs having chemical and temperature sensors can be utilized to monitor skin temperature, skin integrity, and/or the presence of an infection or a developing infection. ISM sensors positioned on casts and splints in contact with the skin are ideally located to serve this function.

Figure 26A:
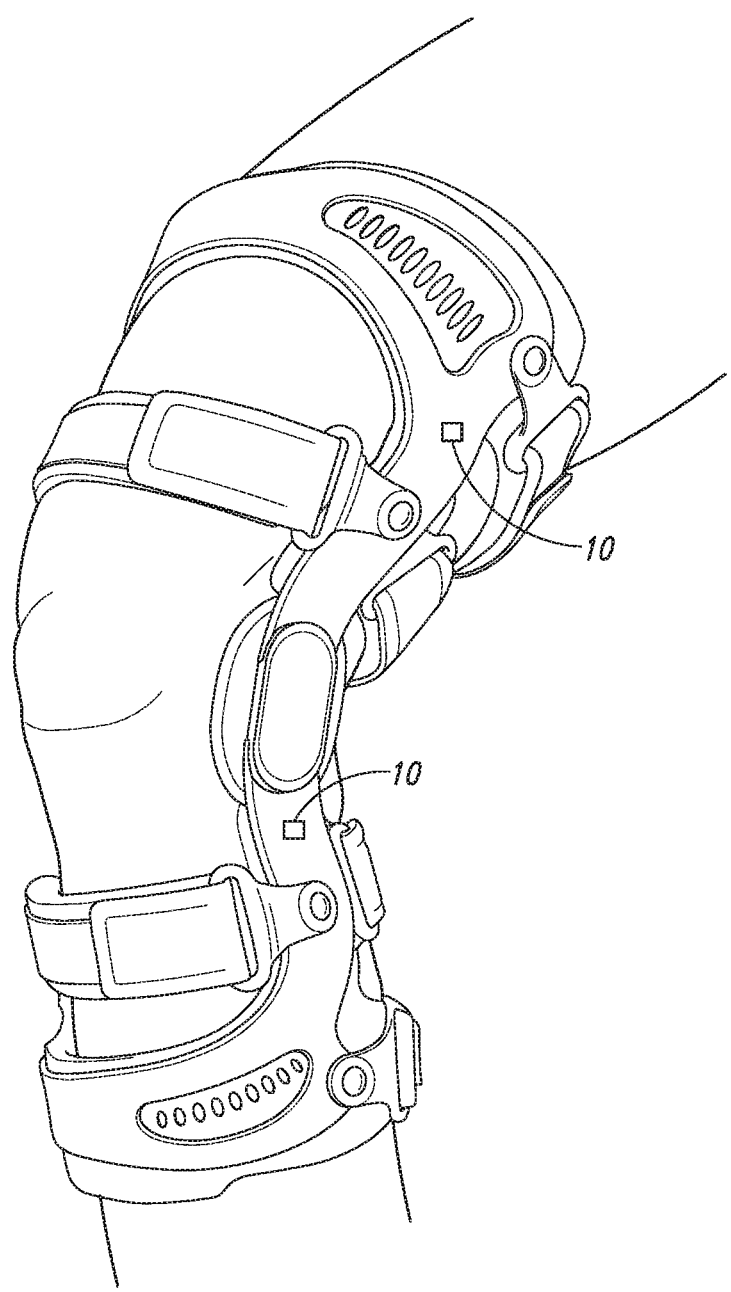
FIGS. 26A and 26B illustrate a variety of braces and slings.
Figure 26B:
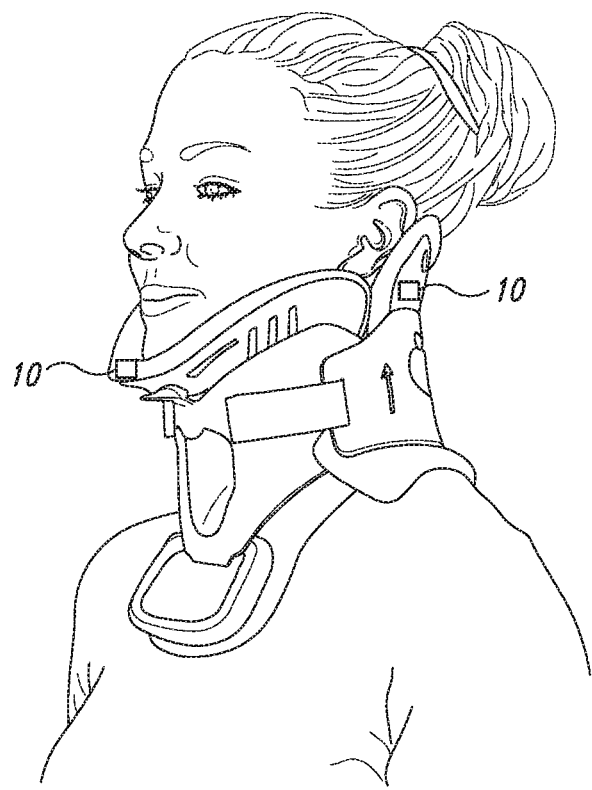

Within other embodiments of the invention, ISMs can be placed on a variety of supports, braces, slings, splints, and tensors. For example, as shown in FIG. 26, one or more ISMs can be placed on knee braces (FIG. 26A), head and neck braces (FIG. 26B), tensor bandages (not shown), arm slings (not shown) and back braces (not shown).

Within other embodiments of the invention, ISMs can be placed at a variety of locations within a sports helmet designed to protect the sporting participant such as but not limited to football, ice hockey, and lacrosse helmets. ISMs with accelerometers and gyroscopes can measure impact G-force sustained during play and monitor acute and cumulative concussive effects for real time assessment of potential brain injury.

Within various embodiments, ISMs having one or more pressure sensors can be placed in any of the braces, tensors, slings or supports provided herein. ISMs with pressure sensors can be utilized to measure compression, rotation and axial loading, and the amount of support. Detection of increased pressure can indicate the possibility of, or potential for, skin and or tissue damage. Detection of decreased pressure can indicate that the device might be ineffective and/or need reapplication or replacement. A rapid increase or decrease in pressure can indicate a traumatic event. For example, detection of a rapid increase in pressure could indicate swelling, inappropriate motion, and/or a risk of breakage or injury, or even the development of a compartment syndrome. A rapid decrease in pressure could indicate a total failure of the device.

Within other embodiments of the invention, ISMs having accelerometers (and strain gauges) can be placed in any of the braces, tensors, slings, splints or supports provided herein. ISMs containing accelerometers can be utilized to monitor alignment, stability and healing. They can also be utilized to monitor and assess patient activity levels (e.g., daily function, range of motion, physiotherapy, rehab and exercise), and to monitor for rotation, bending, breakage, movement and/or slippage of the device.

Within other embodiments of the invention, ISMs having position sensors (and locations markers such as GPS) can be placed in any of the braces, tensors, slings, splints or supports provided herein. ISMs containing position sensors (and location markers) can be utilized to monitor for example, any changes in anatomy, alignment, or mobility. In addition, through the use of location sensors, patient activity, compliance, mobility/immobility, the effect of rehab, and falls, breakage or emergencies can all be monitored.

Within yet other embodiments ISMs having chemical and temperature sensors can be utilized to monitor skin temperature, skin integrity, and/or the presence of an infection or a developing infection.

In summary, ISMs having a wide variety of sensors may be placed on and/or within the external orthopedic hardware described herein, in order to provide "real time" information and feedback to a health care provider (or a surgeon during a surgical procedure), to detect proper placement, anatomy, alignment, mobility/immobility (of injured tissues and related joints), forces exerted on surrounding tissues, and to detect the strain encountered in an surgical procedure. For example, the external orthopedic hardware provided herein (e.g., casts, splints, braces, tensors, slings and supports) can have one or more ISMs which contain a combination of contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. ISMs can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above described ISMs may be continuously or intermittently monitored in order to provide 'real-world' activity (of affected limbs, joints etc.), fixation, mobility/immobility, healing, progressive rehabilitation and function and to collect and compare procedure performance data over time, to evaluate patient activity, and to better understand the conditions which implants are exposed to in the real world.

B.8.B. Internal Orthopedic Hardware: K-wires, Pins, Screws, Plates, and Intramedullary Devices Within other aspects of the invention, ISMs are provided for incorporation into a wide variety of internal orthopedic devices. For example, Kirschner-wires or "K-wires", pins, screws, plates, and intramedullary devices (e.g., rods and nails) used to repair fractured, dislocated and injured musculoskeletal tissues.

B.8.B.1. Pins

Figure 27:
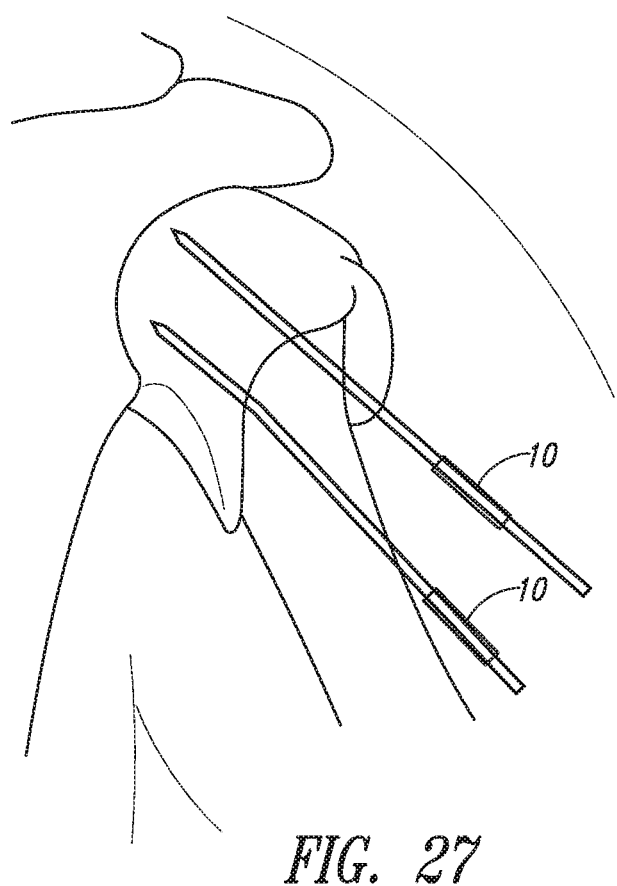
FIG. 27 illustrates one embodiment wherein an ISM is placed on or within several pins (Steinmann pins) inserted to reduce a humeral fracture.

Pins are a common orthopedic device, and are typically utilized as a way to stabilize bone fractures. One of the most common pins is the Steinmann Pin (also sometimes referred to as Intramedullary Pins or IM Pins), which is driven through the skin and into the bone in order to provide an anchor or support for the patient's fracture. Most commonly, pins have either a two-sided (chisel) or a three-sided trocar tip (which is better suited to penetrating cortical bone). FIG. 27 illustrates one embodiment wherein an ISM is placed on or within several pins.

Within one embodiment of the invention, Pins are provided with an ISM having one or more pressure sensors. The pressure sensors can be distributed on, or within, the Pin at specific or randomized locations. Within certain embodiments the ISM may be concentrated on the cutting end of the Pin. The ISM pressure sensors can be useful during placement and removal (if necessary) of the Pin, during movement through different tissues [e.g., in order to determine soft tissue (low pressure), cortical bone (high pressure), cancellous bone (moderate pressure), marrow (low pressure), fracture planes (little to no pressure)—in order to assist in detection, placement and anatomical location].

ISM pressure sensors can also be useful after placement of a Pin. For example, detection of increased pressure on the Pin, or across the fracture plane, can indicate the potential for stress shielding (e.g., a reduction of bone density due to too much stress being borne by the implanted Pin and not enough being borne by the bone tissue) and/or increased potential for the Pin to bend, crack or break. Detection of increased pressure on the Pin in soft tissues can indicate the potential for the development of compartment syndrome. Detection of reduced pressure on the Pin, or across the fracture plane, can indicate the potential for non-union of the fracture (early in the healing process) or the successful completion of healing (later in the healing process when the bone has assumed normal support functions). Unequal and/or unbalanced pressures on the Pin, or across the fracture plane, can be a sign of poor alignment, shifting, and/or the application of torque on the healing bone. In all cases, identifying the presence of improper pressure forces across the fracture plane can allow for preemptive intervention to better stabilize the injury and prevent further damage to the bone.

Within other embodiments Pins are provided with an ISM having accelerometers (and strain gauges). ISMs having accelerometers (and strain gauges) can be distributed on, or within the Pin at specific or randomized locations. However, within certain embodiments the ISM may be concentrated on the cutting end of the Pin. The ISM accelerometer sensors can be useful during placement and removal (if necessary) of the Pin by being able to detect movement through different tissues; they can also assist with achieving correct anatomical placement, alignment and imaging intraoperatively.

ISM accelerometers and strain gauges can also be useful after insertion of a Pin. For example, they can be utilized post-operatively to monitor alignment, stability, fragment mobility/immobility, healing, patient activities, stresses across the fracture, and related joint immobilization (or lack thereof).

Within another embodiment of the invention, Pins are provided with one or more ISMs having one or more position sensors/location marker sensors. The ISM containing position sensors/location marker sensors can be distributed on, or within the Pin at specific or randomized locations. Within certain embodiments the ISM may be concentrated on the cutting end of the Pin. The position sensors/location marker sensors can be useful during placement and removal (if necessary) of the Pin, during movement through different tissues (e.g., in order to determine soft tissue, cortical bone, cancellous bone, marrow, fracture planes—to assist in detection and determination of anatomical location, fracture anatomy, and correct post-surgical alignment), as well as in imaging and functional monitoring after placement.

ISM position sensors/location marker sensors can also be useful after placement of a Pin. For example, they can be utilized to monitor healing anatomy, and compare changes in location over time (e.g., post-surgery). They can also be utilized to monitor alignment, shifting and migration, to confirm joint immobilization, and to detect wire bending and/or breakage.

Within yet other embodiments of the invention, Pins are provided with ISMs having temperature sensors and or chemical sensors. Briefly, temperature and/or chemical sensors can be utilized to monitor skin and tissue temperature, skin and tissue integrity, and/or the presence of an infection or a developing infection [e.g., bone infections (Osteomyelitis), and/or tissue necrosis].

As should be readily evident given the disclosure provided herein, the Pins of the present invention can have one or more ISMs having a combination of one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above ISMs containing sensors may be continuously or intermittently monitored in order to provide a 'real-world' assessment of alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

B.8.B.2. Kirschner Wires

Kirschner wires (or K-wires) are sharpened, sterilized steel wires that were originally developed by Martin Kirschner in 1909. K-wires came along after Steinmann Pins, when Dr. Kirschner recognized that larger pins caused more bone damage, as well as infection. Dr. Kirschner created his own device made of chrome piano wire to provide better tension when aligning fractured fragments of bone into place. Hence, the principle difference between wires and pins is one of size. Smaller diameters are referred to as wires and larger diameters are referred to as pins. Although there is no standardized definition of diameter cut off, typically pins are between 1.5 mm and 6.5 mm in diameter, wherein K-wires are 0.9 to 1.5 mm in diameter.

Figure 28:
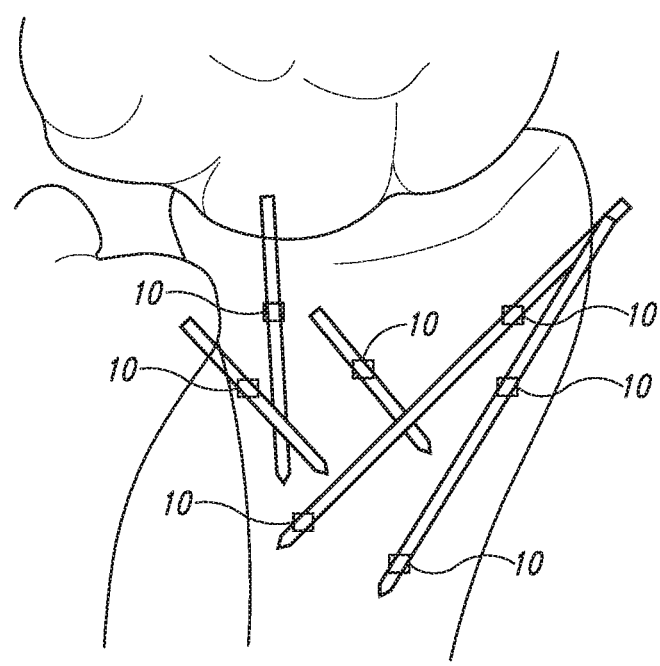
FIG. 28 illustrates one embodiment wherein an ISM is placed on and/or within several K-wires (Kirschner wires) inserted to reduce a radial fracture.

K-wires are typically made of metal (e.g., stainless steel or nitinol), and come in a variety of sizes, diameters and lengths. They are commonly utilized to hold together bone fragments, to provide an anchor for skeletal fixation, or as a guide for screw placement, and are often driven into bone using a power or hand drill. FIG. 28 illustrates one embodiment wherein an ISM is placed on and/or within several K-wires.

Within one embodiment of the invention K-wires are provided with an ISM having one or more pressure sensors. The ISM can have pressure sensors can be distributed on, or within the K-wire at specific or randomized locations. Within certain embodiments the ISM may be concentrated on the cutting end of the K-wire. The ISM pressure sensors can be useful during placement and removal (if necessary) of the K-wire, during movement through different tissues [e.g., in order to determine soft tissue (low pressure), cortical bone (high pressure), cancellous bone (moderate pressure), marrow (low pressure), fracture planes (little to no pressure)—in order to assist in detection, placement and anatomical location].

ISM pressure sensors can also be useful after placement of a K-wire. For example, detection of increased pressure on the K-wire, or across the fracture plane, can indicate the potential for stress shielding and/or increased potential for the Pin to bend, crack or break. Detection of increased pressure on the K-wire in soft tissues can indicate the potential for the development of compartment syndrome. Detection of reduced pressure on the K-wire, or across the fracture plane, can indicate the potential for non-union of the fracture (early in the healing process) or the successful completion of healing (later in the healing process when the bone has assumed normal support functions). Unequal and/or unbalanced pressures on the K-wire, or across the fracture plane, can be a sign of poor alignment, shifting, and/or the application of torque on the healing bone. In all cases, identifying the presence of improper pressure forces across the fracture plane can allow for preemptive intervention to better stabilize the injury and prevent further damage to the bone.

Within other embodiments K-wires are provided with an ISM having accelerometers (and strain gauges). Similar to ISMs having pressure sensors, ISMs having accelerometers (and strain gauges) can be distributed on, or within the K-wire at specific or randomized locations. However, within certain embodiments the ISM may be concentrated on the cutting end of the K-wire. The ISM accelerometer sensors can be useful during placement and removal (if necessary) of the K-wire by being able to detect movement through different tissues; they can also assist with achieving correct anatomical placement, alignment and imaging intraoperatively.

ISM accelerometers and strain gauges can also be useful after insertion of a K-wire. For example, they can be utilized post-operatively to monitor alignment, stability, fragment mobility/immobility, healing, patient activities, stresses across the fracture, and related joint immobilization (or lack thereof).

Within another embodiment of the invention, K-wires are provided with one or more ISMs having one or more position sensors/location marker sensors. The ISMs having position sensors/location marker sensors can be distributed on, or within the K-wire at specific or randomized locations. Within certain embodiments the ISM may be concentrated on the cutting end of the K-wire. The position sensors/location marker sensors can be useful during placement and removal (if necessary) of the K-wire, during movement through different tissues (e.g., in order to determine soft tissue, cortical bone, cancellous bone, marrow, fracture planes—to assist in detection and determination of anatomical location, fracture anatomy, and correct post-surgical alignment), as well as in imaging and functional monitoring after placement.

ISM position sensors/location marker sensors can also be useful after placement of a K-wire. For example, they can be utilized to monitor healing anatomy, and compare changes in location over time (e.g., post-surgery). They can also be utilized to monitor alignment, shifting and migration, to confirm joint immobilization, and to detect wire bending and/or breakage.

Within yet other embodiments of the invention, K-wires are provided with ISMs having temperature sensors and or chemical sensors. Briefly, temperature and/or chemical sensors can be utilized to monitor skin and tissue temperature, skin and tissue integrity, and/or the presence of an infection or a developing infection [e.g., bone infections (Osteomyelitis), and/or tissue necrosis].

As should be readily evident given the disclosure provided herein, the K-wires of the present invention can have one or more ISMs having a combination of one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above ISMs can be continuously monitored in order to provide a 'real-world' assessment of alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

B.8.B.3. Screws

Bone screws are one of the most common devices used in orthopedic surgery. In 1850 two French surgeons (Cucel and Rigaud) are credited with performing the first internal fixation procedure with 2 transcutaneous screws fastened by string. Subsequently, in 1866 German surgeon Carl Hansmann performed an internal plate fixation using a removable steel plate and nickel-plated screws. It wasn't until the 1940s however that surgeons began to advocate for screws that were specifically designed for human bone. For example, Belgian surgeon Robert Danis proposed three key design features for bone screws: 1) a ratio of exterior diameter to core diameter of 3:2, not 4:3 as was typical to common metal screws; 2) a reduction of thread surface area to one-sixth that of metal screws (because bone is not as strong as metal); and 3) a buttress thread design to replace standard V-shaped threads, hence enhancing holding power.

Bone screws now come in a variety of sizes and shapes. They may be composed of a wide variety of polymers, metals and metal alloys, and a variety of shapes, configurations and sizes (e.g., polyaxial screws, monoaxial screws, locking screws, self-drilling screws, self-locking screws, self-tapping screws, cannulated screws, screws with a low-profile, hex heads, etc.).

In addition, screws may be designed for a particular purpose. For example, cortical screws (for use in cortical bone) are typically fully threaded and require a tap to cut threads prior to insertion.

Cancellous screws (which are designed for cancellous bone) are typically self-tapping screws with a relatively thin core and wide deep threads. They may be fully threaded (e.g., ideally for use in fastening devices such as plates into the metaphyseal or epiphyseal areas of bone), or partially threaded (they may be utilized for an area far from the cortex, but do not, however, have as much holding power).

In addition to more common screw types (such as the cancellous and cortical screws), there are a large number of specialty bone screws. For example, dynamic hip screws ("DHS") are a type of orthopedic implant composed of a plate, along with different types of bone screws that are specifically designed for certain types of hip fractures (typically intertrochanteric fractures). More specifically, a DHS side plate is aligned to a joint (e.g., a broken femoral head), and a hole is prepared utilizing a reamer. The sideplate, lag screw and cortical screws are attached to the bone. The idea of this implant is to cause dynamic compression of the femur and the femoral head, causing them to move along one plane (thereby hopefully allowing the native femur to undergo remodeling and proper fracture healing).

Other specialty bone screws include the Herbert screws and Acutrak screws which are cannulated and threaded at both ends, and typically utilized in fractures of small articular bones (e.g., carpal and scaphoid fractures). Interference screws can be specifically designed for certain procedures (e.g., soft tissue and bone-tendon-bone grafts), and are commonly comprised of polymers (e.g., PLDLA) and other components (e.g., Tri-Calcium Phosphate), (see, e.g., U.S. Patent Pub. No. 2009/0198288).

Within one embodiment of the invention ISMs having pressure sensors are provided on or within a bone screw (e.g., cancellous or cortical screw, interference screw, or dynamic hip screw). The ISM can be positioned within specific locations (e.g., at the point and/or head), or distributed throughout the screw. They can be utilized to assist in implanting the screw by detecting various tissue types (e.g., cancellous/cortical bone and bone marrow), detecting fracture planes, and assisting in the determination of anatomy and location. They can also be utilized to prevent accidental placement (e.g., into the articular cartilage; i.e. the pressure would drop from higher to lower when the screw moved from cortical bone into the articular cartilage). For example, detection of increased pressure on the screw, or across the fracture plane, can indicate the potential for stress shielding and/or increased potential for the screw to bend, crack or break. Detection of two much pressure on a DHS can be an indicator of impaction (with the risk of bone shortening). Detection of reduced pressure on the screw, or across the fracture plane, can indicate the potential for non-union of the fracture (early in the healing process) or the successful completion of healing (later in the healing process when the bone has assumed normal support functions; monitoring this can be helpful in determining the timing of ambulation). Unequal and/or unbalanced pressures on the screw, or across the fracture plane, can be a sign of poor alignment, shifting, and/or the application of torque on the healing bone. In all cases, identifying the presence of improper pressure forces across the fracture plane can allow for preemptive intervention to better stabilize the injury and prevent further damage to the bone.

Within another embodiment bone screws are provided with ISMs having accelerometers (and strain gauges). Similar to ISMs having pressure sensors, ISMs having accelerometers (and strain gauges) can be distributed on, or within the bone screw at specific or randomized locations. However, within certain embodiments the ISM may be concentrated on the point or head of the screw. The ISM accelerometer sensors can be useful during placement and removal (if necessary) of the screw by being able to detect movement through different tissues; they can also assist with achieving correct anatomical placement, alignment and imaging intraoperatively.

ISM accelerometers and strain gauges can also be useful after insertion of a screw. For example, they can be utilized post-operatively to monitor alignment, stability, fragment mobility/immobility, healing, patient activities, stresses across the fracture, and related joint immobilization (or lack thereof).

Within another embodiment of the invention, screws are provided with one or more ISMs having position sensors/location marker sensors. The ISMs having position sensors/location marker sensors can be distributed on, or within the screw at specific or randomized locations. Within certain embodiments the ISM may be concentrated on the cutting end of the screw. The ISM position sensors/location marker sensors can be useful during placement and removal (if necessary) of the screw, during movement through different tissues (e.g., in order to determine soft tissue, cortical bone, cancellous bone, marrow, fracture planes—to assist in detection and determination of anatomical location, fracture anatomy, and correct post-surgical alignment), as well as in imaging and functional monitoring after placement.

ISM position sensors/location marker sensors can also be useful after placement of a bone screw. For example, they can be utilized to monitor healing anatomy, and compare changes in location over time (e.g., post-surgery). They can also be utilized to monitor alignment, shifting and migration, to confirm joint immobilization, and to detect screw bending and/or breakage. Importantly, bone screws with position sensors/location markers can be utilized to detect movement (e.g., 'backing out') of the screw before serious complications arise. In DHS, lack of movement of the screw in the tunnel is a sign of non-union or of advancement of the screw into the articular cartilage, while excessive movement of the screw in the tunnel is inactive of shortening (and impaction). Similarly, for screws that are utilized with plates, a bone screw with ISMs containing sensors can be utilized to detect plate movement, and allow intervention prior to serious complications.

Within yet other embodiments of the invention bone screws are provided with one or more ISMs having temperature sensors and or chemical sensors. Briefly, temperature and/or chemical sensors can be utilized to monitor mineralization, tissue health, bleeding, tissue temperature, tissue health (such as avascular necrosis of the hip), and/or the presence of an infection or a developing infection [e.g., bone infections (Osteomyelitis), and/or tissue necrosis].

Figure 29A:
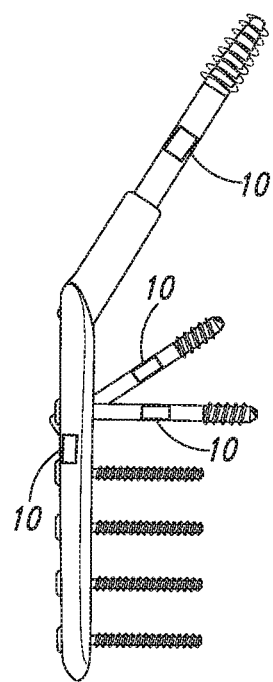
FIGS. 29A and 29B illustrate representative dynamic hip screws having ISMs, including cortical screws inserted into the sideplate (FIG. 29A), and an illustration of the device inserted into a subject (FIG. 29B).
Figure 29B:
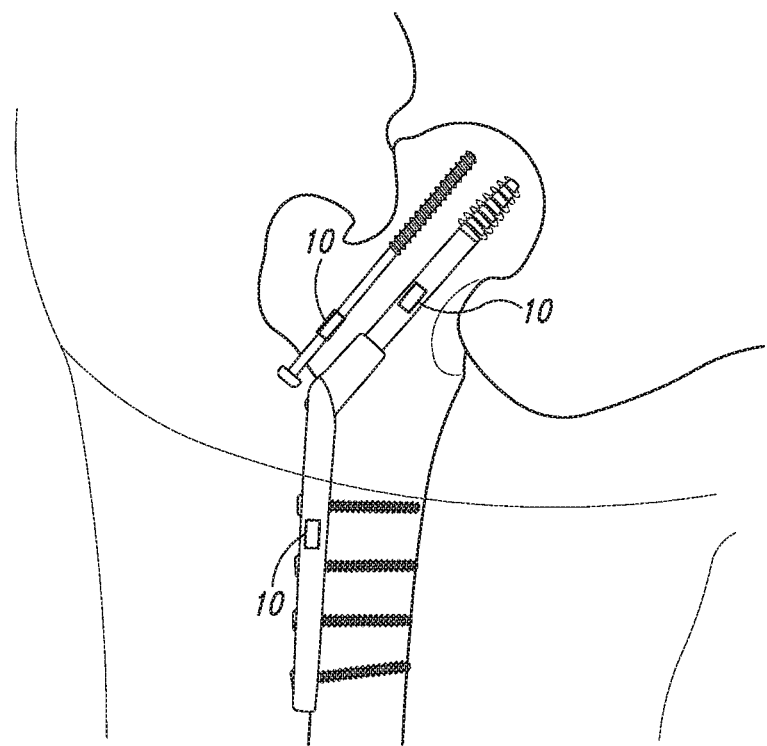

In a particularly preferred embodiment, a dynamic hip screw is provided with an ISM containing multiple sensors located in the "shaft" of the screw (see FIGS. 29A and 29B). For an ISM collecting mechanical data (position, motion, vibration, rotation, shock, tilt, steps), the implanted ISM sensors (accelerometers, position sensors, pedometers) have the advantage of not requiring either direct physical contact with the surface of the device or with patient tissues; only a secure and immobile attachment within the dynamic hip screw is needed. In this preferred embodiment, the ISM containing multiple mechanical sensors (as described above) is placed within the internal canal of the dynamic hip screw; a location that provides more than enough space to insert and seal an ISM with multiple sensor functions and battery capability. Furthermore, the motion of the screw as the hip joint goes through its range of motion during normal activities (such as walking) can provide opportunities to power the ISM.

As should be readily evident given the disclosure provided herein, the bone screws of the present invention can have one or more ISMs having a combination of one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above ISM sensors may be continuously monitored in order to provide a 'real-world' assessment of the alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

B.8.B.4. Plates

Orthopedic plates (also referred to as 'fixation plates' and 'trauma plates') have been utilized to fix fractures for over a hundred years. The first metal plate was introduced by Dr. Lane in 1895 for the internal fixation of fractures.

Figure 29C:
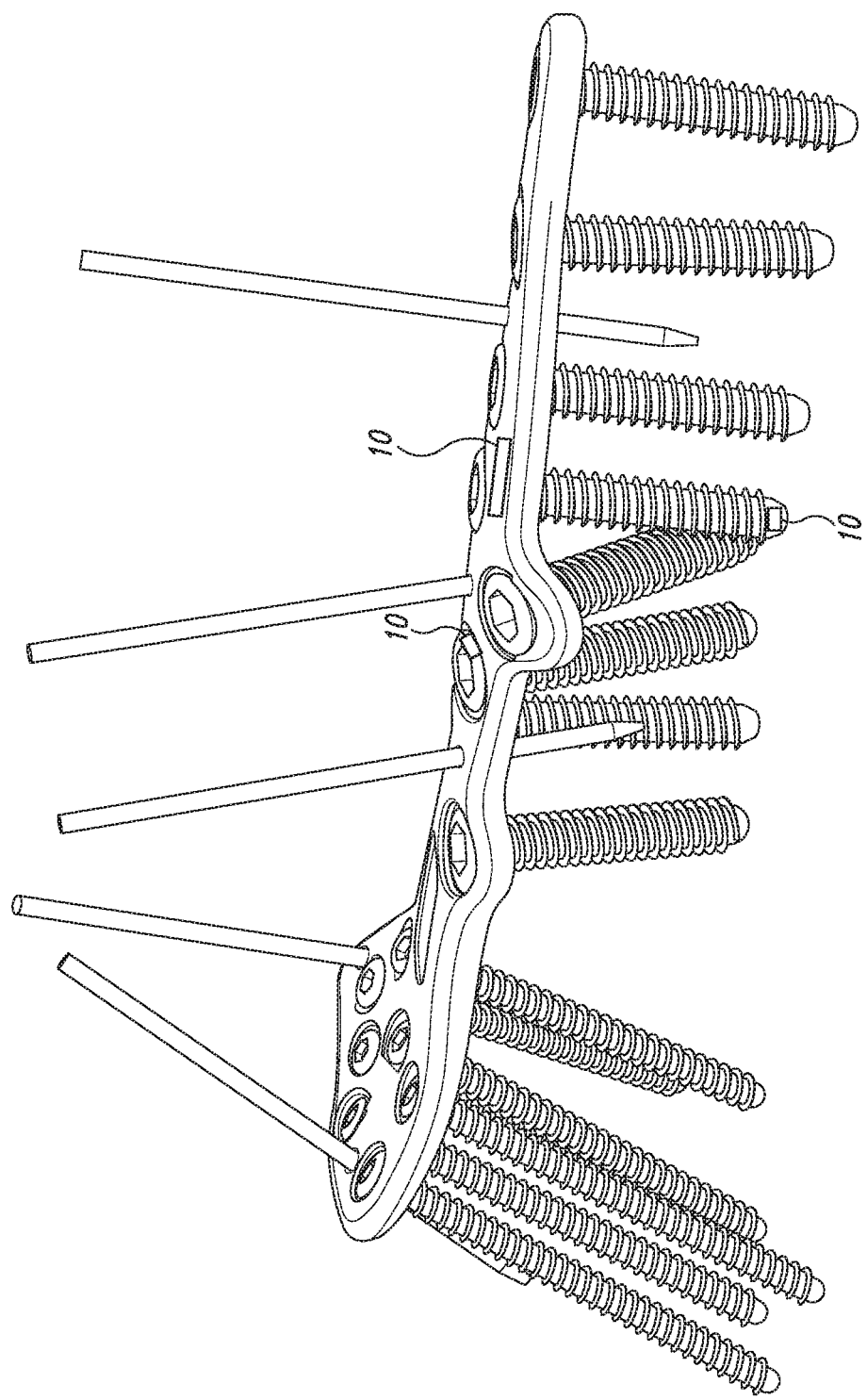
FIG. 29C illustrates an embodiment wherein ISMs are placed on a representative fixation plate.

Fixation plates now come in a wide variety of shapes and sizes, for a variety of specific indications. Representative examples include: 1) the DHS sideplate shown in FIG. 29A for the fixation of fractures at or near the femoral head; 2) DC plates (typically used for the ulna and radius repairs); 3) Buttress plates (e.g., for the repair of comminuted tibial fractures); L-Buttress plates (for complicated surgeries); 4) Clavicle Hook plates; 5) Clover Leaf plates; 6) Condylus Humerus Bone plates; and 7) Humerus and Tibial Compression plates (too name a few). Typically plates are comprised of metals such as stainless steel or titanium. FIG. 29 illustrates an embodiment wherein an ISM is placed on or within a representative fixation plate.

Within one embodiment of the invention an ISM having pressure sensors are provided on or within a plate. The ISM having pressure sensors can be positioned within specific locations (e.g., on the bone or tissue surface, around screw holes), or distributed throughout the plate. They can be utilized to assist in implanting the plate by detecting adherence to or contact with bone (e.g., for malleable plates like reconstruction plates), and or movement through tissue or bone during placement (e.g. on the chisel of blade plates). They can also be useful after placement. For example, detection of increased pressure can indicate the potential for stress shielding or the potential for bending cracking or fracture of the plate. Detection of increased pressure on the tissue surface could be an indicator of compartment syndrome. Detection of a rapid change in pressure can indicate plate breakage. Detecting a slow decrease in pressure can indicate that healing is occurring and can assist in decisions on weight bearing and rehabilitation. Monitoring the pressure around the screw holes can assist with appropriate tightening during placement; later it can be used to detect "backing out" of the screws or other complications such as breakage.

Within another embodiment plates are provided with one or more ISMs having accelerometers (and strain gauges). Such ISMs can be distributed on, or within the plate at specific or randomized locations. Within certain embodiments they may be concentrated on specific locations (e.g., on both the bone and tissue surface, at the ends, and/or around screw holes). The ISM accelerometers can be useful during placement and removal (if necessary) of the plate, for proper alignment, fit, contour, blade placement and imaging.

ISM accelerometers and strain gauges can also be useful after placement of a plate. For example, they can be utilized post-operatively to monitor alignment, stability, healing, patient activities, stresses across the fracture, rotation, bending, breakage, plate movement/slippage, and joint immobilization (or lack thereof).

Within another embodiment of the invention, plates are provided with one or more ISMs having position sensors/location marker sensors. Such ISMs can be distributed on, or within the plate at specific or randomized locations. Within certain embodiments they may be concentrated on specific locations (e.g., on both the bone and tissue surface, plate ends, and/or around screw holes). The ISM position sensors/location marker sensors can be useful during placement and removal (if necessary) of the plate, during movement through different tissues (for blade plates), to monitor alignment and molding to the bone surface, and in an imaging function after placement.

ISM position sensors/location marker sensors can also be useful after placement of a plate. For example, they can be utilized to monitor healing anatomy, and compare changes in location over time (e.g., post-surgery). They can also be utilized to monitor alignment, shifting and migration, to confirm joint immobilization, and to detect plate bending and/or breakage. Importantly, plates with position sensors/location markers can be utilized to detect movement (e.g., 'backing out') of the screw before serious complications arise.

Within yet other embodiments of the invention plates are provided with an ISM having temperature sensors and or chemical sensors. Briefly, temperature and/or chemical sensors can be utilized to monitor mineralization, galvanic corrosion, tissue health, bleeding, tissue temperature, tissue integrity, and/or the presence of an infection or a developing infection [e.g., bone infections (Osteomyelitis), and/or tissue necrosis].

As should be readily evident given the disclosure provided herein, the plates of the present invention can have one or more ISMs having a combination of one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above ISMs may be continuously monitored in order to provide a 'real-world' assessment of alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

B.8.B.5. Intramedullary Fixation: Rods and Nails

Intramedullary rods and nails are long metal rods which are implanted into the medullary cavity of a fractured long bone (e.g., a femur, humerus, or tibia), thereby providing greater stability and support to the bone during healing.

Intramedullary fixation of long bone fractures has been around for centuries. The earliest recorded evidence is that of an anthropologist who in the $16^{th}$ century traveled to Mexico and witnessed Aztec physicians placing wooden sticks into the medullary canals of patients with long bone non-unions. Ivory and metal was also utilized in early treatments, although the rate of infection and complications was very high. During the 1900s, Gerhard Küntscher believed that the same science behind the Smith-Petersen nails might work for diaphyseal fractures, and thus he developed his 'marrow nail'.

Since that time the science of intramedullary devices (e.g., rods and nails) has expanded greatly. Today there are a wide variety of intramedullary rods or nails which are designed for specific applications, including for example, interlocking nails, Küntscher nails, Ender's nail, Grosse-Kempf (GK) nails, Gamma nails, and Rush nails.

Figure 30A:
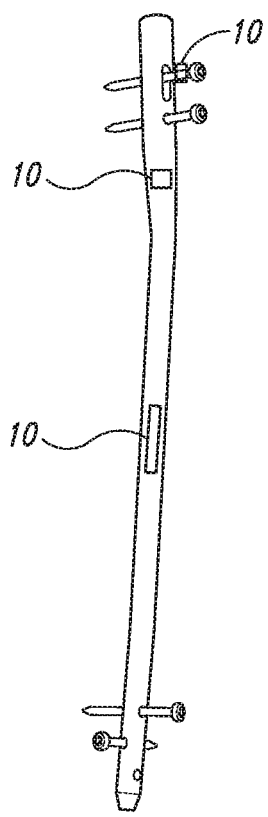
FIGS. 30A and 30B illustrate representative intramedullary rods or nails, including an intramedullary nail (FIG. 30A) having ISMs, and placement of an intramedullary nail having ISMs in the tibia (FIG. 30B).
Figure 30B:
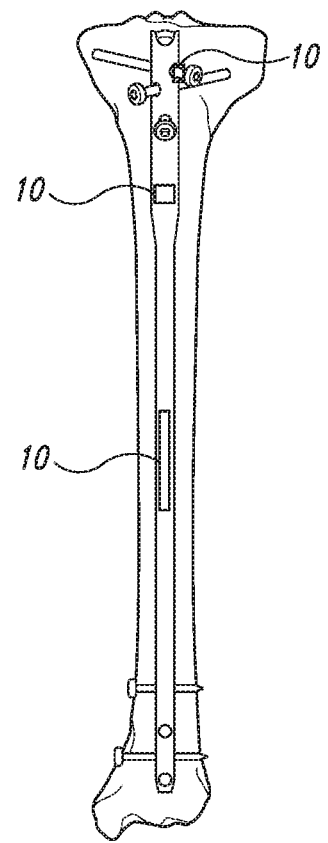

As noted above, the present invention provides intramedullary rods and nails (also referred to as "intramedullary devices") which have ISMs containing a variety of sensors. FIG. 30A illustrates a representative flexible nail or rod having an ISM for intramedullary fixation. FIG. 30B illustrates the rod or nail within the humerus.

Within one embodiment of the invention ISMs having pressure sensors are provided on or within an intramedullary rod or nail device. The ISMs can be positioned within specific locations (e.g., at the ends, on or around screw holes in interlocking nails, or contained within the shaft of the rod or nail), or distributed throughout the intramedullary device. They can be utilized to assist in implanting the intramedullary nail or rod device by detecting soft tissues, bone and marrow, and or movement through tissue or bone during placement. They can also be useful after placement. For example, detection of increased pressure can indicate the potential for stress shielding or the potential for bending cracking or fracture of the rod or nail. Detection of a rapid change in pressure can indicate rod or nail breakage. Detecting a slow decrease in pressure can indicate that healing is occurring and can assist in decisions on weight bearing and rehabilitation. Monitoring the pressure around the screw holes can assist with appropriate tightening during placement; later it can be used to detect "backing out" of the screws or other complications such as breakage.

Within another embodiment intramedullary devices are provided with ISMs having accelerometers (and strain gauges). Such ISMs can be distributed on, or within the intramedullary device at specific or randomized locations. Within certain embodiments they may be concentrated on specific locations (e.g., on both ends, and/or around screw holes, or contained within the shaft of the rod or nail). The accelerometers can be useful during placement and removal (if necessary) of the intramedullary device, during movement through different tissues, and for proper placement, fit, alignment, movement and imaging.

ISM accelerometers and strain gauges can also be useful after placement of an intramedullary device. For example, they can be utilized post-operatively to monitor alignment, stability, healing, patient activities, stresses across the fracture, axial loading, and rod/nail rotation, bending, breakage or slippage.

Within another embodiment of the invention intramedullary devices are provided with one or more ISMs having one or more position sensors/location marker sensors. The ISMs can be distributed on, or within, the intramedullary device at specific or randomized locations. Within certain embodiments they may be concentrated on specific locations (e.g., at the ends, and/or around screw holes, or contained within the shaft of the rod or nail). The ISM position sensors/location marker sensors can be useful during placement and removal (if necessary) of the intramedullary device, during movement through different tissues (soft tissue, cortical bone cancellous bone, marrow, through the fracture plane), to monitor alignment, and in an imaging function after placement.

ISM position sensors/location marker sensors can also be useful after placement of an intramedullary device. For example, they can be utilized to monitor healing anatomy, and compare changes in location over time (e.g., post-surgery). They can also be utilized to monitor alignment, shifting and migration, to confirm fracture immobilization, and to detect rod/nail bending and/or breakage. Importantly, intramedullary devices with position sensors/location markers can be utilized to detect movement, slippage and alignment changes before serious complications arise.

Within yet other embodiments of the invention intramedullary devices are provided with and ISM having temperature sensors and or chemical sensors. Briefly, temperature and/or chemical sensors can be utilized to monitor mineralization, tissue health, bleeding, tissue temperature, tissue integrity, and/or the presence of an infection or a developing infection [e.g., bone infections (Osteomyelitis), and/or tissue necrosis].

In a particularly preferred embodiment, an intramedullary rod or nail is provided with an ISM containing multiple sensors located in the "shaft" of the shaft of the rod or nail. For an ISM collecting mechanical data (position, motion, vibration, rotation, shock, tilt, steps), the implanted ISM sensors (accelerometers, position sensors, pedometers) have the advantage of not requiring either direct physical contact with the surface of the device or with patient tissues; only a secure and immobile attachment within the intramedullary rod or nail is needed. In this preferred embodiment, the ISM containing multiple mechanical sensors (as described above) is placed within the internal canal of the intramedullary rod or nail; a location that provides more than enough space to insert and seal an ISM with multiple sensor functions and battery capability. Furthermore, the motion of the intramedullary rod or nail as the lower limb goes through its range of motion during normal activities (such as walking) can provide opportunities to power the ISM.

As should be readily evident given the disclosure provided herein, the intramedullary devices of the present invention can have one or more ISMs having a combination of one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' assessment of the alignment of the bone, to assist in detecting mobility/immobility of the fracture (and associated joints), to monitor healing and the development of complications, to collect and compare procedure performance data over time, to evaluate patient function, and to better understand the conditions which implants are exposed to in the real world.

B.8.B.6. General Considerations

In summary, one or more ISMs having a combination of one or more sensors may be placed on and/or within internal orthopedic hardware in order to provide "real time" information and feedback to the surgeon during and after the procedure, to detect proper device placement, to achieve proper fracture reduction and alignment during and after surgery, and to detect and monitor the forces the implant will be subjected to in the activities of daily life.

As will be readily evident given the disclosure provided herein, the ISMs described and claimed herein can comprise a variety of different sensors within different locations of the ISM. In addition, within various embodiments of the invention one or more sensors may be placed separate from the ISM (but still be, optionally, able to communicate with and be controlled by the ISM). Representative examples of sensors placed on an orthopedic hardware device, or an orthopedic hardware surgical delivery device are provided in U.S. Provisional No. 62/017,106, which is hereby incorporated by reference in its entirety.

B.9. Medical Polymers

Within another aspect of the invention, ISMs as described herein are provided for use in one or more polymers. "Polymer" refers to a macromolecule, typically in excess of 1,000 g/mol, or in excess of 5,000 g/mol molecular weight, or in excess of 10,000 g/mol, which comprises a plurality of repeating units that are present as part of the backbone of the polymer, the plurality typically in excess of 10, or in excess of 20, or in excess of 50.

Polymers may be composed of synthetic materials (e.g., silicone, polyurethane and rubber), composed of non-synthetic components (e.g., collagen, fibrin, hyaluronic acid, chitosan, and harvested grafts for bypass), or some combination of these (e.g., artificial blood vessels having a synthetic polymer scaffold, and naturally occurring cells (e.g., fibroblasts) which produce matrix materials for the vessel (e.g., collagen). Representative examples of polymers include polyester, polyurethanes, silicones, epoxy resin, melamine formaldehyde resin, acetal, polyethyelene terephthalate, polysulphone, polystyrene, polyvinyl chloride, polyamide, polyolefins, polycarbonate, polyethylene, polyamides, polimides, polypropylene, polytetrafluoroethylene, ethylene propylene diene rubber, styrenes (e.g., styrene butadiene rubber), nitriles (e.g., nitrile rubber), hypalon, polysulphide, butyl rubber, silicone rubber, cellulose, chitosan, fibrinogen, collagen, hyaluronic acid, PEEK, PTFE, PLA, PLGA, PCL and PMMA.

The polymer containing sensors of the present invention are preferably suitable for medical applications (e.g., medical devices and/or implants as described herein), and hence are preferably sterile, non-pyrogenic, and/or suitable for use and/or implantation into humans. However, within certain embodiments of the invention the polymer can be made in a non-sterilized environment (or even customized or "printed" for an individual subject), and sterilized at a later point in time.

B.9.A. Polymers

A wide variety of polymers can be utilized with the ISMs described herein. Examples include polyester, polyurethane, silicone, epoxy resin, melamine formaldehyde resin, acetal, polyethyelene terephthalate, polysulphone, polystyrene, polyvinyl chloride, polyamide, polycarbonate, polyethylene, polypropylene, polytetrafluoroethylene, ethylene propylene diene rubber, polyurethane rubber, styrene butadiene rubber, nitrile rubber, hypalon, polysulphide, butyl rubber, and silicone rubber. The polymer may be classified by whether it is synthetic or non-synthetic. In addition, or alternatively, it may be classified as being biodegradable or non-biodegradable. In one embodiment, the polymer is a synthetic biodegradable polymer, for example, a co-polymer of lactide and glycolide. In another embodiment, the polymer is a synthetic non-biodegradable polymer, such as polyvinyl chloride. In another embodiment, the polymer is a non-synthetic, i.e., a natural occurring polymer that is biodegradable, such as collagen, fibrinogen, and/or hyaluronic acid. In another aspect, the polymer is a non-synthetic polymer that is non-biodegradable, e.g., cellulose and chitin. Some of these, as well as additional examples, are discussed further below.

In one embodiment ISMs may be contained in a polymer such as a polyester. Polyesters contain repeating ester groups separated by aliphatic or aromatic groups. Polyesters may be formed by reaction between a di-acid (e.g., adipic acid, phthalic acid) and a di-alcohol (e.g., ethylene glycol, butylene glycol), or reactive equivalents thereof. The polyester may be biodegradable, such as polylactic acid (PLA), poly (lactic-co-glycolic) acid (PLGA), and polycaprolactone (PCL).

In another embodiment ISMs may be contained in a polymer such as a polyether, optionally including other repeating units. For example, the polymer may be a polyetherimide, having both repeating ether and imide groups. As another example, the polymer may be a polyethersulfone, with repeating ether and sulfone groups.

The polymer may be characterized in terms of its thermal properties. For example, in one embodiment the polymer is a thermoplastic. A thermoplastic becomes plastic (i.e., fluid) upon heating and hardens upon cooling and is able to repeat this phase change multiple times in response to changes in temperature. Examples of thermoplastics include PET, polysulphone, polystyrene, UPVC, polyamides, polycarbonates, polyethylene, polypropylene and PTFE. In another embodiment the polymer is a thermoset. A thermoset is does not become fluid upon heating, but instead retains it hardened form even at elevated temperature. Examples of thermosets include epoxy and phenolics.

In another embodiment ISMs may be contained in a polymer such as a phenolic. Many phenolic polymers are thermoset. Phenolic resins are typically formed between a phenol and formaldehyde, and is sometimes referred to a phenol formaldehyde resin. Novolacs are phenolics made with a formaldehyde to phenol molar ratio of less than one, while resoles are phenolics made with a formaldehyde to phenol ratio of greater than one (usually around 1.5).

The polymer may be an epoxy. Many epoxy polymers are thermoset. Hardened epoxy resins are formed between a polyepoxide compound (often a di-epoxide) and a curing agent such as a poly-hydroxyl or poly-amine. A common epoxy resin is the reaction product between epichlorohydrin and bisphenol A to form diglycidyl ethers of bisphenol A. A common curing agent is triethylenetetramine. Epoxy resins may also be thermally cured. Epoxy resins are tough and resistant to many environments, making them useful components of many medical polymers.

ISMs may also be incorporated in to a polymer such as a polyolefin. Many polyolefin polymers are thermoplastic. Exemplary polyolefins are polyethylene (PE) and polypropylene (PP). Polyolefins are commercially available in a wide range of molecular weights, and different molecular weights have different properties and different applications. For example, ultra-high molecular weight PE can be used to prepare load bearing materials in total joint replacements.

In one aspect, the invention utilizes ISMs in polyethylene, for example crosslinked polyethylene (XLPE) and ultra high molecular weight polyethylene (UHMWPE) which may be crosslinked. The crosslinked polyethylene may be so-called highly-crosslinked polyethylene. (See, e.g., Lachiewicz et al. "The use of highly cross-linked polyethylene in total knee arthroplasty" *J Am Acad Orthop Surg.* 2011 March; 19(3): 143-51, and Journal of the AAOS (Vol. 16, Supplement 1, 2008), providing the proceedings of a symposium titled 2007 AAOS/NIH Osteolysis and Implant Wear: Biological, Biomedical Engineering, and Surgical Principles, and Glyn-Jones et al. "The creep and wear of highly cross-linked polyethylene: a three-year randomized controlled trial using radiostereometric analysis" *J Bone Joint Surg Br.* 2008 May; 90(5):556-61, and Hodrick et al. "Highly crosslinked polyethyelene is safe for use in total knee arthroplasty" Clin Orthop Relat Res. November 2008; 466(11): 2806-2812. See also PCT Publication WO2013/124577 and U.S. Pat. Nos. 8,728,379; 8,663,335; 8,653,154; 7,431,874; 7,182,784; and 6,726,727, all of the above of which are incorporated by reference in their entirety.

In another embodiment ISMs may be contained in a polymer such as an acrylonitrile butadiene styrene (ABS), which is typically a thermoplastic. As its name suggests, ABS is formed by copolymerization of the monomers acrylonitrile, butadiene and styrene. ABS may be viewed as a styrene-acrylonitrile copolymer modified by butadiene rubber. ABS combines the resilience of polybutadiene with the hardness and rigidity of polyacrylonitrile and polystyrene. The properties of the ABS polymer depend to a large extent on the relative amount of each of the monomers used in its preparation. Acrylonitrile tends to impart chemical resistance, heat stability, increased tensile strength, and aging resistance. Styrene tends to impart gloss and rigidity, and also help aid is processing the plastic. Butadiene imparts toughness, impact strength, good low temperature properties.

In another embodiment ISMs may be contained in a polymer such as an ethylene vinyl alcohol (EVA, or EVAL or EVOH) copolymer which is formed by copolymerization of ethylene and vinyl acetate, whereupon the acetate groups are hydrolyzed to hydroxyl (alcohol) groups. EVOH is biocompatible and biodegradable. EVOH is recognized as having excellent barrier properties to oxygen, and accordingly is often used as a coating to provide this desirable function.

In another embodiment ISMs may be contained in a polymer such as a fluoroplastic. As used herein, a fluoroplastic refers to a polymer that is a thermoplastic and which contains carbon-fluorine bonds. Examples are poly(tetrafluoroethylene), also known as PTFE.

The polymer may be polyvinyl chloride (PVC). PVC comes in two basic grades: flexible and rigid. The flexible form is typically prepared by incorporation of various additives into the PVC, where exemplary additives are plasticizers (e.g., phthalates) and stabilizers. Flexible PVC is used in many medical applications due to its biocompatibility, transparency, softness, light weight, high tear strength, kink resistance, and suitability for sterilization. PVC may be chlorinated to increase its chlorine content, thereby creating CPVC.

In another embodiment ISMs may be contained in a polymer such as a polysulfone (PS). For example, the polymer may be a polyphenylsulfone. Westlake Plastics (Lenni, Pa.) markets medical grade Radel R5500 polyphenylsulfone resin. This polymer provides hydrolytic stability, toughness, and good impact strength over a wide temperature range. Recommended sterilization techniques for Radel R5500 include EtO gas, radiation, steam autoclaving, dry heat and cold sterilization.

In another embodiment ISMs may be contained in a polymer such as a polyether ether ketone (PEEK). An exemplary PEEK polymer is formed by reaction of 4,4'-difluorobenzophenone with the disodium salt of hydroquinone. PEEK is a semicrystalline, high-temperature (up to 500° F.) engineering thermoplastic that is useful in applications where thermal, chemical, and combustion properties are important to performance. PEEK also resists radiation and a wide range of solvents including water. With its resistance to hydrolysis, PEEK can withstand boiling water and superheated steam used with autoclave and sterilization equipment at temperatures higher than 482° F., thus making it useful in the manufacture of many medical parts.

In another embodiment ISMs may be contained in a polymer such as a polycarbonate (PC). For example, Westlake Plastics (Lenni, Pa.) markets medical grade Zelux GS polycarbonate which may be sterilized by EtO gas and limited autoclaving sterilization.

In another embodiment ISMs may be contained in a polymer such as a polyimide, such as a polyetherimide. For example, Westlake Plastics (Lenni, Pa.) markets medical grade Tempalux polyetherimide. This polymer maintains its size and shape over a broad temperature range as well as tolerates a high amount of stress over extended periods of time. Recommended sterilization techniques for Tempalux include EtO gas, radiation, steam autoclaving, dry heat and cold sterilization.

In another embodiment ISMs may be contained in a polymer such as a one with repeating oxymethylene units. For example, the polymer may be a homopolymer of oxymethylene units, which is known polyoxymethylene (POM) or acetal or polyacetal. The term POM will be used to refer to homopolymers prepared from formaldehyde or equivalent, which may have various endgroups to enhance the stability of the homopolymer. When a high molecular weight version of the homopolymer is reacted with acetic anhydride, the resulting product is hard, rigid and has high strength. A version is sold by du Pont (Wilmington Del.) as their Delrin polymer and advertised for use in medical products. The polymer may be a copolymer including repeating oxymethylene units. For example, formaldehyde may be converted to 1,3,5-trioxane, which in turn is reacted with a suitable co-monomer such as ethylene oxide or dioxolane. Hostaform from Ticona (now Celanese, Irving, Tex.) and Ultraform from BASF (Florham Park, N.J.) are two examples of commercially available oxymethylene copolymers. Polyplastics (Taipei, Taiwan) manufactures DURACON POM, which may be used in medical products. TECAFORM MT is a POM manufactured by Ensinger Inc. (Washington, Pa.) which is particularly suited for use as sizing trials in knee, hip and shoulder replacement procedures.

The polymer may be characterized in terms of its viscoelastic properties. For example, in one embodiment the polymer is elastic, in which case the polymer may be referred to as an elastomer. At ambient temperatures, elastomers are relatively soft and deformable, i.e., they may be stretched and will return back to its original shape after the stretching force is removed. One type of elastomer is a rubber, where a rubber is typically formed by a process that includes vulcanization. Alternatively, the polymer may be rigid and non-deformable.

In another embodiment ISMs may be contained in a polymer such as a polyurethane. Polyurethanes are formed when a polyol (i.e., a polyhydroxylated compound) reacts with a diisocyanate or a polymeric isocyanate when there are suitable catalysts and additives present. The polyurethane may be a thermoset, particularly when crosslinking reactants are used in its preparation. Alternatively, the polyurethane polymer may be an elastomer. For example, Bayer (Leverkusen, Germany) markets Vulkollan® polymer which is produced by reacting polyesterpolyols, Desmodur® 15 (one or both of MDI (diphenylmethane diisocyanate) and TDI (toluylene diisocyanate) and glycols at temperatures exceeding 100° C. in a multistage process. Vulkollan® polymer may be formed into parts and is particularly well-suited when high mechanical load bearing and high dynamic load bearing capacity is needed. Another suitable polyurethane elastomer, also from Bayer, is Baytec® Spray, a material consisting of two liquid, polyurethane-based components. Baytec® Spray can be used to provide an elastomeric coating on the surface of a polymer.

In another embodiment ISMs may be contained in a polymer such as a may be a natural polymer or a synthetic polymer. A natural polymer is found in nature, where rubber is an example of a natural polymer. A synthetic polymer is not found in nature but is instead made through human-controlled chemical reactions. Polyurethanes are exemplary synthetic polymers. Carbohydrates (e.g., cellulose, hyaluronic acid) and poly(amino acid) (e.g., protein, collagen) are examples of natural polymers. Cellulose finds use in, e.g., the manufacture of dialysis membranes. Chitin is a natural polymer, however the synthetic deacylation of chitin produces the synthetic polymer chitosan. Hyaluronic acid is a natural polymer that finds use in the treatment of osteoarthritis and other joint disorders.

In another embodiment ISMs may be contained in a polymer such as a synthetic elastomer, also known as a synthetic rubber. There are several well-known synthetic elastomers, which are named from the monomer(s) from which they are produced. Those elastomers include cis-polybutadiene (butadiene rubber, BR), styrene-butadiene rubber (SBR), ethylene-propylene monomer (EPM), acrylonitrile-butadiene copolymer (nitrile rubber), isobutylene-isoprene copolymer (butyl rubber), ethylene-propylene-diene monomer (EPDM, where the diene may be, e.g., butadiene), and polychloroprene (neoprene). In large part these synthetic rubbers consist of two or more different monomer units, e.g., styrene and butadiene, arranged randomly along the molecular chain. EPM and nitrile rubber also consist of a random arrangement of two monomers—in this case, ethylene and propylene (which form EPM) and butadiene and acrylonitrile (which form nitrile rubber). Another suitable rubber is silicon rubber, which finds widespread use in catheters and other types of medical tubing. Silicon rubber may be prepared by curing a liquid precursor, e.g., with a platinum catalyst, usually at elevated temperature. The glass transition temperatures of all these polymers are quite low, well below room temperature, so that all of them are soft, highly flexible, and elastic. The present disclosure provides that any one or more of the named synthetic rubbers may be used in the compositions and methods as identified herein.

Instead of an organic polymer, the polymer or coating may be formed in whole or in part from a ceramic biomaterial, sometimes referred to as a bioceramic. An example of a ceramic biomaterial is hydroxyapatite, which may be combined with a binder to create a solid mass or a coating. Suitable binders include collagen, gelatin, and polyvinylalcohol. A sol-gel process may be used to prepare the final product. Other examples of bioceramics include alumina ($Al_2O_3$) and zirconia ($ZrO_2$), tricalcium phosphate ($Ca_3(PO_4)_2$), and bioglass ($Na_2OCaOP_2O_3$—SiO). The bioceramic may be biodegradable (e.g., tricalcium phosphate) or biostable (e.g., alumina). The bioceramics alumina and zirconia are used in orthopedics to produce, for example, femoral heads, artificial knees, bone screws and bone plates, and in dental applications are used to produce crowns and bridges.

The medical polymer may be multi-component. For example, it may be a blend of two or more polymers. As another example, it may be a composite of organic and inorganic materials. For example, the medical polymer may be a blend of polyester and a mineral component, or a blend of silicone and a mineral component.

B.9.B. Bone Cement and Other Implantable Materials

As described herein bone cement and other implantable materials can be utilized in a large number of orthopedic procedures (including for example, hip and knee procedures, spinal procedures and orthopedic procedures as described herein. Most typically, methylmethacrylates are utilized (e.g., polymethylmethacrylate, or amethylmethacrylate—styrene copolymer), although other materials can also be utilized.

However, a wide variety of implantable materials can also be utilized (see generally US 2007/0100449). For example, suitable materials include both biocompatible polymers, therapeutic agents, and naturally occurring materials. Biocompatible polymers may be both bioabsorbable and/or nonbioabsorbable. Typically, the polymers will be synthetics (e.g., aliphatic polyesters, poly(amino acids), copoly(etheresters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), copolymers of lactide (e.g., D,L lactide), glycolides, caprolactones and blends and copolymers thereof. However, in certain embodiments natural polymers can also be utilized (e.g., fibrin-based materials, collagen-based materials, hyaluronic acid-based materials, glycoprotein-based materials, cellulose-based materials, silks and combinations thereof).

Within certain embodiments of the invention the bone cement or implantable material may contain a desired agent, compound, or matrix, such as, for example, bone morphogenic protein or "BMP", bone graft material, and calcium phosphate.

The bone cement and other implantable materials described herein may contain one or more ISMs having one or more sensors, including for example, fluid pressure sensors, contact sensors, position sensors, pulse pressure sensors, fluid (e.g., blood, urine, bile) volume sensors, fluid (e.g. blood, urine, bile) flow sensors, air flow sensors, chemistry sensors (e.g., for blood, urine, bile and/or other fluids), metabolic sensors (e.g., for blood, urine, bile and/or other fluids), accelerometers, mechanical stress sensors and temperature sensors. Within certain embodiments the bone cement or implantable material will sensors at a density of greater than 1, 2, 3, 4, 5, 6, 7, 8, 9, 10 or 20 sensors per square centimeter; and or sensors a density of greater than 1, 2, 3, 4, 5, 6, 7, 8, 9, 10 or 20 sensors per cubic centimeter.

B.9.C. Manufacture of Medical Polymers

A polymer may be fabricated into a desired shape for a medical polymer by various methods including extrusion, molding (e.g., injection molding, compression molding) thermoforming, electrospinning, and cutting (e.g., stamping, die cutting). During the fabrication process, a sensor may be incorporated into the polymer.

For example, the polymer may be fabricated by a thermoforming technique, including vacuum, pressure and mechanical types of thermoforming. In general, thermoforming refers to a process of converting an initially flat thermoplastic sheet into a desired three-dimensional shape, where the process includes at least two stages: softening the sheet by heating, followed by forming it in a mold cavity. In vacuum thermoforming, the heated thermoplastic sheet is held in the cavity by means of vacuum produced between the sheet and the surface of the mold cavity space. In pressure thermoforming, gas pressure is applied against the heated sheet in the direction of the mold cavity, thereby forcing the sheet against the contours of the cavity. In mechanical thermoforming, a solid object is pushed against the sheet so that the sheet is forced against the contour of the mold. Upon cooling, the thermoplastic sheet adopts the shape of the mold. A sensor may be placed in the heated sheet before or during the forming process, so that upon cooling, the sheet adopts a desired shape and the sensor is embedded in whole or in part in the thermoplastic sheet.

As another example, the polymer may be fabricated by a molding process, whereby solid or molten polymer or prepolymer is placed within a mold. Upon cooling, the polymer will adopt the configuration of the mold. Various types of molding process that may be used. For example, compression molding squeezes a pre-polymer into a pre-heated mold and then applies heat and pressure to the pre-polymer, causing the pre-polymer to cure into the shape of the mold. This process may be used for both thermoplastic and thermosetting polymer. In blow molding, a heated hollow thermoplastic tube is inflated within a closed mold until it adopts the shape of the mold. Upon cooling, the newly shaped tube will retain the shape of the mold.

Electrospinning is particularly suited for preparing polymeric fibers, and represents another example of fabricating a polymer. For example, it can be used to form nanofibers from various organic polymers. See, e.g., Doshi, J. and Reneker, D. H., Journal of Electrostatics 35(2-3):151-160, 1995. Fibers formed from electrospinning may be made into various shapes, including matrices formed from woven and non-woven fibers. Sensors may be embedded within the matrix formed from the electrospun fibers.

As yet another example, the medical article may be formed by any of weaving, plying, braiding, knitting, and stitching of polymeric fibers. These processes may be used to form various shapes, including a sheet (as found, e.g., in a mesh), filament (as found, e.g., in a suture), and a tube (as found, e.g., in a graft). See, e.g., U.S. Pat. No. 5,378,469 directed to high strength collagen threads, which are optionally crosslinked, where the threads may be used to form braided constructs, plied into yarn, and knitted to provide an implant. A sensor as described herein can be incorporated in, or associated with, the braided, knitted, or woven materials.

The medical polymer may be sterilized by techniques known in the art. For example, the medical polymer may be exposed to ionizing radiation, such as gamma radiation and electron beam radiation. While ionizing radiation may sterilize the medical polymer, it can also cause some breakdown of the polymer's basic structure. To combat this problem, stabilizers may be added to the polymer, where examples include antioxidants such as phenolics that react with free radicals, and organo-phosphorous compounds which react with peroxide and hydroperoxides generated by the reaction of oxygen with reactive sites generated by the ionizing radiation. Another sterilization technique is to expose the medical polymer to ethyelene oxide. An advantage of ethylene oxide sterilization is that it is not harmful to the structure of the polymer, and accordingly is a suitable sterilization technique when a medical polymer must be repeated sterilized. Another sterilization technique is to expose the medical polymer to high temperature, optionally in the presence of steam, e.g., in an autoclave.

B.9.D. Use of Medical Polymers in Medical Polymers and Implants

Polymers containing ISMs can be utilized in a wide variety of medical devices and implants, including for example, hip and knee prosthesis, tubes (e.g., grafts and catheters), implants (e.g., breast implants), spinal implants, orthopedic and general surgery implants, and cardiovascular implants (e.g., stents, stent grafts, and heart valves). Representative examples of such implants are discussed in more detail in International Patent Application No. PCT/US2013/077356; International Patent Application No. PCT/US2014/028323; International Patent Application No. PCT/US2014/028381; International Patent Application No. PCT/US2014/043736; U.S. Provisional Patent Application No. 62/017,086 Entitled 'Devices, Systems and Methods for Using and Monitoring Catheters', filed Jun. 25, 2014; U.S. Patent Provisional Application No. 62/017,099 Entitled 'Devices, Systems and Methods for Using and Monitoring Implants, filed Jun. 25, 2014; U.S. Patent Provisional Application No. 62/017,106 Entitled 'Devices, Systems and Methods for Using and Monitoring Spinal Implants', filed Jun. 25, 2014; U.S. Patent Provisional Application No. 62/017,116 Entitled 'Devices, Systems and Methods for Using and Monitoring Orthopedic Hardware', filed Jun. 25, 2014; U.S. Patent Provisional Application No. 62/017,161 Entitled 'Devices, Systems and Methods for Monitoring Heart Valves', filed Jun. 25, 2014; all of the aforementioned patent applications incorporated herein by reference in their entireties for all purposes.

Some additional discussion of medical polymers and devices that can be used in the present invention is as follows:

B 9.D.1. Glues, Adhesives and Cements

The medical polymer may be useful to hold tissue together, or to hold tissue together with a medical implant, such as a glue or adhesive, where the tissue includes soft tissue or bone. When used in bone, the medical polymer is frequently referred to as a bone cement, where bone cement is also used to fill in cavities of bone. For example, the polymer may be the reaction product of two synthetic polyethylene glycols which have reactive endgroups such that upon forming a mixture of the two components, the two materials react with one another and form a crosslinked film. A version of this material is commercially available as COSEAL (Baxter Healthcare, Fremont, Calif., USA). See, e.g., Cannata, A., et al., Ann. Thorac. Surg. 2013, 95:1818-1826. COSEAL may be spayed over a large area, and to varying depths, to provide a glue or adhesive layer on living tissue. A modified chitosan-dextran gel as prepared by the process described in Liu G., et al. Macromolecular Symposia 2009 279:151. See, e.g., Lauder, C. I. W., et al. Journal of Surgical Research 2012 176:448-454. This material may be applied to soft tissue and will function to hold the tissue together. A sprayable material that functions primarily as a barrier but also has some adhesive properties is marketed by Covidien and known as SprayShield. SprayShield is a synthetic two-component product that forms a gel when applied to an organ.

As an example, a syringe containing a product such as COSEAL can be delivered along with, or admixed with an ISM as provided herein. Within various embodiments one or more ISMs having sensors (e.g., fluid pressure sensors, contact sensors, position sensors, pulse pressure sensors, liquid (e.g., blood) volume sensors, liquid (e.g., blood) flow sensors, chemistry sensors (e.g., for blood and/or other fluids), metabolic sensors (e.g., for blood and/or other fluids), accelerometers, mechanical stress sensors and temperature sensors) can be incorporated into one or more polymers.

B.9.D.2. Medical Polymers—Meshes and Films

Various medical polymers are used to form implantable films of meshes. For example, the biodegradable copolymer of hydroxybutyrate and hydroxyvalerate known as (PHBV) is available from Metabolix, Inc. (Cambridge, N.J., USA) and can function as a barrier film. Oxidized regenerated cellulose is commercially available as Interceed (Johnson & Johnson, Canada), which is a knitted fabric that converts to a gel within 8 hours and is completely cleared from the body within 28 days. See, e.g., Larsson B., J. Reprod. Med. 1996, 41:27-34 and ten Broek R. P. G., et al., The Lancet 2014 383:48-59. Collagen foil in combination with polypropylene mesh is commercially available as TissueFoil E from Baxter (Germany). See, e.g., Schonleben, F., Int. J. Colorectal Dis. 2006, 21(8):840-6. INTERCOAT, also known as OXIPLEX AP, made by Johnson & Johnson and licensed from Fziomed, may be used as an implantable film. PREVADH, made by Sofradim-Covidien in France is a collagen film and fleece composite that may be used as an implantable filem. W.L. Gore manufactures and sells non-absorbable adhesion barrier films using expanded polytetrafluoroethylene film, sometimes referred to as GoreTex Surgical Membrane or as Preclude. Each of these films may be used as a medical polymer according to the present invention.

Meshes are available from various vendors. For example, Ethicon markets a synthetic mesh, PROLENE mesh, made from polypropylene. Biological meshes are also known and may be used in the present invention. Examples are meshes formed from human or animal dermis or porcine small intestinal submucosa. See, e.g., Nguyen et al., JAMA Surg., epub Feb. 19, 2014 and Carbonell et al., J. Am. Coll. Surg., 217(6):991-998, 2013.

Within one embodiment of the invention one or more ISMs can be incorporated into a mesh (e.g., by interweaving, attaching, interlayering, or otherwise securing the ISM to the mesh). Representative examples of ISMs have one or more sensors such as fluid pressure sensors, contact sensors, position sensors, pulse pressure sensors, liquid (e.g., blood) volume sensors, liquid (e.g., blood) flow sensors, chemistry sensors (e.g., for blood and/or other fluids), metabolic sensors (e.g., for blood and/or other fluids), accelerometers, mechanical stress sensors and temperature sensors. Sensors within a mesh or film can be utilized to determine contact between various organs or anatomical structures (e.g. utilizing contact sensors and/or pressure sensors); the presence of or development of an infection (e.g., utilizing temperature and/or metabolic sensors), to determine degradation, wear, movement and/or fracture (e.g., utilizing contact sensors, pressure sensors, and/or location sensors).

B.9.D.3. Medical Polymers—Suture and Staples

The medical polymer may be formed into a device for securing or fastening tissue, such as a staple or a suture. See, e.g., U.S. Pat. Nos. 8,506,591 and 8,721,681 as well as U.S. Publication Nos. 2001/0027322, 2006/0253131, 2011/0093010, 2013/0165971, and 2014/0130326 for exemplary suitable staples and discussion of insertion devices. The medical polymer may be formed into a suture, e.g., PROLENE polypropylene suture by Ethicon (New Jersey), or DEKLENE polypropylene suture sold by Teleflex Medical (North Carolina). See also, e.g., U.S. Pat. Nos. 6,908,466; 4,750,492; 4,662,068 for medical fasteners prepared in whole or part from polymer.

Within one embodiment of the invention one or more ISMs can be incorporated into, or otherwise attached or secured to a fixation device such as a suture or staple. The Isms can have one or more sensors such as fluid pressure sensors, contact sensors, position sensors, pulse pressure sensors, liquid (e.g., blood) volume sensors, liquid (e.g., blood) flow sensors, chemistry sensors (e.g., for blood and/or other fluids), metabolic sensors (e.g., for blood and/or other fluids), accelerometers, mechanical stress sensors and temperature sensors. Sensors within a suture or staple can be utilized to determine contact with various organs or anatomical structures (e.g. utilizing contact sensors and/or pressure sensors); the presence of or development of an infection (e.g., utilizing temperature and/or metabolic sensors), to determine degradation, wear, movement and/or fracture (e.g., utilizing contact sensors, pressure sensors, and/or location sensors).

As will be readily evident given the disclosure provided herein, the ISMs described and claimed herein can comprise a variety of different sensors within different locations of the ISM. In addition, within various embodiments of the invention one or more sensors may be placed separate from the ISM (but still be, optionally, able to communicate with and be controlled by the ISM). Representative examples of polymers for use with ISMs are provided in U.S. Provisional No. 62/017,159, which is hereby incorporated by reference in its entirety).

B.10. Heart Valves

Within another aspect of the invention, ISMs as described herein are provided for use in one or more types of heart valves. As utilized herein "heart valve" refers to a device which can be implanted into the heart of a patient with valvular disease. There are three principle types of heart valves: mechanical, biological, and tissue-engineered (although, for purposes of this disclosure tissue-engineered valves will be considered along with other biological valves). Mechanical and biological valves typically fall into two categories: 1) heart valves for surgical procedures utilizing a sternotomy or "open heart" procedure (e.g., 'caged ball', 'tilting disc', bileaflet and trileaflet biologic designs with sewing rings for attachment in the valvular annulus); and 2) heart valves which are percutaneously implanted [e.g., either a stent framed (self-expanding stent or balloon-expandable stent) or non-stent framed design] that can often contain valve cusps which are fabricated from biological sources (bovine or porcine pericardium). Tissue-based or 'biological' valves are typically made from either porcine or bovine sources, and are usually prepared either from the valve of the animal (e.g., a porcine valve), or from tissue of the pericardial sac (e.g., a bovine pericardial valve or a porcine pericardial valve). Tissue-engineered valves are valves that have been artificially created on a scaffold (e.g., through the growth of suitable cells on a tissue scaffold). Tissue-engineered valves have not yet been commercially adopted.

In addition to heart valves, delivery devices are also provided. In the context of percutaneous heart valve delivery, particularly preferred delivery devices comprise a guidewire, delivery catheter, catheters with a "sheath" that deploy self-expanding devices, catheters with an expandable balloon, and anchoring suture devices. By utilizing such devices and methods heart valves can be replaced without the need for open heart surgery.

Representative examples of heart valves and associated delivery devices are described in U.S. Pat. Nos. 6,564,805, 6,730,122, 7,033,090, 7,578,842, 8,142,497, 8,287,591, and 8,568,474; U.S. Publication Nos. 2010/0076548, 2010/0161046, 2010/117471, 2011/0009818, 2011/0190897, 2012/0179243, 2013/0096671, 2013/0166023, 2013/0268066; and PCT Publication Nos. WO 2012/011108, and WO 2013/021374; all of the above of which are incorporated by reference in their entirety.

The present invention provides heart valves and related delivery devices, all of which have sensors as described in further detail below. The heart valve and related delivery devices are preferably sterile, non-pyrogenic, and/or suitable for use and/or implantation into humans. However, within certain embodiments of the invention the heart valve and/or delivery device can be made in a non-sterilized environment (or even customized or "printed" for an individual subject), and sterilized at a later point in time.

B.10.A. Heart Valves and their Use

B.10.A.1. Mechanical Heart Valves and their Use

B.10.A.1.1. 'Open Heart' Surgery Heart Valves: "Caged Ball", "Tilting Disc", and Bi and Tri-Leaflet Designs As noted above, within various embodiments of the invention, mechanical heart valves are provided with one or more ISMs as described herein. Representative examples include: 1) heart valves based upon a "caged ball" design [e.g., these devices have a restraining cage (typically made of metal), an occluder ball (typically made from a silicone elastomer), and a suture ring) such as the Starr-Edwards valve and the Smeloff-Cutter valve]; 2) heart valves based upon a "tilting disc" design [typically including an occluder disc that rotates on a flange and 2 metal struts (an inlet and an outlet strut) which stop the occluder disc in either the open or the closed position; additionally, there is a metal ring covered by ePTFE that is used as a suture ring to anchor the valve in place]; and 3) bileaflet and trileaflet valves (with two or three hinged leaflets and a anchoring suture ring).

Mechanical valves have improved greatly since their introduction, yet they still suffer from numerous complications. For example, the caged-ball design can last for a long time, but require a lifetime of anticoagulation for the patient. Red blood cells and platelets get damaged flowing through the mechanical valves which can lead to a hypercoagulative state that can result in thrombus and embolis formation (necessitating blood thinner therapy) and can even result in anemia. The leaflet (bileaflet and trileaflet) mechanical valves cause less damage to blood cells (and are less thrombogenic and require lower levels of anticoagulation therapy), but they are vulnerable to backflow. Mechanical valves are also subject to impact wear (occurs in the hinges of bileaflet valves, between the occluder and ring in tilting disc valves, and between the ball and cage in ball-cage valves) and frictional wear (occurs between the occluder and the struts in tilting disc valves and between the leaflet pivots and hinge cavities in bileaflet valves), and can cause 'cavitation' (i.e., the formation of microbubbles, which can erode the valve surface, increase blood cell damage and increase the incidence of thromboembolic events).

Hence, the present invention provides mechanical heart valves which have one or more ISMs having one or more sensors, including for example, fluid pressure sensors, contact sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, mechanical stress sensors, and temperature sensors. Such sensors can be placed on, in, or within the various components of the heart valve, and can be utilized to monitor, amongst other things, thrombogenesis, wear, blockage, sticking (impaired movement of the 'valve'), trans-valvular pressure gradients (an indicator of the potential for cavitation), cardiac function, leakage (backflow or regurgitation), detachment of the suture ring (from, for example, suture breakage), assembly of the device (where possible), correct anatomical placement of the device, failure, and safety. Within preferred embodiments of the invention ISMs can be provided on the sewing ring or other sites that are utilized to attach the valve to the heart.

Figure 31B:
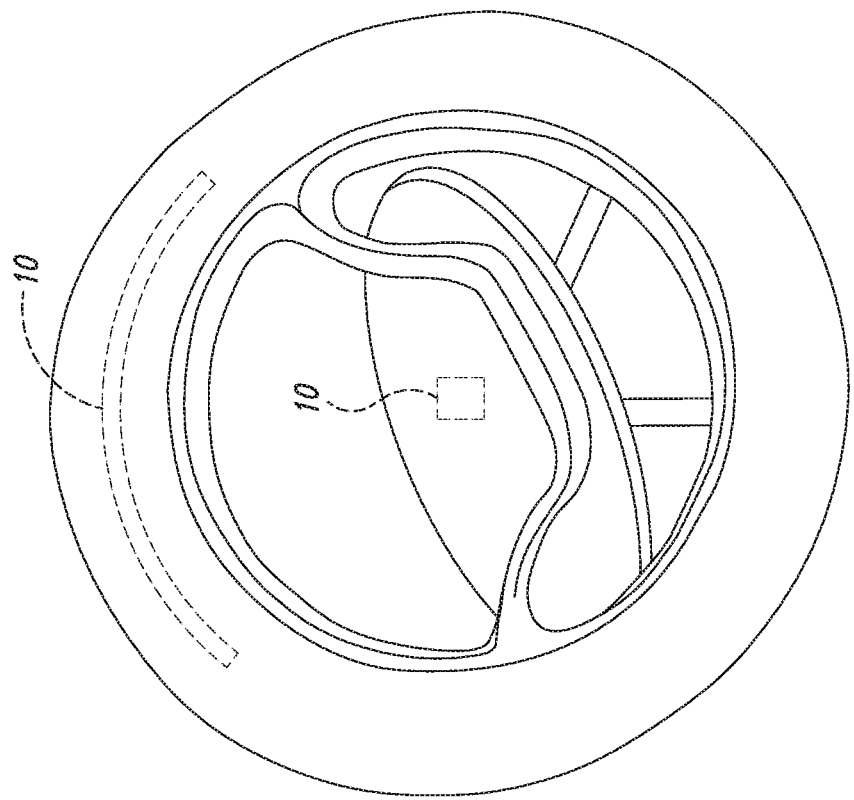
FIG. 31B illustrates a tilting disc mechanical valve with an ISM.
Figure 31A:
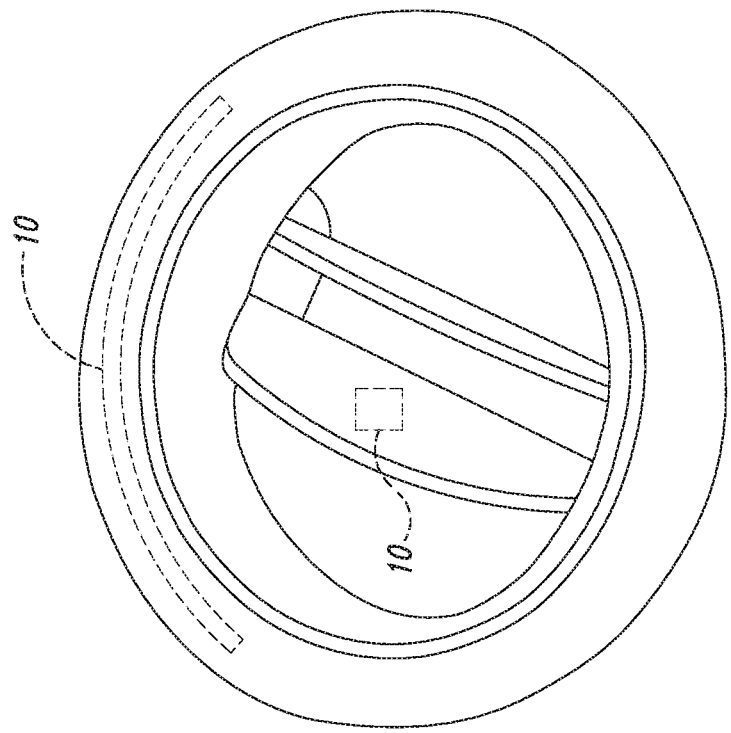
FIG. 31A illustrates a representative bileaflet mechanical valve with an ISM.

For example, as shown in FIGS. 31A and 31B, mechanical valves are illustrated with an ISM incorporated. Within one embodiment, an ISM containing blood flow (motion) sensors are provided on a mechanical heart valve (e.g., 'caged-ball', 'tilting disc', bi or tri-leaflet valves).

ISMs having blood flow sensors can be utilized to measure fluid flow through the mechanical valve, and to detect abnormalities that occur acutely, or gradually over time. The ISMs can be provided in a variety of locations, but are preferred within the suture ring ('10' as shown in FIGS. 31A and 31B); other preferred location include incorporation into the leaflets, the occluder disc/ring, the cage/ball, and the struts. For example, a decrease in forward flow may suggest the development of a stenosis [from thrombus formation, infection (biofilm or vegetations)], sticking of moving components (the ball, disc, or leaflets), or failure of the device. Increases in backwards flow can be suggestive of regurgitation, due to sticking, thrombus, infection or failure of the moving components. ISM blood flow sensors can show real-time movement of blood through the valve, and permit hemodynamic monitoring and determination of cardiac output (similar to an echocardiogram), ejection fraction and cardiac index (key clinical measurements that are valuable in monitoring cardiac-compromised patients, which many valvular patients are).

Within other embodiments, ISMs are provided having one or more pressure sensors which can be utilized to measure pressure on both sides of the valve, and to detect abnormalities that occur acutely, or gradually over time. The ISMs containing pressure sensors can be provided in a variety of locations (particularly such that sensors are located on both the atrial and ventricular side of the valve), but are preferred within the suture ring ('10' as shown in FIGS. 31A and 31B); other preferred location include incorporation into the leaflets, the occluder disc/ring, the cage/ball, and the struts. For example, an increased pressure gradient across the valve can indicate occlusion due to thrombus, panus, or in the case of biologic valves restrictive leaflet immobility due to calcification. Excessive regurgitation can be an indication of the prosthetic valve leaflet's inability to seat on the housing (mechanical valves) or coapt (biological valves) properly due to thrombus, panus, and/or calcification. Valvular regurgitation can also occur due to perivalvular leakage at the interface of the valve's suture ring with the host annulus. ISM pressure sensors on the ventricular side of a valve can measure systolic and diastolic pressure, and estimate systemic vascular resistance and pulmonary vascular resistance (depending upon the valve). These sensor readings can also be utilized to calculate cardiac output, ejection fraction and cardiac index and permit in situ hemodynamic monitoring.

Within further embodiments ISMs are provided having one or more blood volume sensors which can be utilized to measure fluid flow through the valve, and to detect abnormalities that occur acutely, or gradually over time. The ISMs containing blood volume sensors can be provided in a variety of locations (particularly such that sensors are located on both the atrial and ventricular side of the valve), but are preferred within the suture ring ('10' as shown in FIGS. 31A and 31B); other preferred location include incorporation into the leaflets, the occluder disc/ring, the cage/ball, and the struts. For example, a decrease in forward blood volume may suggest the development of a stenosis [from thrombus formation, infection (biofilm or vegetations)], sticking of moving components (the ball, disc, or leaflets), or failure of the device. Increases in backwards blood volume (>5 ml) can be suggestive of regurgitation, due to sticking, thrombus, infection or failure of the moving components. ISM blood volume sensors (e.g., to measure blood volume over a unit of time) can show real-time movement of blood through the valve, and permit hemodynamic monitoring and determination of cardiac output (similar to an echocardiogram), ejection fraction and cardiac index and permit in situ hemodynamic monitoring.

Within yet other embodiments ISMs are provided having metabolic (or chemical) sensors on mechanical valves which can be utilized to measure metabolic parameters important in vascular function. The ISMs containing metabolic can be provided in a variety of locations, but are preferred within the suture ring ('10' as shown in FIGS. 31A and 31B); other preferred location include incorporation into the leaflets, the occluder disc/ring, the cage/ball, and the struts; they must be blood contacting. Representative examples include coagulation/clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.).

Within other embodiments, ISMs are provided with position sensors that can be utilized to measure the location of fixed and moving components of the mechanical valve. The ISMs can be provided in a variety of locations, but are preferred within the suture ring ('10' as shown in FIGS. 31A and 31B); other preferred location include incorporation into the leaflets, the occluder disc/ring, the cage/ball, and the struts. For example, gaps in the leaflets, occluder disc/ring and cage/ball are suggestive of leakage and regurgitation. ISM position sensors can also be utilized to 'image' valvular motion (opening, closing, and integrity of the seal). Changes in ISM position sensors on the suture ring can show slippage, migration, failure, and suture breakage. Dilation of the ring can indicate possible dilative cardiomyopathy, whereas narrowing of the ring can indicate myocardial hypertrophy.

Within further embodiments ISMs are provided with contact sensors that can be utilized to measure the contact between fixed and moving components of a mechanical valve. For example, incomplete contact between the leaflets, between the occluder disc and the ring, and between the ball and cage are suggestive of leakage and regurgitation. The ISMs containing contact sensors can be provided in a variety of locations, but are preferred within the suture ring ('10' as shown in FIGS. 31A and 31B); other preferred locations include incorporation into the leaflets, the occluder disc/ring, the cage/ball, and the struts. Contact sensors can also be utilized to 'image' valvular motion (opening, closing, and integrity of the seal). Changes in contact sensors on the suture ring can show slippage, migration, failure, and suture breakage. ISM contact sensors can also be utilized to monitor the surface of the valve (e.g., to detect the presence of surface anomalies such as the formation of clot or thombi, biofilm or vegetations on the valve surface), and to monitor for friction wear, impact wear, and breakage (e.g., contact sensors can be placed at various depths of any of the various components (e.g., occluder disc, strut, occluder ring, leaflets, leaflet pivots, hinges, ball and/or cage).

Within yet other embodiments ISMs are provided with accelerometers which can be utilized to measure the location and movement of fixed and moving components of a mechanical valve. The ISMs containing accelerometers can be provided in a variety of locations, but are preferred within the suture ring ('10' as shown in FIGS. 31A and 31B); other preferred locations include incorporation into the leaflets, the occluder disc/ring, the cage/ball, and the struts. For example, gaps in the leaflets, occluder disc and ring, and ball and cage are suggestive of leakage and regurgitation. Accelerometers can also be utilized to 'image' real time valvular motion (opening, closing, and integrity of the seal), and to image changes that might occur in the mechanical valve over time. Changes in accelerometers on the suture ring can show slippage, migration, failure, and suture breakage.

B.10.A.1.2. Biological (Tissue-Based) Heart Valves and their Use

As noted above, within various embodiments of the invention biological (tissue-based) heart valves are provided with one or more ISMs as described herein. Briefly, biological valves are heart valves that are typically designed from xenographic (i.e., from a different species) tissue. Most typically, biological heart valves are constructed from porcine or bovine (usually either valvular or pericardial) tissue, although other animal tissues (e.g., equine) have also been utilized.

For purposes of this disclosure, tissue-engineered valves can also be considered to be a biological valve. Briefly, tissue-engineered valves generally comprise a layer of cells (e.g., fibroblasts, stem cells, or some combination of cells), that are grown over a tissue scaffold (typically a synthetic polymer-based scaffold, see generally Lichtenberg et al., "Biological scaffolds for heart valve tissue engineering", Methods Mol. Med. 2007; 140:309-17; see also U.S. Pub. No. 2010/117471).

Biological valves have a number of advantages in that they do not damage red blood cells or platelets (and therefore do not require anticoagulation therapy) after the healing of the suture ring and they do not cause cavitation like mechanical valves. However, they still suffer from several complications, including for example: 1) they have a more limited lifespan than mechanical valves; 2) they can cause an immune reaction; 3) they can clot and form emboli (causing strokes or myocardial infarction); 4) they can also become infected and form septic emboli; 5) they can become covered with fibrous tissue; and 6) they can become calcified. Common biological valves are currently made by Edwards Lifesciences, Medtronic, St. Jude, Sorin, 3F Therapeutics, CryoLife and LifeNet Health.

Hence, the present invention provides biological heart valves which have one or more ISMs having one or more sensors, including for example, fluid pressure sensors, contact sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, biological stress sensors, and temperature sensors. Such ISMs can be placed on, in, or within the various components of the heart valve, and can be utilized to monitor, amongst other things, thrombogenesis, infection (vegetations), wear, blockage, sticking (impaired movement of the valve leaflets), trans-valvular pressure gradients, leakage (backflow or regurgitation), detachment of the suture ring (from, for example, suture breakage), correct anatomical placement of the device, failure, and safety.

Figure 32B:
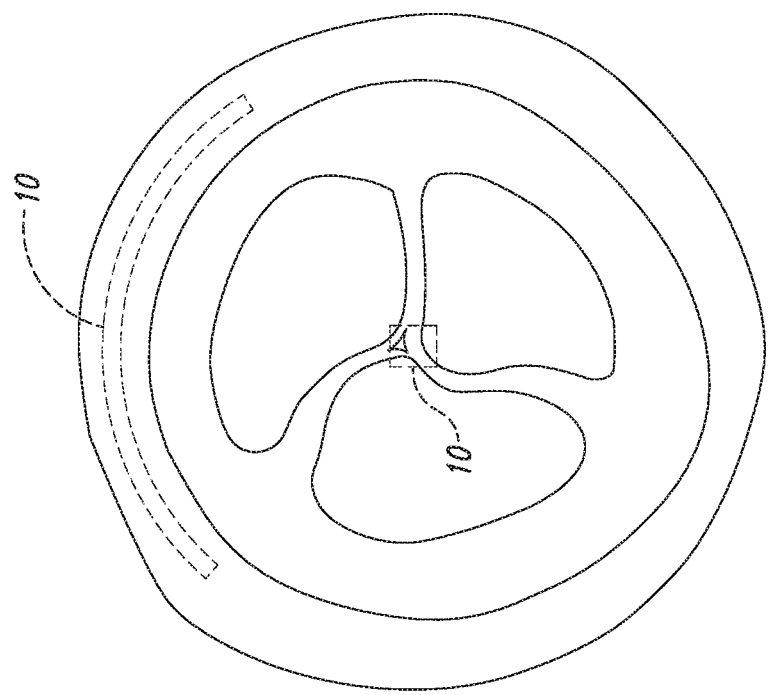
FIG. 32B illustrates a representative bovine valve with an ISM.
Figure 32A:
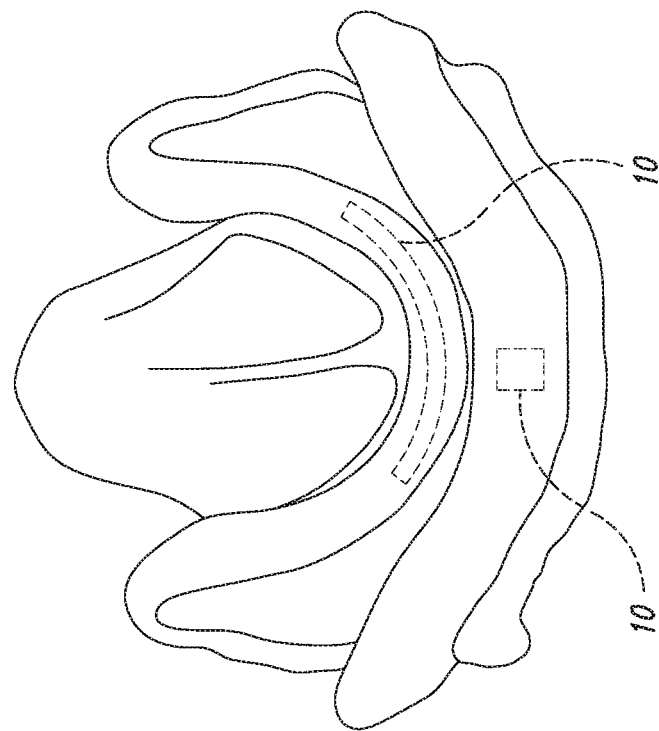
FIG. 32A illustrates a representative porcine valve with an ISM.

FIGS. 32A and 32B schematically illustrate biological valves with representative ISMs. Within one embodiment ISMs are provided with blood flow (motion) sensors on a biological heart valve. The ISMs containing blood flow sensors can be provided in a variety of locations (particularly such that sensors are located on both the atrial and ventricular side of the valve), but are preferred within the suture ring ('10' as shown in FIG. 32A) and the leaflet supports ('10' in FIG. 32B); another preferred location includes incorporation into the leaflets (for pericardial valves). ISM blood flow sensors can be utilized to measure fluid flow through the valve, and to detect abnormalities that occur acutely, or gradually over time. For example, a decrease in forward flow may suggest the development of a stenosis [from thrombus formation, infection (biofilm or vegetations), fibrosis, or calcification], sticking of the leaflets, or failure of the device. Increases in backwards flow can be suggestive of regurgitation, due to sticking, thrombus, infection, fibrosis, calcification or failure of the moving components. ISM blood flow sensors can show real-time movement of blood through the valve, and permit hemodynamic monitoring and determination of cardiac output (similar to an echocardiogram), ejection fraction and cardiac index (key clinical measurements that are valuable in monitoring cardiac-compromised patients, which many valvular patients are).

Within other embodiments, ISMs are provided with pressure sensors which can measure pressure on both sides of the valve, and to detect abnormalities that occur acutely, or gradually over time. The ISMs containing pressure sensors can be provided in a variety of locations (particularly such that sensors are located on both the atrial and ventricular side of the valve), but are preferred within the suture ring ('10' as shown in FIG. 32A) and the leaflet supports ('10' in FIG. 32B); another preferred location includes incorporation into the leaflets (for pericardial valves). Excessive regurgitation can be an indication of the prosthetic valve leaflet's inability to coapt properly due to thrombus, panus, and/or calcification. Valvular regurgitation can also occur due to perivalvular leakage at the interface of the valve's suture ring with the host annulus. ISM pressure sensors on the ventricular side of a biological valve can measure systolic and diastolic pressure, and estimate systemic vascular resistance and pulmonary vascular resistance (depending upon the valve). These sensor readings can also be utilized to calculate cardiac output, ejection fraction and cardiac index and permit in situ hemodynamic monitoring.

Within further embodiments ISMs are provided with blood volume sensors which can be utilized to measure fluid volume through the valve, and to detect abnormalities that occur acutely, or gradually over time. The ISMs containing blood volume sensors can be provided in a variety of locations (particularly such that sensors are located on both the atrial and ventricular side of the valve), but are preferred within the suture ring ('10' as shown in FIG. 32A) and the leaflet supports ('10' in FIG. 32B); another preferred location includes incorporation into the leaflets (for pericardial valves). For example, a decrease in forward blood volume may suggest the development of a stenosis [from thrombus formation, infection (biofilm or vegetations), fibrosis, calcification], sticking of the leaflets, or failure of the device. Increases in backwards blood volume (>5 ml) can be suggestive of regurgitation, due to sticking, thrombus, infection, fibrosis, calcification, or failure of the moving components. ISM blood volume sensors (e.g., to measure blood volume over a unit of time) can show real-time movement of blood through the valve, and permit hemodynamic monitoring and determination of cardiac output (similar to an echocardiogram), ejection fraction and cardiac index and permit in situ hemodynamic monitoring.

Within yet other embodiments ISMs are provided with metabolic (or chemical) sensors can be utilized to measure metabolic parameters important in vascular function. Representative examples include: Coagulation/Clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.).

Within other embodiments ISMs are provided with position sensors that can be utilized to measure location of fixed and moving components of a biological valve. The ISMs containing position sensors can be provided in a variety of locations (particularly such that sensors are located on both the atrial and ventricular side of the valve), but are preferred within the suture ring ('10' as shown in FIG. 32A) and the leaflet supports ('10' in FIG. 32B); another preferred location includes incorporation into the leaflets (for pericardial valves). For example, gaps in the leaflets (upon closing of the valve) are suggestive of leakage and regurgitation. ISM position sensors can also be utilized to 'image' valvular motion (opening, closing, and integrity of the seal). Changes in position sensors on the suture ring can show slippage, migration, failure, and suture breakage. Dilation of the ring can indicate possible cardiomyopathy, whereas narrowing of the ring can indicate myocardial hypertrophy.

Within further embodiments ISMs are provided with contact sensors that can be utilized to measure location of fixed and moving components. The ISMs containing contact sensors can be provided in a variety of locations (particularly such that sensors are located on both the atrial and ventricular side of the valve), but are preferred within the suture ring ('10' as shown in FIG. 32A) and the leaflet supports ('10' in FIG. 32B); another preferred location includes incorporation into the leaflets (for pericardial valves). For example, gaps in the leaflets (upon closing of the valve) are suggestive of leakage and regurgitation. ISM contact sensors can also be utilized to 'image' valvular motion (opening, closing, and integrity of the valvular seal). Changes in contact sensors on the suture ring can show slippage, migration, failure, and suture breakage. ISM contact sensors can also be utilized to monitor the surface of the valve (e.g., to detect the presence of surface anomalies such as the formation of clot or thombi, biofilm or vegetations, fibrosis or calcification on the valve surface), and to monitor for friction wear, impact wear, tears and breakage of the leaflets.

Within yet other embodiments ISMs are provided with accelerometers which can be utilized to measure the location and movement of fixed and moving components of a biological valve. The ISMs containing accelerometers can be provided in a variety of locations (particularly such that sensors are located on both the atrial and ventricular side of the valve), but are preferred within the suture ring ('10' as shown in FIG. 32A) and the leaflet supports ('10' in FIG. 32B); another preferred location includes incorporation into the leaflets (for pericardial valves). For example, gaps in the leaflets during valve closure are suggestive of leakage and regurgitation and integrity of the seal), and to image changes that might occur over time. Changes in accelerometers on the suture ring can show slippage, migration, failure, and suture breakage.

Within yet other embodiments of the invention any of the ISMs described herein can be placed in mitral or tri-cuspid annuloplasty rings (e.g., 2-D Carpentier Edwards rings and 3-D MDT Colvin-Gallaway or Duran rings).

B.10.A.1.3. Percutaneous Heart Valves and their Use

Within other aspects of the invention percutaneous heart valves (and their associated delivery devices) are provided with a variety of sensors described herein. Briefly, percutaneous aortic valve replacement (PAVR) or transcatheter aortic valve replacement (TAVR) is the replacement of the aortic valve through blood vessels or other minimally invasive techniques (thus eliminating a need for 'open-heart' surgery). Typically, the heart is accessed through the femoral artery in the leg, apically (through the apex of the heart), through the subclavian arteries, or via the aorta. Two companies have currently approved devices for aortic valve replacement: 1) COREVALVE (Medtronic); and 2) SAPIEN (Edwards Lifesciences). Other percutaneous aortic valves, percutaneous mitral valves and other percutaneous heart valves are under development.

Figure 33A:
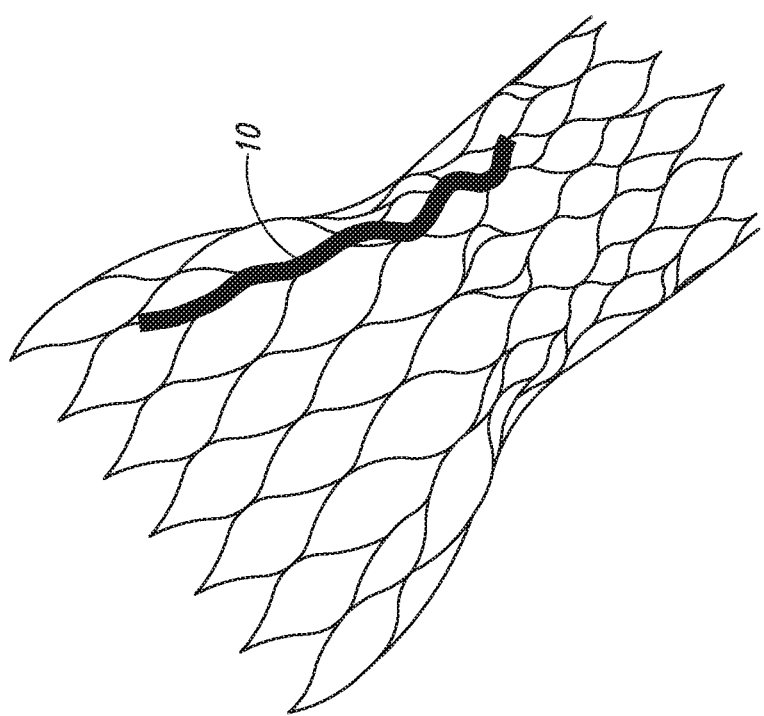
FIG. 33A illustrates an ISM on an expanded (stent) scaffold.
Figure 33B:
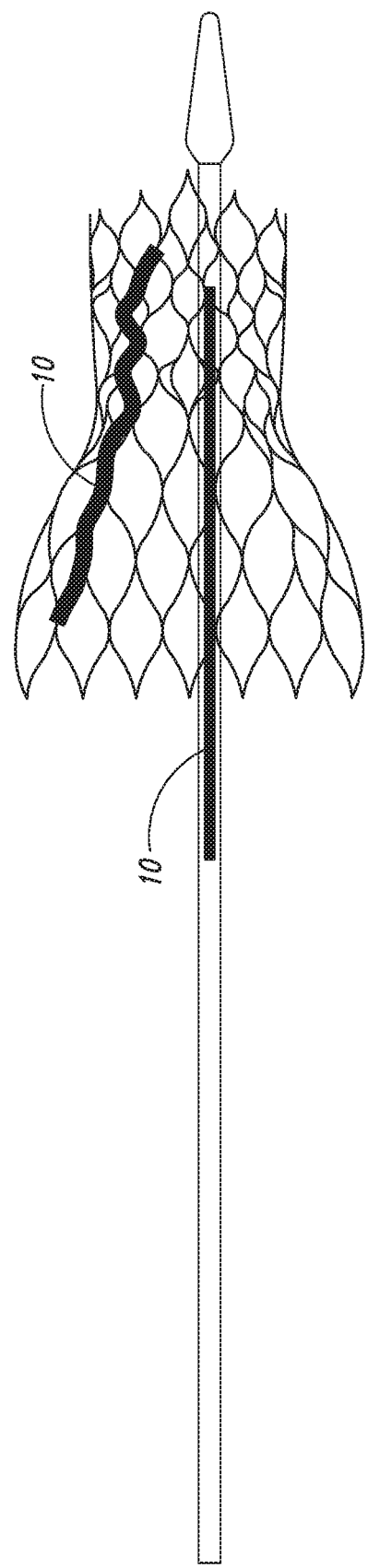
FIG. 33B illustrates a representative percutaneous heart valve with an ISM and a representative delivery system with an ISM.

The COREVALVE (Medtronic) is schematically illustrated in FIGS. 33A and 33B. Briefly, it is composed of a self-expanding nitinol support frame (stent) with cells in a diamond design (see FIG. 33A). It is fitted with bovine or procine pericardium shaped into valve leaflets, and provided along with a 18F delivery catheter. The SAPIEN (Edwards Lifesciences) is a trileaflet heart valve constructed of bovine pericardium which is mounted on a balloon-expandable stainless steel stent (see FIGS. 34A and 34B).

Percutaneous heart valve delivery has a number distinct advantages, including the fact that they do not require open heart surgery for placement, and hence can be utilized in high-risk patients that might not live through such a surgery. However, they still suffer from complications, including for example: 1) cardiogenic shock, stroke and/or death; 2) perforation of the myocardium; 3) cardiac tamponade; 4) ascending aorta trauma; 5) embolism; 6) thrombosis; 7) valve migration; 8) valve regurgitation; and 9) a variety of other valve dysfunctions [e.g., breaking or fracturing of the valve frame, incomplete expansion, bending, build-up of minerals (calcification) or clots (thrombosis), wear and tear, pannus (fibrous tissue) formation that might block the valve, and failures during the surgical procedure (e.g., failure to properly size and/or place the valve)].

Hence, the present invention provides percutaneous heart valves and/or their associated delivery devices (guidewires, catheters, balloon catheters, anchoring devices) which have one or more ISMs having one or more sensors, including for example, fluid pressure sensors, contact sensors, position sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, stress sensors, and temperature sensors. Such sensors can be place on, in, or within the various components of the heart valve, and can be utilized to monitor, amongst other things, proper placement of the valve, anatomical location of the valve, pressure exerted on surrounding tissues, balloon inflation/deflation, stent scaffold expansion, deployment of the valve, migration, thrombogenesis, infection (vegetations), calcification, fibrous tissue accumulation, wear, blockage, sticking (impaired movement of the 'valve'), trans-valvular pressure gradients, leakage (backflow or regurgitation), detachment, leaflet damage, assembly of the device (where possible), failure, and safety.

FIGS. 33A, 33B, 34A and 34B schematically illustrate percutaneous valves and their associated delivery devices (guidewires, catheters, balloon catheters, anchoring devices) with a variety of ISM sensors. Within one embodiment ISMs are provided with one or more blood flow (motion) sensors are provided on a percutaneous heart valve and/or delivery device. The ISMs containing blood flow sensors can be provided in a variety of locations on the percutaneous valve (particularly such that sensors are located on both the atrial and ventricular side of the valve), but are preferred within the stent support, stent covering, anchoring ring and leaflet supports. ISMs with blood flow sensors can also be provided on a variety of locations on the delivery devices such as on/in the guidewires, catheters, balloon catheters, anchoring devices. ISM blood flow sensors can be utilized to measure fluid flow through the valve and/or delivery device, and to detect abnormalities that occur acutely, or gradually over time. During percuatenous placement of the valve, ISM blood flow sensors on the valve and/or delivery devices can be used to ensure that adequate blood circulation is being maintained and that the device assembly is not critically obstructing cardiac outflow and output. After deployment, changes in flow through the implanted valve can provide valuable clinical information. For example, a decrease in forward flow through the valve leaflets may suggest the development of a stenosis [from thrombus formation, infection (biofilm or vegetations), fibrosis, or calcification], sticking of the leaflets, or failure of the device. Increases in backwards flow can be suggestive of regurgitation, due to sticking, thrombus, infection, fibrosis, calcification or failure of the moving components. Blood flow sensors can also detect leakage through or around the valve frame. ISM blood flow sensors can show real-time movement of blood through the valve, and permit hemodynamic monitoring and determination of cardiac output (similar to an echocardiogram), ejection fraction and cardiac index (key clinical measurements that are valuable in monitoring cardiac-compromised patients, which many valvular patients are).

Within other embodiments, ISMs are provided with one or more pressure sensors which can be utilized to measure pressure on both sides of the valve and/or delivery device, and to detect abnormalities that occur acutely, or gradually over time. The ISMs containing pressure sensors can be provided in a variety of locations on the percutaneous valve (particularly such that sensors are located on both the atrial and ventricular side of the valve), but are preferred within the stent support, stent covering, anchoring ring and leaflet supports. ISMs with pressure sensors can also be provided on a variety of locations on the delivery devices such as on/in the guidewires, catheters, balloon catheters, anchoring devices. During percuatenous placement of the valve, ISM pressure sensors on the valve (particularly the metallic stent scaffold) and/or delivery devices (particularly the delivery balloon) can be used to monitor the pressure being applied to surrounding tissues. This can help prevent procedural complications such as damage to the wall of the aorta or myocardium and/or perforation of these tissues. After deployment, changes in pressures across the implanted valve can provide valuable clinical information. For example, an increased pressure gradient across the valve can indicate stenosis. A low, or decreasing, pressure gradient can indicate regurgitation and/or possible valve failure. ISM pressure sensors on the ventricular and aortic side of a percutaneous valve can measure systolic and diastolic pressure, and estimate systemic vascular resistance. These sensor readings can also be utilized to calculate cardiac output, ejection fraction and cardiac index and permit in situ hemodynamic monitoring.

Within further embodiments ISMs are provided with blood volume sensors which can be utilized to measure fluid flow through the percutaneous valve and/or associated delivery devices, and to detect abnormalities that occur acutely, or gradually over time. The ISMs containing blood volume sensors can be provided in a variety of locations on the percutaneous valve (particularly such that sensors are located on both the atrial and ventricular side of the valve), but are preferred within the stent support, stent covering, anchoring ring and leaflet supports. ISMs with blood volume sensors can also be provided on a variety of locations on the delivery devices such as on/in the guidewires, catheters, balloon catheters, anchoring devices. During percuatenous placement of the valve, ISM blood volume sensors on the valve and/or delivery devices can be used to ensure that adequate systemic blood volume is being maintained and that the device assembly is not critically obstructing cardiac outflow and output. After deployment, changes in blood volume through the implanted valve can provide valuable clinical information. For example, a decrease in forward blood volume may suggest the development of a stenosis [from thrombus formation, infection (biofilm or vegetations), fibrosis, calcification], sticking of the leaflets, or failure of the device. Increases in backwards blood volume (>5 ml) can be suggestive of regurgitation, due to sticking, thrombus, infection, fibrosis, calcification, or failure of the moving components. ISM blood volume sensors (e.g., to measure blood volume over a unit of time) can show real-time movement of blood through the valve, and permit hemodynamic monitoring and determination of cardiac output (similar to an echocardiogram), ejection fraction and cardiac index and permit in situ hemodynamic monitoring.

Within yet other embodiments ISMs are provided with metabolic (or chemical) sensors which can be utilized on the valve and/or delivery devices to measure metabolic parameters important in vascular function. Representative examples include Coagulation/Clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.).

Within other embodiments ISMs are provided with position sensors that can be utilized on the percutaneous valve and/or associated delivery devices to measure the location of fixed and moving components. The ISMs with position sensors can be provided in a variety of locations on the percutaneous valve (particularly such that sensors are located on both the atrial and ventricular side of the valve), but are preferred within the stent support, stent covering, anchoring ring and leaflet supports. ISMs containing position sensors can also be provided on a variety of locations on the delivery devices such as on/in the guidewires, catheters, balloon catheters, anchoring devices. During percuatenous placement of the valve, ISM position sensors on the valve and/or delivery devices are invaluable in assisting in correct anatomical placement of the artificial valve across the native valve. Monitoring position changes of the device in "real time" during deployment can help the clinician place and secure the device correctly. After deployment, changes in position of the implanted valve can indicate migration of the device away (upstream or downstream) from its original placement site. ISM position sensors can also be utilized to monitor valve function after implantation. For example, gaps in the leaflets upon closing of the valve are suggestive of leakage and regurgitation. ISM position sensors can also be utilized to 'image' valvular leaflet motion (opening, closing, and integrity of the seal). Changes in ISM position sensors located on the stent scaffold can show slippage, migration, failure, and anchoring suture breakage. Dilation of the scaffold can indicate possible overexpansion, breakage or failure; whereas narrowing of the scaffold can indicate possible underexpansion, collapse, breakage, or failure.

Within further embodiments ISMs are provided with contact sensors that can be utilized on the percutaneous valve and/or associated delivery devices to measure the contact between the device and the surrounding tissues, the contact between related device components/moving pieces, and the status of blood-contacting surface of the device. The ISMs containing contact sensors can be provided in a variety of locations on the percutaneous valve (particularly such that sensors are located on both the atrial and ventricular side of the valve), but are preferred within the stent support, stent covering, anchoring ring and leaflet supports. ISMs with contact sensors can also be provided on a variety of locations on the delivery devices such as on/in the guidewires, catheters, balloon catheters, anchoring devices. During percuatenous placement of the valve, ISM contact sensors on the valve and/or delivery devices are invaluable in assisting in correct anatomical placement of the artificial valve across the native valve. Monitoring contact changes of the device in "real time" during deployment can help the clinician place, size, and secure the device correctly. In addition, ISM contact sensors on the valve (particularly the metallic stent scaffold) and/or delivery devices (particularly the delivery balloon) can be used to monitor the amount and extent of contact with surrounding tissues. This can help prevent procedural complications such as damage to the wall of the aorta or myocardium (and/or perforation of these tissues), monitor for correct inflation and full deflation of the balloon catheter (if present), and full deployment of the stent scaffold across the native valve. After deployment, changes in contact between the implanted valve and surrounding tissues can indicate migration of the device away (upstream or downstream) from its original placement site. ISM contact sensors can also be utilized to monitor valve function after implantation. For example, gaps in the valve leaflets (upon closing) are suggestive of leakage and regurgitation. ISM contact sensors can also be utilized to 'image' valvular motion (opening, closing, and integrity of the seal) in real time. Increased contact between the stent scaffold and the vascular wall can indicate possible overexpansion, breakage or failure; whereas decreased contact between the stent scaffold and the vascular wall can indicate possible underexpansion, collapse, breakage, or failure. ISM contact sensors can also be utilized to monitor the blood-contacting surface of the valve (e.g., to detect the presence of surface anomalies such as the formation of clot or thombi, biofilm or vegetations, fibrosis or calcification on the valve surface), and to monitor for friction wear, impact wear, tears and breakage of the leaflets.

Within yet other embodiments ISMs are provided with accelerometers which can be utilized to measure the location and movement of fixed and moving components on the valve and/or delivery devices. The ISMs containing accelerometers can be provided in a variety of locations on the percutaneous valve (particularly such that sensors are located on both the atrial and ventricular side of the valve), but are preferred within the stent support, stent covering, anchoring ring and leaflet supports. ISMs with accelerometers can also be provided on a variety of locations on the delivery devices such as on/in the guidewires, catheters, balloon catheters, anchoring devices. During percuatenous placement of the valve, accelerometers on the valve and/or delivery devices are invaluable in assisting in correct anatomical placement of the artificial valve across the native valve. Monitoring movement of the device in "real time" during deployment can help the clinician place, size, and secure the device correctly. In addition, accelerometers on the valve (particularly the metallic stent scaffold) and/or delivery devices (particularly the delivery balloon) can be used to monitor the interaction between the device(s) and surrounding tissues. This can help prevent procedural complications such as damage to the wall of the aorta or myocardium (and/or perforation of these tissues), monitor for correct inflation and full deflation of the balloon catheter (if present), and full deployment of the stent scaffold across the native valve. After deployment, movement of the implanted valve can indicate migration of the device away (upstream or downstream) from its original placement site. ISM accelerometers can also be utilized to monitor valve function after implantation. For example, gaps in the valve leaflets (when in the closed position) are suggestive of leakage and regurgitation. ISM accelerometers can also be utilized to 'image' valvular motion (opening, closing, and integrity of the seal), and to image changes that might occur over time. ISM accelerometers can detect changes in the stent scaffold: increases in diameter are indicative of possible overexpansion, breakage or failure; whereas decreases in the diameter can indicate possible underexpansion, collapse, breakage, or failure.

Figure 34B:
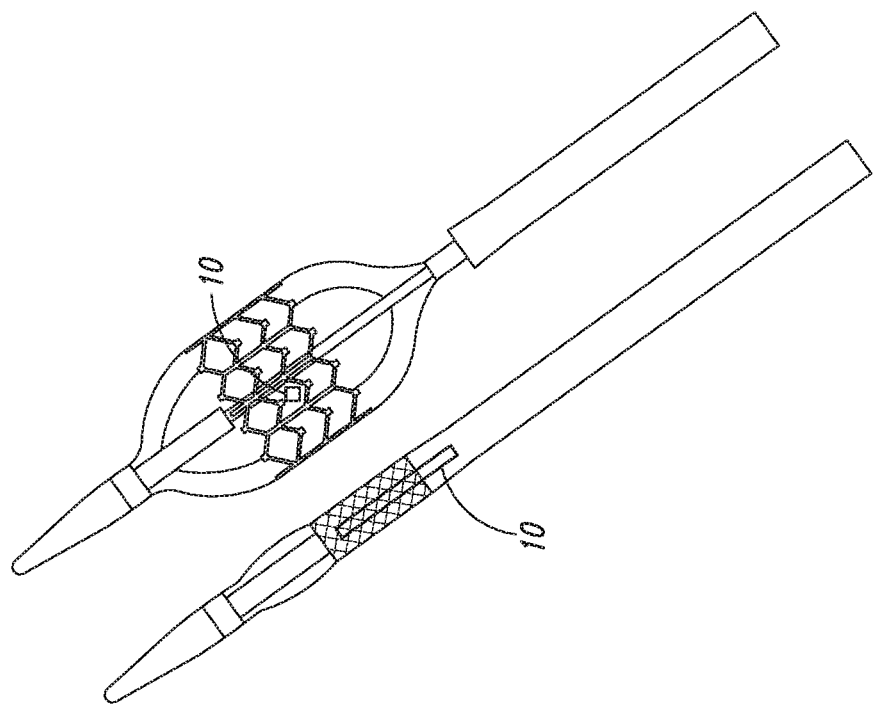
FIG. 34B illustrates an ISM on a balloon-expandable percutaneous heart valve.
Figure 34A:
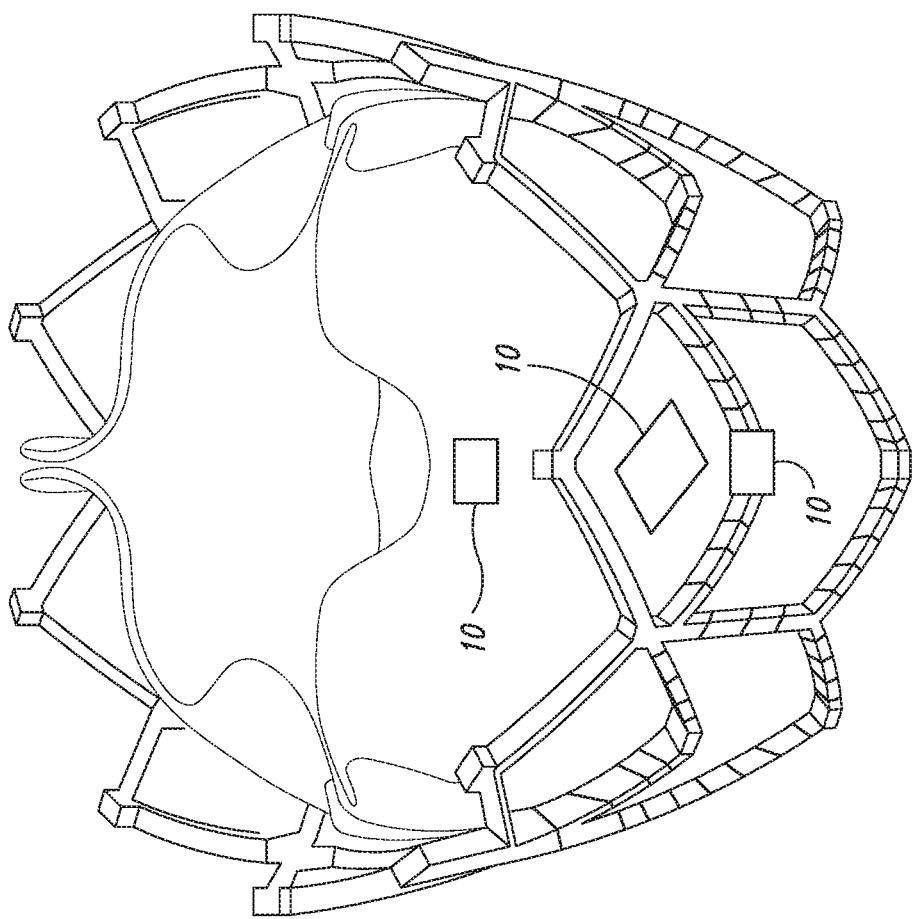
FIG. 34A illustrates an ISM on a balloon delivery device for a balloon-expandable percutaneous heart valve, as well as an ISM on the balloon itself.

Within further embodiments of the invention ISMs are provided with sensors that can be utilized on the heart valve and delivery devices in tandem in order to ensure proper placement and deployment of the heart valve (see FIGS. 33B and 34B). Utilizing for example, ISMs having one or more position sensors, accelerometers, and/or contact sensors, a physician can help to ensure: 1) accurate placement across the native valve; 2) imaging during placement; 3) full balloon deployment and deflation; 4) full stent (heart valve) deployment and expansion; and 5) movement or migration during or subsequent to the procedure.

B.10.A.1.4. General Consideration Regarding Heart Valves

As briefly noted above, heart valves (e.g., mechanical, biological or percutaneous heart valves) and their associated delivery devices (guidewires, catheters, balloon catheters, and anchoring devices if present) of the present invention can have one or more ISMs having one or more of the sensors provided herein. The ISMs can be incorporated on the surface of (in or on), or within the heart valve or delivery devices. Representative examples of sensors include contact sensors, strain gauge sensors, pressure sensors, fluid pressure sensors, position sensors, accelerometers, shock sensors, rotation sensors, vibration sensors, tilt sensors, pressure sensors, blood chemistry sensors, blood metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

ISMs having one or more of the sensors described herein can be continuously or intermittently monitored in order to provide analysis of 'real-world' activity, healing, and changes in function over time, to evaluate patient activity, patient cardiac function, and to better understand the conditions under which artificial heart valves are exposed to in the real world. They can be utilized to detect, monitor and report, a wide variety of metabolic parameters, including for example: Coagulation/Clotting parameters such as PT, PTT, clotting time and INR; Blood Oxygen content; Blood $CO_2$ content; Blood pH; Blood cholesterol; Blood lipids (HDL, LDL); Blood Glucose; Cardiac enzymes; Hepatic Enzymes; Electrolytes; Blood Cell Counts; and Kidney Function parameters (BUN, Creatinine, etc.). They can also be utilized to detect, monitor and report measurements of cardiac output, ejection fraction and cardiac index; permit in situ hemodynamic monitoring of parameters such as systolic and diastolic pressure, transvalvular pressure and regurgitation; and estimate parameters such systemic (or pulmonary) vascular resistance.

As will be readily evident given the disclosure provided herein, the ISMs described and claimed herein can comprise a variety of different sensors within different locations of the ISM. In addition, within various embodiments of the invention one or more sensors may be placed separate from the ISM (but still be, optionally, able to communicate with and be controlled by the ISM). For example, a relatively small ISM having a relatively small battery may be placed in the tibial component of a knee replacement prosthesis, and a regular sized ISM having a regular sized battery may be placed in the femoral component of a knee replacement prosthesis. The ISM in the tibial component will send information wirelessly to the ISM in the femoral component, and the ISM in the femoral component will send information wirelessly to a remote device. Each of the ISMs in the femoral and tibial units will receive unique information from their own unique surroundings, which when combined provides a physician or other interested party with a more complete understanding of the action of the knee replacement prosthesis. For example, by combining information from an ISM in a tibial unit and an ISM in a femoral unit, an evaluation of gait may be obtained. Representative examples of ISMs for use with heart valves are provided in U.S. Provisional No. 62/017,161, which is hereby incorporated by reference in its entirety).

B.11. Methods of Manufacture

Within various embodiments of the invention, methods are also provided for manufacturing a medical device having one of the sensor or ISMs provided herein. For example, within one embodiment of the invention a medical device is constructed such that one or more sensor or ISMs provided herein are placed directly into, onto, or within the medical device at the time of manufacture, and subsequently sterilized in a manner suitable for use in subjects.

Within other embodiments, scaffolds can be prepared for medical devices (see, e.g., U.S. Pat. No. 8,562,671, and WO 2013/142879 which are incorporated by reference in their entirety). Briefly, scaffolds composed of one or more polymers can be prepared in order to mimic the shape of a biological structure (e.g., vessel), or a portion thereof. Sensors or ISMs can be placed into the structure before, during, or subsequent to manufacture of the valve (e.g., in the case or electro-spinning or molding of polymer fibers, or in the case of 3D printing as described in more detail below). Within certain preferred embodiments the scaffold can be seeded with stem cells suitable for growth of tissue on the artificial medical device (see, e.g., WO 1999/003973 and U.S. Pat. No. 8,852,571, which are incorporated by reference in their entirety).

Within further embodiments, the present disclosure provides a method of making a medical device by 3D printing, additive manufacturing, or a similar process whereby the medical device is formed from powder or filament that is converted to a fluid form such subsequently solidifies as the desired shape. For convenience, such processes will be referred to herein as printing processes or 3D printing processes. The present disclosure provides a method of making a medical device by a printing process, where that medical device includes a sensor or ISM. The sensor or ISM may be separately produced and then incorporated into the medical device during the printing process. For example, a sensor or ISM may be placed into a desired position and the printing process is carried out around the sensor or ISM so that the sensor or ISM becomes embedded in the printed medical device. Alternatively, the printing process may be started and then at appropriate times, the process is paused to allow a sensor or ISM to be placed adjacent to the partially completed medical device. The printing process is then re-started and construction of the medical device is completed. The software that directs the printing process may be programmed to pause at appropriate predetermined times to allow a sensor or ISM to be added to the partially printed medical device.

In addition, or alternatively, the sensor or ISM itself, or a portion thereof may be printed by the 3D printing process. Likewise, electronic connectively to, or from, or between, sensor or ISMs may be printed by the 3D printing process. For example, conductive silver inks may be deposited during the printing process to thereby allow conductivity to, or from, or between sensor or ISMs of a medical device. See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides medical devices wherein the sensor or ISM is printed onto a substrate, or a substrate is printed and a sensor or ISM is embedded or otherwise incorporated into or onto the substrate, or both the substrate and the sensor or ISM are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the medical device is of a particularly intricate shape, it may be printed with two materials. The first material is cured (using, e.g., actinic radiation) as it is deposited, while the second material is uncured and can be washed away after the medical device has been finally printed. In this way, significant hollow spaces may be incorporated into the medical device.

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor or ISM may be embedded into the alloy powder bed, and the laser melts the powder around the sensor or ISM so as to incorporate the sensor or ISM into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating a sensor or ISM-containing medical device, the method comprising forming at least one of a sensor or ISM and a support for the sensor or ISM using a 3D printing technique. Optionally, the 3D printing technique may be an additive manufacturing technique. In a related embodiment, the present disclosure provides a medical device that is produced by a process comprising a 3D printing process, such as an additive manufacturing process, where the medical device includes a sensor or ISM.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

Within yet other embodiments of the invention methods of fabricating a medical device having a sensor or one or more ISMs are provided comprising the steps of forming an implantable medical device (e.g., as described herein), and implanting a sensor into the device during the fabrication process. Within further embodiments, such methods further comprise the steps of determining a medical device shape that is suitable for a particular subject, or a particular group of subjects (e.g., by imaging a subject, and utilizing CAD programs or other 3-D design programs to design a suitable medical device for a particular subject, or, for a group of subjects. Within yet further embodiments, one or more ISMs can be implanted onto a medical device in a particular location for a particular subject. For example, based upon imaging (e.g., CT, MRI, ultrasound, or other forms of analysis), stent grafts can be designed so that one or more ISMs, or components thereof (e.g., communication modules and/or batteries) can be placed on a stent graft so that, once implanted, they would fall within an aneurysm sac of a subject.

C. Use of Medical Devices or Implants Having ISMs to Deliver Therapeutic Agent(s)

As noted above, the present invention also provides drug-eluting medical devices or implants which comprise one or more ISMs, and which can be utilized to release a therapeutic agent (e.g., a drug) to a desired location within the body (e.g., a body tissue such as bone marrow, or sites of possible or typical infection or inflammation). Within related embodiments, a drug-eluting delivery device may be included within the medical device in order to release a desired drug upon demand (e.g., upon remote activation/demand, or based upon a timed schedule), or upon detection of an activating event (e.g., detection of an accelerometer of a significant impact event, or detection of loosening by a contact sensor) (see generally U.S. Patent App. No. 2011/0092948 entitled "Remotely Activated Piezoelectric Pump For Delivery of Biological Agents to the Intervertebral Disc and Bone", which is incorporated by reference in its entirety).

For example, within certain embodiments of the invention, biological agents can be administered along with or released from an orthopedic implant in order to increase bone growth, fibrosis or scarring within the implant. Representative examples of suitable agents include, for example, irritants, silk, wool, talcum powder, metallic beryllium, and silica. Other agents which may be released by the orthopedic implant include components of extracellular matrix, fibronectin, polylysine, ethylenevinylacetate, and inflammatory cytokines such as TGFβ, PDGF, VEGF, bFGF, TNFα, NGF, GM-CSF, IGF-a, IL-1, IL-8, IL-6, BMP and growth hormone, and adhesives such as cyanoacrylate (see U.S. Patent App. Nos. 2005/0149173 and 2005/0021126, both of which are incorporated by reference in their entirety).

Within other embodiments of the invention anti-scarring biological agents (e.g., drugs such as paclitaxel, sirolimus, or an analog or derivative of these), can be administered along with or released from an orthopedic implant or a vascular implant in order to prevent scarring of the implant inappropriately (see, e.g., U.S. Pat. No. 7,491,188, U.S. Patent Application Nos. 2005/0152945, 2005/0187639, 2006/0079836, US 2009/0254063, US 2010/0023108, and US 2010/0042121).

Within other embodiments of the invention, anti-inflammatory agents, local anesthetics and pain-relief medications (e.g., drugs such as cortisone, dexamethasone, nonsteroidal anti-inflammatories, lidocaine, bupivacaine, marcaine, morphine, codeine, narcotic pain relievers and analogs or derivatives of these) can be utilized to reduce post-operative pain and swelling and reduce the need for systemic pain relief therapy.

Within other embodiments a wide variety of additional therapeutic agents may be delivered (e.g., to prevent or treat an infection such as osteomyelitis, myocarditis, biofilm formation, or to treat another disease state such as a primary or secondary bone tumor), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g., clindamycin); lipopeptides; macrolides (e.g., azithromycin); monobactams; nitrofurans; polypeptides (e.g., bacitracin); and tetracyclines.

Within preferred embodiments one or more ISMs can be utilized to determine appropriate placement of the desired drug, as well as the quantity and release kinetics of drug to be released at a desired site.

D. Methods for Monitoring Infection in Medical Devices or Implants

Within other embodiments medical devices or implants are provided comprising an ISM having one or more temperature sensors. Such medical devices or implants can be utilized to measure the temperature of the medical device, and in the local tissue adjacent to the medical device. Methods are also provided for monitoring changes in temperature over time, in order to determine and/or provide notice (e.g., to a patient or a healthcare provider) that an infection may be imminent. For example, an ISM having temperature sensors can be included within one or more components of the medical device in order to allow early detection of infection could allow preemptive treatment with antibiotics or surgical drainage and eliminate the need to surgically remove the medical device.

In certain embodiments of the present invention, ISMs having metabolic and physical sensors can also be placed on or within the various components of a device or implant in order to monitor for rare, but potentially life-threatening complications of medical devices. In some patients, the medical device and surrounding tissues can become infected; typically from bacteria colonizing the patient's own skin that contaminate the surgical field or the device surface (often *Staphylococcus aureus* or *Staphylococcus epidermidis*). ISMs having sensors such as temperature sensors (detecting temperature increases), pH sensors (detecting pH decreases), and other metabolic sensors (e.g. oxygen content, $CO_2$ content, bacterial DNA detection assays) can be used to suggest the presence of infection on or around the medical device.

Hence, within one embodiment of the invention methods are provided for determining an infection associated with a medical device, comprising the steps of a) providing to a patient an medical device as described herein, wherein the medical device comprises an ISM having at least one temperature sensor and/or metabolic sensor, and b) detecting a change in said temperature sensor and/or metabolic sensor, and thus determining the presence of an infection. Within various embodiments of the invention the step of detecting may be a series of detections over time, and a change in the sensor is utilized to assess the presence or development of an infection. Within further embodiments a change of 0.5%, 1.0%, or 1.5% elevation of temperature or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section C (the "Therapeutic Agents")

E. Further Uses of ISM-Containing Medical Devices in Healthcare

ISM having sensors on medical devices, and any associated medical device have a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the ISM sensors on a selected or randomized basis, and captures and/or stores the collected sensor data. This data may then be downloaded to another system or device (as described in further detail below).

Integrating the data collected by the ISM sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion and medical device performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, anti-inflammatory medication, rest, etc.), and to compare patient progress versus previous function and future expected function. Better therapeutic decisions and better patient compliance can be expected when both the doctor and the patient have the benefit of observing the impact of various treatment modalities on patient rehabilitation, activity, function and overall performance.

F. Generation of Power from Medical Devices or Implants

Within certain aspects of the invention, a small electrical generation unit can be positioned along an outer, or alternatively an inner, surface of the medical device, or associated medical device. Briefly, a variety of techniques have been described for scavenging power from small mechanical movements or mechanical vibration. See, for example, the article entitled "Piezoelectric Power Scavenging of Mechanical Vibration Energy," by U.K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283,793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces within the body and movements within the body.

After the electricity is generated by one or more generators, the electricity can be transmitted to any one of the variety of sensors which is described herein. For example, it can be transmitted to any of the sensors shown in Figures. It may also be transmitted to the other sensors described herein. The transmission of the power can be carried out by any acceptable technique. For example, if a ISM sensor is physically coupled to the medical device, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Medical Imaging and Self-Diagnosis of Assemblies Comprising Medical Devices or Implants; Predictive Analysis and Predictive Maintenance Within other aspects of the invention methods are provided for imaging the medical device as provided herein, comprising the steps of (a) detecting the location of one or more ISM sensors in the medical device, and/or associated medical device; and (b) visually displaying the location of said one or more ISM sensors, such that an image of the medical device and/or medical device is created. Within various embodiments, the step of detecting may be done over time, and the visual display may thus show positional movement over time. Within certain preferred embodiments the image which is displayed is a three-dimensional image. Within preferred embodiments the various images (e.g., 2D or 3D) may be collected and displayed in a time-sequence (e.g., as a moving image or 'movie-like' image). Within other embodiment, the imaging techniques may be utilized post-operatively in order to examine the medical device, and/or to compare operation and/or movement of the device over time such as during placement (intra-operatively) or during the post-operative (rehabilitative) period.

The present invention provides medical devices and associated medical devices which are capable of imaging through the use of ISM having sensors over a wide variety of conditions. For example, within various aspects of the invention methods are provided for imaging the medical device (or portion thereof) having an ISM (and/or delivery device, comprising the steps of detecting the changes in the ISM in, on, and or within the medical device, medical device or kit over time, and wherein the medical device, medical device or kit comprises one or more ISM having sensors at a density of greater than 1, 2, 3, 4, 5, 6, 7, 8, 9, 10 or greater than 10 sensors per square centimeter. Within other aspects the medical device medical device or kit comprises an ISM having sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the medical device, medical device, or kit as described herein. As noted above, a wide variety of sensors can be utilized therein, including for example, contact sensors, strain gauge sensors, pressure sensors, fluid pressure sensors, position sensors, tissue chemistry sensors, tissue metabolic sensors, mechanical stress sensors, and temperature sensors.

For example, the medical device, medical device, or kit comprising sensors as described herein can be utilized to image anatomy through sensors which can detect positional movement. The sensors used can also include accelerometers and motion sensors to detect movement of the medical device due to a variety of physical changes. Changes in the position of the accelerometers and/or motion sensors over time can be used as a measurement of changes in the position of the medical device over time. Such positional changes can be used as a surrogate marker of medical device anatomy—i.e. they can form an "image" of the medical device to provide information on the size, shape, integrity, alignment and location of changes to the medical device, and/or medical device movement/migration. In particular, as noted above the image data can be collected over time, in order to visually show changes (e.g., a "movie" or "moving images", which may be in 2D or 3D).

Certain exemplary embodiments will now be explained in more detail. One particular benefit is the live and in-situ monitoring of the patient's recovery with a medical device having an ISM as described herein. The ISM can, optionally, collect data on a constant basis, during normal daily activities and even during the night if desired. For example, contact sensors within an ISM can obtain and report data once every 10 seconds, once a minute, or once a day. Other sensors can collect data more frequently, such as several times a second. For example, it would be expected that the temperature, contact, and/or position data could be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, instability, etc.)— and signals the device to obtain a reading at that time in order to allow the comparison of subjective/symptomatic data to objective/sensor data in an effort to better understand the underlying cause or triggers of the patient's symptoms. All activity can be continuously monitored post operation or post-procedure and the data collected and stored in the memory located inside the medical device.

A patient with a medical device will generally have regular medical checkups. When the patient goes to the doctor's office for a medical checkup, the doctor will bring a reading device closely adjacent to the medical device or ISM 10, in this example the medical device, in order to transfer the data from the internal circuit inside the medical device to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the medical device to the doctor's computer or wireless device. The computer therefore analyzes the data for anomalies, unexpected changes over time, positive or negative trends, and other signs which may be indicative of the health of the patient and the operability of the medical device. For example, if the patient has decided to go skiing or jogging, the doctor will be able to monitor the effect of such activity on the medical device having an ISM, including the accelerations and strains during the event itself. The doctor can then look at the health of the medical device in the hours and days after the event and compare it to data prior to the event to determine if any particular event caused long term damage, or if the activities subjected the medical device to forces beyond the manufacturer's performance specifications for that particular medical device. Data can be collected and compared with respect to the ongoing and long term performance of the medical device from the strain gauges, the contact sensors, the surface wear sensors, or other sensors which may be present. Hence, within preferred embodiments the data can be collected over time, in order to visually show changes (e.g., a 2D or 3D "movie" or "moving images").

In one alternative, the patient may also have such a reading device in their home which collates the data from the medical device on a periodic basis, such as once per day or once per week. As described above, the patient may also be able to "trigger" a device reading (via an external signaling/triggering device) as part of "event recording." Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different medical devices can be compared in different patients (different sexes, weights, activity levels, etc.) to help manufacturers design better devices and assist surgeons and other healthcare providers in the selection of the right medical device for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

H. Methods of Monitoring Assemblies Comprising Medical Devices with ISMs

Figure 35:
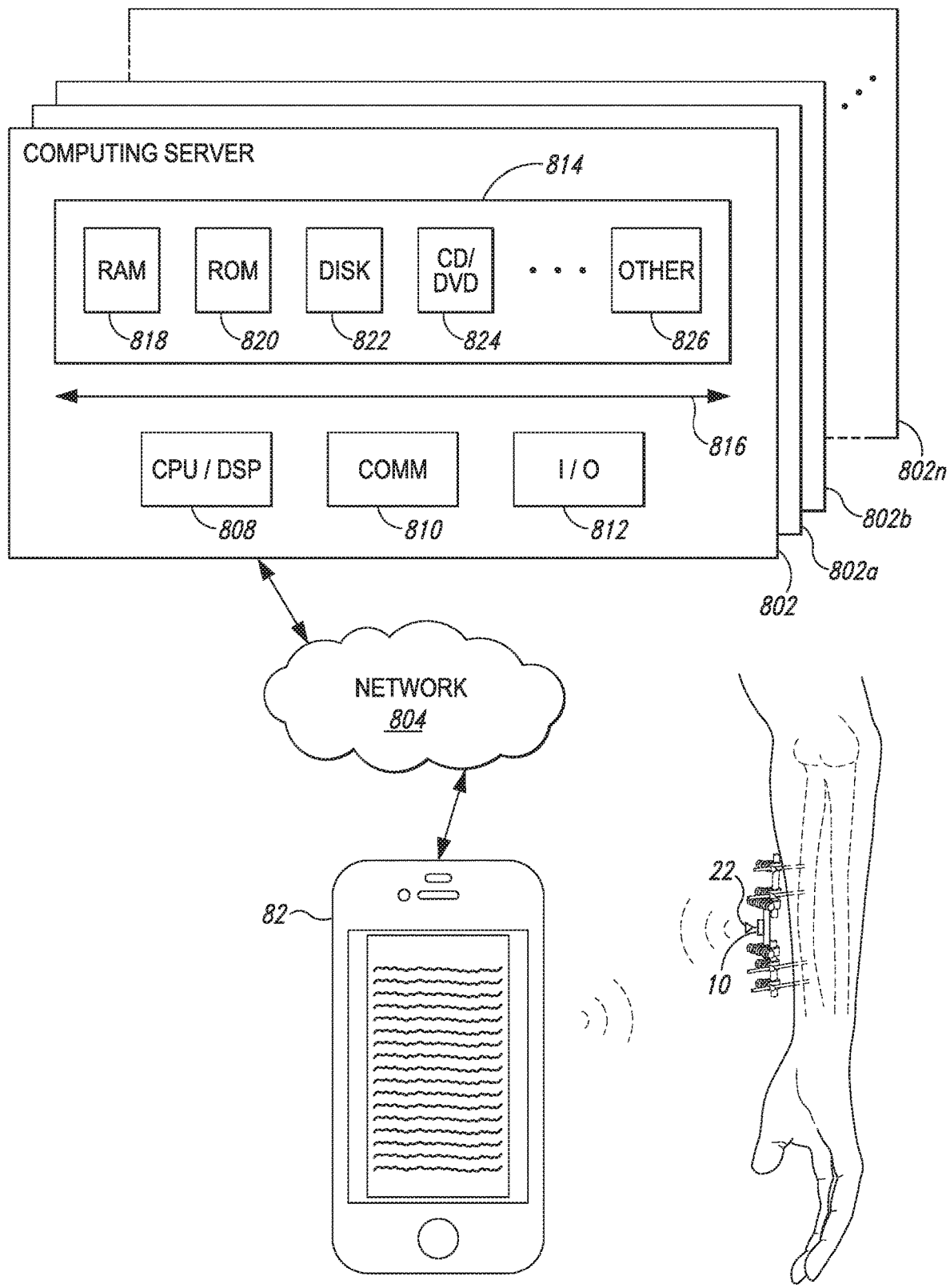
FIG. 35 is a schematic illustration of an ISM on a medical device as described herein within a subject which is being probed for data and outputting data, according to one embodiment of the invention.

As noted above, the present invention also provides methods for monitoring one or more of the medical devices or implants with ISMs provided herein. For example, FIG. 35 illustrates a monitoring system usable with the medical device or ISM 10 as of the type shown in any one of the Figures described herein.

Within other embodiments, the monitoring system however may be composed of passive sensors, which respond to an external signal. For example, according to one embodiment, sufficient signal strength is provided in the initial signal to provide power for the sensor and to carry out the sensing operation and output the signal back to an interrogation module. In other embodiments, two or more signals are sent, each signal providing additional power to the sensor to permit it to complete the sensing operation and then provide sufficient power to transfer the data via the signal path back to the interrogation module. For example, the signal can be sent continuously, with a sensing request component at the first part of the signal and then continued providing, either as a steady signal or pulses to provide power to operate the sensor. When the sensor is ready to output the data, it sends a signal alerting the interrogation module that data is coming and the signal can be turned off to avoid interference. Alternatively, the integration signal can be at a first frequency and the output signal at a second frequency separated sufficiently that they do not interfere with each other. In a preferred embodiment, they are both the same frequency so that the same antenna on the sensor can receive the signal and send signal.

The interrogation signal may contain data to select specific sensors on the medical device. For example, the signal may power up all sensors on the medical device at the same time and then send requests for data from each at different selected times so that with one interrogation signal provided for a set time, such as 1-2 seconds, results in each of the sensors on the medical device collecting data during this time period and then, at the end of the period, reporting the data out on respective signals at different times over the next 0.5 to 2 seconds so that with one interrogation signal, the data from all sensors is collected.

While the wireless signal can be in any frequency range, within certain embodiments an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

The interrogation module is operating under control of the control unit which has a microprocessor for the controller, a memory, an I/O circuit to interface with the interrogation module and a power supply. The control unit may output data to a computer or other device for display and use by the physician to treat the subject.

I. Collection, Transmission, Analysis, and Distribution of Data from Assemblies Comprising Medical Devices or Implants FIG. 35 illustrates one embodiment of an information and communication technology (ICT) system 800 arranged to process sensor data (e.g., data from the ISM 10). In FIG. 35, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 35 include computing servers 802, and other devices that are not shown for simplicity.

In FIG. 35, one or more ISMs 10 communicate with a remote data receiving device 82. The remote data receiving device can be a wearable device (e.g., a watch-like device, a wrist-band, or other device that may be carried or worn by the subject) can interrogate the ISMs over a set (or random) period of time, collect the data, and forward the data on to one or more networks (804). Alternatively, the remote data receiving device 82 can be a stationary device in a hospital, home, or office. The remote data receiving device 82 may collect data of its own accord which can also be transmitted to the network. Representative examples of data that may be collected include location (e.g., a GPS), body or skin temperature, and other physiologic data (e.g., pulse). Within yet other embodiments, the remote data receiving device may notify the subject directly of any of a number of prescribed conditions, including but not limited to possible or actual failure of the device.

The information that is communicated between the ISM 10 and the data receiving device 82 may be useful for many purposes as described herein. In some cases, for example, sensor data information is collected and analyzed expressly for the health of an individual subject. In other cases, sensor data is collected and transmitted to another computing device to be aggregated with other data (for example, the ISM data may be collected and aggregated with other data collected from an additional data receiving device (e.g., a device that may, in certain embodiments, include GPS data and the like).

FIG. 35 illustrates aspects of a computing server 802 as a cooperative bank of servers further including computing servers 802*a*, 802*b*, and one or more other servers 802*n*. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 35 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., medical device sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 35, sensor data from, e.g., ISM 10 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various ISMs is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPAA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data $806a$, $806b$) is optionally encrypted before being communicated to a computing device.

In one embodiment, the operation of the information and communication technology (ICT) system 800 of FIG. 35 includes one or more sensor data computer programs stored on a computer-readable medium. The computer program may optionally direct and/or receive data from one or more medical device sensors medical devices in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of medical device sensor data is stored on a non-transitory computer-readable medium in storage module 814. The computer program is configured to identify a subject who has a wireless medical device inserted in his or her body. The wireless medical device may include one or more wireless sensors.

In some cases, the computer program identifies one subject, and in other cases, two or more subjects are identified. The subjects may each have one or more medical devices or implants, and each medical device may have one or more ISMs of the type described herein.

The computer program is arranged to direct the collection of sensor data from the ISM containing medical device. Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 35:

```
Start
    Open a secure socket layer (SSL)
    Identify a subject
    Communicate with a predetermined control unit
    Request sensor data from the subject via the control unit
    Receive sensor data
    If the sensor data is encrypted
        THEN decrypt the sensor data
    Store encrypted data in the selected storage locations
    Aggregate the sensor data with other sensor data
    Store encrypted data in the selected storage locations
    Maintain a record of the storage transaction
    Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, ambulance, truck, locomotive, tank, armored personnel carrier, etc.), (c) a building (e.g., a home, hospital, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, medical devices utilizing a variety of ISMs can be utilized to serve a variety of critical clinical functions, such as safe, accurate and less traumatic placement and deployment of the medical device, procedural and post-operative "real time" imaging of the medical device and the surrounding anatomy, the early identification of the development of medical device complications (often prior to becoming evident by other medical diagnostic procedures), and the patient's overall health status and response to treatment. Currently, post-operative (both in hospital and out-patient) evaluation of medical device patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes, radiation exposure). It can, therefore, be very difficult to accurately measure and follow the development or worsening of symptoms and evaluate "real life" medical device performance, particularly as they relate to patient activity levels, exercise tolerance, and the effectiveness of rehabilitation efforts and medications.

At present, neither the physician nor the patient has access to the type of "real time," continuous, objective, medical device performance measurements that they might otherwise like to have. Being able to monitor in situ medical device function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the medical device on a periodic basis, such as once per day or once per week. For example, within certain embodiments the devices and systems provided herein can instruct or otherwise notify the patient, or a permitted third-party as to deviations (e.g., greater than 10%, 20%, 25%, 50%, 70%, and or 100%) from normal, and/or, set parameters. In addition to empowering the patient to follow their own rehabilitation—and enabling them to see the positive (and negative) effects of various lifestyle choices on their health and rehabilitation—such information access can be expected to improve compliance and improve patient outcomes. Furthermore, their recovery experience can be shared via the web with other patients to compare their progress versus expected "norms" for function and rehabilitation and alert them to signs and symptoms that should be brought to their doctor's attention. From a public health perspective, the performance of different medical devices can be compared in different patients (different sexes, disease severity, activity levels, concurrent diseases such as hypertension and diabetes, smoking status, obesity, etc.) to help manufacturers design better medical devices and assist physicians in the selection of the right medical device for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

Conventions

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (latin, exempli gratia) is used herein to refer to a non-limiting example, and effectively means "for example". In addition, the Figures, while being understood to generally show the subject matter being described, should not be seen as limiting. For example, while ISMs can be shown as a block, linear, or rectangular symbolically, they can in practice look quite differently, and be attached differently than shown. For example, where ISMs are shown diagrammatically on stents as relatively linear objects, they can follow the struts or tynes of a stent and in practice be non-linear on the stent.

"Subjects" or "Patients" refers to an organism for which the medical device can be utilized. Representative organisms include horses, cows, sheep, pigs, dogs, cats, rats and mice. Within one embodiment a particularly preferred organisms are humans.

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the devices, methods, systems and processes disclosed herein. These embodiments are exemplary only. It will be understood that the invention is not limited to the embodiments set forth herein for illustration, but embraces all such forms thereof as come within the scope of the above disclosure.

1. A sensor module, comprising: a sensor channel; and a communication interface coupled to the sensor channel.

2. The sensor module of embodiment 1 wherein the sensor channel includes a sensor and a sensor channel coupled to the sensor and to the communication interface.

3. The sensor module of embodiments 1 or 2 wherein the sensor includes one or more of the following sensors: a global-positioning-system (GPS), accelerometer, Hall-effect, electrical, magnetic, thermal, pressure, radiation, optical, quantity-differential, capacitive, inductive, and time.

4. The sensor module of any one of embodiments 1 to 3 wherein the sensor is a microelectromechanical sensor. (MEMS).

5. The sensor module of any one of embodiments 1 to 4 wherein said sensor module includes one or more of the following sensors: fluid pressure sensors, fluid volume sensors, contact sensors, position sensors, pulse pressure sensors, blood volume sensors, blood flow sensors, chemistry sensors, metabolic sensors, accelerometers, mechanical stress sensors and temperature sensors. Within preferred embodiments the sensor module includes an accelerometer, gyroscope, and optionally, a temperature sensor.

6. The sensor module of any one of embodiments 1 to 5 wherein the communication interface includes a wireless interface.

7. The sensor module of any one of embodiments 1 to 6 wherein the communication interface is configured to communicate with another sensor module.

8. The sensor module of any one of embodiments 1 to 7, further comprising a power supply coupled to the sensor channel and the communication interface.

9. The sensor module of any one of embodiments 1 to 8, further comprising a power supply coupled to the sensor and the communication interface and configured to harvest energy from an organism in which the sensor module is implanted. Within further embodiments the power supply is a battery, which optionally, can power the sensor module continuously or intermittently. Within yet other embodiments the battery can power the sensor module in response to a signal.

10. The sensor module of any one of embodiments 1 to 9, further comprising a power supply coupled to the sensor channel and to the communication interface and configured to receive energy wirelessly.

11. The sensor module of any one of embodiments 1 to 10, further comprising a controller coupled to the sensor channel and the communication interface.

12. The sensor module of any one of embodiments 1 to 11, further comprising: an implantable housing; and wherein the sensor channel and the communication interface are disposed within the housing. Within certain embodiments of the invention, the sensor module is less than less than 5.0, 4.5, 4.0, 3.5, 3.0, 2.5, 2.0, 1.5, 1.0, 0.9, 0.8. 0.7, 0.6, 0.5, 0.4, 0.3, 0.2, or 0.1 cubic centimeters in size.

13. A medical device, comprising a medical device and a sensor module according to any one of embodiments 1 to 12.

14. The medical device according to embodiment 13, wherein said medical device is a cardiovascular device, orthopedic device, spinal device, intrauterine device, cochlear implant, aesthetic implant, dental implant, medical polymer or artificial eye lense.

15. The medical device according to embodiment 14 wherein said cardiovascular device is an implantable cardioverter defibrillator, pacemaker, stent, stent graft, bypass graft, catheter, or heart valve 16. The medical device according to embodiment 14, wherein said orthopedic device is a cast, brace, tensor bandage, support, sling, tensor bandage, hip or knee prosthesis, orthopedic plate, bone screw, spinal cage, artificial disc, orthopedic pin, intramedullary device, K-wire, or orthopedic plate. Within one embodiment the medical device is a tibial extension on a total arthroplastic joint (e.g, total hip or knee joint).

17. The medical device according to embodiment 14, wherein said medical polymer is a biodegradable polymer.

18. The medical device according to embodiment 14, wherein said medical polymer is a non-biodegradable polymer.

19. The medical device according to embodiment 14, wherein said medical polymer is a polymethylmethacrylate, a methylmethacrylate—styrene copolymer, fibrin, polyethylene glycol, carboxymethylcellulose, and polyvinylalcohol.

20. The medical device according to any one of embodiments 13 to 19 wherein said sensor module is located within said implant.

21. The medical device according to any one of embodiments 13 to 20 wherein said medical device is sterile.

22. The medical device according to any one of embodiments 13 to 21, further comprising one or more passive sensors.

23. The medical device according to embodiment 22 wherein said passive sensors are selected from the group consisting of fluid pressure sensors, fluid volume sensors, contact sensors, position sensors, pulse pressure sensors, blood volume sensors, blood flow sensors, chemistry sensors, metabolic sensors, accelerometers, mechanical stress sensors and temperature sensors.

24. A method, comprising: sensing a physical quantity; and generating a representation of the sensed quantity.

25. The method of embodiment 24 wherein the physical quantity relates to an organism.

26. The method of embodiment 24 wherein sensing the physical quantity includes sensing the physical quantity from inside of an organism.

27. The method of embodiment 24, further comprising storing the representation of the sensed quantity.

28. The method of embodiment 24, further comprising transmitting wirelessly the representation of the sensed quantity to a device.

29. The method of embodiment 24, further comprising receiving wirelessly data from a device.

30. The method of embodiment 24, further comprising: wherein the sensing and generating are performed by a first sensor module; and transmitting wirelessly the representation of the sensed quantity to a second sensor module that is remote from the first sensor module.

31. The method of embodiment 24, further comprising: wherein the sensing and generating are performed by a first sensor module; and receiving with the first sensor module data from a second sensor module that is remote from the first sensor module.

32. The method according to embodiment 30 or embodiment 31 wherein said first sensor module is a sensor module according to any one of embodiments 1 to 12.

33. A system, comprising: a sensor module including a battery; and a battery charger configured to charge the battery wirelessly.

34. The system according to embodiment 33 wherein said sensor module is a sensor module according to any one of embodiments 1 to 12.

35. A system, comprising: a first sensor module; and a second sensor module configured to communicate with the first sensor module.

36. The system according to embodiment 35 wherein said sensor module is a sensor module according to any one of embodiments 1 to 12.

37. The system of embodiment 35 wherein at least one of the first and second sensor modules is configured to be attached to an organism.

38. The system of embodiment 35 wherein at least one of the first and second sensor modules is configured to be implanted in an organism.

39. The system of embodiment 35 wherein one of the first and second sensor modules is configured to power the other of the first and second sensor modules.

40. The medical device according to any one of embodiments 13 to 23 wherein said sensor is a plurality of sensors which are positioned on or within said medical device at a density of greater than 1, 2, 3, 4, 5, 6, 7, 8, 9, 10 or 20 sensors per square centimeter.

41. The medical device according to any one of embodiments 13 to 23 wherein said sensor is a plurality of sensors which are positioned on or within said medical device at a density of greater than 1, 2, 3, 4, 5, 6, 7, 8, 9, 10 or 20 sensors per cubic centimeter.

42. A method comprising:
obtaining data from sensors positioned at a plurality of locations between, on, and/or within the medical device according to any one of embodiments 13 to 23 of a subject;
storing the data in a memory device located on or within the medical device; and
transferring the data from the memory to a location outside the medical device.

43. The method according to embodiment 42 further comprising the step of analyzing said data.

44. A method for detecting and/or recording an event in a subject with the medical device according to any one of embodiments 13 to 23, comprising the step of interrogating at a desired point in time the activity of one or more sensors within the medical device, and recording said activity.

45. The method according to embodiment 44 wherein the step of interrogating is performed by a subject which has said medical device.

46. The method according to embodiment 44 or 45 wherein said recording is performed on a wearable device.

47. The method according to any one of embodiments 43 to 45 wherein said recording, or a portion thereof, is provided to a health care provider.

48. A method for imaging the medical device in the bone, comprising the steps of
(a) detecting the location of one or more sensors in the medical device according to any one of embodiments 13 to 23; and
(b) visually displaying the location of said one or more sensors, such that an image of the medical device, or a portion thereof, in the bone is created.

49. The method according to embodiment 48 wherein the step of detecting occurs over time.

50. The method according to embodiment 47 or 48 wherein said visual display shows changes in the positions of said sensors over time, and/or changes in temperature of the sensors or surrounding tissue over time.

51. The method according to any one of embodiments 47 to 50 wherein said visual display is a three-dimensional image of said medical device in the bone.

52. A method for inserting the medical device according to any one of embodiments 13 to 23, comprising the steps of (a) inserting a medical device according to any one of embodiments 13 to 23 into a subject; and (b) imaging the placement of said medical device according to the method of an one of embodiments 47 to 50.

53. A method for examining the medical device according to any one of embodiments 13 to 23 which has been previously inserted into a patient, comprising the step of imaging the medical device according to the method of any one of embodiments 47 to 50.

54. A method of monitoring a medical device within a subject, comprising:
(a) transmitting a wireless electrical signal from a location outside the body to a location inside the subject's body;
(b) receiving the signal at a sensor positioned on a medical device according to any one of embodiments 13 to 23 located inside the body;
(c) powering the sensor using the received signal;
(d) sensing data at the sensor; and
(e) outputting the sensed data from the sensor to a receiving unit located outside of the body.

55. The method according to embodiment 54 wherein said receiving unit is a watch, wrist band, cell phone or glasses.

56. The method according to embodiments 54 or 55 wherein said receiving unit is located within a subject's residence or office.

57. The method according to embodiments any one of embodiments 54 to 56 wherein said sensed data is provided to a health care provider.

58. The method according to any one of embodiments 54 to 57 wherein said sensed data is posted to one or more websites.

59. A non-transitory computer-readable storage medium whose stored contents configure a computing system to perform a method, the method comprising:
(a) identifying a subject, the identified subject having at least one wireless medical device according to any one of embodiments 13 to 23, each wireless medical device having one or more wireless sensors;
(b) directing a wireless interrogation unit to collect sensor data from at least one of the respective one or more wireless sensors; and
(c) receiving the collected sensor data.

60. The non-transitory computer-readable storage medium of embodiment 59 whose stored contents configure a computing system to perform a method, the method further comprising:
(a) identifying a plurality of subjects, each identified subject having at least one medical device, each medical device having one or more wireless sensors;
(b) directing a wireless interrogation unit associated with each identified subject to collect sensor data from at least one of the respective one or more wireless sensors;
(c) receiving the collected sensor data; and
(d) aggregating the collected sensor data.

61. The non-transitory computer-readable storage medium of embodiment 60 whose stored contents configure a computing system to perform a method, the method further comprising:
(a) removing sensitive subject data from the collected sensor data; and
(b) parsing the aggregated data according to a type of sensor.

62. The non-transitory computer-readable storage medium of embodiment 60 whose stored contents configure a computing system to perform a method, wherein directing the wireless interrogation unit includes directing a control unit associated with the wireless interrogation unit.

63. The non-transitory computer readable storage medium according to any one of embodiments 60 to 62, wherein said medical device is according to any one of embodiments 13 to 23.

64. The storage medium according to any one of embodiments 60 to 63 wherein said collected sensor data is received on a watch, wrist band, cell phone or glasses.

65. The storage medium according to any one of embodiments 60 to 64 wherein said collected sensor data is received within a subject's residence or office.

66. The storage medium according to any one of embodiments 60 to 65 wherein said collected sensed data is provided to a health care provider.

67. The storage medium according to any one of embodiments 60 to 66 wherein said sensed data is posted to one or more websites.

68. The method according to any one of embodiments 54 to 58, or storage medium according to any one of embodiments 60 to 67, wherein said data is analyzed.

69. The method or storage medium according to embodiment 68 wherein said data is plotted to enable visualization of change over time.

70. The method or storage medium according to embodiments 68 or 69 wherein said data is plotted to provide a three-dimensional image.

71. A method for determining degradation of a medical device, comprising the steps of a) providing to a subject a medical device according to any one of embodiments 13 to 23, and b) detecting a change in a sensor, and thus determining degradation of the medical device.

72. The method according to embodiment 71 wherein said sensor is capable of detecting one or more physiological and/or locational parameters.

73. The method according to embodiments 71 or 72 wherein said sensor detects a location within the subject.

74. The method according to any one of embodiments 71 to 73 wherein said sensor moves from its original location, thereby indicating degradation of the medical device.

75. The method according to any one of embodiments 71 to 74 wherein the step of detecting is a series of detections over time.

76. A method for determining an infection associated with a medical device, comprising the steps of a) providing to a subject a medical device according to any one of embodiments 13 to 23, wherein said medical device comprises at least one temperature sensor and/or metabolic sensor, and b) detecting a change in said temperature sensor and/or metabolic sensor, and thus determining the presence of an infection.

77. The method according to embodiment 76 wherein the step of detecting is a series of detections over time.

78. The method according to embodiments 76 or 77 wherein said change is greater than a 1% change over the period of one hour.

79. The method according to any one of embodiments 76 to 78 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A medical device, comprising:
a tibial extension capable of being joined to a tibial component of an implantable knee prosthesis, where the tibial extension is configured to be placed into the medullary canal of a tibia and used to seat the medical device in a patient, the tibial extension comprising a housing and a body located within the housing, the housing having an outer surface; and
a first sensor module located entirely within the body of the tibial extension, the first sensor module comprising components, the components comprising a first power supply, a first sensor channel and a first communication interface, the first power supply comprising a first battery; the first sensor channel comprising a first power management circuit to manage transport of voltage from the first battery to a sensor of the first sensor channel via a first conductor, the sensor comprising sensors including both of a gyroscope and an accelerometer;
the tibial component comprising a second sensor module located entirely within the body of the tibial component, the second sensor module comprising a second power supply, a second sensor channel and a second communication interface, the second power supply comprising a second battery; the second sensor channel comprising a second power management circuit to manage transport of voltage from the second batter to a sensor of the second sensor channel via a second conductor;
wherein the second communication interface is a wireless interface configured to send information only to the first sensor module; and
wherein the first communication interface is a wireless interface configured to send information to a location outside of the medical device.

2. The medical device of claim 1 wherein the sensor of the first sensor channel is a microelectromechanical sensor (MEMS).

3. The medical device of claim 1, wherein the second power management circuit provides intermittent voltage to the sensor of the second sensor module in response to a signal.

4. The medical device of claim 1, wherein an antenna for receiving and transmitting wireless signal is located within the body of the tibial extension.

5. The medical device of claim 1 wherein the tibial component is to a tibial stem.

6. The medical device of claim 1 wherein the tibial component is to a tibial plate.

7. The medical device of claim 1, wherein the tibial extension comprises a screw engagement for joining to at least one of a tibial plate and a tibial stem.

8. The medical device of claim 1, wherein the tibial extension comprises a press-fit cylinder that can be accepted into a mating unit on at least one of a tibial plate or a tibial stem to effect joining of the tibial extension to the tibial plate or tibial stem, respectively.

9. The medical device of claim 1, wherein the tibial extension comprises a threaded cylinder that can be accepted into a mating unit on at last one of a tibial plate or a tibial stem to effect joining of the tibial extension to the tibial plate or tibial stem, respectively.

10. The medical device of claim 1, wherein the outer surface is ribbed to assist with bone engagement.

11. The medical device of claim 1, wherein the tibial extension is formed from two pieces that are connected together at a joint.

12. The medical device of claim 1, wherein said medical device is sterile.

13. A method, comprising:
(a) sensing a physical quantity using the medical device of claim 1 to obtain a sensed quantity; and
(b) generating a representation of the sensed quantity.

14. The method of claim 13 further comprising storing the representation of the sensed quantity.

15. The method of claim 13, further comprising transmitting wirelessly the representation of the sensed quantity to a device.

16. The method of claim 13, further comprising receiving wirelessly data from a device.

17. A method comprising:
(a) obtaining data from sensors positioned at a plurality of locations within the medical device according to claim 1, where the medical device is implanted within a subject;
(b) storing the data in a memory device located within the medical device; and
(c) transferring the data from the memory to a location outside the medical device.

18. A method for detecting and/or recording an event in a subject with the medical device according to claim 1, comprising the step of interrogating at a desired point in time an activity of one or more sensors within the medical device, and recording said activity.

19. The method according to claim 18 wherein said recording is performed on a wearable device.

20. A method for imaging a medical device in a tibia, comprising the steps of:
(a) detecting a location of one or more sensors in the medical device of claim 1 located in a tibia of a subject; and
(b) visually displaying the location of said one or more sensors, such that an image of the medical device, or a portion thereof, in the tibia is created.

21. The method of claim 20 wherein the step of detecting occurs over time.

22. A method for inserting a medical device comprising the steps of:
(a) inserting the medical device of claim 1 into a tibia of a subject to provide a placement of the medical device in the subject; and
(b) imaging the placement of said medical device according to a method comprising:
i. obtaining data from sensors positioned within the tibial extension located in the subject; and
ii. visually displaying a relative anatomical location of said sensors such that an image of the medical device is created.

23. A method for examining the medical device according to claim 1 which has been previously inserted into a patient, comprising the step of imaging the medical device according to a method comprising:
(a) obtaining data from sensors positioned within the tibial extension located in the tibia of the patient; and
(b) visually displaying a relative anatomical location of said sensors such that an image of the medical device is created.

24. A method of monitoring the medical device of claim 1 within a subject, comprising:
(a) transmitting a wireless electrical signal from a location outside the body to a location inside the subject's body;
(b) receiving the signal at a sensor positioned on the medical device of claim 1 located inside the tibia of the subject;
(c) powering the sensor using the battery;
(d) sensing data at the sensor; and
(e) outputting the sensed data from the sensor to a receiving unit located outside of the subject.

25. The method according to claim 24 wherein said sensed data is provided to a health care provider.

26. The method according to claim 24 wherein said sensed data is posted to one or more websites.

27. A non-transitory computer-readable storage medium whose stored contents configure a computing system to perform a method, the method comprising:
(a) identifying a subject, the identified subject having the tibial extension of the medical implant according to claim 1 inserted into a tibia of the subject, where the communication interface of the tibial extension comprises a wireless interface in communication with the sensor;
(b) directing a wireless interrogation unit to collect sensor data from the sensor; and
(c) receiving the collected sensor data.

28. The non-transitory computer-readable storage medium of claim 27 whose stored contents configure a computing system to perform a method, the method further comprising:
(d) identifying a plurality of subjects, each identified subject having a tibial extension of a respective medical device according to claim 1 inserted into a tibia of each respective identified subject, where the communication interface of the tibial extension comprises a wireless interface in communication with a respective sensor;
(e) directing a wireless interrogation unit associated with each identified subject to collect sensor data from at least one of the respective sensors;
(f) receiving the collected sensor data; and
(g) aggregating the collected sensor data.

29. The non-transitory computer-readable storage medium of claim 28 whose stored contents configure a computing system to perform a method, the method further comprising:
(h) removing sensitive subject data from the collected sensor data; and
(i) parsing the aggregated data according to a type of sensor.

30. A method for determining degradation of a medical device in a subject, comprising the steps of:
(a) providing to a subject a medical device according to claim 1, where the tibial extension of the medical device has been inserted into a tibia of the subject; and
(b) detecting a change in a sensor, and thus determining degradation of the medical device.

* * * * *